(12) United States Patent
Boebel et al.

(10) Patent No.: US 9,204,653 B2
(45) Date of Patent: *Dec. 8, 2015

(54) 5-FLUORO PYRIMIDINE DERIVATIVES

(71) Applicant: DOW AGROSCIENCES LLC, Indianapolis, IN (US)

(72) Inventors: Timothy Boebel, Indianapolis, IN (US); Kristy Bryan, Carmel, IN (US); Carla J. R. Klittich, Zionsville, IN (US); Beth Lorsbach, Indianapolis, IN (US); Timothy P. Martin, Noblesville, IN (US); Mark A. Pobanz, Zionsville, IN (US); Michael T. Sullenberger, Westfield, IN (US); Jeffery D. Webster, New Palestine, IN (US); Chenglin Yao, Westfield, IN (US); W. John Owen, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/031,920

(22) Filed: Sep. 19, 2013

(65) Prior Publication Data
US 2014/0024616 A1    Jan. 23, 2014

Related U.S. Application Data

(60) Division of application No. 12/537,504, filed on Aug. 7, 2009, now abandoned, which is a continuation-in-part of application No. 12/357,710, filed on Jan. 22, 2009, now abandoned.

(60) Provisional application No. 61/011,799, filed on Jan. 22, 2008, provisional application No. 61/115,297, filed on Nov. 17, 2008.

(51) Int. Cl.
| | |
|---|---|
| *C07D 239/47* | (2006.01) |
| *A01N 43/54* | (2006.01) |
| *A01N 55/00* | (2006.01) |
| *C07D 401/12* | (2006.01) |
| *C07D 403/12* | (2006.01) |
| *C07D 405/12* | (2006.01) |
| *C07D 409/12* | (2006.01) |
| *C07D 413/12* | (2006.01) |
| *C07D 417/12* | (2006.01) |
| *A01N 43/60* | (2006.01) |
| *A01N 43/80* | (2006.01) |
| *A01N 47/18* | (2006.01) |
| *A01N 47/24* | (2006.01) |
| *A01N 47/36* | (2006.01) |
| *A01N 47/42* | (2006.01) |
| *A01N 47/44* | (2006.01) |
| *A01N 57/32* | (2006.01) |

(52) U.S. Cl.
CPC ............ *A01N 55/00* (2013.01); *A01N 43/54* (2013.01); *A01N 43/60* (2013.01); *A01N 43/80* (2013.01); *A01N 47/18* (2013.01); *A01N 47/24* (2013.01); *A01N 47/36* (2013.01); *A01N 47/42* (2013.01); *A01N 47/44* (2013.01); *A01N 57/32* (2013.01); *C07D 239/47* (2013.01); *C07D 401/12* (2013.01); *C07D 403/12* (2013.01); *C07D 405/12* (2013.01); *C07D 409/12* (2013.01); *C07D 413/12* (2013.01); *C07D 417/12* (2013.01)

(58) Field of Classification Search
CPC ...... C07D 239/47; C07D 403/12; A01N 43/54; A01N 43/60; A01N 43/80
USPC .......... 544/122, 295, 317; 514/235.8, 252.14, 514/274

See application file for complete search history.

(56) References Cited

U.S. PATENT DOCUMENTS

| | | | |
|---|---|---|---|
| 3,309,359 | A | 3/1967 | Duschinsky et al. |
| 3,354,160 | A | 11/1967 | Duschinsky et al. |
| 3,368,938 | A | 2/1968 | Berger et al. |
| 3,868,373 | A | 2/1975 | Hoffer |
| 4,845,081 | A | 7/1989 | Sloan |
| 4,996,208 | A | 2/1991 | Lindner et al. |
| 5,480,991 | A | 1/1996 | Orvik et al. |
| 5,962,489 | A | 10/1999 | Mueller et al. |
| 6,066,638 | A | 5/2000 | Bereznak et al. |
| 6,072,051 | A | 6/2000 | Kim et al. |
| 6,617,330 | B2 | 9/2003 | Walter |
| 6,897,302 | B2 | 5/2005 | Kowalczyk et al. |
| 7,914,799 | B2 | 3/2011 | Jira et al. |
| 8,912,207 | B2 * | 12/2014 | Boebel et al. ............ 514/274 |
| 2003/0039667 | A1 | 2/2003 | Jira et al. |
| 2008/0004253 | A1 | 1/2008 | Branstetter et al. |
| 2008/0269238 | A1 | 10/2008 | Sugihara et al. |

(Continued)

FOREIGN PATENT DOCUMENTS

| | | |
|---|---|---|
| CA | 2321182 A1 | 8/1999 |
| EP | 0102908 A1 | 3/1984 |

(Continued)

OTHER PUBLICATIONS

International Search Report and Written Opinion for PCT/US2012/050930, Oct. 15, 2012.

(Continued)

*Primary Examiner* — Deepak Rao
(74) *Attorney, Agent, or Firm* — C. W. Arnett; Faegre Baker Daniels LLP

(57) ABSTRACT

This present disclosure is related to the field of 5-fluoro pyrimidines and their derivatives and to the use of these compounds as fungicides.

20 Claims, No Drawings

(56) References Cited

U.S. PATENT DOCUMENTS

| | | | |
|---|---|---|---|
| 2009/0203647 A1 | 8/2009 | Benko et al. |
| 2010/0022538 A1 | 1/2010 | Boebel et al. |
| 2011/0034493 A1 | 2/2011 | Boebel et al. |

FOREIGN PATENT DOCUMENTS

| | | | |
|---|---|---|---|
| EP | 0139613 A1 | 5/1985 |
| EP | 0332579 A2 | 9/1989 |
| EP | 0602478 A1 | 6/1994 |
| EP | 0877022 B1 | 4/2003 |
| GB | 1461184 A | 1/1977 |
| JP | 6001793 A | 1/1994 |
| NZ | 209356 A | 1/1988 |
| WO | WO9733890 A1 | 9/1997 |
| WO | 9856803 | 12/1998 |
| WO | WO 03/059916 A2 | 7/2003 |
| WO | WO 2007/077505 A2 | 7/2007 |
| WO | WO 2008/046757 A1 | 4/2008 |
| WO | WO 2008/131062 A2 | 10/2008 |
| WO | WO 2009/094442 | 7/2009 |
| WO | WO2010047866 A2 | 4/2010 |
| WO | WO2010085377 A2 | 7/2010 |

OTHER PUBLICATIONS

International Search Report for PCT/US2010/044579, Sep. 21, 2010.
Chiacchio U, et al. Enantioselective Syntheses and Cytotoxicity of N,O-Nucleosides. Journal of Medicinal Chemistry, Jan. 1, 2003, vol. 46, pp. 3696-3702.
Morris J Robins, et al. A direct synthesis of 5-fluorocytosine and its nucleosides using trifluoromethyl hypofluorite. Journal of the Chemical Society, Chemical Communications, No. 1, Jan. 1, 1972, p. 18.
Arthur F. Lewis et al. Synthesis and in vitro anti-human cytomegalovirus (hcmv) activity of certain alkenyl substituted cytosines and 5-halocytosines. Journal of Heterocyclic Chemistry, Sep. 1, 1995, vol. 32, Nr:5, pp. 1513-1515.
Kulikowski et al. Methylation and tautomerism of 5-fluorocytosine nucleosides and their analogues. Journal Nucleic Acids Research, Jan. 1, 1978, vol. 4, pp. S7-S10.
Supplemental European Search Report for EP10807172 (PCT/US2010/044579), Dec. 7, 2012.
International Search Report for PCT/US2010/044592, Sep. 21, 2010.
International Search Report for PCT/US/2009/031683, Jan. 22, 2009.
Jaworski et al. Infrared spectra and tautomerism of 5-fluorocytosine, 5-bromocytosine and 5-iodocytosine. Matrix isolation and theoretical ab initio studies. Journal of Molecular Structure, Jan. 1, 1990, vol. 223, pp. 63-92.
Gabriella et al. Some 5-fluorosulfanilamidopyrimidines. Gazzetta Chimica Italiana, Jan. 1, 1963, vol. 93, Nr:10, pp. 1268-1278.
International Search Report for PCT/US2012/050931, Oct. 9, 2012.
International Search Report for PCT/US2011/020351, Mar. 14, 2011.
Liang et al., A facile synthesis and herbicidal activities of novel fluorine-containing thiazolo[4,5-d] pyrimidin-7(6H)-ones. Journal of Fluorine Chemistry [online], Jul. 2007, vol. 128, Iss. 7, pp. 879-884.
Duschinsky et al., Nucleosides. XXXIII. N4-Acylated 5-Fluorocytosines and a Direct Synthesis of 5-Fluoro-2'-deoxycytidine. Journal of Medicinal Chemistry, Jul. 1, 1966, vol. 9, Nr:4, pp. 566-572.
Bera et al., Nucleosides with furanyl scaffolds. Tetrahedron, Jun. 10, 2002, vol. 58, Nr:24, pp. 4865-4871.
Duschinsky et al., Cytosine derivatives. CAPLUS Abstract 61:18527, 1964.
International Search Report for PCT/US2010/044588, Oct. 1, 2010.
Waring, M J, Defining optimum lipophilicity and molecular weight ranges for drug candidates—Molecular weight dependent lower logD limits based on permeability. Bioorganic & Medical Chemistry Letters, May 15, 2009, vol. 19, Nr:10, pp. 2844-2851.
International Search Report for PCT/US2010/060792, Apr. 22, 2011.
International Search Report for PCT/US2010/044576, Sep. 23, 2010.
Wempen, I. et al., Thiation of Nucleosides. IV. The Synthesis of 5-Fluoro-2'-deoxycytidine and Related Compounds, Organic and Biological Chemistry, Dec. 5, 1961, pp. 4755-4766, vol. 83.
Stroeter, T., European Search Report for EP App. No. 12192509.3, Jan. 21, 2013, pp. 1-2, Munich.
European Search Opinion for EP App. No. 12192509.3, pp. 1-3, Jan. 2013.
Stroeter, T., European Search Report for EP App. No. 12192511.9, Jan. 15, 2013, pp. 1-2, Munich.
European Search Opinion for EP App. No. 12192511.9, pp. 1-3, Jan. 2013.
Stroeter, T., European Search Report for EP App. No. 12192512.7, Jan. 15, 2013, pp. 1-2, Munich.
European Search Opinion for EP App. No. 12192512.7, pp. 1-2, Jan. 2013.
Jeong, L.S., et al. Structure-activity relationships of .beta.-D-(2S, 5R)- and .alpha.-D-(2S,5S)-1,3-oxathiolanyl nucleosides as potential anti-HIV agents, Journal of Medicinal Chemistry, Sep. 1, 1993, pp. 2627-2638, vol. 36, No. 18.
Stroeter, T., European Search Report for EP App. No. 12192515.0, Jan. 15, 2013, pp. 1-2, Munich.
European Search Opinion for EP App. No. 12192515.0, pp. 1-3, Jan. 2013.
Stroeter, T., European Search Report for EP App. No. 12192521.8, Jan. 17, 2013, pp. 1-2, Munich.
European Search Opinion for EP App. No. 12192521.8, pp. 1-3, Jan. 2013.
Stroeter, T., European Search Report for EP App. No. 12192549.9, Jan. 17, 2013, pp. 1-3, Munich.
European Search Opinion for EP App. No. 12192549.9, pp. 1-3, Jan. 2013.
Klotzer, Wilhelm, et al., 5-Halogenated N-hydroxypyrimidines. 5-Fluoro-1-hydroxyuracil and 5-fluoro-3-hydroxycytosine, Monatshefte fur Chemie, Jan. 1, 1968, pp. 847-860, vol. 99, No. 2.
Atkins, Paul J., et al., Stereochemistry of the formation of 4-alkoxyimino-5,6-dihydro-6-alkoxyaminopyrimidin-2(1 H)-ones from cytosines and hydroxylamines, Journal of the Chemical Society, Perkin Transactions 2: Physical Organic Chemistry, Jan. 1, 1972, pp. 155-160, No. 2.
Stroeter, T., European Search Report for EP App. No. 12192553.1, Jan. 17, 2013, pp. 1-2, Munich.
European Search Opinion for EP App. No. 12192553.1, pp. 1-2, Jan. 2013.
Stroeter, T., European Search Report for EP App. No. 12192556.4, Jan. 17, 2013, pp. 1-5, Munich.
European Search Opinion for EP App. No. 12192556.4, pp. 1-4, Jan. 2013.
Yamada, H. et al., Product subclass 3: Carbohydrate Derivatives (Including Nucleosides), Science of Synthesis, Jan. 1, 2007, pp. 47-81.
Protsenko, L.D. et al, Amino- and ethylenimino derivatives of 5-fluoropyrimidine, Zhurnal Obshchei Khimii, Jan. 1, 1963, pp. 537-542, vol. 33, No. 2.
Pyrimidines. III. Some transformations of 4-bis(2-chloroethyl)amino-5-fluoropyrimidines, Zhurnal Obshchei Khimii, Jan. 1, 1965, pp. 1303-1307, vol. 35, No. 7.
Kuz'Menko, I.D., et al., Synthesis and antineoplastic properties of pyrimidyl phosphates containing a cytotoxic group, Fiziologiceski Aktivnye Vesestva, Jan. 1, 1988, pp. 7-10, vol. 20.
Saneyoshi, M. et al., Synthetic Nucleosides and Nucleotides. XXXV. Synthesis and Biological Evaluations of 5-Fluoropyrimidine Nucleosides and Nucleotides of 3-Deoxy-Beta-D-Ribofuranose and Related Compounds, Chemical and Pharmaceutical Bulletin, Nov. 1, 1995, pp. 2005-2009, vol. 43, No. 11.
Saneyoshi, M., et al., Synthetic nucleosides and nucleotides. XVIII. Synthesis and cytostatic activity of 5-fluoropyrimidine nucleosides of 3-amino-3-deoxy-.BETA.-D-ribofuranose and related compounds, Chemical and Pharmaceutical Bulletin, 1981, pp. 2769-2775, vol. 29, No. 10.

(56) References Cited

OTHER PUBLICATIONS

Gelijkens, C.F., et al., Capillary gas chromatography of pyrimidines and purines: N,O-peralkyl and trifluoroacetyl-N,O-alkyl derivatives, Journal of Chromatography Biomedical Sciences and Applications, Oct. 1, 1981, pp. 291-299, vol. 225, No. 2.

European Search Opinion for EP App. No. 09704708.8, Apr. 12, 2011, pp. 1-3.

Lee, K., et al., Structure-Activity Relationships of 2'-Fluoro-2',3'-unsaturated D-Nucleosides as Anti-HIV-1 Agents, J. Med. Chem. 2002, pp. 1313-1320, vol. 45.

Saneyoshi, M. et al., Synthetic Nucleosides and Nucleotides. XI. Facile Synthesis and Antitumor Activities of Various 5-Fluoropyrimidine Nucleosides, Chem. Pharm. Bull., 1978, pp. 2990-2997, vol. 26.

Chemical Abstracts, AN 1977:439530 SU551329 A1, 1977, pp. 1-8.

Zhang et al., CAPLUS Abstract 111:134074 (1989).

* cited by examiner

5-FLUORO PYRIMIDINE DERIVATIVES

CROSS REFERENCE TO RELATED APPLICATIONS

This application is a divisional application of U.S. patent application Ser. No. 12/537,504, filed Aug. 7, 2009, which is a continuation-in-part application of U.S. patent application Ser. No. 12/357,710, filed Jan. 22, 2009, which claims the benefit of U.S. Provisional Patent Application Ser. No. 61/011,799 filed Jan. 22, 2008, and U.S. Provisional Patent Application Ser. No. 61/115,297 filed Nov. 17, 2008.

FIELD OF THE INVENTION

This present disclosure is related to the field of 5-fluoro pyrimidines and their derivatives and to the use of these compounds as fungicides.

BACKGROUND AND SUMMARY OF THE INVENTION

Fungicides are compounds, of natural or synthetic origin, which act to protect and cure plants against damage caused by agriculturally relevant fungi. Generally, no single fungicide is useful in all situations. Consequently, research is ongoing to produce fungicides that may have better performance, are easier to use, and cost less.

The present disclosure relates to 5-fluoro pyrimidine compounds and their use as fungicides. The compounds of the present disclosure may offer protection against ascomycetes, basidiomycetes, deuteromycetes and oomycetes.

One embodiment of the present disclosure may include compounds of Formula I:

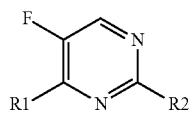

I wherein $R^1$ is —$N(R^3)R^4$;
$R^2$ is —$OR^{21}$;
$R^3$ is:
  H;
  $C_1$-$C_6$ alkyl optionally substituted with 1- to 3 $R^5$;
  $C_2$-$C_6$ alkenyl optionally substituted with 1-3 $R^5$;
  a 5- or 6-membered heteroaromatic ring selected from the group consisting of furanyl, pyridinyl, pyridinyl-N-oxide, pyrimidinyl, pyridazinyl, pyrazinyl, thiazolyl, triazinyl, thiadiazolyl, oxazolyl, isoxazolyl, triazolyl, each heteroaromatic ring being optionally substituted with 1-3 $R^{30}$;
  imidazole fused with an aromatic or heteroaromatic ring selected from the group consisting of benzene, oxazole, isoxazole, furan, thiazole, pyrimidine, pyridine, pyrrole, pyrazine, thiophene, each aromatic or heteroaromatic ring being optionally substituted with 1 to 3 $R^{30}$;
  benzo[1,3]dioxolyl;
  3H-isobenzofuran-1-onyl;
  cyano;
  $C_3$-$C_6$ alkynyl optionally substituted with 1-3 $R^5$;
  —$C(=O)R^6$;
  —$C(=O)OCH_2C(=O)R^8$;
  —$C(=S)R^6$;
  —$C(=S)NHR^8$;
  —$C(=O)N(R^8)R^{10}$;
  —$OR^7$;
  —$P(O)(OR^{15})_2$;
  —$S(O)_2R^8$;
  —$SR^8$;
  —$Si(R^8)_3$;
  —$N(R^9)R^{10}$;
  —$N=C(R^{15})R^{16}$;
  —$(CHR^{22})_m R^{37}$;
  —$(CHR^{24})OR^{29}$;
  —$C(=NR^{16})SR^{16}$; or
  —$C(=NR^{27})NR^{13}R^{28}$;
wherein m is an integer from 1-3;
$R^4$ is:
  H;
  hydroxyl;
  amino;
  $C_1$-$C_6$ alkyl, optionally substituted with 1-3 $R^5$;
  —$C(=O)R^6$; or
  —$C(=O)N(R^8)R^{10}$;
alternatively $R^3$ and $R^4$ may be taken together to form:
  a 5- or 6-membered saturated or unsaturated ring containing 1-3 heteroatoms wherein each ring may be optionally substituted with 1-3 $R^{11}$;
  =$C(R^{12})N(R^{13})R^{14}$;
  =$C(R^{13})(R^{14})$;
  =$C(R^{15})OR^{15}$;
  =$S(R^{34})_2$; or
  =$NR^{35}$;
$R^5$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, —OH, N-methyl piperazine or $C_3$-$C_6$ trialkylsilyl;
$R^6$ is independently H, $C_1$-$C_6$ alkyl, $C_2$-$C_6$ alkenyl optionally substituted with 1-3 $R^{30}$, $C_1$-$C_5$ haloalkyl, $C_1$-$C_5$ alkoxy, $C_1$-$C_5$ haloalkoxy $C_2$-$C_6$ alkoxycarbonyl, $C_1$-$C_4$ alkoxyalkyl, $C_2$-$C_6$ alkylaminocarbonyl; 1-benzo[1,2,3]thiadiazol-7-yl, thiazolyl, benzyl, phenyl, phenoxy, or benzyloxy wherein the thiazolyl, benzyl, phenyl, phenoxy, or benzyloxy may be optionally substituted with 1-3 $R^{20}$, a 5- or 6-membered saturated or unsaturated ring containing 1-3 heteroatoms wherein each ring may be optionally substituted with 1-3 $R^{11}$;
$R^7$ is H, $C_1$-$C_6$ alkyl, $C_2$-$C_6$ alkenyl, $C_1$-$C_5$ haloalkyl, benzyl which may be optionally substituted with 1-5 $R^{20}$, —$CHR^{18}C(O)OR^{19}$, —$(CHR^{27})R^{28}$, —$Si(R^8)_3$, or a 5- or 6-membered saturated or unsaturated ring containing 1-3 heteroatoms wherein each ring may be optionally substituted with 1-3 $R^{11}$;
$R^8$ is independently $C_1$-$C_6$ alkyl, $C_1$-$C_6$ haloalkyl, amino, $C_1$-$C_6$ alkylamino, $C_2$-$C_6$ dialkylamino, methylene-2-furanyl, —$CHR^{15}C(O)OR^{19}$, benzyl optionally substituted with 1-3 $R^{30}$, phenyl optionally substituted with 1-3 $R^{30}$, or a 5- or 6-membered saturated or unsaturated ring containing 1-3 heteroatoms wherein each ring may be optionally substituted with 1-3 $R^{11}$;
$R^9$ is H, $C_1$-$C_6$ alkyl $C_1$-$C_6$ haloalkyl, —$C(=O)R^{17}$, benzothiazoyl, quinazolinyl, or phenyl optionally substituted with 1-3 $R^{20}$, a 5- or 6-membered saturated or unsaturated ring containing 1-3 heteroatoms wherein each ring may be optionally substituted with 1-3 $R^{11}$;
$R^{10}$ is H or $C_1$-$C_6$ alkyl, $C_1$-$C_6$ haloalkyl, or phenyl optionally substituted with 1-3 $R^{20}$;
$R^{11}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, amino, $C_1$-$C_6$ alkylamino, $C_2$-$C_6$ dialkylamino, $C_2$-$C_6$ alkoxycarbonyl, or $C_2$-$C_6$ alkylcarbonyl;

$R^{12}$ is H or $C_1$-$C_4$ alkyl;

$R^{13}$ and $R^{14}$ are independently H, cyano, —OH, $C_1$-$C_4$ alkyl, $C_1$-$C_6$ alkoxy, $C_2$-$C_6$, alkylcarbonyl, phenyl, or benzyl wherein the phenyl or benzyl may be optionally substituted with 1-3 $R^{20}$;

alternatively $R^{13}$ and $R^{14}$ may be taken together to form:
  a 5- or 6-membered saturated or unsaturated ring containing 1-3 heteroatoms wherein each ring may be optionally substituted with 1-3 $R^{11}$, or 3,4-dihydro-1H-isoquinolin-2-yl;

alternatively $R^{12}$ and $R^{13}$ may be taken together to form:
  a 5- or 6-membered saturated or unsaturated ring containing 1-3 heteroatoms wherein each ring may be optionally substituted with 1-3 $R^{11}$;

$R^{15}$ is H or $C_1$-$C_6$ alkyl, $C_2$-$C_6$ alkenyl, 2-benzofuranyl, a 5- or 6-membered saturated or unsaturated ring containing 1-3 heteroatoms wherein each ring may be optionally substituted with 1-3 $R^{11}$;

$R^{16}$ is H, $C_1$-$C_6$ alkyl, or phenyl optionally substituted with 1-3 $R^{20}$;

alternatively $R^{15}$ and $R^{16}$ may be taken together as —(CH$_2$)$_4$— or —(CH$_2$)$_5$—;

$R^{17}$ is H, $C_1$-$C_6$ alkyl, $C_2$-$C_6$ alkenyl, $C_1$-$C_6$ haloalkyl, $C_1$-$C_6$ alkoxy, benzyl, phenyl, phenoxy, or benzyloxy wherein each ring may be optionally substituted with 1-3 $R^{20}$, a 5- or 6-membered saturated or unsaturated ring containing 1-3 heteroatoms wherein each ring may be optionally substituted with 1-3 $R^{11}$;

$R^{18}$ is H, $C_1$-$C_6$ alkyl, or $C_1$-$C_6$ haloalkyl;

$R^{19}$ is H, $C_1$-$C_6$ alkyl, $C_1$-$C_6$ haloalkyl, or benzyl;

$R^{20}$ is independently halogen, cyano, nitro, amino, $C_1$-$C_6$ alkoxyalkoxy, $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ haloalkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$-$C_8$ dialkylamino, $C_3$-$C_8$ dialkylaminocarbonyl, $C_2$-$C_6$ alkoxycarbonyl, $C_2$-$C_6$ alkylcarbonyl, $C_3$-$C_6$ trialkylsilyl, 2-[(E)-methoxyimino]-N-methylacetamidyl, phenyl, benzyl, benzyloxy, phenoxy, or a 5- or 6-membered heteroaromatic ring wherein each phenyl, benzyl, benzyloxy, phenoxy, or 5- or 6-membered heteroaromatic ring may be optionally substituted with 1-3 substitutents independently selected from $R^{31}$;

$R^{21}$ is:
  H;
  $C_1$-$C_{14}$ alkyl;
  $C_1$-$C_6$ haloalkyl;
  $C_2$-$C_4$ alkenyl;
  $C_2$-$C_4$ haloalkenyl;
  $C_3$-$C_4$ alkynyl;
  $C_3$-$C_4$ haloalkynyl;
  phenyl, naphthyl, or tetrahydroquinolinyl each optionally substituted with 1-3 $R^{20}$;
  —(CHR$^{22}$)$_m$R$^{23}$;
  —(CHR$^{24}$)$_m$C(O)OR$^{25}$;
  —(CHR$^{24}$)$_m$C(O)R$^{26}$;
  —(CHR$^{24}$)$_m$C(O)N(R$^{27}$)R$^{28}$;
  —(CHR$^{24}$)$_m$OR$^{29}$;
  —(CHR$^{24}$)$_m$SR$^{29}$;
  —(CHR$^{24}$)$_m$N(R$^{27}$)R$^{28}$;
  —C(=O)R$^{32}$;
  —N=C(R$^{32}$)(R$^{36}$);
  —NR$^{25}$C(=O)OR$^{25}$
  —Si(R$^8$)$_3$;
  —SO$_2$R$^{33}$;
  $C_2$-$C_6$ alkoxy carbonyl;
  $C_2$-$C_6$ alkylaminocarbonyl;
  $C_2$-$C_6$ alkylcarbonyl;
  sugars selected from the group consisting of beta-D-glucose-tetraacetate, rhamnose, fructose, and pentose; or
  a 5- or 6-membered heteroaromatic ring selected from the group consisting of furanyl, pyridinyl, pyridinyl-N-oxide, pyrimidinyl, pyridazinyl, pyrazinyl, pyrazolyl, thiazolyl, triazinyl, thiadiazolyl, oxazolyl, triazolyl or isoxazolyl wherein each 5- or 6-member heteroaromatic ring may be optionally substituted with 1-5 $R^{20}$;

$R^{22}$ is independently:
  H;
  halogen;
  cyano;
  nitro;
  $C_1$-$C_6$ alkyl;
  $C_1$-$C_6$ haloalkyl;
  phenyl or benzyl optionally substituted with 1-3 $R^{20}$;
  $C_1$-$C_6$ hydroxyalkyl;
  $C_2$-$C_6$ alkoxylalkyl;
  $C_3$-$C_6$ haloalkynyl;
  $C_2$-$C_6$ alkenyl;
  $C_2$-$C_6$ haloalkenyl;
  $C_3$-$C_6$ alkynyl;
  $C_1$-$C_6$ alkoxy;
  $C_1$-$C_6$ haloalkoxy;
  $C_1$-$C_6$ alkylthio;
  $C_1$-$C_6$ alkylamino;
  $C_2$-$C_8$ dialkylamino;
  $C_3$-$C_6$ cycloalkylamino;
  $C_4$-$C_6$ (alkyl)cycloalkylamino;
  $C_2$-$C_6$ alkylcarbonyl;
  $C_2$-$C_6$ alkoxycarbonyl;
  $C_2$-$C_6$ alkylaminocarbonyl;
  $C_3$-$C_8$ dialkylaminocarbonyl;
  $C_3$-$C_6$ trialkylsilyl;
  ring-fused heteroaromatic rings selected from the group consisting of benzothiophenyl, quinolinyl, isoquinolinyl, thieno[2,3-b]pyridyl, 1-methyl-1H-thieno[2,3-c]pyrazolyl, and benzoimidazolyl, wherein each of the rings may be further substituted with 1-3 $R^{20}$; or
  a 5- or 6-membered heteroaromatic ring selected from the group consisting of furanyl, pyridinyl, pyridinyl-N-oxide, pyrimidinyl, pyridazinyl, pyrazinyl, thiazolyl, triazinyl, thiadiazolyl, oxazolyl, isoxazolyl, triazolyl and thienyl;

$R^{23}$ is:
  H;
  halogen;
  $C_1$-$C_6$ alkyl;
  $C_1$-$C_6$ haloalkyl;
  $C_2$-$C_6$ dialkylamino;
  phenyl optionally substituted with 1-5 $R^{20}$;
  ring-fused heteroaromatic rings selected from the group consisting of benzothiophenyl, quinolinyl, isoquinolinyl, thieno[2,3-b]pyridyl, 1-methyl-1H-thieno[2,3-c]pyrazolyl, benzofuranyl and benzoimidazolyl, 2,3-dihydrobenzofuran-2-yl, 4-methyl-4H-thieno[3,2-b]pyrrol-5-yl, 1-methyl-1H-indol-5-yl, imidazo[1,2-a]pyridin-2-yl, imidazo[2,1-b]thiazol-6-yl, benzothiazol-2-yl, benzo[b]thiophen-7-yl, and 1-methyl-1H-indazol-3-yl, wherein each of the rings may be further substituted with 1-3 $R^{20}$;

naphthyl;

benzo[1,3]dioxolyl;

pyrrolidinonyl;

oxetanyl;

$C_1$-$C_6$ alkylthio optionally substituted with 1-5 $R^{20}$;

a 5- or 6-membered saturated or unsaturated ring containing 1-3 heteroatoms wherein each ring may be optionally substituted with 1-3 $R^{11}$; or a 5- or 6-membered heteroaromatic ring selected from the group consisting of furanyl, pyridinyl, pyridinyl-N-oxide, pyrimidinyl, pyridazinyl, pyrazinyl, pyrazolyl, thiazolyl, triazinyl, thiadiazolyl, oxazolyl, isoxazolyl, triazolyl, imidazolyl, thiophene-2-yl and thiophen-3-yl wherein each heteroaromatic ring may be optionally substituted with 1-3 $R^{20}$;

$R^{24}$ is H, $C_1$-$C_6$ alkyl, $C_1$-$C_6$ alkoxy, benzyl, or phenyl wherein each of the benzyl or phenyl may be optionally substituted with 1-3 $R^{20}$;

$R^{25}$ is H, $C_1$-$C_6$ alkyl, phenyl or benzyl optionally substituted with 1-3 $R^{20}$;

$R^{26}$ is:
  H;
  $C_1$-$C_6$ alkyl;
  $C_1$-$C_6$ alkoxy;
  phenyl optionally substituted with 1-3 $R^{20}$; or
  a 5- or 6 membered heteroaromatic ring selected from the group consisting of furanyl, pyridinyl, pyridinyl-N-oxide, pyrimidinyl, pyridazinyl, pyrazinyl, thiazolyl, triazinyl, thiadiazolyl, oxazolyl, triazolyl and isoxazolyl;

$R^{27}$ and $R^{28}$ are independently:
  H;
  $C_1$-$C_6$ alkyl;
  benzyl or phenyl wherein each of the benzyl or phenyl may be optionally substituted with 1-3 $R^{20}$; or
  a 5- or 6-membered saturated or unsaturated ring containing 1-3 heteroatoms wherein each ring may be optionally substituted with 1-3 $R^{11}$;

$R^{29}$ is:
  H;
  $C_1$-$C_6$ alkyl;
  $C_1$-$C_6$ haloalkyl;
  $C_1$-$C_6$ alkoxyalkyl;
  $C_2$-$C_6$ alkylcarbonyl;
  benzyl, benzoyl, or phenyl wherein each of the benzyl, benzoyl or phenyl may be optionally substituted with 1-3 $R^{20}$; or
  a 5- or 6-membered saturated or unsaturated ring containing 1-3 heteroatoms wherein each ring may be optionally substituted with 1-3 $R^{11}$;

$R^{30}$ is independently halogen, cyano, nitro, $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$-$C_8$ dialkylamino, $C_3$-$C_8$ dialkylaminocarbonyl, $C_3$-$C_6$ trialkylsilyl, thiazolyl, phenyl, pyrimidinyl, or pyridyl, wherein the thiazolyl, phenyl, pyridyl, or pyrimidinyl may be optionally substituted with 1-3 $R^{20}$;

$R^{31}$ is independently halogen, cyano, nitro, $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$-$C_8$ dialkylamino, $C_3$-$C_8$ dialkylaminocarbonyl, or $C_3$-$C_6$ trialkylsilyl;

$R^{32}$ is independently:
  $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$-$C_8$ dialkylamino, $C_3$-$C_8$ dialkylaminocarbonyl, $C_3$-$C_6$ trialkylsilyl;
  phenyl wherein the phenyl ring may be optionally substituted with 1-3 $R^{20}$; or
  a 5- or 6-membered saturated or unsaturated ring containing 1-3 heteroatoms wherein each ring may be optionally substituted with 1-3 $R^{11}$;

$R^{33}$ is independently:
  $C_1$-$C_6$ alkyl, $C_1$-$C_6$ haloalkyl, phenyl or thienyl optionally substituted with 1-3 $R^{20}$; or
  a 5- or 6-membered saturated or unsaturated ring containing 1-3 heteroatoms wherein each ring may be optionally substituted with 1-3 $R^{11}$;

$R^{34}$ is:
  $C_1$-$C_6$ alkyl, $C_1$-$C_6$ haloalkyl, $C_2$-$C_6$ alkoxyalkyl, $C_1$-$C_6$ alkylamino; or
  a 5- or 6-membered saturated or unsaturated ring containing 1-3 heteroatoms wherein each ring may be optionally substituted with 1-3 $R^{11}$;

$R^{35}$ is:
  $C_1$-$C_6$ alkyl, $C_2$-$C_6$ alkylcarbonyl; or
  a 5- or 6-membered saturated or unsaturated ring containing 1-3 heteroatoms wherein each ring may be optionally substituted with 1-3 $R^{11}$;

$R^{36}$ is H, cyano, $C_1$-$C_6$ alkyl, $C_1$-$C_6$ alkoxy, benzyl, or phenyl wherein each of the benzyl, or phenyl may be optionally substituted with 1-3 $R^{20}$;

alternatively $R^{32}$ and $R^{36}$ may be taken together to form:
  a 5- or 6-membered saturated or unsaturated ring containing 1-3 heteroatoms wherein each ring may be optionally substituted with 1-3 $R^{11}$; and $R^{37}$ is independently:
  H, halogen, or phenyl optionally substituted with 1-5 $R^{20}$;
  $C_1$-$C_6$ alkyl, $C_1$-$C_6$ haloalkyl, hydroxyl, $C_1$-$C_6$ alkoxy, or $C_1$-$C_6$ haloalkoxy; or
  a 5- or 6-membered saturated or unsaturated ring containing 1-3 heteroatoms wherein each ring may be optionally substituted with 1-3 $R^{11}$.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, an area adjacent to the plant, and the seed adapted to produce the plant.

The term "alkyl" refers to an unbranched, branched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to refers to a branched or unbranched carbon chain containing one or more triple bonds including propynyl, butynyl and the like.

As used throughout this specification, the term 'R' refers to the group consisting of $C_{2-8}$ alkyl, $C_{3-8}$ alkenyl or $C_{3-8}$ alkynyl, unless stated otherwise.

The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —SO$_2$—R substituent.

The term "haloalkylsulfonyl" refers to a sulfonyl substitution on an alkyl which is partially substituted with halogen atoms.

The term "alkylthio" refers to an —S—R substituent.

The term "alkylaminocarbonyl" refers to a —C(O)—N(H)—R substituent.

The term "dialkylaminocarbonyl" refers to a —C(O)—NR$_2$ substituent.

The term "alkylcycloalkylamino" refers to a cycloalkylamino substituent that is substituted with an alkyl group.

The term "trialkylsilyl" refers to —SiR$_3$.

The term "cyano" refers to a —C≡N substituent.

The term "hydroxyl" refers to a —OH substituent

The term "amino" refers to a —NH$_2$ substituent

The term "alkylamino" refers to a —N(H)—R substituent

The term "dialkylamino" refers to a —NR$_2$ substituent

The term "alkoxyalkoxy" refers to —O(CH$_2$)$_n$O(CH$_2$)$_n$ where n is an integer from 1-3

The term "alkoxyalkyl" refers to an alkoxy substitution on an alkyl.

The term "haloalkoxyalkyl" refers to an alkoxy substitution on an alkyl which may be partially substituted with halogen atoms The term "hydroxyalkyl" refers to an alkyl which is substituted with a hydroxyl group.

The term "haloalkoxy" refers to a —OR—X substituent, wherein X is Cl, F, Br, or I, or any combination thereof.

The term "haloalkyl" refers to an alkyl, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "hydroxycarbonyl" refers to a —C(O)—OH substituent.

The term "nitro" refers to a —NO$_2$ substituent.

The term "thienyl" refers to a 5-member aromatic ring with one sulfur atom.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION OF THE PRESENT DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendable, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I, and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, IK-1140, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dessicant insecticides such as boric acid, diatomaceous earth and silica gel; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, alpha-endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, isofenphos-methyl, methamidophos and propetamphos; phosphorodiamide insecticides such as dimefox, mazidox, mipafox and schradan; oxadiazine insecticides such as indoxacarb; oxadiazoline insecticides such as metoxadiazone; phthalimide insecticides such as dialifos, phosmet and tetramethrin; pyrazole insecticides such as tebufenpyrad, tolefenpyrad; phenylpyrazole insecticides such as acetoprole, ethiprole, fipronil, pyrafluprole, pyriprole and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spirotetramat; tetronic acid insecticides such as spiromesifen; thiourea insecticides such as diafenthiuron; urea insecticides such as flucofuron and sulcofuron; and unclassified insecticides such as closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene and triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal or grape plants), a fungicidal effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, wheat leaf blotch (*Septoria tritici*, also known as *Mycosphaerella graminicola*), apple scab (*Venturia inaequalis*), and *Cercospora* leaf spots of sugar beets (*Cercospora beticola*), peanuts (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

EXAMPLES

Preparation of
5-Fluoro-2-(4-fluorobenzyloxy)pyrimidin-4-amine
(1)

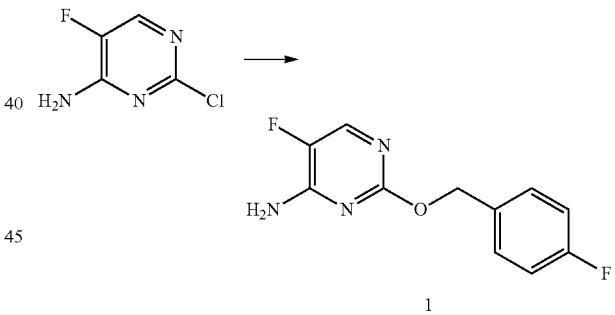

To a solution of 4-fluorobenzyl alcohol (2.56 g, 20.3 mmol) in 1,4-dioxane (20 mL) was added 60% NaH (0.813 g, 20.3 mmol) in several portions over a period of 10 min. To the magnetically stirred solution was added 4-amino-2-chloro-5-fluoropyrimidine* (2.00 g, 13.6 mmol) and the mixture was stirred at room temperature until gas evolution subsided. The reaction mixture was then heated in a CEM Discover microwave reactor at 120° C. for 90 min. The cooled reaction mixture was partitioned between ethyl acetate and water, the organic phase was concentrated, and the product was purified by column chromatography (hexane/ethyl acetate gradient) to yield 5-fluoro-2-(4-fluorobenzyloxy)pyrimidin-4-amine (1.66 g, 52% yield) as a white solid: mp 129-131° C.; $^1$H NMR (300 MHz, CDCl$_3$) δ 7.91 (d, J=2.6 Hz, 1H), 7.42 (m, 2H), 7.03 (m, 2H), 5.27 (s, 2H), 5.05 (br s, 2H); MS (ESI) m/z 238 (M+H)$^+$.

*4-Amino-2-chloro-5-fluoropyrimidine can be purchased commercially or can be prepared through known literature methods. 1. Hayashi, T.; Kawakami, T. JP Patent 2005126389 2. Durr, G. J. *J. Med. Chem.* 1965, 8(2), 253.

2-(3-Bromobenzyloxy)-5-fluoropyrimidin-4-ylamine (2)

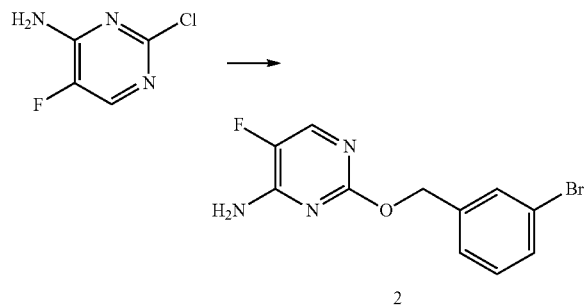

To a magnetically stirred mixture of t-BUOK (1.0 M in t-BuOH, 1.36 ml, 1.36 mmol) was added (3-bromophenyl) methanol (0.25 g, 1.36 mmol). To the resulting solution was added 4-amino-2-chloro-5-fluoropyrimidine (0.10 g, 0.68 mmol) and the mixture was capped and stirred at 90° C. for 4 h. The reaction mixture was cooled to room temperature, diluted with water, and the resulting precipitate was collected by filtration. The solid was washed with water, washed with cyclohexane, and dried in a vacuum oven. A $CH_2Cl_2$ solution of the compound was loaded onto Biotage SCX column and eluted with $CH_2Cl_2$ followed by 2.0 M $NH_3$ in MeOH. The solvent was evaporated under reduced pressure to give the title compound (0.100 g, 49%) as an off-white solid: mp 143-145° C.; $^1$H NMR (400 MHz, DMSO-$d_6$) δ 7.90 (d, J=2.5 Hz, 1H), 7.61 (s, 1H), 7.43 (d, J=8.0 Hz, 1H), 7.36 (d, J=7.7 Hz, 1H), 7.22 (t, J=7.7 Hz, 1H), 5.28 (s, 2H), 5.20 (br s, 2H); GCMS (EI) m/z 297, 299 (M)$^+$.

Preparation of 5-Fluoro-2-[1-(4-fluorophenyl) ethoxy]pyrimidin-4-ylamine (3)

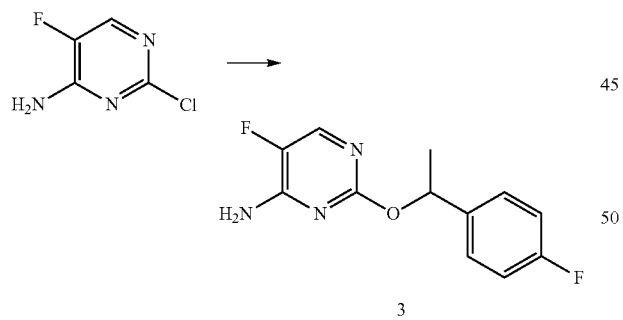

To a magnetically stirred mixture of 4-amino-2-chloro-5-fluoropyrimidine (11.10 g, 75.2 mmol) in 1-(4-fluorophenyl) ethanol (11.70 g, 82.8 mmol) was added a 1.0 M solution of t-BuOK in t-BuOH (82.8 mL, 82.8 mmol) in one portion, and the resulting tan mixture was heated to reflux and stirred for 24 h. The solvent was removed in vacuo and the resulting red-orange oil was purified by flash chromatography ($SiO_2$, 0→10% MeOH/$CH_2Cl_2$) to give 5.5 g of red-orange oil. The oil was suspended in hexanes (100 mL) and stirred for 16 h. Water (100 mL) was added to the unchanged mixture, and the biphasic system was stirred vigorously for 1 h. The resulting cream colored solid was collected by vacuum filtration, washed with warm water (55° C., 2×100 mL), and dried under vacuum at 55° C. for 16 h to give 5-fluoro-2-[1-(4-fluorophenyl)ethoxy]pyrimidin-4-ylamine (3.30 g, 17.2% yield) as a white solid: mp 96-98° C.; $^1$H NMR (300 MHz, CDCl$_3$) δ 7.84 (d, J=2.6 Hz, 1H), 7.42-7.38 (m, 2H), 7.03-6.97 (m, 2H), 5.99 (q, J=6.6 Hz, 1H), 5.09 (br s, 2H), 1.61 (d, J=6.6 Hz, 3H); MS (ESI) m/z 252 (M+H)$^+$, m/z 250 (M−H)$^-$.

Preparation of 1-Phenyl-ethanone-O-(4-amino-5-fluoropyrimidin-2-yl)oxime (4)

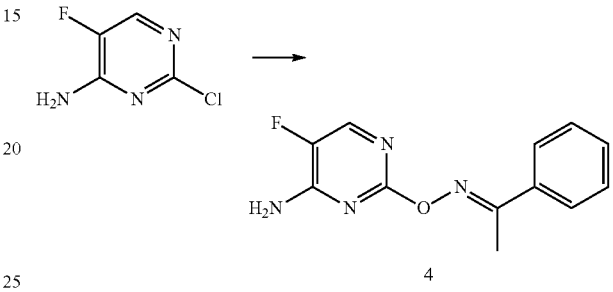

To a magnetically stirred mixture of 4-amino-2-chloro-5-fluoropyrimidine (0.10 g, 0.68 mmol) and acetophenone oxime (0.092 g, 0.68 mmol) in dry DMF (3 mL) in a 5 mL Biotage Iniator microwave vessel was added NaH (0.027 g of a 60 wt. % suspension, 0.68 mmol) under a $N_2$ atmosphere. After gas evolution ceased, the resulting mixture was sealed with a Biotage Initiator microwave septa cap and heated to 100° C. in a Biotage Initiator microwave for 60 min. The contents were poured into a vial with water (5 mL) and $CH_2Cl_2$ (5 mL), and neutralized with a few drops of 2N HCl. The phases were separated and the organic extract was dried over $MgSO_4$, filtered, and evaporated under a stream of nitrogen. The crude contents were purified on silica (EtOAc/hexanes gradient) and evaporation of the product fractions gave 0.057 g (34%) of 1-phenyl-ethanone-O-(4-amino-5-fluoropyrimidin-2-yl)oxime as an off-white solid: mp 163-165° C.; $^1$H NMR (300 MHz, CDCl$_3$) δ 8.04 (d, J=2.6 Hz, 1H), 7.75 (m, 2H), 7.42 (m, 3H), 5.25 (bs, 2H), 2.51 (s, 3H); HPLC-MS (ESI) m/z 247 (M+H)$^+$.

Preparation of 5-Fluoro-2-(thiophen-2-ylmethoxy)-pyrimidin-4-ylamine (5)

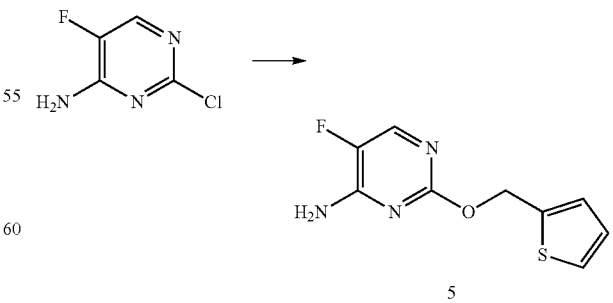

To a mixture of 4-amino-2-chloro-5-fluoropyrimidine (2.00 g, 13.5 mmol) and thiophen-2-ylmethanol (1.92 g, 16.9 mmol) with a magnetic stir bar in a 20 mL Biotage Initiator microwave reaction vessel was added t-BuOK (17.0 mL of 1M in t-BuOH, 17.0 mmol). The resulting mixture was sealed with a Biotage Initiator microwave septa cap and heated in a Biotage Initiator microwave to 100° C. for 30 min. The heating cycle was repeated (2×) for a total reaction time of 90 min. The contents were poured into ice-water and the pH was adjusted to neutral with 2N HCl. The resulting solid was filtered and washed with water (2×) and then 20% ether/hexanes (100 mL). The remaining solid was dried overnight at 50° C. under vacuum to give 4.17 g (68%) of 5-fluoro-2-(thiophen-2-ylmethoxy)pyrimidin-4-ylamine as a pale yellow powder: mp 92-94° C.; $^1$H NMR (300 MHz, CDCl$_3$) δ 7.92 (d, J=2.7 Hz, 1H), 7.29 (m, 1H), 7.13 (d, J=3.6 Hz, 1H), 6.97 (m, 1H), 5.46 (s, 2H), 5.17 (br s, 2H); MS (ESI) m/z 226 (M+H)$^+$.

Preparation of N-[5-Fluoro-2-(thiophen-2-yl-methoxy)pyrimidin-4-yl]acetamide (6)

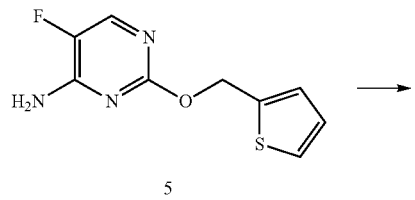

5

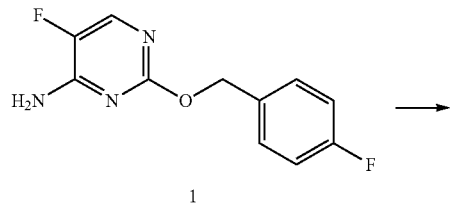

6

In a 2 dram screw cap vial, a solution of 5-fluoro-2-(thiophen-2-ylmethoxy)-pyrimidin-4-ylamine (0.10 g, 0.4 mmol) in CH$_2$Cl$_2$ was treated with acetyl chloride (0.032 g, 0.4 mmol) and PS-NMM (0.42 g, 0.8 mmol), a resin-bound equivalent of N-methyl morpholine (NMM). The mixture was shaken at RT for 12 h. The reaction mixture was filtered and the solvent evaporated to yield 0.084 g (75%) of the title compound as white solid: mp 134-136° C.; $^1$H NMR (300 MHz, CDCl$_3$) δ 8.24 (d, J=2.6 Hz, 1H), 7.86 (bs, 1H), 7.31 (m, 1H), 7.23 (m, 1H), 7.00 (m, 1H), 5.54 (s, 2H), 2.58 (s, 3H); MS (ESI) m/z 268 (M+H)$^+$.

Preparation of [5-Fluoro-2-(4-fluorobenzyloxy)pyrimidin-4-yl]-(4-methylpiperazin-1-ylmethyl)amine (7)

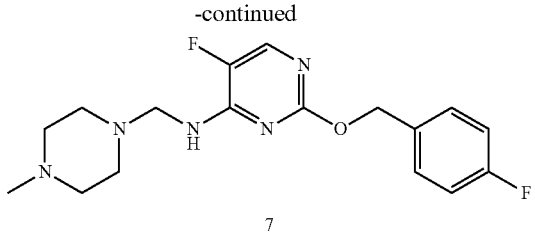

7

To a magnetically stirred mixture of paraformaldehyde (0.24 g, 8 mmol) in CH$_2$Cl$_2$ (20 mL) was added N-methylpiperazine (0.80 g, 8.0 mmol). The suspension was stirred overnight at ambient temperature on an orbital shaker, and then 5-fluoro-2-(4-fluorobenzyloxy)pyrimidin-4-ylamine (0.47 g, 2.0 mmol) was added. The resulting mixture was stirred over the weekend at RT. The solvent was evaporated and the crude residue was washed twice with 50% ether/petroleum ether and dried under a stream of N$_2$ to give 0.21 g (30%) of [5-fluoro-2-(4-fluorobenzyloxy)pyrimidin-4-yl](4-methylpiperazin-1-ylmethyl)amine as a beige solid: mp 125-126° C.; $^1$H NMR (300 MHz, CDCl$_3$) δ 7.83 (d, J=2.3 Hz, 1H), 7.43 (m, 2H), 7.03 (t, J=8.5 Hz, 2H), 5.40 (bs, 1H), 5.27 (s, 2H), 4.41 (d, J=6.8 Hz, 2H), 2.63 (bs, 4H), 2.47 (bs, 4H), 2.30 (s, 3H); HPLC-MS (ESI) m/z 350 (M+H)$^+$.

Preparation of [5-Fluoro-2-(4-fluorobenzyloxy)pyrimidin-4-yl]triethylsilanylamine (8)

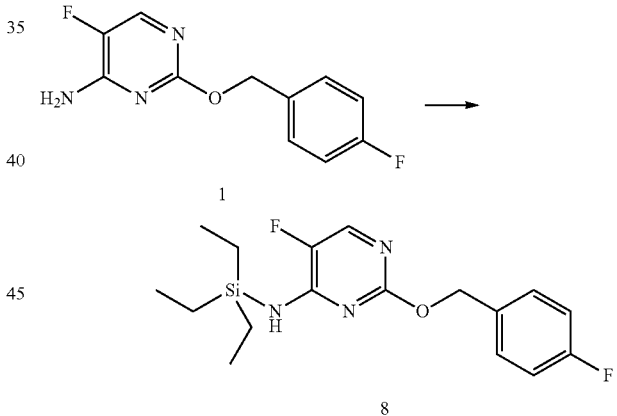

To a magnetically stirred mixture of 5-fluoro-2-(4-fluorobenzyloxy)pyrimidin-4-ylamine (0.25 g, 1.05 mmol) in dry THF (5 mL) at 0° C. was added NaH (0.042 g of 60 wt. % suspension in mineral oil, 1.05 mmol). When bubbling ceased, triethylsilyl chloride (0.158 g, 1.05 mmol) was added dropwise (neat) via syringe. After stirring overnight at ambient temperature, the reaction mixture was poured into ether and washed with a mixture of aqueous saturated sodium bicarbonate and brine solution. The organic layer was separated, dried over Na$_2$SO$_4$, filtered, and evaporated to give a white solid. This crude material was purified on silica by column chromatography (EtOAc/hexanes gradient) to give 0.121 g (33%) of [5-fluoro-2-(4-fluorobenzyloxy)pyrimidin-4-yl]-triethylsilanylamine as a clear yellow oil: $^1$H NMR (300 MHz, CDCl$_3$) δ 7.89 (d, J=2.5 Hz, 1H), 7.39 (m, 2H), 7.03 (t, J=8.6 Hz, 2H), 5.27 (s, 2H), 4.53 (s, 1H), 0.99 (m, 9H), 0.83 (m, 6H); HPLC-MS (ESI) m/z 352 (M+H)+.

Preparation of [5-Fluoro-2-(4-fluorobenzyloxy)pyrimidin-4-yl]bis-carbamic acid 4-fluorophenyl ester (9)

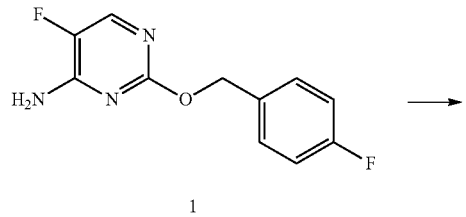

1

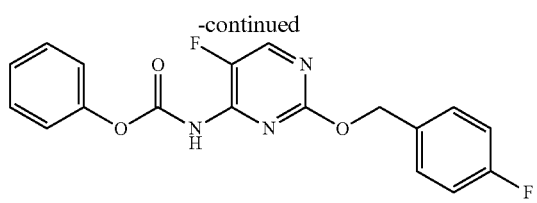

9

To a magnetically stirred ice-cold mixture of 5-fluoro-2-(4-fluorobenzyloxy)pyrimidin-4-ylamine (0.25 g, 1.05 mmol) in dry THF (5 mL) was added NaH (0.042 g of a 60 wt. % suspension in mineral oil, 1.05 mmol). After bubbling ceased, 4-fluorophenyl chloroformate (0.184 g, 1.05 mmol) was added dropwise as a solution in dry THF. After stirring one hour, the reaction was partitioned between EtOAc and brine solution. The organic extract was dried over Na$_2$SO$_4$, filtered, and evaporated. The crude material was purified on silica using a gradient of EtOAc/Hex and then MeOH/EtOAc to give 0.054 g (14%) of [5-fluoro-2-(4-fluorobenzyloxy)pyrimidin-4-yl]bis-carbamic acid 4-fluoro-phenyl ester as a white solid: mp 103-105° C.; $^1$H NMR (300 MHz, CDCl$_3$) δ 8.58 (d, J=2.2 Hz, 1H), 7.43 (m, 2H), 7.08 (m, 10H), 5.40 (s, 2H); HPLC-MS (ESI) m/z 514 (M+H)+.

Preparation of [5-Fluoro-2-(4-fluorobenzyloxy)pyrimidin-4-yl]carbamic acid phenyl ester (10)

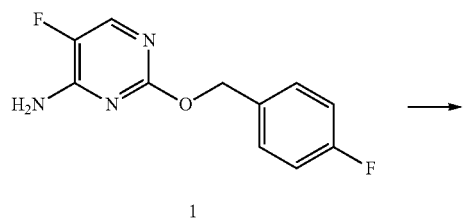

1

10

To a stirred mixture of 5-fluoro-2-(4-fluorobenzyloxy)pyrimidin-4-ylamine (0.20 g, 0.84 mmol) in dry THF (3 mL) at ice-bath temperature was added NaH (0.034 g of 60 wt. % suspension in mineral oil, 0.84 mmol). When bubbling ceased, the resulting mixture was transferred (dropwise) via cannula to an ice-cold, stirred mixture of diphenyl carbonate (1.8 g, 8.4 mmol) in dry THF (5 mL). The mixture was stirred overnight, poured into EtOAc, and washed with saturated aq. NH$_4$Cl solution followed by brine solution. The EtOAc layer was separated, dried over Na$_2$SO$_4$, filtered, and evaporated. The crude material was purified on silica gel using a gradient of EtOAc and hexanes to give 0.063 g (21%) of [5-fluoro-2-(4-fluorobenzyloxy)pyrimidin-4-yl]carbamic acid phenyl ester as a white solid: mp 129-131° C.; $^1$H NMR (300 MHz, CDCl$_3$) δ 8.28 (d, J=2.3 Hz, 1H), 7.43 (m, 5H), 7.30-7.20 (m, 2H), 7.02 (t, J=8.6 Hz, 2H), 5.38 (s, 2H); HPLC-MS (ESI) m/z 358 (M+H)+.

Preparation of N-[5-Fluoro-2-(4-fluorobenzyloxy)pyrimidin-4-yl]oxalamic acid ethyl ester (11)

1

11

To a mixture of 5-fluoro-2-(4-fluorobenzyloxy)pyrimidin-4-ylamine (0.235 g, 0.99 mmol), N-methyl morpholine on polystyrene (0.538 g, 1.24 mmol), and CH$_2$Cl$_2$ (5 mL) was added chloro-oxo-acetic acid ethyl ester (0.135 g, 0.99 mmol) and the resulting mixture was agitated on an orbital shaker for 16 h. The reaction contents were filtered onto an acidic SPE cartridge and eluted with CH$_2$Cl$_2$. The CH$_2$Cl$_2$ filtrate was evaporated to give 0.165 g (50%) of N-[5-fluoro-2-(4-fluorobenzyloxy)pyrimidin-4-yl]oxalamic acid ethyl ester as a clear oil: $^1$H NMR (300 MHz, CDCl$_3$) δ 9.21 (bs, 1H), 8.38 (d, J=2.3 Hz, 1H), 7.48 (m, 2H), 7.03 (t, J=8.5 Hz, 2H), 5.40 (s, 2H), 4.48 (q, J=7.1 Hz, 2H), 1.45 (t, J=7.1 Hz, 3H); HPLC-MS (ESI) m/z 338 (M+H)+.

Preparation of 3,4-Dichloroisothiazole-5-carboxylic acid [5-fluoro-2-(4-fluorobenzyl-oxy)pyrimidin-4-yl]amide (12)

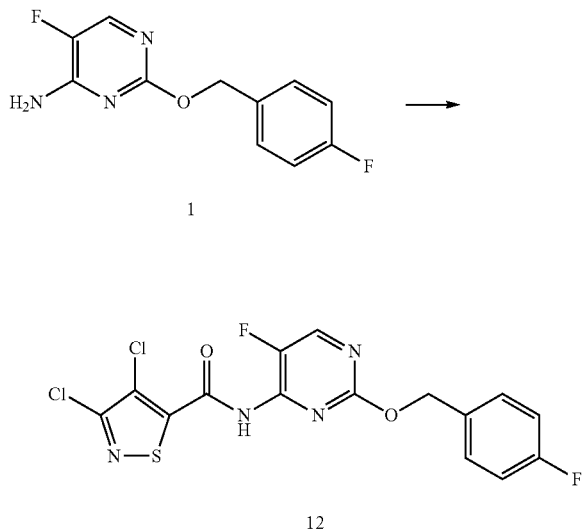

To a suspension of 3,4-dichloroisothiazole-5-carboxylic acid (0.15 g, 0.76 mmol) in oxalyl chloride (2 mL) was added a catalytic amount of dimethylformamide (2 drops) and the mixture was heated to 80° C. and stirred for 2 h. The excess oxalyl chloride was removed on the rotary evaporator. Meanwhile, 5-fluoro-2-(4-fluorobenzyloxy)-pyrimidin-4-ylamine (0.17 g, 0.68 mmol) was dissolved in THF (1 mL), treated with LiHMDS (1M in THF, 0.76 mL, 0.76 mmol) and stirred for 10 min. The freshly prepared 3,4-dichlorothiazole-5-carbonyl chloride*, dissolved in THF (1 mL), was added and the reaction was capped and stirred for 12 h. The reaction was diluted with water and the target compound was extracted with $CH_2Cl_2$ (3×5 mL). The combined extracts were dried over $MgSO_4$ and then evaporated under reduced pressure. The mixture was eluted with $CH_2Cl_2$ through an anionic-exchange solid phase extraction column and then further purified by reverse-phase chromatography to give 3,4-dichloroisothiazole-5-carboxylic acid [5-fluoro-2-(4-fluorobenzyloxy)pyrimidin-4-yl]amide (0.035 g, 12%) as a tan solid: mp 87-90° C.; $^1$H NMR (400 MHz, DMSO-$d_6$) δ 11.78 (s, 1H), 8.67 (s, 1H), 7.51-7.48 (m, 2H), 7.24-7.19 (m, 2H), 5.25 (s, 2H); MS (ESI) m/z 417 (M+H)$^+$, 415 (M−H)$^−$.
*Nagata, T.; Kogure, A.; Yonekura, N.; Hanai, R.; Kaneko, I.; Nakano, Y. JP 2007211002 A

Preparation of [5-Fluoro-2-(4-fluorobenzyloxy)pyrimidin-4-yl]phosphoramidic acid diethyl ester (13)

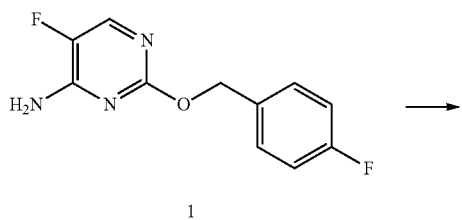

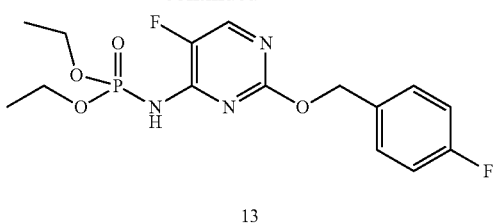

To a magnetically stirred solution of 5-fluoro-2-(4-fluorobenzyloxy)pyrimidin-4-ylamine (0.10 g, 0.42 mmol) in dry THF (5 mL) under a nitrogen atmosphere was added NaH (0.017 g of a 60 wt. % suspension, 0.42 mmol) and the mixture was stirred until bubbling ceased. Diethyl chlorophosphate (0.073 g, 0.42 mmol) was added dropwise, and the mixture was stirred at ambient temperature for 1 h. The reaction mixture was evaporated to dryness and the residue dissolved in EtOAc and washed with saturated aqueous $NH_4Cl$ solution. The organic layer was separated, dried over $Na_2SO_4$, filtered, and evaporated. The crude material was purified on silica (acetone/$CH_2Cl_2$ gradient) to give 0.017 g (11%) of [5-fluoro-2-(4-fluorobenzyloxy)pyrimidin-4-yl] phosphoramidic acid diethyl ester as a white solid: mp 109-111° C.; $^1$H NMR (300 MHz, CDCl$_3$) δ 8.10 (t, J=1.8 Hz, 1H), 7.43 (m, 2H), 7.03 (t, J=8.5 Hz, 2H), 6.18 (br s, 1H), 5.35 (s, 2H), 4.25 (m, 4H), 1.38 (t, J=7.1 Hz, 6H); HPLC-MS (ESI) m/z 374 (M+H)$^+$.

Preparation of [5-Fluoro-2-(4-fluorobenzyloxy)pyrimidin-4-yl](1-methoxypropyl)amine (14)

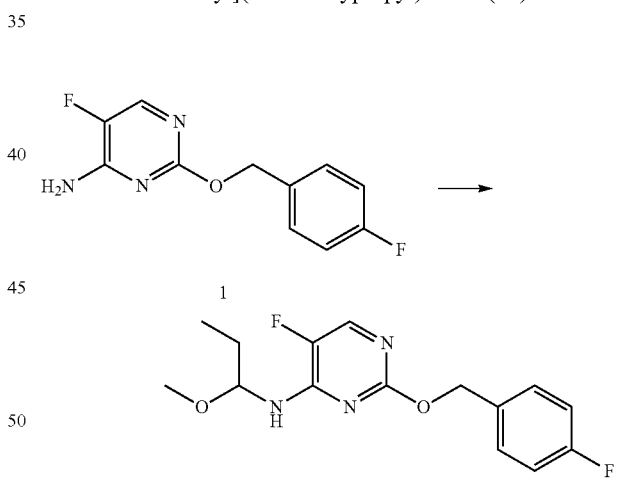

To a solution of 5-fluoro-2-(4-fluorobenzyloxy)pyrimidin-4-ylamine (0.10 g, 0.42 mmol) in propionaldehyde (2 mL) was added a catalytic amount of camphorsulfonic acid. The mixture was agitated on an orbital shaker at room temperature for 4 h and then evaporated to dryness. Methanol (2 mL) was added, and the resulting solution was warmed to 60° C. for 1 h. After evaporation, the crude product was purified by reverse phase chromatography to yield the title compound (0.030 g, 24% yield) as a clear, colorless oil: $^1$H NMR (300 MHz, CDCl$_3$) δ 7.91 (d, J=2.5 Hz, 1H), 7.47-7.41 (m, 2H), 7.09-7.01 (m, 2H), 5.41 (dt, J=9.9 and 6.0 Hz, 1H), 5.30 (s, 2H), 5.2 (bd, J~10 Hz, 1H), 3.12 (s, 3H), 1.88-1.60 (m, 2H), 0.98 (t, J=7.1 Hz, 3H). HPLC-MS 308 (ES⁻), 310 (ES⁺).

Preparation of [5-Fluoro-2-(4-methylbenzyloxy) pyrimidin-4-ylamino]methanol (16)

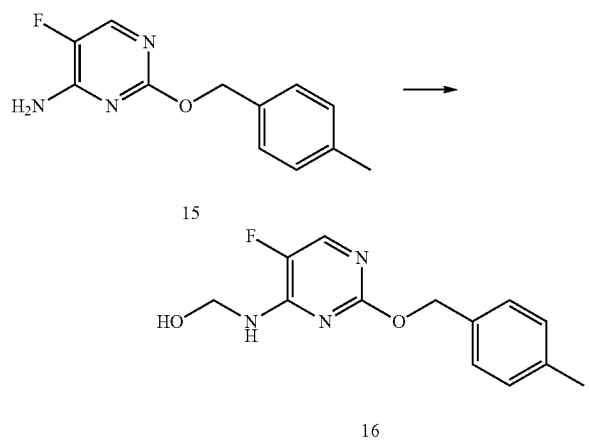

To a solution of 5-fluoro-2-(4-methylbenzyloxy)pyrimidin-4-ylamine (0.10 g, 0.43 mmol) in dioxane (2 mL) was added paraformaldehyde (0.060 g, 2 mmol) and the mixture was agitated on an orbital shaker at 90° C. for 16 h, cooled, and evaporated to dryness. Purification by reverse phase chromatography afforded 0.070 g (63%) of the title compound as a white solid: mp 97-98° C.; ¹H NMR (CDCl₃) δ 7.94 (d, J=2.5 Hz, 1H), 7.36 (d, J=7.9 Hz, 2H), 7.19 (d, J=7.9 Hz, 2H), 5.97 (bs, 1H), 5.33 (s, 2H), 5.04-4.99 (m, 2H), 3.39 (t, J=8.0 Hz, 1H), 2.37 (s, 3H); MS (ESI) m/z 264 (M+H)⁺.

Preparation of Benzyloxymethyl[5-fluoro-2-(4-fluorobenzyloxy)pyrimidin-4-yl]amine (18)

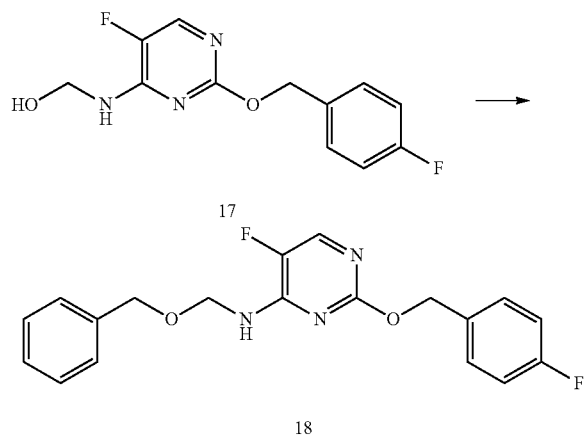

To a mixture of [5-fluoro-2-(4-fluorobenzyloxy)pyrimidin-4-ylamino]methanol (0.10 g, 3.7 mmol) in benzyl alcohol (1 mL) was added a catalytic amount of p-toluene sulfonic acid. After 30 min, the reaction was cooled to room temperature and partitioned between ethyl acetate and saturated sodium bicarbonate. The phases were separated and the organic portion was dried over anhydrous Na₂SO₄, filtered and evaporated to obtain the crude product. Purification by reverse phase chromatography afforded 0.094 g (70%) of the title compound as a white solid: mp 64-66° C.; ¹H NMR (CDCl₃) δ 7.93 (d, J=2.7 Hz, 1H), 7.47-7.40 (m, 2H), 7.37-7.29 (m, 5H), 7.08-7.00 (m, 2H), 5.81-5.70 (bm, 1H), 5.29 (s, 2H), 5.12 (d, J=6.9 Hz, 2H), 4.63 (s, 2H); MS (ESI) m/z 358 (M+H)⁺.

Preparation of 2,2-Dimethylpropionic acid[5-fluoro-2-(4-fluorobenzyloxy)pyrimidin-4-ylamino]methyl ester (19)

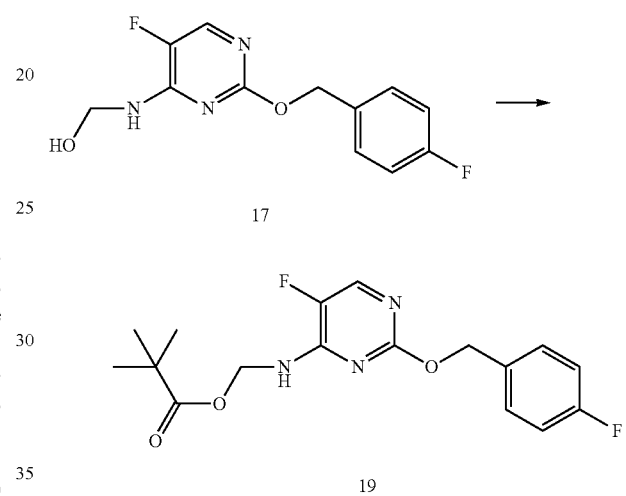

To a mixture of [5-fluoro-2-(4-fluorobenzyloxy)pyrimidin-4-ylamino]methanol (0.10 g, 0.37 mmol) in pyridine (2 mL) was added trimethylacetyl chloride (0.048 g, 0.40 mmol), and the mixture was agitated on an orbital shaker at 60° C. for 4 h. The reaction mixture was cooled, evaporated to dryness, and partitioned between EtOAc and water. The organic layer was dried over Na₂SO₄, filtered, and evaporated to yield the title compound (0.078 g, 60% yield) as a white solid: mp 134-135° C.; ¹H NMR (300 MHz, CDCl₃) δ 7.97 (d, J=2.5 Hz, 1H), 7.49-7.44 (m, 2H), 7.11-7.03 (m, 2H), 6.17 (bt, J≈7 Hz, 1H), 6.17 (d, J=7.4 Hz, 2H), 5.33 (s, 2H), 1.20 (s, 9H); HPLC-MS m/z 352 (M+H)⁺.

Preparation of N-[5-Fluoro-2-(4-fluorobenzyloxy) pyrimidin-4-yl]-N,N dimethyl-formamidine (20)

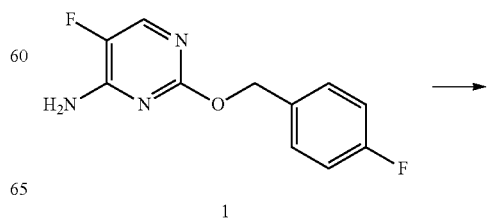

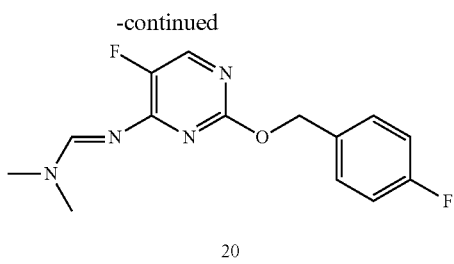

20

To a magnetically stirred solution of 5-fluoro-2-(4-fluorobenzyloxy)pyrimidin-4-ylamine (1.00 g, 4.2 mmol) in N,N-dimethylformamide (DMF, 20 mL) was added N,N-dimethylformamide dimethyl acetal (0.55 g, 4.6 mmol) and stirring was continued 16 h at RT. The solution was poured into 100 mL of ice water, whereupon a white precipitate was produced. The mixture was cooled at 0° C. for 1 h and then filtered to produce the title compound (1.10 g, 89%) as a white solid: mp 113-115° C.; $^1$H NMR (CDCl$_3$) δ 8.65 (s, 1H), 8.04 (d, J=2.6 Hz, 1H), 7.46-7.40 (m, 2H), 7.07-6.98 (m, 2H), 5.30 (s, 2H), 3.17 (s, 3H), 3.16 (s, 3H); MS (ESI) m/z 292 (M+H)$^+$. Anal. Calcd for C$_{14}$H$_{14}$F$_2$N$_4$O: C, 57.53; H, 4.83; N, 19.17. Found: C, 57.67; H, 4.84; N, 19.09.

Preparation of [5-Fluoro-2-(4-fluorobenzyloxy)pyrimidin-4-yl]-[1-pyrrolidin-1-yl-methylidene]amine (21)

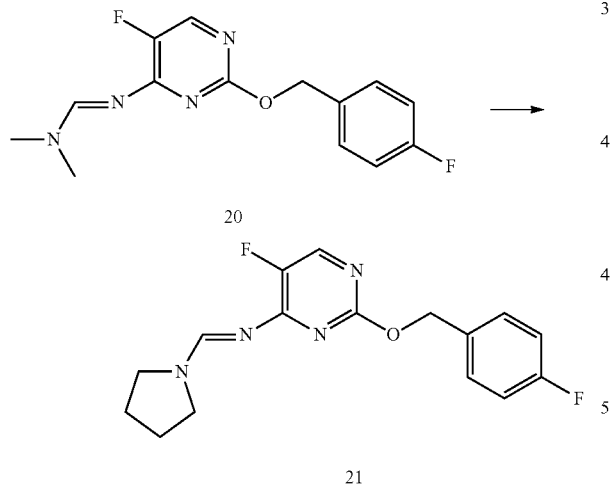

To a solution of N'-[5-fluoro-2-(4-fluorobenzyloxy)pyrimidin-4-yl]-N,N-dimethylformamidine (0.10 g, 0.36 mmol) in toluene (2 mL) was added pyrrolidine (0.051 g, 0.72 mmol) and a catalytic amount of camphorsulfonic acid. The vented vial was placed on an orbital shaker, agitated at 90° C. for 16 h, cooled, and evaporated to dryness. Purification by reverse phase chromatography afforded the title compound (0.060 g, 53% yield) as a white solid: mp 102-103° C.; $^1$H NMR (300 MHz, CDCl$_3$) δ 8.87 (s, 1H), 8.06 (d, J=2.7 Hz, 1H), 7.49-7.42 (m, 2H), 7.09-7.01 (m, 2H), 5.32 (s, 2H), 3.73-3.62 (m, 4H), 2.07-1.96 (m, 4H); HPLC-MS (ESI) m/z 319 (M+H)$^+$.

Preparation of N-[5-Fluoro-2-(4-fluorobenzyloxy)pyrimidin-4-yl]-N'-hydroxy-formamidine (22)

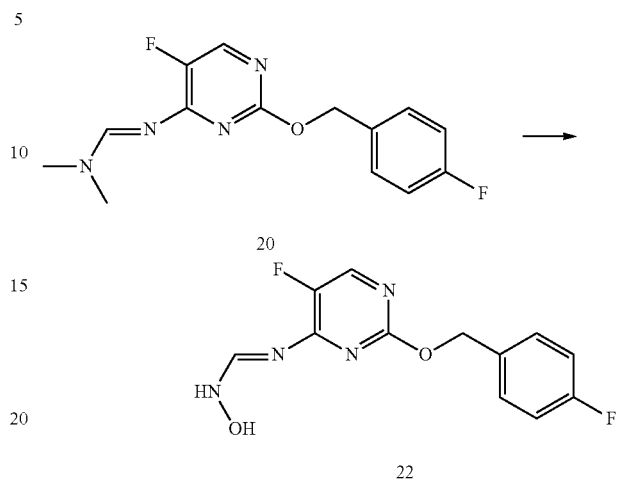

To a solution of N'-[5-fluoro-2-(4-fluorobenzyloxy)pyrimidin-4-yl]-N'-dimethyl-formamidine (0.10 g, 0.34 mmol) in EtOH (2 mL) was added hydroxylamine hydrochloride (0.047 g, 0.68 mmol) and the mixture was agitated on an orbital shaker for 1.5 h at 50° C. The reaction mixture was cooled and evaporated to dryness. Water was added to produce a slurry which was filtered to isolate the title compound (0.090 g, 94% yield) as a white solid: mp 169-171° C.; $^1$H NMR (300 MHz, CDCl$_3$) δ 8.15 (d, J=2.2 Hz, 1H), 8.02 (bs, 2H), 7.49-7.43 (m, 2H), 7.11-7.02 (m, 3H), 5.35 (s, 2H); HPLC-MS (ESI) m/z 281 (M+H)$^+$, 279 (M–H)$^-$.

Preparation of N-[5-Fluoro-2-(4-fluorobenzyloxy)pyrimidin-4-yl]-N'-cyanoformamidine (23)

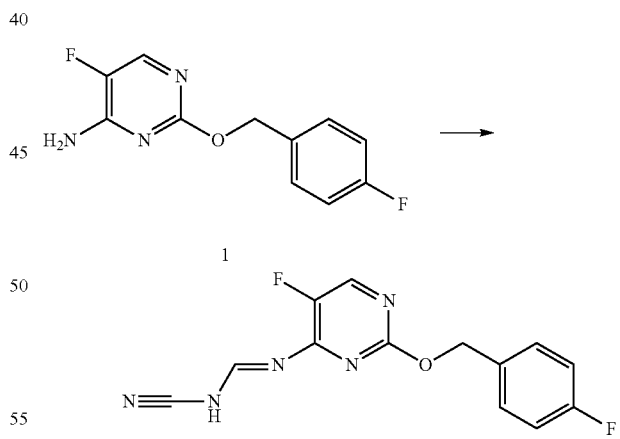

Cyanamide (8.00 g, 190.0 mmol) was stirred at reflux in triethylorthoformate (60 mL) for 2 h. The reaction was cooled to room temperature and distilled to provide ethyl-N-cyanoimidate (12.5 g, bp=110-112° C./45 mm Hg).* To this imidate (1 mL) was added 5-fluoro-2-(4-fluorobenzyloxy) pyrimidin-4-ylamine (0.05 g, 0.2 mmol) and the mixture was heated at 90° C. for 4 h, cooled, diluted with chloroform, filtered, and evaporated. The crude product was purified by reverse phase chromatography to furnish 0.053 g (17%) of the title compound as an off white solid: mp 148-149° C.; $^1$H NMR (300 MHz, CDCl$_3$) δ 9.45 and 9.33 (bd, bs, J=10 Hz, 1H), 8.33 and 8.25 (2d, J≈2 Hz, 1H), 7.46-7.38 (m, 2H), 7.11-7.01 (m, 2H), 5.35 and 5.33 (2s, 2H); HPLC-MS (ESI) m/z 290 (M+H)$^+$, 288 (M−H)$^−$.

*Bridsen, Peter K., and Wang, Xiaodong, *Synthesis*, 1995, 855-8.

Preparation of N'-[5-Fluoro-2-(4-fluorobenzyloxy)pyrimidin-4-yl]-N,N-dimethyl-propionamidine (24)

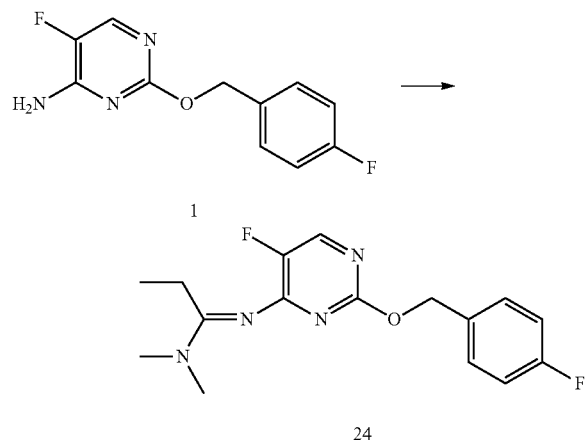

To a solution of N,N-dimethylpropionamide (0.202 g, 2.0 mmol) in CHCl$_3$ (2 mL) was added phosphorous oxychloride (POCl$_3$, 0.066 g, 0.43 mmol) and the mixture was agitated on an orbital shaker at room temperature for 1 h. Triethylamine (0.22 g, 2.2 mmol) and 5-fluoro-2-(4-fluorobenzyloxy)pyrimidin-4-ylamine (0.10 g, 0.40 mmol) were added, and the mixture was agitated at 50° C. for 3 h, cooled to room temperature, partitioned between chloroform and water, the phases separated, and the organics evaporated under reduced pressure. Purification by reverse phase chromatography afforded the title compound (0.042 g, 31% yield) as a yellow oil: $^1$H NMR (300 MHz, CDCl$_3$) δ 8.87 (s, 1H), 8.04 (d, J=2.5 Hz, 1H), 7.46-7.40 (m, 2H), 7.07-6.99 (m, 2H), 5.30 (s, 2H), 3.13 (s, 6H), 2.55 (q, J=7.7 Hz, 2H), 1.15 (t, J=7.7 Hz, 3H); HPLC-MS (ESI) m/z 321 (M+H)$^+$.

Preparation of N'-(5-Fluoro-2-hydroxy-pyrimidin-4-yl)-N,N-dimethyl-formamidine (25)

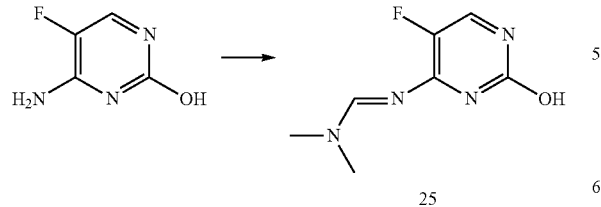

To a magnetically stirred solution of 4-amino-5-fluoropyrimidin-2-ol* (4.00 g, 31.0 mmol) in DMF (100 mL) was added N,N-dimethylformamide dimethyl acetal (4.00 g, 34.0 mmol). The mixture was stirred at room temperature for 72 h, diluted with diethyl ether (200 mL), and filtered. The solid product was washed with heptane to give the title compound (5.23 g, 92% yield) as a white solid: mp 240-243° C.; $^1$H NMR (300 MHz, DMSO-d$_6$) δ 10.7 (bs, 1H), 8.59 (s, 1H), 7.7 (d, J=5.6 Hz, 1H), 3.18 (s, 3H), 3.06 (s, 3H); HPLC-MS (ESI) m/z 185 (M+H)$^+$, 183 (M−H)$^−$.

*4-amino-5-fluoro-pyrimidin-2-ol can be purchased commercially.

Preparation of Carbonic acid 4-(dimethylamino-methyleneamino)-5-fluoropyrimidin-2-yl ester ethyl ester (26)

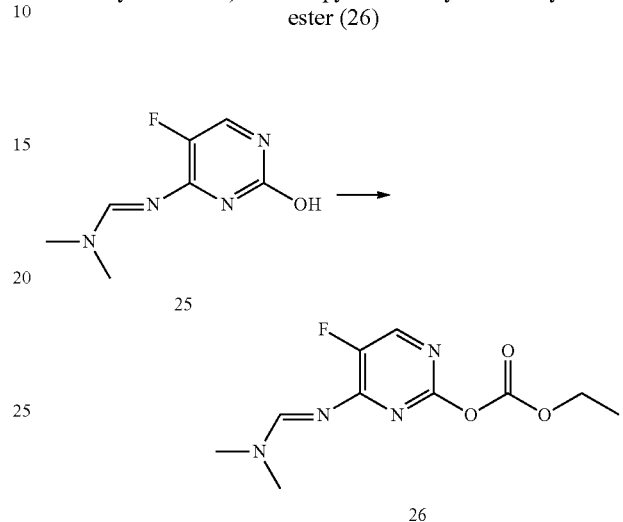

To a solution of N'-(5-fluoro-2-hydroxy-pyrimidin-4-yl)-N,N-dimethylformamidine (0.10, 0.54 mmol) in CH$_2$Cl$_2$ (2 mL) were added triethylamine (0.20 g, 2.0 mmol) and ethyl chloroformate (0.065 g, 0.60 mmol), and the mixture was agitated on an orbital shaker at room temperature overnight. The reaction was diluted with CH$_2$Cl$_2$ and the solution was washed with water, dried over MgSO$_4$, filtered and evaporated. The crude product was purified by silica gel column chromatography (EtOAc/petroleum ether gradient) to yield 0.031 g (22%) of the title compound as a white solid: mp 124-126° C.; $^1$H NMR (300 MHz, CDCl$_3$) δ 8.67 (s, 1H), 8.19 (d, J=2.2 Hz, 1H), 4.35 (q, J=7.14 Hz, 2H), 3.21 (s, 6H), 1.40 (t, J=7.14 Hz, 3H); HPLC-MS (ESI) m/z 258 (M+H)$^+$.

Preparation of Benzoic acid 4-(dimethylamino-methyleneamino)-5-fluoropyrimidin-2-yl ester (27)

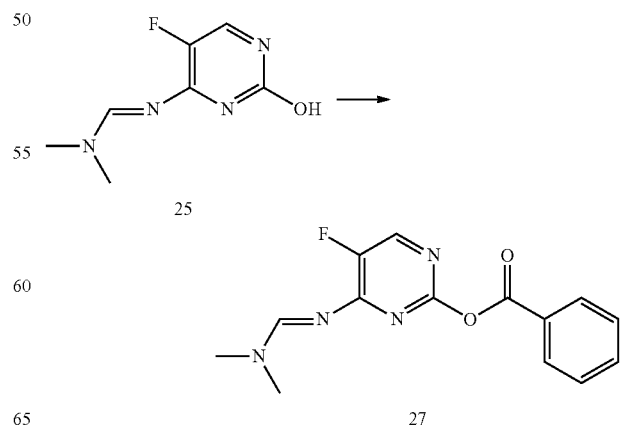

To a suspension of N'-(5-fluoro-2-hydroxypyrimidin-4-yl)-N,N-dimethylformamidine (0.10 g, 0.54 mmol) in pyridine (2 mL) was added benzoyl chloride (0.084 g, 0.60 mmol), and the mixture was agitated on an orbital shaker for 16 h at RT. The reaction mixture was partitioned between EtOAc and saturated aq NaHCO$_3$, and the organic phase was dried over solid MgSO$_4$, filtered, and evaporated to give the title compound (0.147 g 94%) as a white solid: mp 136-138° C.; $^1$H NMR (300 MHz, CDCl$_3$) δ 8.69 (s, 1H), 8.27 (d, J=2.4 Hz, 2H), 8.25-8.20 (m, 2H), 7.69-7.63 (m, 1H), 7.56-7.49 (m, 2H), 3.23 (s, 3H), 3.20 (s, 3H); HPLC-MS (ESI) m/z 289 (M+H)$^+$.

Preparation of Benzenesulfonic acid 4-(dimethylamino-methyleneamino)-5-fluoro-pyrimidin-2-yl ester (28)

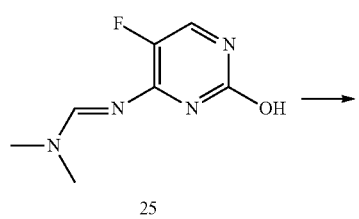

28

To a suspension of N'-(5-fluoro-2-hydroxypyrimidin-4-yl)-N,N-dimethylformamidine (0.10 g, 0.54 mmol) in pyridine (2 mL) was added benzene sulfonyl chloride (0.106 g, 0.60 mmol) and the mixture was agitated on an orbital shaker for 16 h at room temperature. The reaction mixture was partitioned between EtOAc and saturated aq NaHCO$_3$, and the organic phase was dried over solid MgSO$_4$, filtered, and concentrated under reduced pressure. Purification by reverse phase chromatography (H$_2$O/MeCN gradient) afforded the title compound (0.089 g, 46% yield) as a white solid: mp 124-125° C.; $^1$H NMR (300 MHz, CDCl$_3$) δ 8.54 (s, 1H), 8.12-8.07 (m, 3H), 7.73-7.66 (m, 1H), 7.62-7.56 (m, 2H), 3.21 (s, 6H); HPLC-MS (ESI) m/z 325 (M+H)$^+$.

Preparation of Benzenesulfonic acid 4-amino-5-fluoropyrimidin-2-yl ester (29)

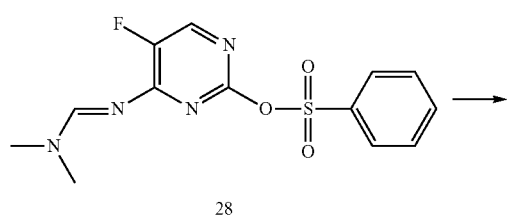

28

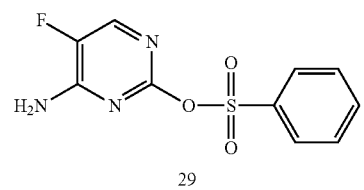

29

To a solution of 10% 1N HCl in doxane (3 mL) was added benzenesulfonic acid 4-(dimethylamino-methyleneamino)-5-fluoropyrimidin-2-yl ester (0.090, 0.3 mmol) and the mixture was agitated on an orbital shaker at room temperature for 1.5 h. The solvent was removed by evaporation and the residue was dissolved in a 1:1 solution of dioxane and water (2.5 mL) and treated with saturated aq NaHCO$_3$ (0.5 mL). After 16 h, the reaction mixture was partitioned between EtOAc and water and the organic phase was dried over Na$_2$SO$_4$, filtered, and the solvent evaporated to yield the title compound (0.059 g, 79% yield) as a white solid: mp 139-141° C.; $^1$H NMR (300 MHz, DMSO-d$_6$) δ 8.05-8.00 (m, 3H), 7.90-7.75 (m, 3H), 7.70-7.63 (m, 2H); HPLC-MS (ESI) m/z 268 (M–H)$^-$, 270 (M+H)$^+$.

Preparation of Benzenesulfonic acid 4-amino-5-fluoropyrimidin-2-yl ester (29)

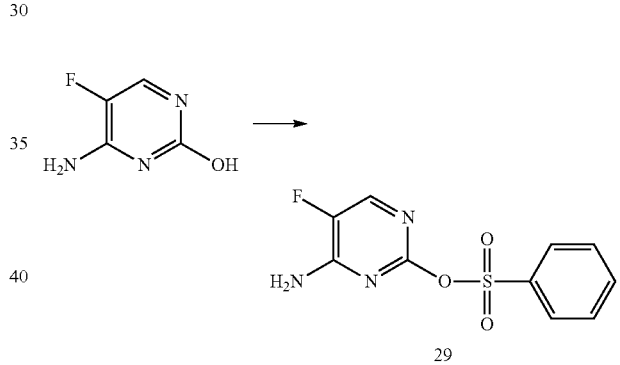

29

To a suspension of 4-amino-5-fluoro-pyrimidin-2-ol (0.177 g, 1.4 mmol) in pyridine (5 mL) was added benzene sulfonyl chloride (0.284 g, 1.6 mmol) and the mixture was stirred at room temperature for 2 h. The reaction mixture was evaporated to dryness and the crude material purified by reverse phase chromatography to yield the title compound (0.106 g, 29% yield) as a white solid: mp 145-146° C.; $^1$H NMR (300 MHz, DMSO-d$_6$) δ 8.05-8.00 (m, 3H), 7.9-7.75 (m, 3H), 7.70-7.63 (m, 2H); HPLC-MS (ESI) m/z 270 (M+H)$^+$, 268 (M–H)$^-$.

Preparation of (2-Fluorobenzyl)-[5-fluoro-2-(4-fluorobenzyloxy)pyrimidin-4-yl]amine (30)

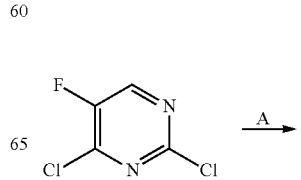

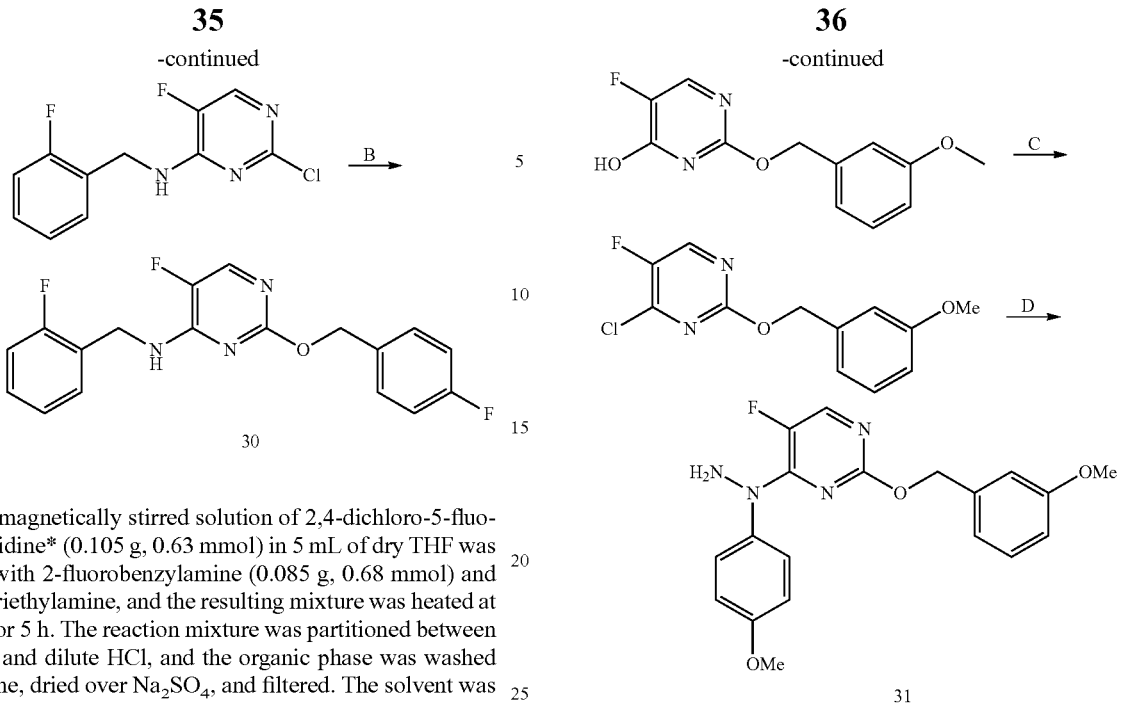

A) A magnetically stirred solution of 2,4-dichloro-5-fluoropyrimidine* (0.105 g, 0.63 mmol) in 5 mL of dry THF was treated with 2-fluorobenzylamine (0.085 g, 0.68 mmol) and excess triethylamine, and the resulting mixture was heated at 80° C. for 5 h. The reaction mixture was partitioned between $CH_2Cl_2$ and dilute HCl, and the organic phase was washed with brine, dried over $Na_2SO_4$, and filtered. The solvent was removed under reduced pressure to yield 0.157 g (97%) of the title compound as a yellow solid: mp 117-118° C.; $^1$H NMR (300 MHz, $CDCl_3$) δ 7.90 (d, J=2.6, 1H), 7.47-7.27 (m, 2H), 7.21-7.01 (m, 2H), 5.54 (s, 1H), 4.76 (d, J=5.9, 2H); MS (ESI) m/z 256 (M+H)$^+$.

*2,4-Dichloro-5-fluoropyrimidine can be purchased commercially.

B) A solution of (2-chloro-5-fluoropyrimidin-4-yl)-(2-fluorobenzyl)amine* (0.103 g, 0.40 mmol) in 5 mL of dry THF was treated with 4-fluorobenzylalcohol (0.062 g, 0.49 mmol) and a 1.0 M solution of KO$^t$Bu in $^t$BuOH (0.4 mL, 0.4 mmol). The mixture was heated at 80° C. in a sealed vial for 18 h, partitioned between $CH_2Cl_2$ and water, and the organic phase was washed with brine, dried over $Na_2SO_4$, and filtered. The solvent was removed under reduced pressure and the residue purified by flash column chromatography ($SiO_2$, 10→20% EtOAc/petroleum ether) to yield the title compound (0.157 g, 42%) as a white solid: mp 83-84° C.; $^1$H NMR (300 MHz, $CDCl_3$) δ 7.83 (d, J=2.8, 1H), 7.45-7.27 (m, 5H), 7.15-6.96 (m, 5H), 5.37 (br s, 1H), 5.29 (s, 3H), 4.74 (d, J=5.9, 3H); MS (ESI) m/z 346 (M+H)$^+$.

*Singh, R.; Argade, A.; Payan, D. G.; Clough, J.; Keim, H.; Sylvain, C.; Li, H.; Bhamidipati, S., WO 2004014382 A1 20040219

Preparation of 5-Fluoro-2-(3-methoxybenzyloxy)-4-(1-(4-methoxyphenyl)-hydrazinyl)pyrimidine (31)

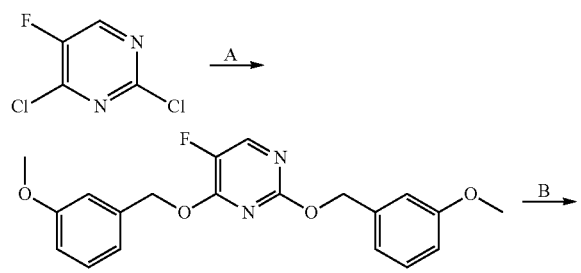

A) A 1.0 M solution of t-BuOK in t-BuOH (66 mL, 66 mmol) was added to a mixture of 2,4-dichloro-5-fluoropyrimidine (5.04 g, 30.1 mmol) and 3-methoxybenzyl alcohol (7.8 mL, 62.8 mmol) in a 250 mL round bottom flask. A significant exotherm was observed and the resulting mixture was stirred at room temperature for 2 h. The reaction was diluted with EtOAc (100 mL) and washed with brine (50 mL×2). The organic layer was dried over $MgSO_4$, filtered, and concentrated under reduced pressure. Crystallization from hot EtOH provided a material which was collected on a fritted funnel and rinsed with ice-cold EtOH to provide the title compound (7.94 g, 71%) as a white solid: mp 81-83° C.; $^1$H NMR (300 MHz, $CDCl_3$) δ 8.10 (d, J=2.3 Hz, 1H), 7.29 (m, 2H), 7.02 (m, 4H), 6.87 (dt, J=2.2, 7.8 Hz, 2H), 5.44 (s, 2H), 5.35 (s, 2H), 3.82 (s, 3H), 3.82 (s, 3H); MS (ESI) m/z 371 (M+H)$^+$.

B) A solution of 2.0 N KOH in water (85 mL, 170 mmol) was added to a mixture of 5-fluoro-2,4-bis(3-methoxybenzyloxy)pyrimidine (7.9 g, 21.3 mmol) and EtOH (21 mL) in a 500 mL round bottom flask. A reflux condenser was attached, and the reaction was heated at 95° C. for 16 h. After cooling to room temperature, the reaction mixture was washed with $Et_2O$ (2×50 mL), and then acidified with 1 N HCl to pH 3. The resulting solid material was collected on a fritted funnel. Subsequent extraction with excess EtOAC, and concentration under reduced pressure provided the title compound (3.63 g, 68%) as a white solid: mp 136-139; $^1$H NMR (300 MHz, DMSO-d$_6$) δ 12.97 (br s, 1H), 7.87 (d, J=3.7 Hz, 1H), 7.30 (t, J=7.9 Hz, 1H), 7.00 (m, 2H), 6.91 (dd, J=1.8, 8.0 Hz, 1H), 5.29 (s, 2H), 3.74 (s, 3H); MS (ESI) m/z 251 (M+H)$^+$.

C) An oven-dried 100 mL Schlenk flask was charged with 5-fluoro-2-(3-methoxybenzyloxy)pyrimidin-4-ol (3.63 g, 14.5 mmol) and N,N-dimethylaniline (3.7 mL, 29.2 mL). Phosphorous oxychloride ($POCl_3$, 40 mL, 429 mmol) was added, and resulting solution was heated to 95° C. under nitrogen. After 2 h, the reaction was cooled to room temperature and concentrated to constant volume under reduced pressure at 50° C. The remaining residue was diluted with $Et_2O$ (50 mL) and washed with 1 N HCl (2×50 mL). Concentration at reduced pressure provided a solid, which was washed with water and collected by vacuum filtration. The title compound (4.09 g, 105%) was isolated as a white solid: mp 96-100° C.; ¹H NMR (300 MHz, DMSO-d₆) δ 8.81 (d, J=0.8 Hz, 1H), 7.30 (t, J=8.1 Hz, 1H), 7.02 (m, 2H), 6.91 (dd, J=2.3, 8.3 Hz, 1H), 5.34 (s, 2H), 3.75 (s, 3H); MS (ESI) m/z 269 (M+H)⁺.

D) To a mixture of 4-chloro-2-(3-methoxybenzyl)-5-fluoropyrimidine (0.153 g, 0.568 mmol) and 4-methoxyphenylhydrazine hydrochloride (0.324 g, 1.85 mmol) in ethanol (5 mL) was added triethylamine (0.272, 2.69 mmol) and the mixture was heated to 50° C. for 16 h. The reaction was cooled to room temperature and diluted with Et₂O (50 mL). The Et₂O solution was washed with water (2×50 mL), dried over MgSO₄, filtered, and concentrated. The residue was triturated with Et₂O to obtain 5-fluoro-2-(3-methoxy-benzyloxy)-4-(1-(4-methoxyphenyl)hydrazinyl)pyrimidine (0.113 g, 54% yield) as a white solid: mp 121-123.5° C.; ¹H NMR (300 MHz, DMSO-d₆) δ 8.02 (d, J=5.4 Hz, 1H), 7.28 (t, J=8.1 Hz, 1H), 7.22 (d, J=8.5 Hz, 2H), 6.99-6.93 (m, 2H), 6.93-6.85 (m, 3H), 5.25 (s, 2H), 3.75 (s, 3H), 3.74 (s, 3H); MS (ESI) m/z 371 (M+H)⁺, 354 (M-NH₂)⁻.

Preparation of O-Allyl-N-(5-fluoro-2-(3-methoxy-benzyloxy)pyrimidin-4-yl)hydroxylamine (32)

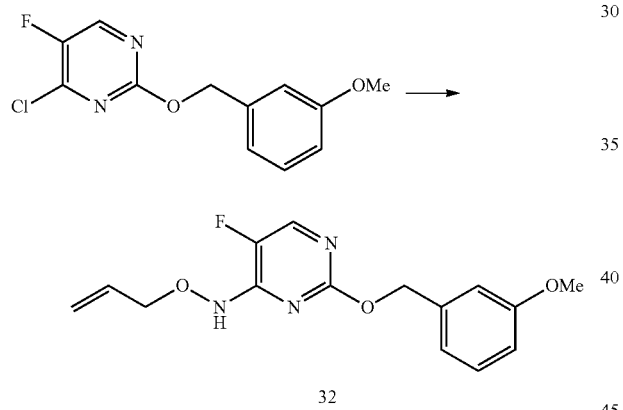

To a mixture of 4-chloro-2-(3-methoxybenzyl)-5-fluoropyrimidine (0.151 g, 0.558 mmol) and O-allyl hydroxylamine hydrochloride (0.201 g, 1.83 mmol) in 5:1 MeOH: CH₃CN (5 mL) was added triethylamine (0.273 g, 2.70 mmol) and the mixture was heated at 50° C. for 18 h. The reaction was cooled to room temperature and diluted with Et₂O (50 mL). The organic solution was washed with water (2×50 mL), dried over MgSO₄, filtered, and concentrated. Purification by flash chromatography (SiO₂, 17%→50% EtOAc/hexane) afforded O-allyl-N-(5-fluoro-2-(3-methoxy-benzyloxy)-pyrimidin-4-yl)hydroxylamine (0.113 g, 66% yield) as a colorless oil: ¹H NMR (300 MHz, DMSO-d₆) δ 10.94 (broad singlet, 1H), 7.94 (broad singlet, 1H), 7.28 (t, J=8.0 Hz, 1H), 6.95-7.03 (m, 2H), 6.88 (dd, J=2.5, 7.9 Hz, 1H), 5.97 (tdd, J=5.8, 10.6, 17.0 Hz, 1H), 5.32 (dd, J=1.5, 17.4 Hz, 1H), 5.24 (s, 2H), 5.22 (dd, J=1.2, 10.6 Hz, 1H), 4.39 (d, J=6.0 Hz, 2H), 3.74 (s, 3H); MS (ESI) m/z 306 (M+H)⁺, 304 (M-H)⁻.

Preparation of 1-[2-(3-Cyanobenzyloxy)-5-fluoropyrimidin-4-yl]-3-(2-fluorobenzyl)urea (34)

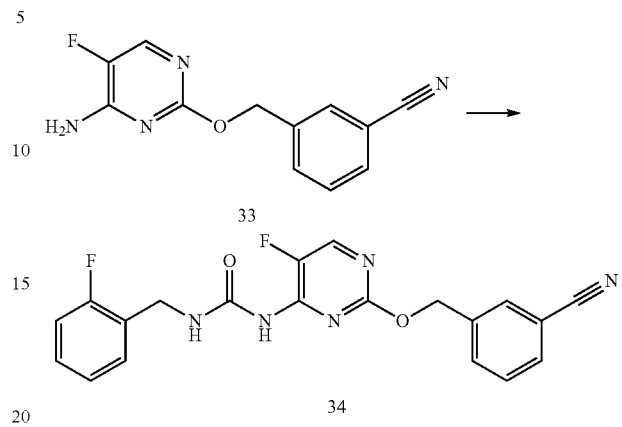

To a magnetically stirred mixture of 3-(4-amino-5-fluoro-pyrimidin-2-yloxymethyl)-benzonitrile (0.075 g, 0.31 mmol) and 2-fluorobenzylisocyanate (0.59 mL, 0.46 mmol) in dry DMF (1.5 mL) was added LiHMDS (1.0 M in THF, 0.31 ml, 0.30 mmol). The vial was capped and the mixture stirred at room temperature for 8 h. Saturated aq. NH₄Cl (3 ml) was added and the mixture was stirred for 4 h. The heterogeneous mixture was filtered, and the solid was washed with hot water, washed with E₂O, and then dried under vacuum to give the title compound (0.075 g, 62%) as a white solid: mp 177-178° C.; ¹H NMR (400 MHz, DMSO-d₆) δ 10.04 (s, 1H), 8.90 (t, J=5.7 Hz, 1H), 8.37 (d, J=2.8 Hz, 1H), 7.85 (br s, 1H), 7.80 (d, J=7.5 Hz, 1H), 7.74 (d, J=8.0 Hz, 1H), 7.60 (t, J=7.8 Hz, 1H), 7.42-7.38 (m, 1H), 7.35-7.29 (m, 1H), 7.20-7.14 (m, 2H), 5.33 (s, 2H), 4.49 (d, J=5.8 Hz, 2H); HPLC-MS (ESI) m/z 396.3 (M+H)⁺, 394.3 (M-H)⁻.

Preparation of 1-[5-Fluoro-2-(3-methoxybenzyloxy)pyrimidin-4-yl](3'-propyl carbamoyl)-3-propyl-urea (36)

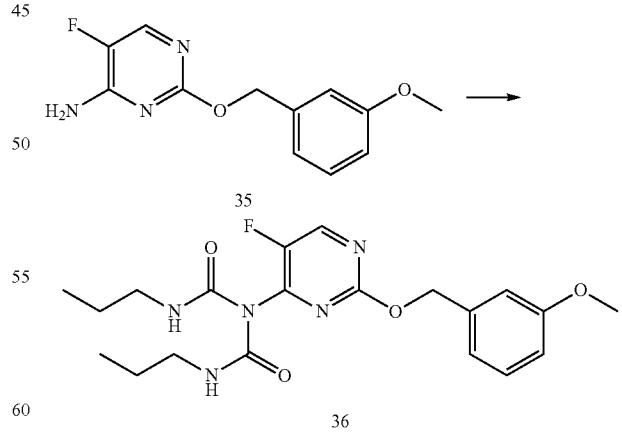

To a magnetically stirred mixture of 5-fluoro-2-(3-methoxybenzyloxy)pyrimidin-4-ylamine (0.075 g, 0.30 mmol) and propylisocyanate (0.057 mL, 0.60 mmol) in dry DMF (1.5 mL) was added LiHMDS (1.0 M in THF, 0.60 ml, 0.60 mmol). The vial was capped and the reaction was stirred at room temperature for 8 h. The solvent was evaporated under reduced pressure and the crude material was purified by reverse-phase chromatography to give the title compound (0.043 g, 10%) as a tan solid: mp 75-78° C.; $^1$H NMR (400 MHz, DMSO-$d_6$) δ 12.34 (s, 1H), 8.49 (s, 1H), 7.89 (s, 1H), 7.29 (t, J=7.8 Hz, 1H), 7.05-7.01 (m, 2H), 6.90 (dd, J=6.9 Hz, J=2.5 Hz, 1H), 5.30 (s, 2H), 3.75 (s, 3H), 3.74-3.68 (m, 2H), 3.15-3.10 (m, 2H), 1.58-1.44 (m, 4H), 0.89-0.85 (m, 6H); HPLC-MS (ESI) m/z 420.4 (M+H)$^+$, 418.4 (M−H)$^−$.

Preparation of 1-[2-(3-Cyanobenzyloxy)-5-fluoropyrimidin-4-yl]-3-propylthiourea (37)

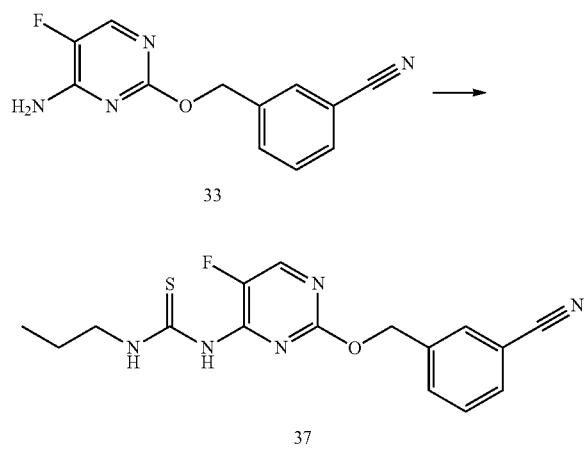

To a magnetically stirred mixture of 3-(4-amino-5-fluoropyrimidin-2-yloxymethyl)-benzonitrile (0.075 g, 0.31 mmol) and propylisothiocyanate (0.047 mL, 0.46 mmol) in dry DMF (1.5 mL) was added LiHMDS (1.0 M in THF, 0.31 ml, 0.31 mmol). The vial was capped and reaction was stirred for 8 h. Saturated aq NH$_4$Cl (3 ml) was added to the vial and the mixture was stirred for 4 h. The heterogeneous mixture was filtered and the solid was washed with hot water, washed with hexanes, and dried under vacuum to give the title compound (0.055 g, 52%) as a pale-yellow solid: mp 163-165° C.; $^1$H NMR (400 MHz, DMSO-$d_6$) δ 10.77 (s, 1H), 10.38 (s, 1H), 8.47 (d, J=2.7 Hz, 1H), 7.90 (s, 1H), 7.82 (d, J=7.5 Hz, 1H), 7.78 (d, J=8.1 Hz, 1H), 7.62 (t, J=7.7 Hz, 1H), 5.42 (s, 2H), 3.55 (dd, J=12.4, 6.8 Hz, 2H), 1.65-1.59 (m, 2H), 0.95 (t, J=7.5 Hz, 3H): HPLC-MS (ESI) m/z 346.3 (M+H)$^+$, 344.2 (M−H)$^−$.

Preparation of N-[5-Fluoro-2-(4-methylbenzyloxy)pyrimidin-4-yl]methanesulfonamide (38)

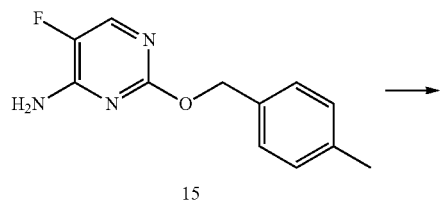

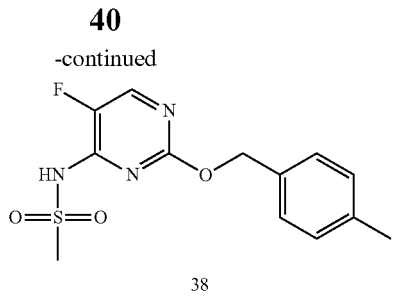

To a solution of 5-fluoro-2-(4-methylbenzyloxy)pyrimidin-4-ylamine (0.100 g, 0.43 mmol) in anhydrous THF (4 mL) was added LiHMDS (1.07 mL of 1.0M, 1.07 mmol) dropwise at room temperature, and the resulting orange solution was stirred for 20 min. Methanesulfonyl chloride (0.108 g, 0.94 mmol) was added in one portion and the turbid, light orange solution was stirred for 60 min. The reaction was quenched with brine (5 mL) and the THF phase was separated. The aq. phase was extracted w/EtOAc (5 mL), and the organics were combined, dried over Na$_2$SO$_4$, filtered, and concentrated to an orange gummy residue. The residue was purified by flash chromatography (SiO$_2$, 0→100% EtOac/hexanes) to give 0.034 g (26%) of the title compound as a white solid: mp 145-148° C.; $^1$H NMR (400 MHz, CDCl$_3$) δ 8.19 (s, 1H), 7.33 (d, J=7.9 Hz, 2H), 7.17 (d, J=7.9 Hz, 2H), 5.35 (s, 2H), 3.37 (s, 3H), 2.35 (s, 3H); HPLC-MS (ESI) m/z 312 (M+H)$^+$, 310 (M−H)$^−$.

Preparation of N-[5-Fluoro-2-(4-fluorobenzyloxy)-pyrimidin-4-yl]-S-(2-nitrophenyl)-thiohydroxylamine (39)

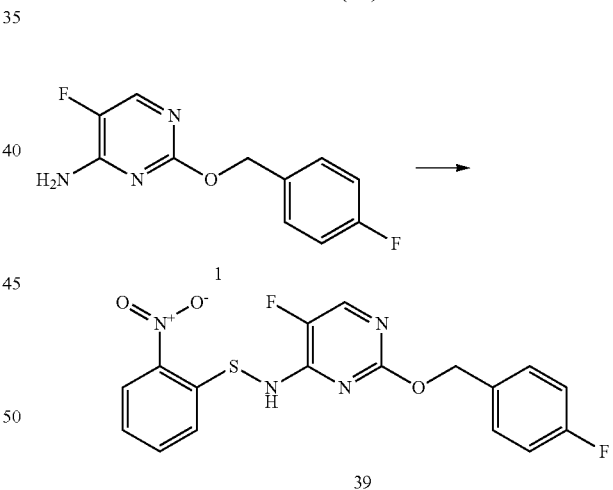

To a solution of 5-fluoro-2-(4-fluorobenzyloxy)pyrimidin-4-ylamine (0.05 g, 0.2 mmol) and a 1.0 M solution of t-BuOK in t-BuOH (1.0 mL, 1.0 mmol) was added nitrobenzenesulfenyl chloride (0.044 g, 0.23 mmol) in one portion, and the resulting brown solution was stirred for 60 min. The reaction was diluted with water (2 mL) and neutralized to pH 7 with 1N HCl. The aq. phase was extracted with EtOAc (5 mL), and the organics were combined, dried over Na$_2$SO$_4$, filtered, and concentrated. The crude material was purified by reverse phase chromatography to yield the title compound (0.020 g, 26%) as a yellow solid: mp 184° C.; $^1$H NMR (300 MHz, CDCl$_3$) δ 8.36 (d, J=7.25 Hz, 1H), 8.09 (d, J=2.3 Hz, 1H), 7.59 (m, 1H), 7.36 (m 2H), 7.29 (m, 2H), 6.88 (m, 2H), 6.23 (bs, 1H), 5.19 (s, 2H); HPLC-MS (ESI) m/z 391 (M+H)$^+$, 389 (M−H)$^-$.

Preparation of Benzenesulfonic acid 4-acetylamino-5-fluoro-pyrimidin-2-yl ester (40)

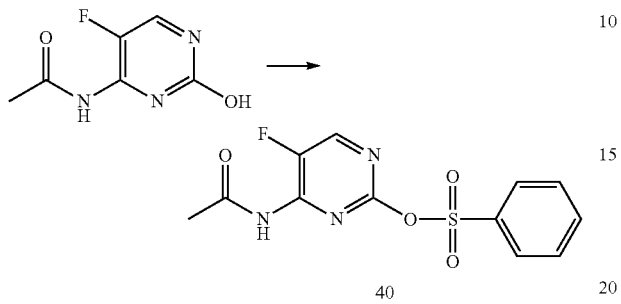

N-(5-Fluoro-2-hydroxypyrimidin-4-yl)-acetamide* (200 mg, 1.17 mmol) was suspended in pyridine (5 mL) and stirred at ambient temperature. To the stirred suspension was added benzenesulfonyl chloride (226 mg, 1.29 mmol) and agitation was continued for 16 hours. The solvent was evaporated under a stream of nitrogen and the residue was suspended in dichloromethane (2-3 mL), placed directly onto a silica gel column, and eluted with ethyl acetate in petroleum ether (0-50% gradient) to isolate 180 mg, 0.58 mmol (49%) of the title compound as a white solid: mp 142-143° C.; $^1$H NMR (DMSO-d$_6$) δ 10.96 (s, 1H), 8.67 (d, J=2.6 Hz, 1H), 8.12-8.06 (m, 2H), 7.86-7.79 (m, 1H), 7.73-7.65 (m, 2H), 2.98 (s, 3H); HPLC-MS (ESI) m/z 312 (M+H)$^+$, 310 (M−H)$^-$.

*N-(5-Fluoro-2-hydroxypyrimidin-4-yl)-acetamide can be prepared through known literature methods. 1. Duschinsky, R., Fells, E., Hoffer, M. U.S. Pat. No. 3,309,359

Preparation of 2,2-Dimethylpropionic acid 4-(dimethylamino-methyleneamino)-5-fluoro-pyrimidin-2-yloxymethyl ester (41)

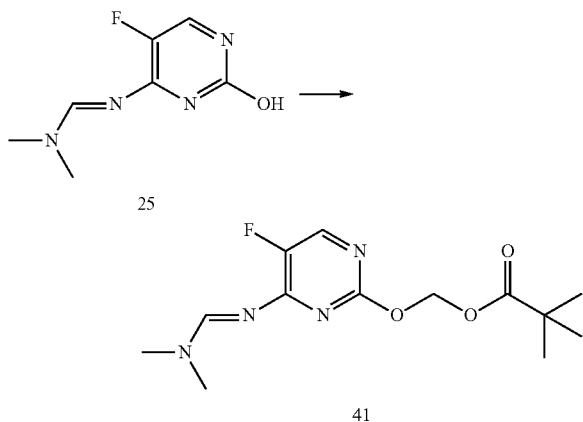

N'-(5-Fluoro-2-hydroxypyrimidin-4-yl)-N,N-dimethyl-formamidine (100 mg, 0.54 mmol), cesium carbonate (196 mg, 0.60 mmol), and chloromethyl pivalate (90 mg, 0.6 mmol) were shaken together in DMF (3 mL) at ambient temperature for 16 hours. The reaction mixture was partitioned between ethyl acetate and water, dried over magnesium sulfate, filtered and evaporated to yield a colorless oil which was treated with diethyl ether (3-4 mL) to produce a solid. The solid was removed and the ether solution was placed onto a silica gel column and eluted with ethyl acetate in petroleum ether (0-50% gradient) to isolate 14 mg, 0.05 mmol (9%) of the title compound as a white solid: mp 86-88° C.; $^1$H NMR (CDCl$_3$) δ 8.73 (s, 1H), 8.06 (d, J=2.6 Hz, 1H), 6.04 (s, 2H), 3.20 (s, 3H), 3.18 (s, 3H), 1.16 (s, 9H); HPLC-MS (ESI) m/z 299 (M+H)$^+$.

Preparation of N'-(5-Fluoro-2-methoxymethoxypyrimidin-4-yl)-N,N-dimethyl-formamidine (42)

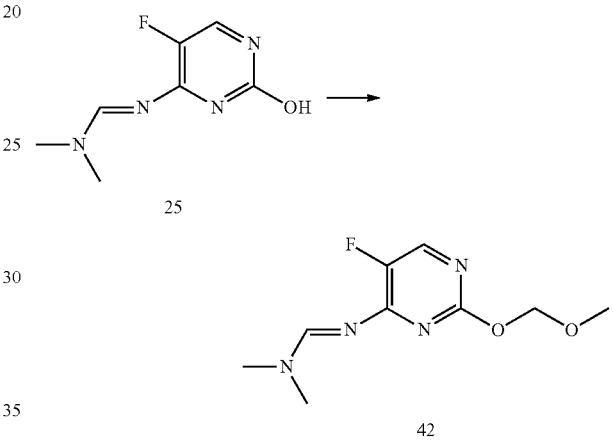

N'-(5-Fluoro-2-hydroxypyrimidin-4-yl)-N,N-dimethyl-formamidine (100 mg, 0.54 mmol), cesium carbonate (196 mg, 0.60 mmol), and bromomethyl methyl ether (75 mg, 0.6 mmol) were shaken together in DMF (3 mL) at ambient temperature for 4 hours. The reaction mixture was partitioned between ethyl acetate and water, dried over magnesium sulfate, filtered and evaporated to yield a colorless oil which was placed directly onto a silica gel column and eluted with ethyl acetate in petroleum ether (0-80% gradient) to isolate 23 mg, 0.1 mmol (19%) of the title compound as a colorless oil: $^1$H NMR (CDCl$_3$) δ 8.66 (s, 1H), 8.05 (d, J=2.6 Hz, 1H), 5.46 (s, 2H), 3.53 (s, 3H), 3.17 (s, 3H), 3.16 (s, 3H); HPLC-MS (ESI) m/z 229 (M+H)$^+$.

Preparation of [5-Fluoro-2-(3-methoxybenzyloxy)pyrimidin-4-yl]sulfamide (43)

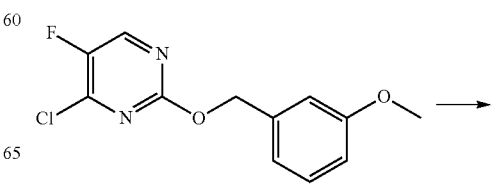

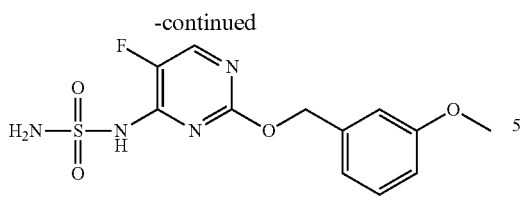

43

To a magnetically stirred solution of 4-chloro-5-fluoro-2-(3-methoxybenzyloxy)pyrimidine* (1.3 g, 4.84 mmol) in dry DMF (5 mL) was added a pre-mixed suspension of 60% NaH (0.45 g, 10.65 mmol) and sulfamide (0.93 g, 9.68 mmol) in dry DMF (5 mL). The resulting off-white suspension was stirred at room temperature for 72 hrs. The orange suspension was then heated to 50° C. for 48 hours and cooled to room temperature. The reaction mixture was partitioned between ethyl acetate and brine solution. The organic extract was dried over Na$_2$SO$_4$, filtered, and evaporated. The crude material was purified by column chromatography on normal phase silica using a gradient of EtOAc/Hex and reverse phase using a gradient of H$_2$O/CH$_3$CN to yield [5-fluoro-2-(3-methoxybenzyloxy)pyrimidin-4-yl]sulfamide (115 mg, 7.2% yield) as a white solid: mp 126-130° C.; $^1$H NMR (300 MHz, CD$_3$OD) δ 8.01 (d, J=3.63 Hz, 1H), 7.25 (m, 1H), 7.01 (m, 2H), 6.88 (m, 1H), 5.37 (s, 2H), 3.78 (s, 3H); MS (ESI) m/z 326.9 (M–H)⁻.

*The 4-chloro-5-fluoro-2-(3-methoxybenzyloxy)pyrimidine intermediate was prepared as described in the synthesis of 31.

Preparation of 5-Fluoro-4-hydrazinyl-2-(3-methoxybenzyloxy)pyrimidine (44)

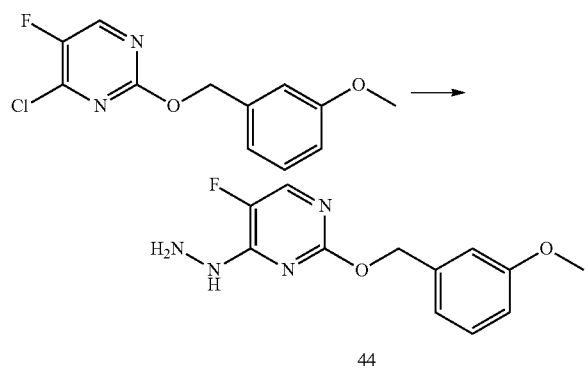

A 125 mL Erlenmeyer flask was charged with 4-chloro-5-fluoro-2-(3-methoxybenzyl-oxy)pyrimidine (1.50 g, 5.58 mmol) and EtOH (50 mL). Hydrazine monohydrate (900 μL, 18.5 mmol) was added, and the resulting mixture was allowed to stir at room temperature. After 22 h, the reaction was transferred to a 500 mL Erlenmeyer flask and diluted with water (200 mL), whereupon a white solid began to precipitate from solution. After stirring for 7 h, solid product was collected in a fritted funnel and rinsed with excess water. After drying on the frit, the title compound was obtained (1.23 g, 83%) as a white solid: mp 103-106° C.; $^1$H NMR (300 MHz, DMSO-d$_6$) δ 8.92 (bs, 1H), 7.86 (d, J=3.6 Hz, 1H), 7.27 (t, J=8.1 Hz, 1H), 6.94-7.01 (m, 2H), 6.87 (dd, J=2.4, 7.9 Hz, 1H), 5.24 (s, 2H), 4.46 (bs, 2H), 3.74 (s, 3H); MS (ESI) m/z 265.2 (M+H)⁺, 263.2 (M–H)⁻.

Preparation of (E)-5-Fluoro-2-(3-methoxybenzyloxy)-4-(2-(thiophen-2-ylmethylene)-hydrazinyl)pyrimidine(45)

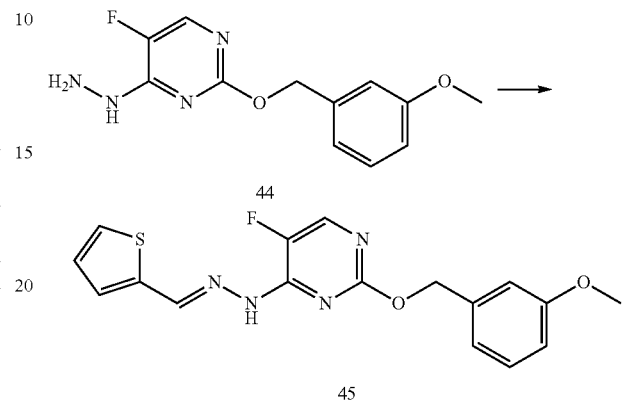

A 20 mL vial was charged with 5-fluoro-4-hydrazinyl-2-(3-methoxybenzyloxy)-pyrimidine (74.7 mg, 0.283 mmol), EtOH (2 mL), thiophene-2-carbaldehyde (26 μL, 0.284 mmol) and 1 M HCl in Et$_2$O (14 μL, 0.014 mmol) and heated at 50° C. on shaker. After 90 minutes, the reaction was cooled to room temperature concentrated on high vacuum to provide the title compound (77.8 mg, 77%) as a yellow solid: mp 136-139° C.; $^1$H NMR (300 MHz, DMSO-d$_6$) δ 11.46 (bs, 1H), 8.50 (bs, 1H), 8.16 (d, J=3.6 Hz, 1H), 7.64 (d, J=5.0 Hz, 1H), 7.41 (d, J=3.4 Hz, 1H), 7.28 (t, J=8.0 Hz, 1H), 7.12 (dd, J=3.8, 4.8 Hz, 1H), 7.04 (m, 2H), 6.88 (dd, J=2.4, 8.3 Hz, 1H), 5.27 (s, 2H), 3.73 (s, 3H); MS (ESI) m/z 359.2 (M+H)⁺, 357.2 (M–H)⁻.

Preparation of 2-(Benzyloxy)-4-[(dimethyl-λ$^4$-sulfanylidene)amino]-5-fluoropyrimidine (47)

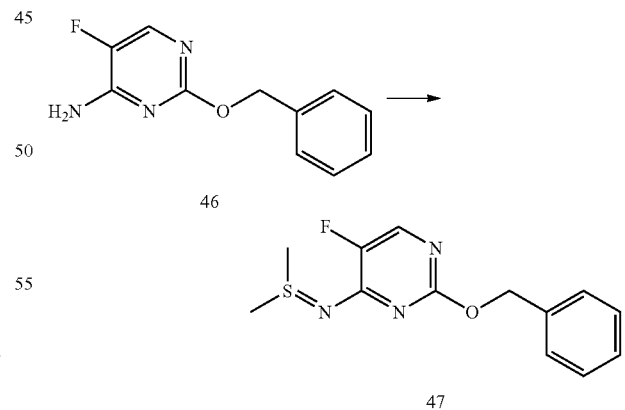

A 10 mL oven-dried Schlenk flask was charged with 2-(benzyloxy)-5-fluoropyrimidin-4-amine (101 mg, 0.462 mmol), CH$_2$Cl$_2$ (2 mL), and dimethylsulfide (75.0 μL, 1.02 mmol) and was cooled to 0° C. in an ice bath. N-Chlorosuccinimide (122 mg, 0.914 mmol) was added and the resulting mixture was allowed to stir at 0° C. for 45 minutes, and then at room temperature for 30 minutes. A solution of NaOMe in MeOH (25%, 360 µL, 1.35 mmol) was added. After 20 minutes, the reaction was quenched with water (3 mL) and allowed to stir for 1 hour. The crude reaction mixture was then diluted with $CH_2Cl_2$ and washed with water (50 mL×2), dried over anhydrous $Na_2SO_4$, filtered, and concentrated by rotary evaporation and then on high vacuum to give the title compound (120 mg, 93%) as an off white solid: mp 125-129° C.; $^1$H NMR (300 MHz, DMSO-$d_6$): δ 7.70 (d, J=3.9 Hz, 1H), 7.25-7.44 (m, 5H), 5.21 (s, 2H), 2.75 (s, 6H); MS (ESI) m/z 281.1 (M+H)$^+$.

*Yamamoto, Y.; Yamamoto, H. *J. Am. Chem. Soc.* 2004, 126, 4128-4129.

Preparation of 1-[5-Fluoro-2-(4-methylbenzyloxy)-pyrimidin-4-yl]-2,3-dipropyl-isothiourea (49)

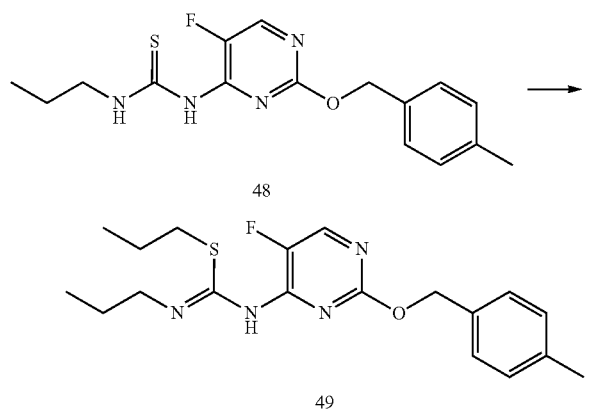

To a magnetically stirred solution of 1-[5-fluoro-2-(4-methyl-benzyloxy)-pyrimidin-4-yl]-3-propyl-thiourea (0.50 g, 1.40 mmol) in $CH_3CN$ (4 mL), was added potassium carbonate (0.20 g, 1.40 mmol) at room temperature and the mixture was stirred for 20 min. N-propylbromide (0.19 g, 1.40 mmol) was added at room temperature and the resulting mixture stirred for 15 h. The reaction mixture was diluted with $H_2O$ and extracted with $CH_2Cl_2$ (3×20 mL). The combined organic layers were dried over $Na_2SO_4$, filtered, and the solvent evaporated. The crude mixture was purified on silica (EtOAc/hexanes gradient) and evaporation of the product fractions gave 0.335 g (63%) of 1-[5-fluoro-2-(4-methyl-benzyloxy)-pyrimidin-4-yl]-2,3-dipropyl-isothiourea as a pale yellow viscous liquid: $^1$H NMR (300 MHz, CDCl$_3$) δ 10.56 (bs, 1H), 8.09 (d, J=2.6 Hz, 1H), 7.31 (m, 2H), 7.24 (m, 2H), 5.28 (s, 2H), 3.28 (dd, J=13.6, 6.5 Hz, 4H), 2.36 (s, 3H), 1.62 (m, 4H), 1.0 (t, J=7.4 Hz, 4H); HPLC-MS (ESI) m/z 377 (M+H)$^+$.

Preparation of O-(4-Amino-5-fluoropyrimidin-2-yl)-t-butyl N-methyl-N-hydroxycarbamate (50)

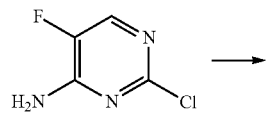

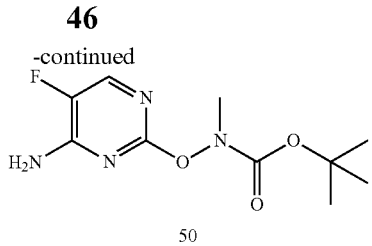

In a 2 dram screw cap vial, a solution of 4-amino-2-chloro-5-fluoropyrimidine (0.1 g, 0.68 mmol) and t-butyl N-methyl-N-hydroxycarbamate* (0.11 g, 0.75 mmol) was treated with a 1.0 M solution of t-BuOK in t-BuOH (1.0 mL, 1.0 mmol) in one portion, and the resulting yellow solution was heated at 100° C. and shaken for 24 h. The reaction mixture was cooled, extracted with EtOAc (3×5 mL), and the solvent evaporated. The crude mixture was purified via reverse phase chromatography to yield 0.10 g (56.9%) of the title compound as yellow solid: mp 123-125° C.; $^1$H NMR (300 MHz, CDCl$_3$) δ 7.96 (d, J=2.3 Hz, 1H), 5.26 (bs, 2H), 3.32 (s, 3H), 1.43 (s, 9H); MS (ESI) m/z 259 (M+H)$^+$.

*t-butyl N-methyl-N-hydroxycarbamate can be prepared through known literature methods: 1. Carrasco, M. R.; Brown, R, T.; Serafimova, I. M.; Silva O. *J. Org. Chem.*, 2003, 68 (1), 195.

Preparation of O-ethyl 5-fluoro-2-(4-fluorobenzy-loxy)pyrimidin-4-ylcarbamothioate (51)

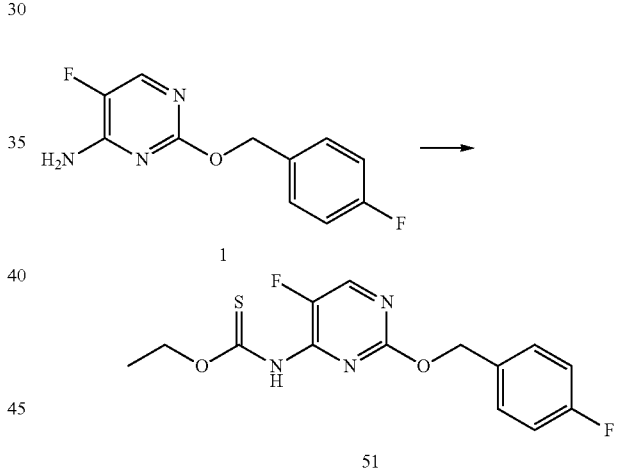

5-Fluoro-2-(4-fluorobenzyloxy)pyrimidin-4-amine (300 mg, 1.26 mmol) was stirred in chloroform (25 mL) and water (12 mL). Sodium bicarbonate (870 mg, 10.12 mmol) was added followed by dropwise addition of thiophosgene (218 mg, 1.9 mmol). The reaction mixture was stirred at room temperature for 16 hours, then diluted with chloroform (20 mL) and the phases were separated. The organic extract was dried over sodium sulfate, filtered, and concentrated by rotary evaporation to ⅓ volume. To this chloroform solution of crude isothiocyanate was added abs. ethanol (10 mL) and the mixture was heated in a sealed tube for 1 h. The reaction mixture was cooled to room temperature, concentrated and purified by flash chromatography on silica, to give 45 mg (11%) of O-ethyl 5-fluoro-2-(4-fluorobenzyloxy)pyrimidin-4-ylcarbamothioate as a pale yellow solid: mp 109-119° C.; $^1$H NMR (CDCl$_3$) δ 8.30 (bs, 2H), 7.44 (m, 2H), 7.06 (m, 2H), 5.36 (s, 2H), 4.66 (q, J=6 Hz, 2H), 1.45 (t, J=6 Hz, 3H); HPLC-MS (ESI): m/z 326 (ES$^+$).

Preparation of N-(5-Fluoro-2-(4-fluorobenzyloxy)pyrimidin-4-yl)ethanethioamide (53)

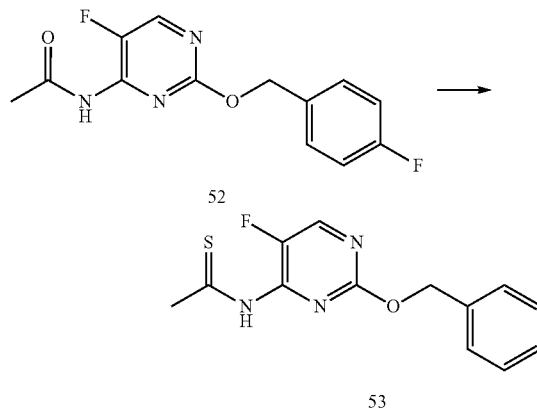

N-(5-Fluoro-2-(4-fluorobenzyloxy)pyrimidin-4-yl)acetamide (50 mg, 0.42 mmol) was stirred in a Biotage Initiator® microwave vessel with 1,2-dichloroethane (3 mL) and Lawesson's reagent (170 mg, 0.42 mmol). The vessel was heated in a Biotage Initiator® microwave to 100° C. for 5 minutes then cooled room temperature, filtered, and diluted with CH$_2$Cl$_2$. The reaction mixture was then washed brine, and the layers were separated. The organic extract was dried onto silica and purified by flash chromatography. The product-containing fractions were then evaporated to dryness and purified again by reverse-phase HPLC to give 4 mg of N-(5-fluoro-2-(4-fluorobenzyl-oxy)pyrimidin-4-yl)ethanethioamide (4%) as a yellow glass: $^1$H NMR (CDCl$_3$) δ 9.34 (b, 1H), 8.29 (d, J=3 Hz, 1H), 7.41 (m, 2H), 7.06 (m, 2H), 5.33 (s, 2H), 3.13 (s, 3H); HPLC-MS (ESI): m/z 294 (ES$^-$).

Preparation of 1-(5-Fluoro-2-hydroxypyrimidin-4-yl)-3-(2-methoxyphenyl)urea (954)

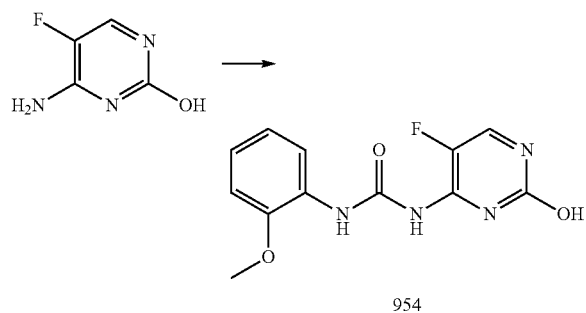

To a magnetically stirred mixture of 4-amino-2-hydroxy-5-fluoropyrimidine (150 mg, 1.16 mmol) in dry DMF (3.5 mL) was added 2-methoxyphenyl isocyanate (170 μL, 1.28 mmol) and the white suspension was allowed to stir at room temperature for 60 min. The mixture was heated to 55° C. for 3 h, and then allowed to stir at room temperature overnight. The precipitate was collected by vacuum filtration and washed with Et$_2$O (10×3 mL) to give a solid material, which was air dried for 1 h to give 1-(5-fluoro-2-hydroxypyrimidin-4-yl)-3-(2-methoxyphenyl)urea (269 mg, 83%) as a white solid: mp 247-250° C.; $^1$H NMR (300 MHz, DMSO-d$_6$) δ 12.24 (bs, 1H), 11.31 (bs, 1H), 10.16 (bs, 1H), 8.14 (d, J=7.91 Hz, 1H) 8.0 (d, J=5.6, 1H), 7.03-6.99 (m, 2H), 6.95-6.88 (m, 1H), 3.87 (s, 3H) MS (ESI) m/z 276.9 (M–H)$^-$.

Preparation of N-(5-Fluoro-2-(4-methylbenzyloxy)pyrimidin-4-yl)-4-methylbenzenesulfonamide (955)

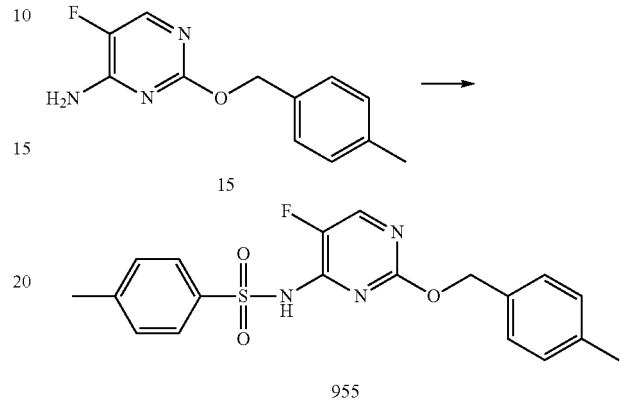

To a magnetically stirred solution of 5-fluoro-2-(4-methylbenzyloxy)pyrimidin-4-amine (200 mg, 0.857 mmol) in sure seal THF (4 mL) was added 1M lithium bis(trimethylsilyl)amide (LiHMDS) solution in THF (1.28 mL, 1.28 mmol) causing a slight exotherm. After stirring for 5 min, p-toluenesulfonyl chloride (196.65 mg, 1.028 mmol) was added and after 10 min the orange solution turned light yellow and turbid. The mixture was stirred at room temperature for 4 h. The solvent was removed in vacuo and the resulting viscous gold oil was diluted in EtOAc (50 mL), poured into a separatory funnel containing EtOAc (75 mL) and washed with 1N HCl aqueous solution (4×75 mL) followed by brine solution (1×100 mL). The organic extract was dried over Na$_2$SO$_4$, filtered, and evaporated. To the crude oil material was added distilled water (150 mL) and the resulting mixture was vigorously stirred at room temperature over 72 h forming an off-white solid. The solid was collected by vacuum filtration and air dried for 1 hour followed by drying under vacuum for 24 hours. The white solid was then suspended in Et$_2$O (2 mL) for 1 h, then collected by vacuum filtration washed with Et$_2$O (1×1 mL), and air dried for 1 h to yield N-(5-fluoro-2-(4-methylbenzyloxy)pyrimidin-4-yl)-4-methylbenzenesulfonamide (150 mg, 45.2% yield) as a white solid: mp 120-122° C.; $^1$H NMR (300 MHz, DMSO-d$_6$) δ 8.28 (d, J=2.9 Hz, 1H), 7.83 (d, J=8.1 Hz, 2H), 7.33 (d, J=8.0 Hz, 2H), 7.23 (d, J=8.23 Hz, 2H), 7.16 (d, J=7.92 Hz, 2H), 5.08 (s, 2H), 2.33 (s, 3H), 2.29 (s, 3H) MS (ESI) m/z 386.3 (M–H)$^-$.

Preparation of N-(5-Fluoro-2-hydroxypyrimidin-4-yl)benzenesulfonamide (956)

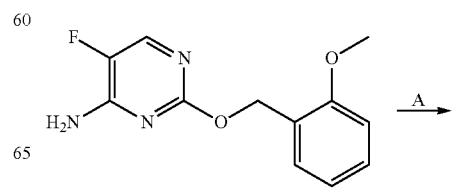

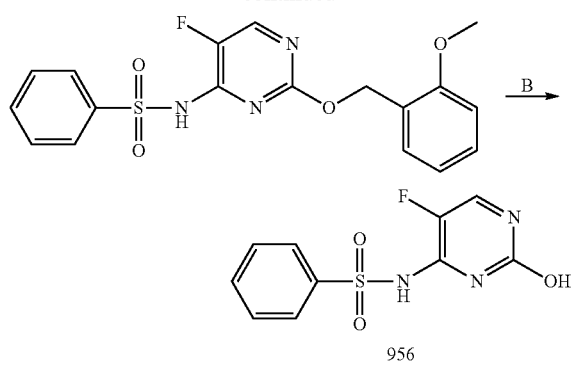

956

A) To a magnetically stirred solution of 5-fluoro-2-(2-methoxybenzyloxy)pyrimidin-4-amine (500 mg, 2.01 mmol) in dry THF (10 mL) was added 1M LiHMDS solution in THF (3.21 mL, 3.21 mmol) causing a slight exotherm. After stirring for 5 min, benzenesulfonyl chloride (0.346 mL, 2.71 mmol) was added and after 10 min the orange solution turned light orange and turbid. The mixture was stirred at room temperature for 5 h. The solvent was removed in vacuo and the resulting viscous gold oil was diluted in EtOAc (10 mL), poured into a separatory funnel containing EtOAc (100 mL) and washed with 1N HCl aqueous solution (4×50 mL) and brine solution (1×50 mL). The organic extract was dried over $Na_2SO_4$, filtered, and evaporated to yield N-(5-fluoro-2-(2-methoxybenzyloxy)pyrimidin-4-yl)benzenesulfonamide (714 mg, 91% yield) as a light tan solid. MS (ESI) m/z 387.99 (M–H)⁻.

B) The solid N-(5-fluoro-2-(2-methoxybenzyloxy)pyrimidin-4-yl)benzenesulfonamide (714 mg, 1.83 mmol) was dissolved in dichloromethane (10 mL) followed by the addition of trifluoroacetic acid (1.0 mL, 13.5 mmol) and allowed to stir at room temperature for 1 h. The solvent was removed in vacuo and the resulting residue was dissolved in dichloromethane:methanol in a 10:1 ratio. The product was purified by column chromatography (dichloromethane/methanol gradient) to yield N-(5-fluoro-2-hydroxypyrimidin-4-yl)benzenesulfonamide (251 mg, 51% yield) as a white solid: mp 221-223° C.; ¹H NMR (300 MHz) δ 11.57 (bs, 1H), 11.11 (bs, 1H), 8.04 (d, J=6.1 Hz, 1H), 7.94-7.84 (m, 2H), 7.71-7.51 (m, 3H).

Preparation of 4-(Benzylmethylamino)-5-fluoropyrimidin-2-ol (957)

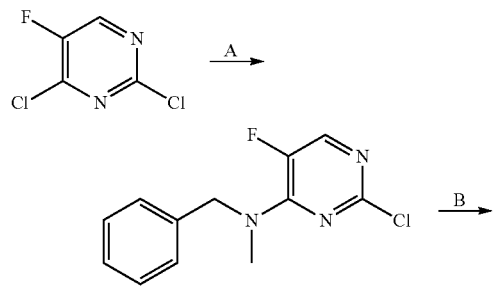

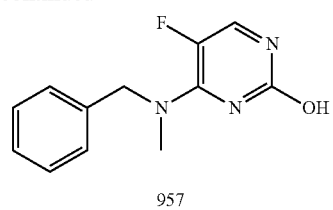

957

A) To a suspension of 2,4-dichloro-5-fluoropyrimidine (0.30 g, 1.80 mmol) in dioxane (3.6 mL) were added N-ethyl-N-isopropylpropan-2-amine (0.23 g, 1.80 mmol) and N-methyl-1-phenylmethanamine (0.24 g, 1.98 mmol), and the resulting mixture was stirred at room temperature for 16 h. The reaction was diluted with EtOAc (15 mL) and the resulting solution was washed with $H_2O$ (2×5 mL). The organic phase was dried over $Na_2SO_4$, filtered, and concentrated to a light yellow oil which was purified by flash chromatography (40 g $SiO_2$, EtOAc/Hexanes gradient) to give a colorless oil which solidified upon cooling. The solid was dried under high vacuum at 23° C. for 16 h to give N-benzyl-2-chloro-5-fluoro-N-methylpyrimidin-4-amine (0.34 g, 76%) as a white solid: mp 47-49° C.; ¹H NMR (300 MHz, CDCl₃) δ 8.18 (d, J=6.4, 1H), 7.43-7.23 (m, 5H), 4.82 (s, 2H), 3.17 (d, J=3.3, 3H); MS (EI) m/z 251 (M)⁺.

B) To a suspension of N-benzyl-2-chloro-5-fluoro-N-methylpyrimidin-4-amine (0.075 g, 0.30 mmol) in dioxane/H₂O (1:1, 2 mL total volume) was added KOH (0.17 g, 3.0 mmol) and the mixture was warmed to 100° C. and stirred for 72 h. The reaction was diluted with H₂O (5 mL) and the pH was adjusted to 7 with 2 N HCl. The resulting white precipitate was collected by vacuum filtration, but the majority of the product remained in the aqueous phase. The solid and filtrate were combined and the solvent was removed by azeotropic distillation with CH₃CN on the rotary evaporator. The residue was dissolved/suspended in CH₂Cl₂ (25 mL), adsorbed onto Celite (3.0 g) and purified by flash chromatography (24 g SiO₂, MeOH/CH₂Cl₂ gradient) to give 4-(benzylmethylamino)-5-fluoropyrimidin-2-ol (0.016 g, 23%) as a white solid: mp 175-178° C.; ¹H NMR (300 MHz, CDCl₃) δ 12.72 (s, 1H), 7.42-7.14 (m, 6H), 4.88 (s, 2H), 3.20 (d, J=3.2, 3H); MS (ESI) m/z 235 (M+2)⁺, m/z 232 (M–H)⁻.

Preparation of 2-Benzyloxy-5-fluoro-pyrimidin-4-yl)-(3-trifluoromethyl-phenyl)-diazene (958)

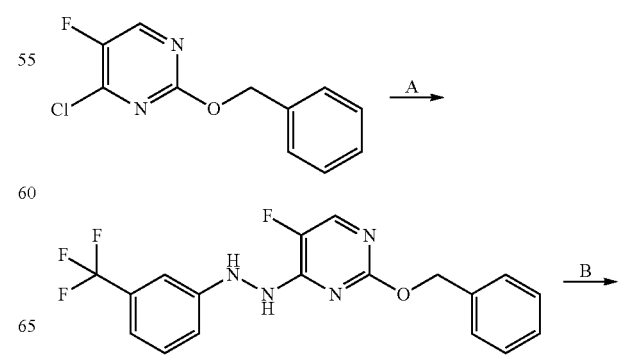

-continued

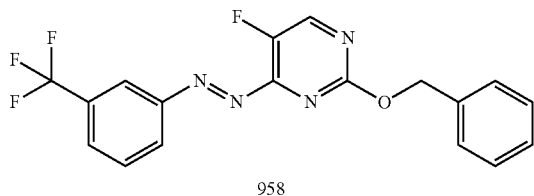

958

-continued

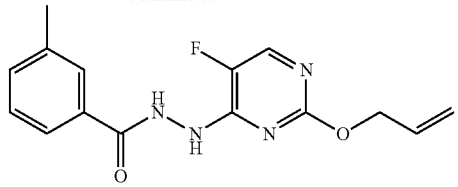

959

A) A 25 mL vial was charged with 2-(benzyloxy)-4-chloro-5-fluoropyrimidine (153 mg, 0.639 mmol), (3-(trifluoromethyl)phenyl)hydrazine (338 mg, 1.92 mmol), ethanol (8 mL), and triethylamine (140 µL, 1.00 mmol). The resulting yellow solution was heated at 50° C. on an orbital shaker for 16 h. The crude material was then diluted with Et$_2$O (100 mL) and washed with 1.0 M aqueous NaH$_2$PO$_4$ (50 mL) and then water (50 mL). The organic phase was dried over MgSO$_4$, filtered, and concentrated under reduced pressure. The crude material was purified by flash column chromatography (EtOAc/hexane gradient) to afford 2-(benzyloxy)-5-fluoro-4-(2-(3-(trifluoromethyl)phenyl)hydrazinyl)pyrimidine (186 mg, 77%) as a brown oil: $^1$H NMR (300 MHz, DMSO-d$_6$) δ 9.74 (bs, 1H), 8.38 (s, 1H), 8.07 (s, 1H), 7.36 (m, 1H), 7.26 (bs, 5H), 7.01 (m, 3H), 5.14 (s, 2H); MS (ESI) m/z 379 (M+H)$^+$, 377 (M−H)$^-$.

B) A 25 mL vial was charged with 2-(benzyloxy)-5-fluoro-4-(2-(3-(trifluoromethyl)phenyl)hydrazinyl)pyrimidine (140 mg, 0.371 mmol), methanol (4.6 mL), titanium(III) chloride (12% in HCl, 5.0 µL, 0.0047 mmol), hydrogen bromide (33% in acetic acid, 4.0 µL, 0.022 mmol), and 35% hydrogen peroxide (64 µL, 0.744 mmol).* The resulting dark brown, homogeneous solution was agitated on an orbital shaker for 16 h at room temperature, after which a crystalline red solid was found to have formed. This solid was collected in a fritted funnel and was rinsed with a minimal amount of methanol to afford the title compound (54.5 mg, 39%) as a crystalline red solid: mp 123-125° C.; $^1$H NMR (300 MHz, DMSO-d$_6$) δ 9.07 (s, 1H), 8.22-8.37 (m, 2H), 8.12 (d, J=7.8 Hz, 1H), 7.94 (t, J=7.8 Hz, 1H), 7.46-7.53 (m, 2H), 7.30-7.44 (m, 3H), 5.43 (s, 2H); MS (ESI) ink 377 (M+H)$^+$.

*Drug, E.; Gozin, M. J. Am. Chem. Soc. 2007, 129, 13784-13785.

Preparation of N'-(2-(allyloxy)-5-fluoropyrimidin-4-yl)-3-methylbenzohydrazide (959)

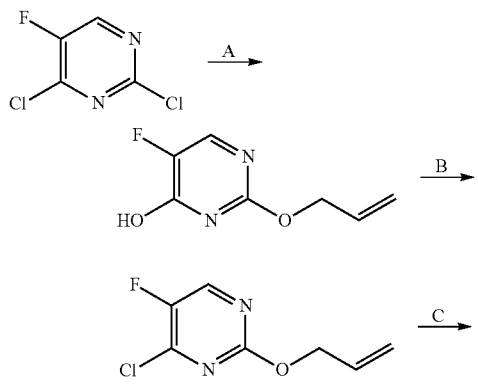

A) A 250 mL round bottom flask was charged with 2,4-dichloro-5-fluoropyrimidine (10.0 g, 59.9 mmol) and allyl alcohol (8.60 mL, 126 mmol). t-BuOK (1.0 M in t-BuOH, 132 mL, 132 mmol) was then added, and a significant exotherm was observed. The resulting mixture was allowed to stir at room temperature for 5 h. The crude reaction mixture was then diluted with EtOAc (300 mL) and washed with saturated aqueous NaCl solution (200 mL×2). The organic layer was dried over MgSO$_4$, filtered, and concentrated in a 500 mL round bottom flask. The crude mixture was diluted with ethanol (60 mL) and aqueous potassium hydroxide (2.0 M, 240 mL, 480 mmol), and the resulting biphasic mixture was heated at reflux for 18 h. After cooling to room temperature, the crude material was washed with Et$_2$O (200 mL×2) and then acidified with 2.0 M HCl (~215 mL) to obtain a turbid solution with a pH of 3. This mixture was then diluted with saturated aqueous NaCl solution (200 mL) and extracted with EtOAc (200 mL×2). The combined organic layers were dried over MgSO$_4$, filtered, and concentrated under reduced pressure to obtain 2-(allyloxy)-5-fluoropyrimidin-4-ol (6.47 g, 64%) as an off white solid: mp 138-141° C.; $^1$H NMR (300 MHz, DMSO-d$_6$) δ 13.00 (bs, 1H), 7.84 (d, J=3.7 Hz, 1H), 5.99 (m, 1H), 5.38 (m, 1H), 5.26 (m, 1H), 4.78 (m, 2H); MS (ESI) m/z 171 (M+H)$^+$, 169 (M−H)$^-$.

B) A 250 mL round bottom flask was charged with 2-(allyloxy)-5-fluoropyrimidin-4-ol 4.96 g, 29.2 mmol), N,N-dimethylaniline (5.45 mL, 43.0 mmol), phosphorous oxychloride (3.30 mL, 35.4 mmol), and acetonitrile (60 mL). The resulting solution was heated at 80° C. for 1 h. After cooling to room temperature, the crude material was diluted with Et$_2$O (300 mL) and was washed with 1.0 M aqueous NaH$_2$PO$_4$ (150 mL×2) and saturated aqueous NaCl (150 mL). The organic layers were dried over MgSO$_4$, filtered, and concentrated under reduced pressure to obtain 2-(allyloxy)-4-chloro-5-fluoropyrimidine contaminated with N,N-dimethylaniline (6.71 g, 72.5% pure, 89% calcd.) as a brown oil: $^1$H NMR (300 MHz, DMSO-d$_6$) δ 8.78 (bs, 1H), 6.04 (m, 1H), 5.38 (d, J=16.8 Hz, 1H), 5.26 (d, J=10.3 Hz, 1H), 4.82 (dd, J=0.8, 5.3 Hz, 2H); MS (EI) m/z 187 (M+H)$^+$.

C) A 25 mL vial was charged with 2-(allyloxy)-4-chloro-5-fluoropyrimidine (72.5% pure, 175 mg, 0.673 mmol), ethanol (4 mL), triethylamine (234 µL, 1.68 mmol), and hydrazine monohydrate (34 µL, 0.706 mmol). The resulting solution was then agitated on an orbital shaker at room temperature for 90 min. 3-Methylbenzoyl chloride (93 µL, 0.706 mmol) was then added, and the reaction was further agitated for 16 h. The crude reaction mixture was concentrated under reduced pressure, and then purified by flash column chromatography (EtOAc/hexane gradient) to afford the title compound (95.8 mg, 47%) as a pale yellow solid: mp 181-185° C.; $^1$H NMR (300 MHz, DMSO-d$_6$) δ 10.44 (bs, 1H), 9.75 (bs, 1H), 8.10 (d, J=3.5 Hz, 1H), 7.65-7.75 (m, 2H), 7.37-7.43 (m, 2H), 5.95 (m, 1H). 5.25 (m, 1H), 5.15 (m, 1H), 4.63 (m, 2H), 2.37 (s, 3H); MS (ESI) m/z 303 (M+H)$^+$, 301 (M−H)$^-$.

Preparation of (E)-5-Fluoro-4-(2-(4-methoxyben-zylidene)hydrazinyl)pyrimidin-2(1H)-one (960)

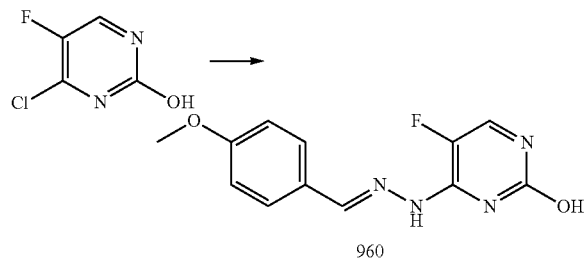

A 25 mL vial was charged with 4-chloro-5-fluoropyrimidin-2(1H)-one (149 mg, 1.00 mmol),* ethanol (4 mL), triethylamine (148 µL, 1.06 mmol), and hydrazine monohydrate (52 µL, 1.07 mmol). The resulting yellow solution was agitated on an orbital shaker at room temperature for 3 h. 4-Methoxybenzaldehyde (123 µL, 1.01 mmol) was added, and the reaction mixture was heated at 50° C. for 16 h. After cooling to room temperature, the crude material was concentrated under reduced pressure and purified by reverse phase flash column chromatography to afford the title compound (49.3 mg, 19%) as a yellow solid: mp 202-208° C.; $^1$H NMR (300 MHz, DMSO-$d_6$) δ 10.60 (bs, 1H), 10.14 (s, 1H), 8.35 (s, 1H), 7.97 (d, J=8.8 Hz, 2H), 7.38 (t, J=5.9 Hz, 1H), 6.97 (d, J=8.9 Hz, 2H), 3.80 (s, 3H); MS (ESI) ink 263 (M+H)$^+$, 261 (M−H)$^-$.

*Driscoll, J. S.; Marquez, V. E.; Plowman, J.; Liu, P. S.; Kelley, J. A.; Barchi, J. J. *J. Med. Chem.* 1991, 34, 3280-3284. Yamashita, J.; Yamawaki, I; Ueda, S.; Yasumoto, M.; Unemi, N.; Hashimoto, S. *Chem. Pharm. Bull.* 1982, 30, 4258-4267.

Preparation of N-(2-(Benzyloxy)-5-fluoropyrimidin-4-yl)formamide (961)

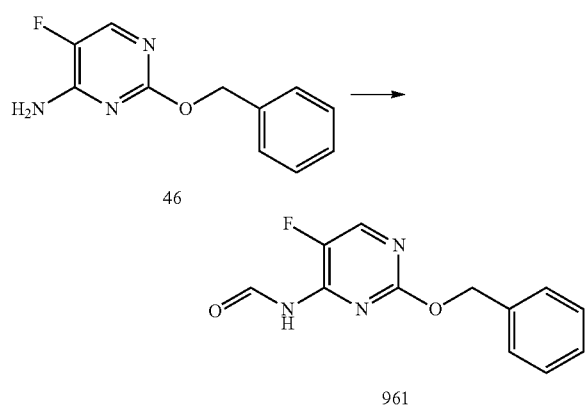

A 10 mL Schlenk-type flask was charged with acetic anhydride (4.0 mL, 42 mmol), formic acid (2.0 mL, 53 mmol), and CH$_2$Cl$_2$ (20 mL), and was cooled to 0° C. under nitrogen. N,N-Dimethylpyridin-4-amine (275 mg, 2.25 mmol) was added, and the resulting solution was allowed to stir at room temperature for 10 min. Solid 2-(benzyloxy)-5-fluoropyrimidin-4-amine (495 mg, 2.26 mmol) was added, and the reaction stirred for another 21 h at room temperature. The crude reaction mixture was diluted with CH$_2$Cl$_2$ (50 mL) and washed with water (50 mL), saturated aqueous NaHCO$_3$ (50 mL), and water (50 mL). The organic solution was dried over MgSO$_4$, filtered, and concentrated under reduced pressure. The crude material was then purified by flash column chromatography (EtOAc/hexane gradient) to afford the title compound (295.8 mg, 53%) as a white solid: mp 153-157° C.; $^1$H NMR (300 MHz, DMSO-$d_6$) δ 11.29 (bs, 1H), 9.34 (s, 1H), 8.48 (d, J=2.6 Hz, 1H), 7.29-7.46 (m, 5H), 5.32 (s, 2H); MS (ESI) m/z 248 (M+H)$^+$, 246 (M−H)$^-$.

Preparation of (4-amino-5-fluoropyrimidin-2-yloxy)methyl cyclopentanecarboxylate (962)

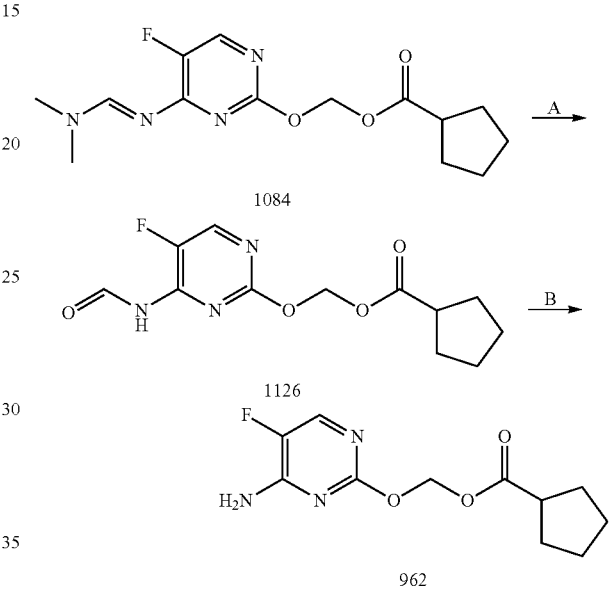

A) A 25 mL vial was charged with (E)-(4-((dimethylamino)methyleneamino)-5-fluoropyrimidin-2-yloxy)methyl cyclopentanecarboxylate (50.0 mg, 0.161 mmol), 1,4-dioxane (4 mL), and 1.0 M aqueous HCl (78 µL, 0.078 mmol) and was agitated on an orbital shaker for 5 h. The reaction was monitored by ultra performance liquid chromatography (UPLC) and determined to be incomplete, therefore an additional portion of 1.0 M aqueous HCl (78 µL, 0.078 mmol) was added. After 1 h, the reaction was quenched by the addition of 1.0 M aqueous NaHCO$_3$ (260 µL, 0.260 mmol) and concentrated under reduced pressure at 45° C. The dried residue was then extracted with EtOAc (5 mL×4), and concentrated to dryness under reduced pressure to obtain (5-fluoro-4-formamidopyrimidin-2-yloxy)methyl cyclopentanecarboxylate (43.5 mg, 95%) as a white solid: mp 76-79° C.; $^1$H NMR (300 MHz, DMSO-$d_6$) δ 11.38 (bs, 1H), 9.31 (d, J=5.7 Hz, 1H), 8.52 (d, J=2.6 Hz, 1H), 5.97 (s, 2H), 2.71-2.85 (m, 1H), 1.40-1.89 (m, 8H); MS (ESI) m/z 306 (M+Na)$^+$, 282 (M−H)$^-$.

B) A 25 mL vial was charged with (5-fluoro-4-formamidopyrimidin-2-yloxy)methyl cyclopentanecarboxylate (34.0 mg, 0.120 mmol), ethanol (1 mL), and hydrazine monohydrate (23.3 µL, 0.479 mmol). The resulting clear, colorless solution was then agitated on an orbital shaker at room temperature for 45 min. The crude reaction mixture was diluted with Et$_2$O (50 mL) and was washed with saturated aqueous NaCl solution (50 mL×2). The organic was dried over MgSO$_4$, filtered, and concentrated under reduced pressure to give the title compound (11.2 mg, 36%) as a white solid: mp 101-104° C.; $^1$H NMR (300 MHz, DMSO-$d_6$) δ 7.97 (d, J=3.4

Hz, 1H), 7.44 (bs, 1H), 5.86 (s, 2H), 2.69-2.83 (m, 1H), 1.42-1.91 (m, 8H); MS (ESI) m/z 256 (M+H)$^+$, 254 (M−H)$^−$.

Preparation of 2-Benzyloxy-5-fluoro-pyrimidin-4-yl-cyanamide (963)

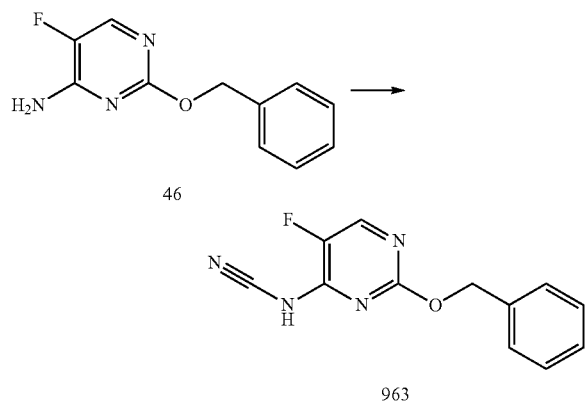

To a mixture of sodium hydride (0.65 g, 0.27 mol) in dry THF (10 mL), was added 2-benzyloxy-5-fluoro-pyrimidin-4-yl amine (2.0 g, 0.009 mol) dissolved in THF (15 mL) at room temperature under nitrogen. The mixture was allowed to stir at room temperature for 30 min and then cyanogen bromide (1.45 g, 0.0136 mol) in THF (10 ml) was added to the reaction mixture and allowed stir at room temperature for 16 h. The reaction was diluted with sat. sodium bicarbonate (2×5 mL) and extracted with EtOAc (3×40 mL). The organic phase was dried over Na$_2$SO$_4$, and concentrated to a give a crude solid which was recrystallized by adding minimum quantity of ethyl acetate and hexane until solution became turbid. The solvent was decanted and a gummy brown solid was obtained. The gummy brown solid was rinsed with Et$_2$O (2×10 mL) and allowed to stand in Et$_2$O while stirring for 1 h, until a free solid formed. The resulting solid was filtered and dried to give the title compound (1.7 g, 77%) as a pale brown solid: mp 150-152 dec.; $^1$H NMR (300 MHz, DMSO-d$_6$) δ 7.80 (bs, 1H), 7.43 (m, 5H), 5.20 (s, 2H); MS (EI) m/z 245 (M)$^+$.

Preparation of 1-[2-(Benzyloxy)-5-fluoropyrimidin-4-yl]-3-hydroxyguanidine (964)

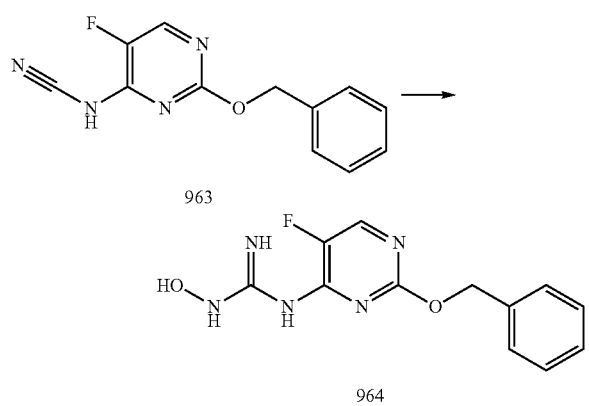

To a solution of 2-benzyloxy-5-fluoro-pyrimidin-4-yl-cyanamide (2.9 g, 0.012 mol) in n-butanol (30 mL) in a 100 mL sealed tube was added hydroxylamine hydrochloride (4.1 g, 0.059 mol) and the solution was heated at 110° C. for 2 h. The reaction was cooled and checked by TLC and was determined to be complete. The solvent was removed in vacuo and the resulting mixture was diluted with water and extracted with EtOAc (3×30 mL). The organic layers were dried over Na$_2$SO$_4$, filtered, and evaporated. The crude product was purified further with reverse phase chromatography to yield the title compound (500 mg, 15% yield) as an off white solid; mp 150-152 dec.; $^1$H NMR (300 MHz, DMSO-d$_6$) δ 8.72 (s, 2H), 8.44 (d, J=2.6 Hz, 1H), 7.41 (m, J=13.8, 6.3 Hz, 5H), 5.34 (s, 2H); MS (EI) m/z 278 (M)$^+$.

Biological Testing Protocols:

1. Evaluation of Fungicidal Activity: Leaf Blotch of Wheat (*Mycosphaerella graminicola*; Anamorph: *Septoria tritici*; Bayer Code SEPTTR):

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber) to permit spores to germinate and infect the leaf. The plants were then transferred to a greenhouse for disease to develop.

2. Evaluation of Fungicidal Activity: Leaf Spot of Sugar Beets (*Cercospora beticola*; Bayer Code CERCBE):

Sugar beets (variety HH-88) were grown in soil-less Metro mix in a greenhouse. The spores were harvested from moisturized infected leaf surface by washing whole leaves in water, and then filtered through two layers of cheesecloth. The young seedlings were inoculated with the spore suspension. The plants were kept in a dark dew room for 48 hrs, and then placed under a plastic hood in a greenhouse with a temperature of 26° C.

3. Evaluation of Fungicidal Activity: Leaf Spot of Peanut (*Mycosphaerella arachidis*; Bayer Code MYCOAR; Anamorph: *Cercospora arachidicola*):

Peanuts seedlings (variety Star) were grown in soil-less Metro mix. The spores were harvested from moisturized infected leaf surface by washing whole leaves in water, and then filtered through two layers of cheesecloth. The young seedlings were inoculated with the spore suspension. The plants were kept in a dark dew room for 48 hrs, and then placed under a plastic hood in a greenhouse with a temperature of 26° C.

4. Evaluation of Fungicidal Activity: Apple Scab (*Venturia inaequalis*; Bayer Code VENTIN):

Apple seedlings (McIntosh or Golden Delicious) were grown in Metro mix in a greenhouse. Fungal spores were collected from infected leaf tissue. Plants were inoculated with the spore suspension. Plants were placed in a dew room for 24 hours with 100% relative humidity and then transferred to a greenhouse with a temperature of 18° C. for disease to develop.

5. Evaluation of Fungicidal Activity: Black Sigatoka Disease of Banana (*Mycosphaerella fijiensis*; BAYER Code MYCOFI):

Efficacy against *Mycosphaerella fijiensis* was tested using newly emerged leaves of field grown banana plants. 20 ml of a diluted formulation of compound 1 of the required concentration were sprayed onto each test leaf over a delineated area of 20×20 cm. The leaves were subsequently allowed to become infected by natural inoculum, and were visually assessed for percent disease control ~40-45 days later.

6. Evaluation of Fungicidal Activity as a Seed Treatment: Leaf Blotch of Wheat (*Mycosphaerella graminicola*; Anamorph: *Septoria tritici*; Bayer Code SEPTTR)

Seeds of wheat variety Yuma were treated with 10% SC formulation of compound 15 (Table 1) at rates of 120, 40, 13.3, 4.44, 1.48, and 0 g ai/100 kg seeds. Seeds (10 seeds/pot) were planted in 1 inch pot containing 50% mineral soil/50% soil-less Metro mix. 8-day old seedlings were inoculated with an aqueous spore suspension of *Septoria tritici*, and 8 pots of plants were inoculated for each fungicide rate. After inoculation, plants were kept in 100% relative humidity (one day in a dark dew chamber followed by two days in a lighted mist room) to allow establishment of infection. The plants were then transferred to a greenhouse for disease to develop. When infection levels on untreated plants reached 95 to 100%, disease severities on treated plants were assessed. At the lowest test rate of 1.48 g ai/100 kg seeds, compound 15 (Table 1) provided nearly complete control of SEPTTR (Table V), indicating that aminopyrimidine fungicides can efficiently deliver SEPTTR efficacy via seed treatment.

The following tables present the activity of typical compounds of the present disclosure when evaluated in these experiments. The effectiveness of the test compounds in controlling disease was determined by assessing the severity of disease on treated plants, then converting the severity to percent control based on the level of disease on untreated, inoculated plants.

In each case of Tables I-V the rating scale is as follows:

| % Disease Control | Rating |
|---|---|
| 76-100 | A |
| 51-75 | B |
| 26-50 | C |
| 0-25 | D |
| Not Tested | E |

TABLE I

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|------|-----------|-------------------|---------------------|-------------------|---------------------|------------|------|------------------|------------------|------|
| 1 | *structure: 4-amino-5-fluoro-2-(4-fluorobenzyloxy)pyrimidine* | A | A | A | A | white solid | 130-132 | 238 | | 236 |
| 2 | *structure: 4-amino-5-fluoro-2-(3-bromobenzyloxy)pyrimidine* | A | A | A | A | off-white powder | 143-145 | | | 297, 298 |
| 3 | *structure: 3-amino-5-fluoro-2-(1-(4-fluorophenyl)ethoxy)pyrazine* | A | A | A | A | oil product | | | 250 | |
| 4 | *structure: 4-amino-5-fluoro-2-(phenyl methyl ketoxime-O-yl)pyrimidine* | A | A | A | A | off-white solid | 163-165 | 247 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SEPTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 5 | (2-thienylmethoxy)-5-fluoro-4-aminopyrimidine | A | A | A | A | White Solid | 90-92 | 226 | | |
| 6 | N-acetyl (2-thienylmethoxy)-5-fluoropyrimidin-4-amine | A | A | A | A | white solid | 134-136 | 268 | 266 | |
| 7 | 2-(4-fluorobenzyloxy)-5-fluoro-4-((4-methylpiperazin-1-yl)methylamino)pyrimidine | A | A | A | A | beige solid | 125-126 | 350 | 348 | |
| 8 | 2-(4-fluorobenzyloxy)-5-fluoro-4-(triethylsilylamino)pyrimidine | A | A | A | A | clear yellow oil | | 352 | 350 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 9 | 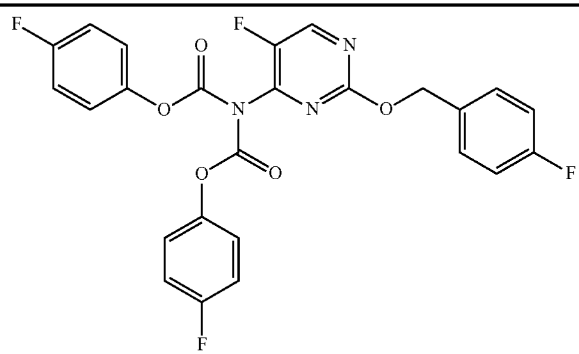 | A | A | A | A | white solid | 103-105 | 514 | | |
| 10 | 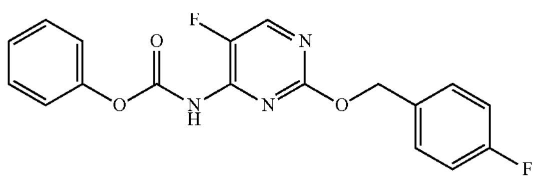 [SMILES: O=C(Nc1nc(OCc2ccc(F)cc2)ncc1F)Oc1ccccc1] | | A | A | A | white solid | 129-131 | 358 | 356 | |
| 11 | 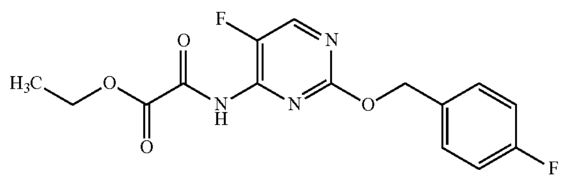 [SMILES: CCOC(=O)C(=O)Nc1nc(OCc2ccc(F)cc2)ncc1F] | A | A | A | A | clear oil | | 338 | 336 | |
| 12 | 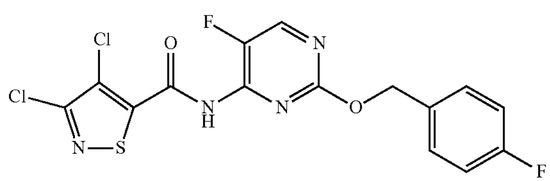 [SMILES: O=C(Nc1nc(OCc2ccc(F)cc2)ncc1F)c1snc(Cl)c1Cl] | A | A | A | A | tan solid | 87-90 | 417 | 415 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 13 | 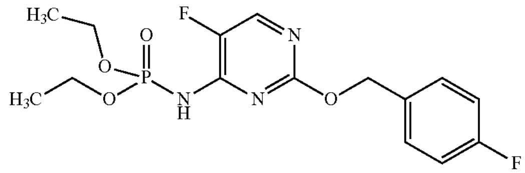 [SMILES: CCOP(=O)(Nc1nc(OCc2ccc(F)cc2)ncc1F)OCC] | D | D | C | B | white solid | 109-111 | 374 | 372 | |
| 14 | 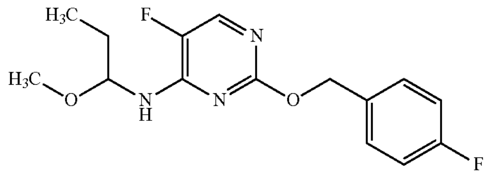 [SMILES: CCC(Nc1nc(OCc2ccc(F)cc2)ncc1F)OC] | A | A | A | A | clear colorless oil | | 310 | 308 | |
| 15 | 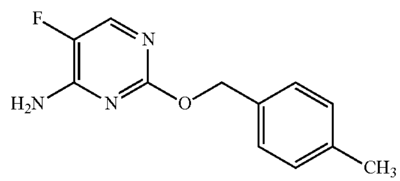 [SMILES: Cc1ccc(COc2ncc(F)c(N)n2)cc1] | A | A | A | A | White Solid | 135-137 | 234 | 232 | |
| 16 | 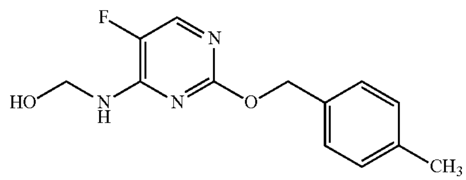 | A | A | A | A | white solid | 97-98 | 264 | 262 | |
| 17 | 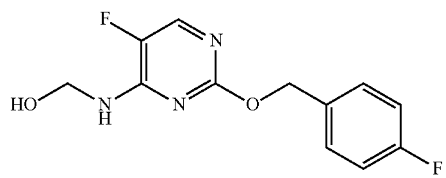 [SMILES: OCNc1nc(OCc2ccc(F)cc2)ncc1F] | A | A | A | A | white solid | 108-110 | 268 | 266 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 18 | 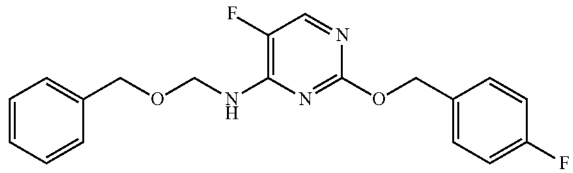 [SMILES: Fc1ccc(COc2ncc(F)c(NCOCc3ccccc3)n2)cc1] | B | B | B | A | white solid | 64-66 | 358 | 356 | |
| 19 | 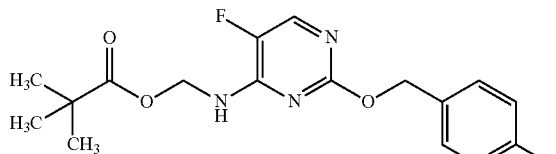 | B | A | A | A | white solid | 134-135 | 352 | | |
| 20 | 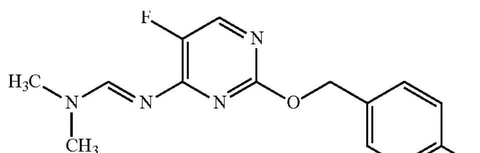 | A | A | A | A | white powder | 115-116 | 293 | | |
| 21 | 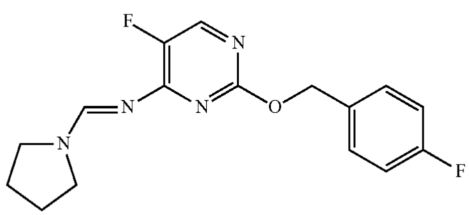 [SMILES: Fc1ccc(COc2ncc(F)c(/N=C/N3CCCC3)n2)cc1] | A | A | A | A | off white solid | 102-103 | 319 | | |
| 22 | 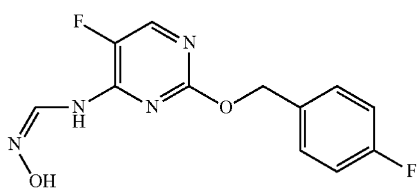 [SMILES: O/N=C\Nc1nc(OCc2ccc(F)cc2)ncc1F] | A | A | A | A | white solid | 169-171 | 281 | 279 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 23 | 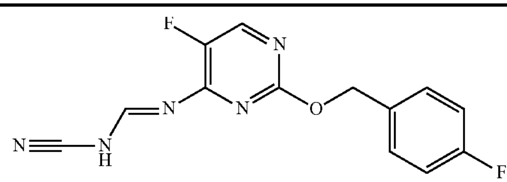 | A | A | A | A | off white solid | 148-149 | 290 | 288 | |
| 24 | 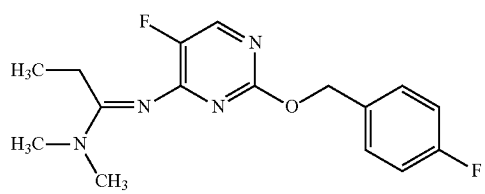 | A | A | A | A | clear yellow oil | | 321 | | |
| 25 | 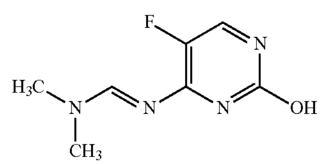 | A | A | A | A | tan solid | 240-243 | | 183 | |
| 26 | 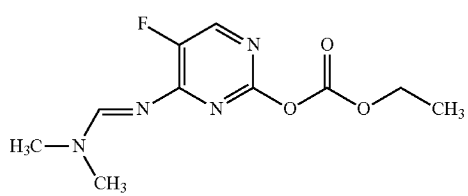 | A | A | A | A | white solid | 124-126 | 258 | | |
| 27 | 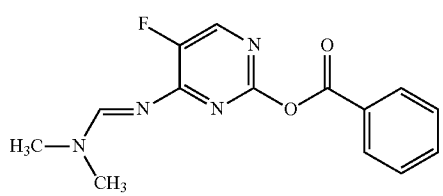 | A | A | A | A | white crystalline solid | 136-138 | 289 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 28 | 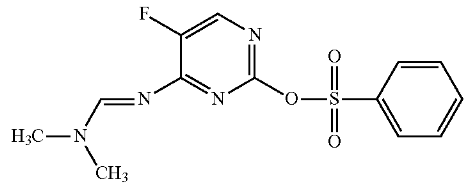 | A | A | A | A | white solid | 124-125 | 325 | | |
| 29 | 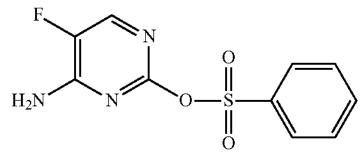 | B | A | A | A | white solid | 139-140 | 270 | 268 | |
| 30 | 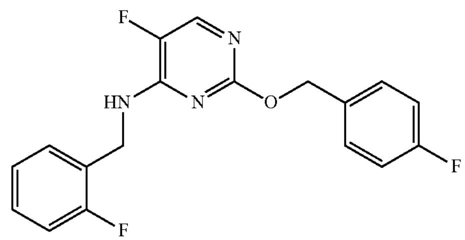 [SMILES: Fc1ccc(COc2ncc(F)c(NCc3ccccc3F)n2)cc1] | B | A | B | A | white solid | 88-90 | 346 | 344 | |
| 31 | 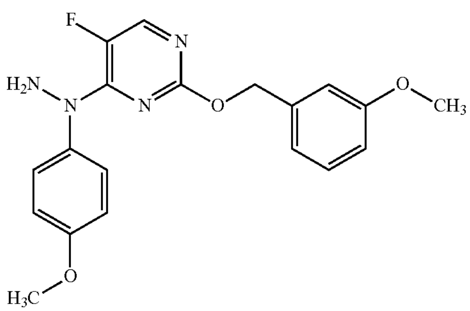 | D | D | D | D | off white solid | 121-123.5 | 371 | 354 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 32 | 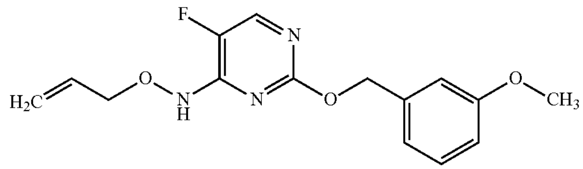 [SMILES: C=CCONc1nc(OCc2cccc(OC)c2)ncc1F] | D | A | C | A | colorless oil | | 306 | | 304 |
| 33 | 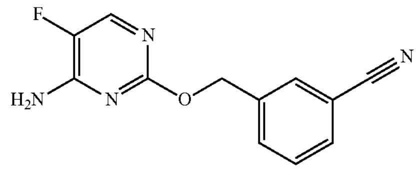 [SMILES: N#Cc1cccc(COc2ncc(F)c(N)n2)c1] | A | A | A | A | fluffy white solid | 184-186 | 243 | 245 | |
| 34 | 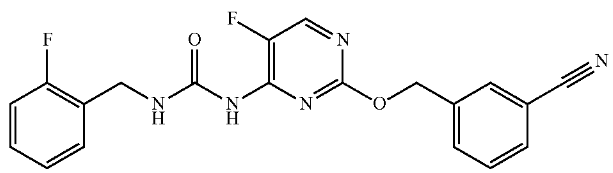 | D | D | D | D | white solid | 177-178 | 396 | 394 | |
| 35 | 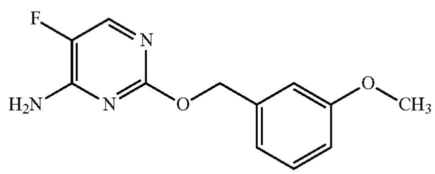 [SMILES: COc1cccc(COc2ncc(F)c(N)n2)c1] | A | A | A | A | yellow solid | 104-106 | 250 | 248 | |
| 36 | 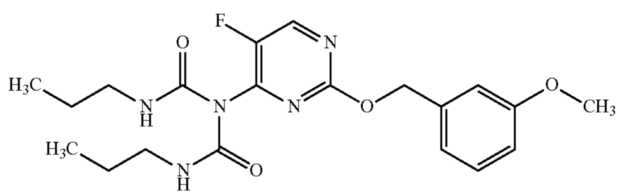 [SMILES: CCCNC(=O)N(C(=O)NCCC)c1nc(OCc2cccc(OC)c2)ncc1F] | B | A | C | A | tan solid | 75-78 | 420 | 418 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 37 | 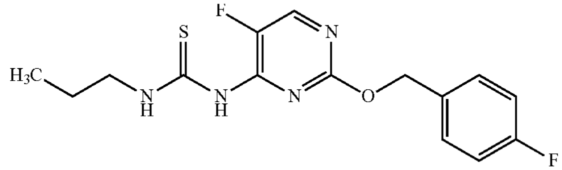 [SMILES: CCCNC(=S)Nc1nc(OCc2ccc(F)cc2)ncc1F] | A | A | A | A | white needles | 150-151 | 339 | 337 | |
| 38 | 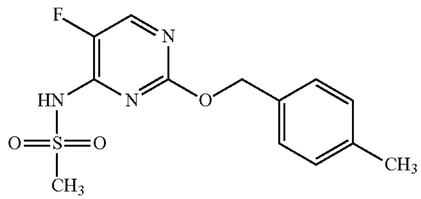 | D | C | C | C | White Solid | 145-148 | 312 | 310 | |
| 39 | 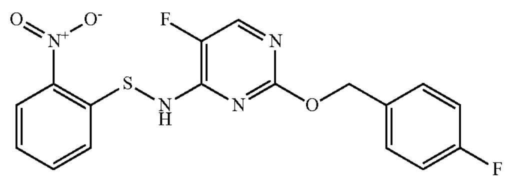 [SMILES: O=[N+]([O-])c1ccccc1SNc1nc(OCc2ccc(F)cc2)ncc1F] | D | D | A | A | yellow solid | 184 | 391 | 389 | |
| 40 | 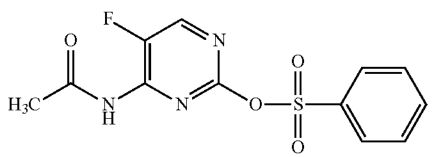 [SMILES: CC(=O)Nc1nc(OS(=O)(=O)c2ccccc2)ncc1F] | E | E | E | E | white solid | 142-143 | 312 | 310 | |
| 41 | 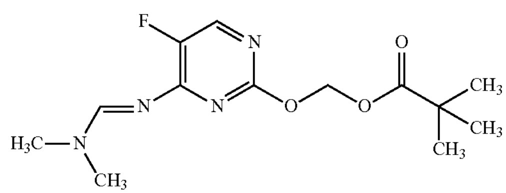 | E | E | E | E | white solid | 86-88 | 299 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 42 | 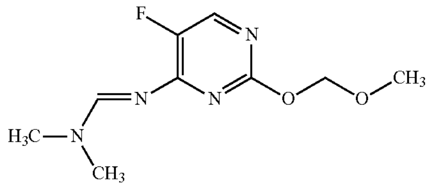 | E | E | E | E | colorless oil | | 229 | | |
| 43 | 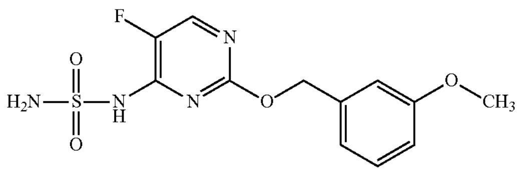 | B | B | C | B | yellow glassy solid | 126-130 | | 327 | |
| 44 | 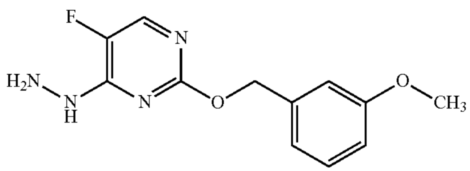 [SMILES: COc1cccc(COc2ncc(F)c(NN)n2)c1] | B | A | D | A | off white solid | 102-105 | 265 | 263 | |
| 45 | 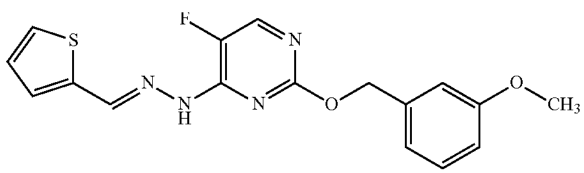 [SMILES: COc1cccc(COc2ncc(F)c(N/N=C/c3cccs3)n2)c1] | C | C | B | A | yellow solid | 136-139 | 359 | 357 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 46 | 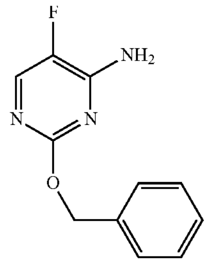 [SMILES: Nc1nc(OCc2ccccc2)ncc1F] | A | A | A | A | orange-white solid | | 220 | | 218 |
| 47 | 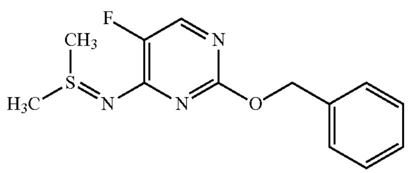 [SMILES: CS(C)=Nc1nc(OCc2ccccc2)ncc1F] | E | E | E | E | off white solid | 125-129 | 281 | | |
| 48 | 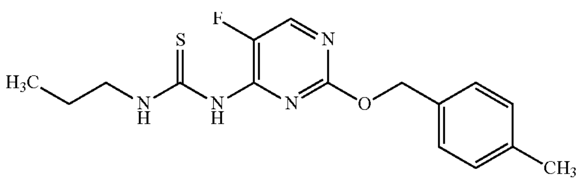 [SMILES: CCCNC(=S)Nc1nc(OCc2ccc(C)cc2)ncc1F] | A | A | A | A | off-white solid | 149-150 | 335 | 333 | |
| 49 | 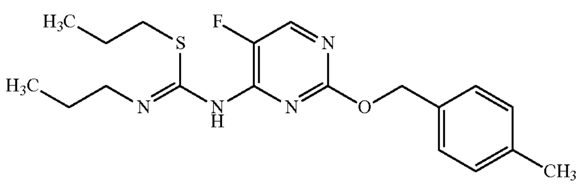 [SMILES: CCC/N=C(/Nc1nc(OCc2ccc(C)cc2)ncc1F)SCCC] | E | E | E | E | Pale yellow viscous liquid | | 377 | | |
| 50 | 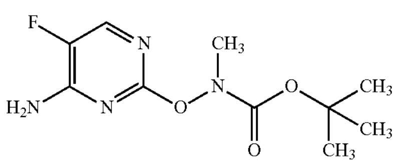 | C | A | C | A | pale yellow solid | 123-125 | 259 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 51 | 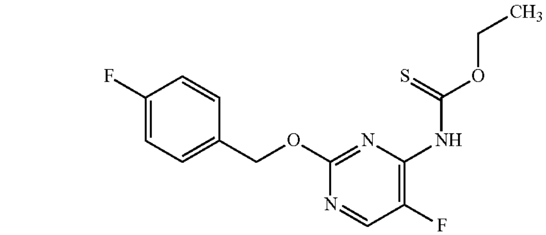 [SMILES: CCOC(=S)Nc1nc(OCc2ccc(F)cc2)ncc1F] | E | E | E | E | Pale yellow solid | | 326 | | |
| 52 | 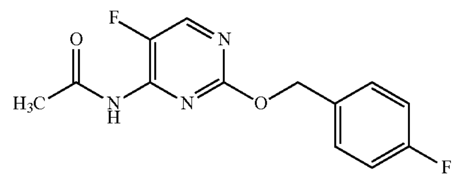 | B | B | A | A | white solid | 160-162 | 280 | 278 | |
| 53 | 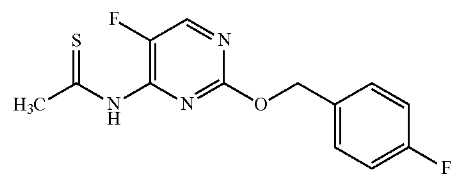 [SMILES: CC(=S)Nc1nc(OCc2ccc(F)cc2)ncc1F] | A | A | A | A | yellow glass | | | 294 | |
| 54 | 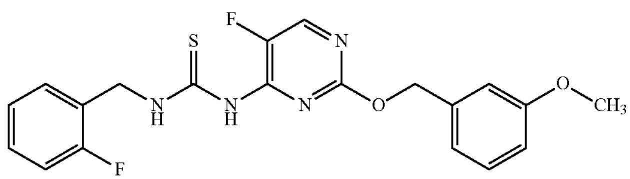 [SMILES: COc1cccc(COc2ncc(F)c(NC(=S)NCc3ccccc3F)n2)c1] | D | D | B | A | white solid | 118-121 | 417 | 415 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 55 | 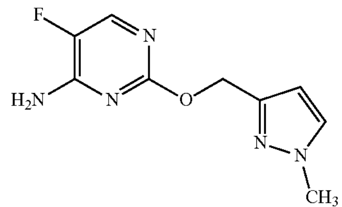 | A | A | A | A | white solid | 124 | 224 | | |
| 56 | 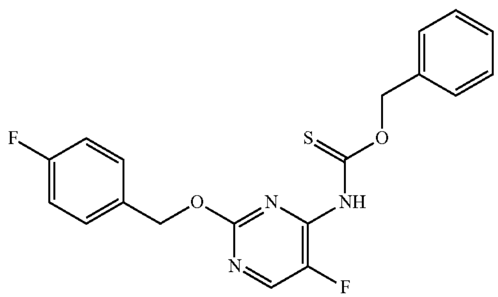 [SMILES: Fc1ccc(COc2ncc(F)c(NC(=S)OCc3ccccc3)n2)cc1] | E | E | E | E | Pale yellow solid | | 338 | | |
| 57 | 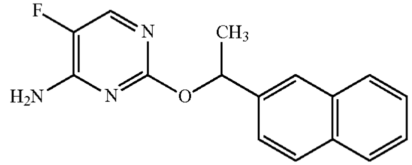 [SMILES: CC(Oc1ncc(F)c(N)n1)c1ccc2ccccc2c1] | A | A | A | A | white solid | 122-124 | | 282 | |
| 58 | 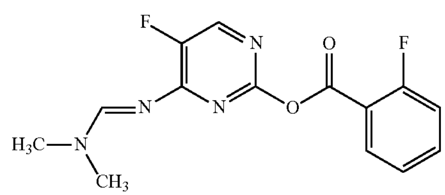 | A | A | A | A | white solid | 170 (dec) | 307 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 59 | 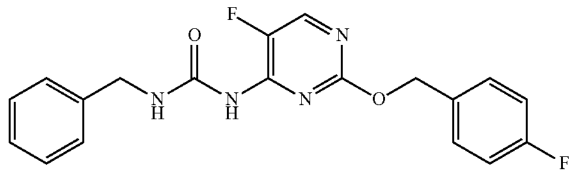 [SMILES: O=C(NCc1ccccc1)Nc1nc(OCc2ccc(F)cc2)ncc1F] | D | C | D | D | white solid | 190-191 | 371 | 369 | |
| 60 | 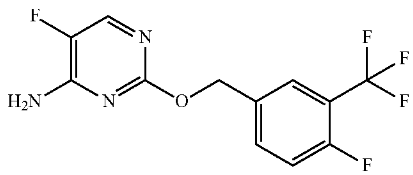 [SMILES: Nc1nc(OCc2ccc(F)c(C(F)(F)F)c2)ncc1F] | A | A | A | A | white solid | 143 | 306 | 304 | |
| 61 | 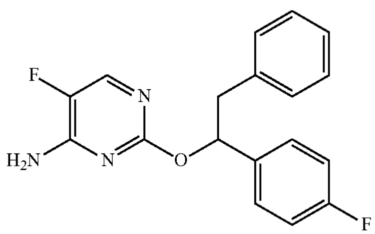 [SMILES: Nc1nc(OC(Cc2ccccc2)c2ccc(F)cc2)ncc1F] | D | D | A | A | white solid | 111-113 | | 326 | |
| 62 | 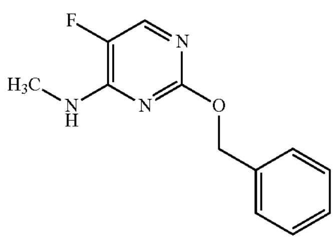 [SMILES: CNc1nc(OCc2ccccc2)ncc1F] | E | E | E | E | Off white solid | | 234 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 63 | 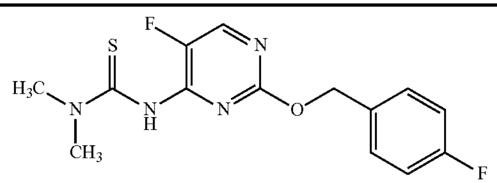 | E | E | E | E | yellow oil | | 325 | | |
| 64 | 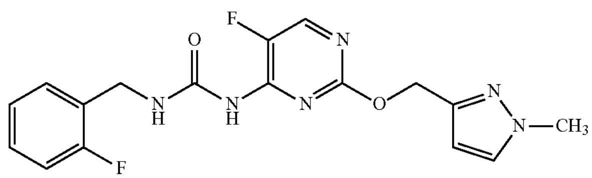 [SMILES: Cn1ccc(COc2ncc(F)c(NC(=O)NCc3ccccc3F)n2)n1] | D | C | D | D | white solid | 170-172 | 375 | 373 | |
| 65 | 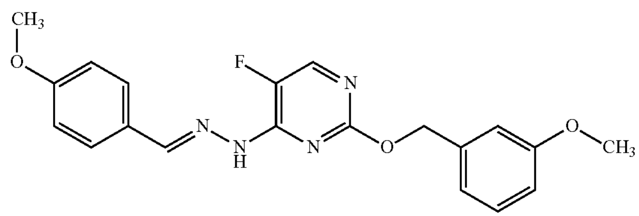 [SMILES: COc1ccc(/C=N/Nc2nc(OCc3cccc(OC)c3)ncc2F)cc1] | C | B | C | B | brown/orange solid | 60-64 | 383 | 381 | |
| 66 | 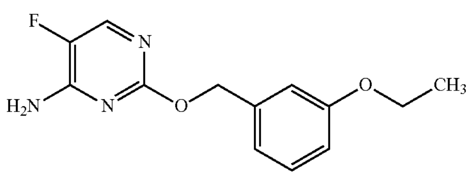 [SMILES: CCOc1cccc(COc2ncc(F)c(N)n2)c1] | A | A | A | A | yellow solid | 76-79 | 264 | 262 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 67 | 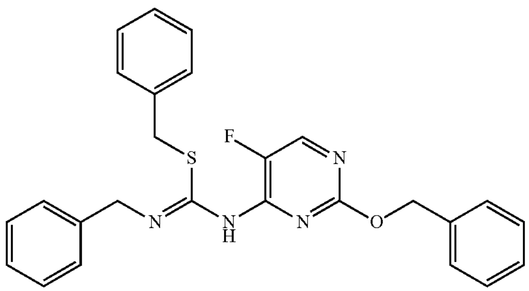 [SMILES: Fc1cnc(OCc2ccccc2)nc1N/C(=N/Cc1ccccc1)SCc1ccccc1] | E | E | E | E | Pale yellow solid | | 459 | | |
| 68 | 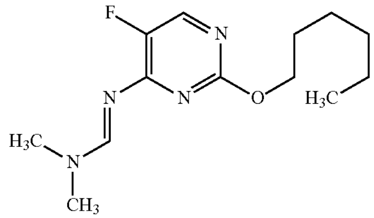 | D | B | D | B | WHITE SOLID | 128-130 | 269 | | |
| 69 | 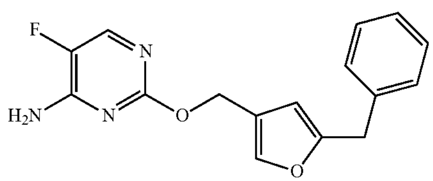 [SMILES: Nc1nc(OCc2coc(Cc3ccccc3)c2)ncc1F] | B | A | A | A | beige wax | | 300 | 298 | |
| 70 | 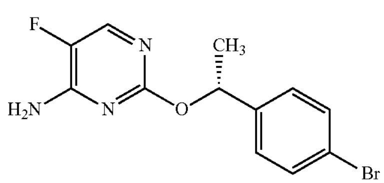 | C | A | C | A | white solid | 94-97 | | 312 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 71 | 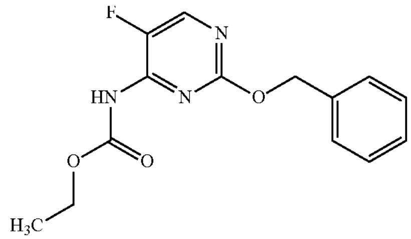 [SMILES: CCOC(=O)Nc1nc(OCc2ccccc2)ncc1F] | A | A | A | A | | | 292 | 290 | |
| 72 | 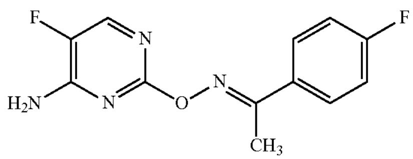 [SMILES: C/C(=N\Oc1ncc(F)c(N)n1)c1ccc(F)cc1] | A | A | A | A | beige solid | 155-156 | 265 | 263 | |
| 73 | 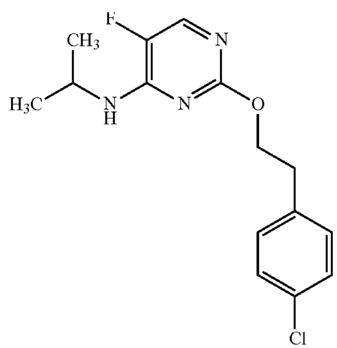 [SMILES: CC(C)Nc1nc(OCCc2ccc(Cl)cc2)ncc1F] | E | E | E | E | Gummy liquid | | 310 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 74 | 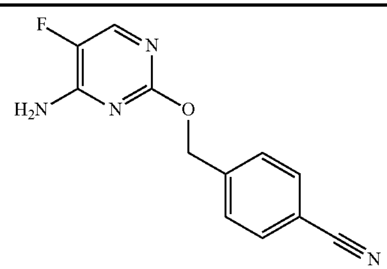 | D | D | B | A | white solid | | 245 | 243 | |
| 75 | 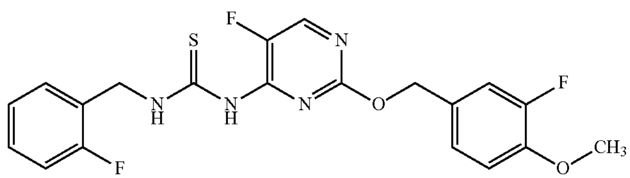 | A | A | C | A | off-white solid | 164-166 | 435 | 433 | |
| 76 | 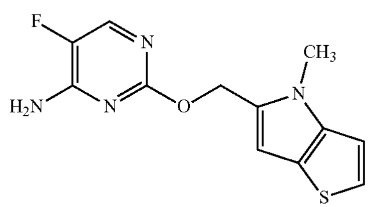 [SMILES: Cn1c(COc2ncc(F)c(N)n2)cc2sccc21] | C | C | C | C | black semi-solid | | | 277 | |
| 77 | 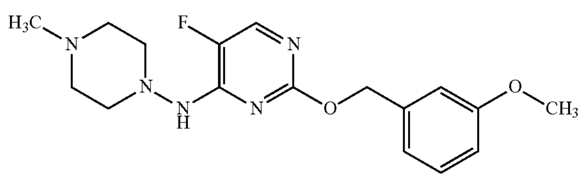 | C | A | D | A | colorless oil | | 348 | 346 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 78 | 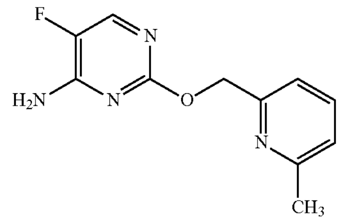 [SMILES: Cc1cccc(COc2ncc(F)c(N)n2)n1] | A | A | A | A | white solid | 125-127 | 234 | | |
| 79 | 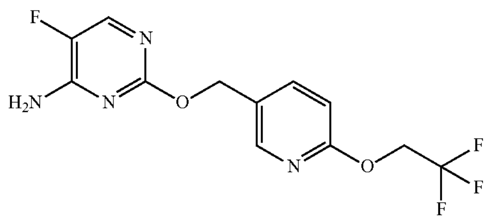 [SMILES: Nc1nc(OCc2ccc(OCC(F)(F)F)nc2)ncc1F] | A | A | A | A | white solid | 134-135 | 319 | | |
| 80 | 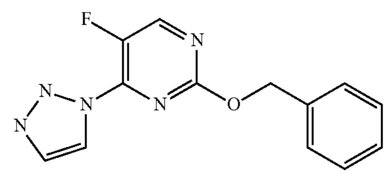 [SMILES: Fc1cnc(OCc2ccccc2)nc1N1C=CNN1] | D | B | D | D | white solid | 63-69* | 272 | | |
| 81 | 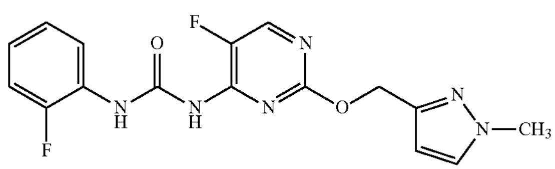 [SMILES: Cn1ccc(COc2ncc(F)c(NC(=O)Nc3ccccc3F)n2)n1] | D | D | D | D | off-white solid | 187-189 | 361 | 359 | |
| 82 | 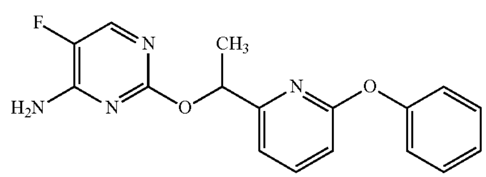 [SMILES: CC(Oc1ncc(F)c(N)n1)c1cccc(Oc2ccccc2)n1] | D | C | C | C | orange oil | | | 325 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 83 | 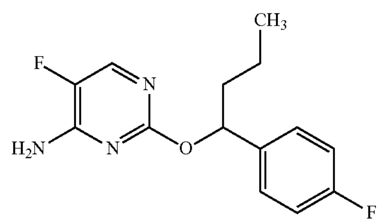 [SMILES: CCCC(Oc1ncc(F)c(N)n1)c1ccc(F)cc1] | A | A | A | A | clear oil | | | 278 | |
| 84 | 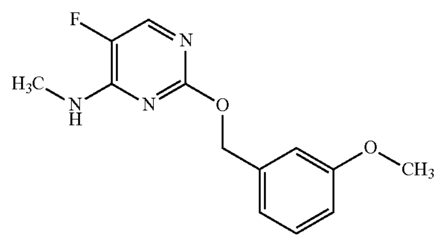 | E | E | E | E | Gummy liquid | | | 262 | |
| 85 | 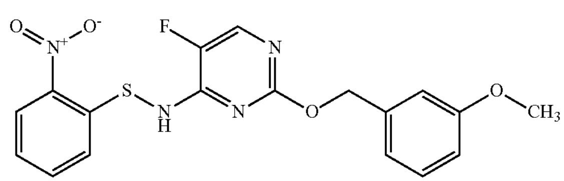 [SMILES: COc1cccc(COc2ncc(F)c(NSc3ccccc3[N+](=O)[O-])n2)c1] | A | A | C | A | yellow solid | 151-156 | 403 | 401 | |
| 86 | 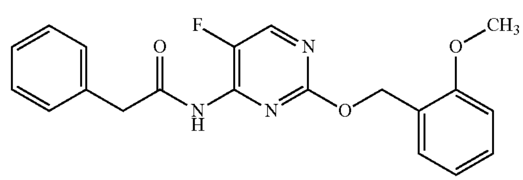 [SMILES: COc1ccccc1COc1ncc(F)c(NC(=O)Cc2ccccc2)n1] | D | D | C | B | white solid | | 368 | 366 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 87 | 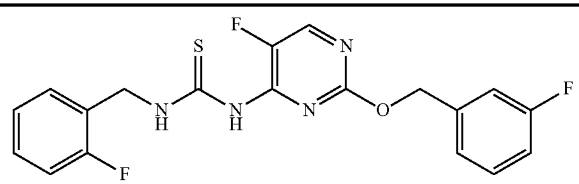 | D | A | B | A | yellow solid | 154-155 | 379 | 377 | |
| 88 | 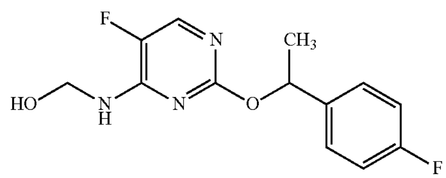 [SMILES: CC(Oc1ncc(F)c(NCO)n1)c1ccc(F)cc1] | C | A | C | A | clear colorless oil | | 282 | 280 | |
| 89 | 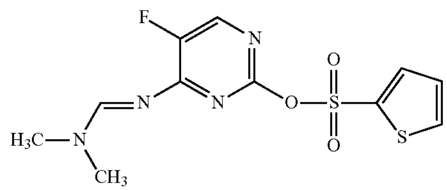 | A | A | A | A | tan solid | 129-130 | 331 | | |
| 90 | 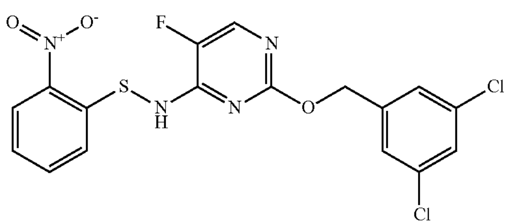 [SMILES: O=[N+]([O-])c1ccccc1SNc1nc(OCc2cc(Cl)cc(Cl)c2)ncc1F] | C | B | A | A | yellow solid | 180-187 | 441 | 439 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 91 | 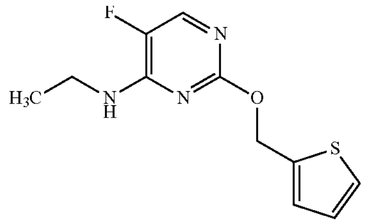 [SMILES: CCNc1nc(OCc2cccs2)ncc1F] | E | E | E | E | Gummy liquid | | 276 [M + Na] | | |
| 92 | 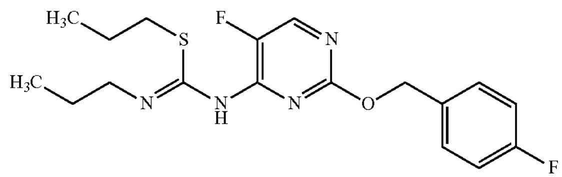 [SMILES: CCC/N=C(/Nc1nc(OCc2ccc(F)cc2)ncc1F)SCCC] | E | E | E | E | Off white solid | | 381 | | |
| 93 | 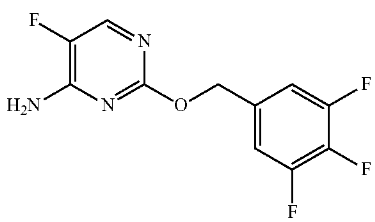 [SMILES: Nc1nc(OCc2cc(F)c(F)c(F)c2)ncc1F] | A | A | A | A | white solid | 122 | 274 | 272 | |
| 94 | 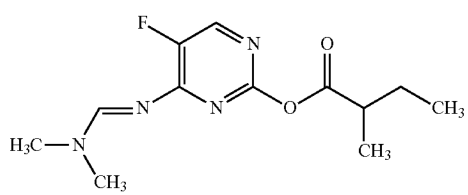 [SMILES: CCC(C)C(=O)Oc1ncc(F)c(/N=C/N(C)C)n1] | A | A | A | A | off white solid | 63-65 | 291 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 95 | 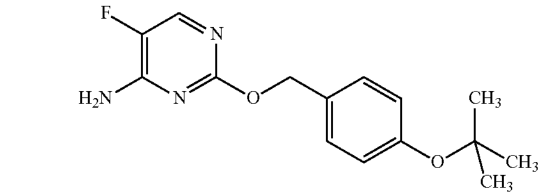 [SMILES: CC(C)(C)Oc1ccc(COc2ncc(F)c(N)n2)cc1] | A | A | A | A | yellow solid | 118-120 | 292 | — | |
| 96 | 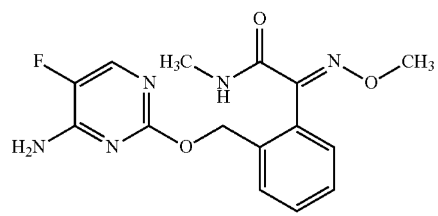 [SMILES: CNC(=O)/C(=N/OC)c1ccccc1COc1ncc(F)c(N)n1] | D | D | D | D | brown oil | | 334 | | |
| 97 | 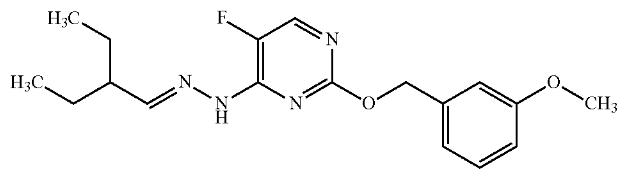 [SMILES: CCC(/C=N/Nc1nc(OCc2cccc(OC)c2)ncc1F)CC] | D | D | D | B | white solid | 104-107 | 348 | 345 | |
| 98 | 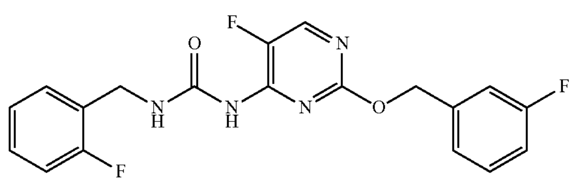 | D | D | D | D | white solid | 168-169 | 389 | 387 | |
| 99 | 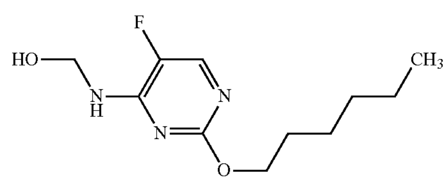 [SMILES: CCCCCCOc1ncc(F)c(NCO)n1] | D | B | D | A | white solid | 74-77 | 244 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 100 | 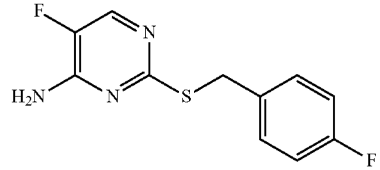 [SMILES: Nc1nc(SCc2ccc(F)cc2)ncc1F] | D | D | D | D | white solid | 163-164 | 254 | | 252 |
| 101 | 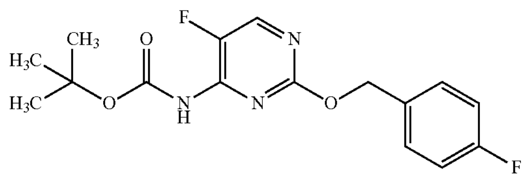 [SMILES: CC(C)(C)OC(=O)Nc1nc(OCc2ccc(F)cc2)ncc1F] | D | D | B | B | white solid | 127-129 | 338 | | |
| 102 | 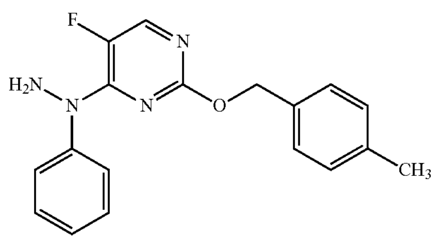 [SMILES: Cc1ccc(COc2ncc(F)c(N(N)c3ccccc3)n2)cc1] | D | C | D | D | dark brown solid | 118-122 | 325 | | |
| 103 | 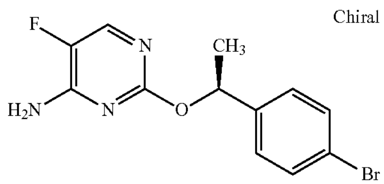 [SMILES: C[C@H](Oc1ncc(F)c(N)n1)c1ccc(Br)cc1] | B | A | A | A | yellow solid | 90-92 | | 312 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 104 | 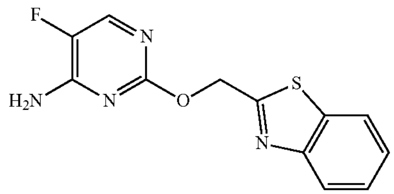 [SMILES: Nc1nc(OCc2nc3ccccc3s2)ncc1F] | A | A | A | A | yellow solid | 179-181 | 277 | | 275 |
| 105 | 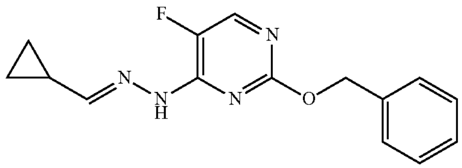 [SMILES: Fc1cnc(OCc2ccccc2)nc1N/N=C/C1CC1] | D | D | D | D | brown solid | 143-148 | 288 | 285 | |
| 106 | 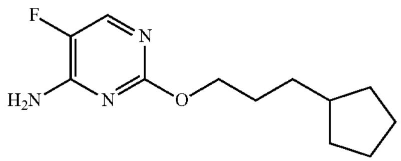 [SMILES: Nc1nc(OCCCC2CCCC2)ncc1F] | D | C | D | D | yellow clear oil | | 240 | 238 | |
| 107 | 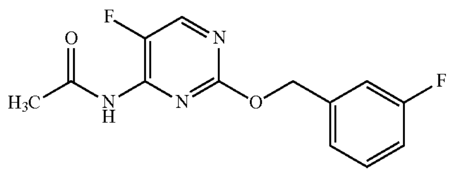 [SMILES: CC(=O)Nc1nc(OCc2cccc(F)c2)ncc1F] | A | A | A | A | white solid | | 280 | 278 | |
| 108 | 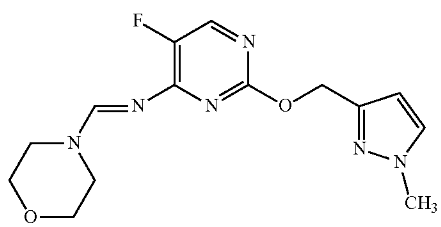 [SMILES: Cn1ccc(COc2ncc(F)c(/N=C/N3CCOCC3)n2)n1] | A | A | A | A | white solid | 123-124 | 321 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 109 | 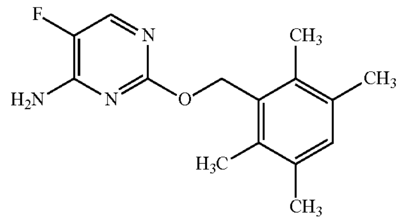 | E | E | E | E | white solid | 188-192 | 276 | 274 | |
| 110 | 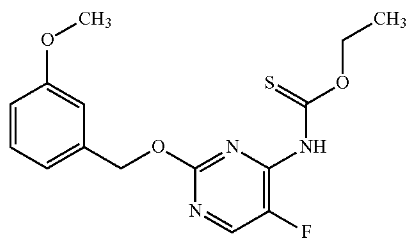 [SMILES: CCOC(=S)Nc1nc(OCc2cccc(OC)c2)ncc1F] | E | E | E | E | Pale yellow solid | | 338 | | |
| 111 | 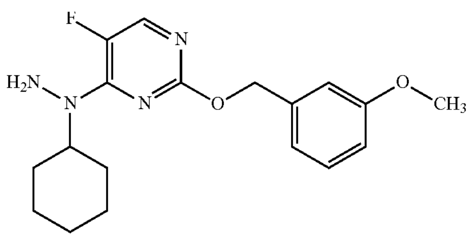 [SMILES: COc1cccc(COc2ncc(F)c(N(N)C3CCCCC3)n2)c1] | D | D | D | D | pale yellow oil | | 347 | | |
| 112 | 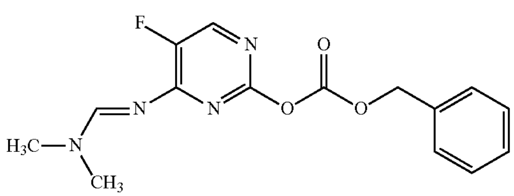 [SMILES: CN(C)/C=N/c1nc(OC(=O)OCc2ccccc2)ncc1F] | A | A | A | A | white solid | 128-131 | 340.8 (Na+) | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|------|-----------|-------------------|--------------------|--------------------|--------------------|------------|-----|------------------|------------------|------|
| 113 | 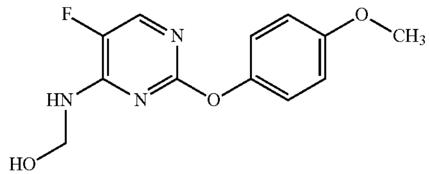 [SMILES: COc1ccc(Oc2ncc(F)c(NCO)n2)cc1] | D | C | B | A | pale yellow gummy solid | | 266 | | |
| 114 | 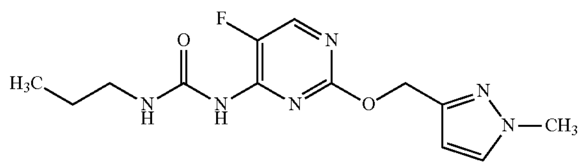 [SMILES: CCCNC(=O)Nc1nc(OCc2ccn(C)n2)ncc1F] | D | D | D | D | white solid | 133-135 | 389 | 307 | |
| 115 | 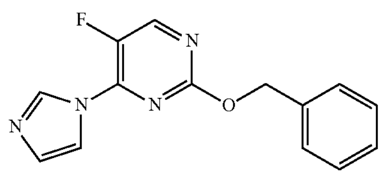 [SMILES: Fc1cnc(OCc2ccccc2)nc1-n1ccnc1] | A | A | A | A | yellow-white wax | | 271 | | |
| 116 | 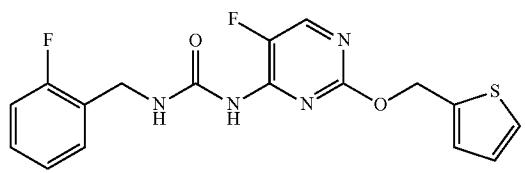 | D | D | D | D | white solid | 162-164 | 377 | 375 | |
| 117 | 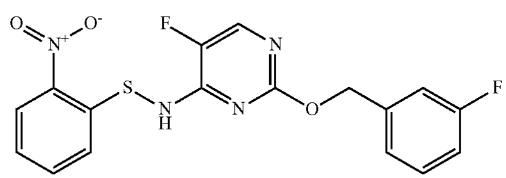 [SMILES: O=[N+]([O-])c1ccccc1SNc1nc(OCc2cccc(F)c2)ncc1F] | C | C | C | B | yellow solid | 173-178 | 391 | 389 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 118 | 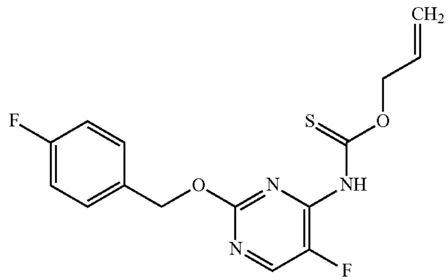 [SMILES: C=CCOC(=S)Nc1nc(OCc2ccc(F)cc2)ncc1F] | E | E | E | E | Off white solid | | 338 | | |
| 119 | 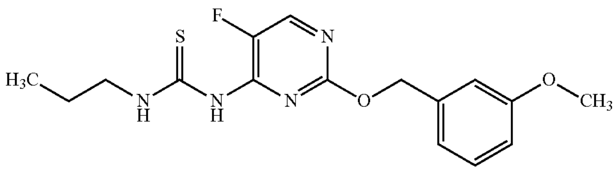 | B | A | C | A | white powder | 122-123 | 351 | 349 | |
| 120 | 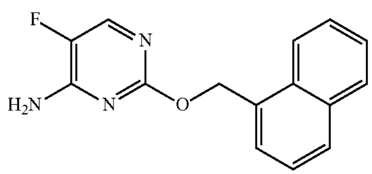 [SMILES: Nc1nc(OCc2cccc3ccccc23)ncc1F] | A | A | A | A | off-white solid | 173-174 | 270 | 268 | |
| 121 | 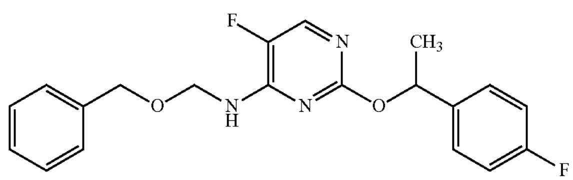 [SMILES: CC(Oc1ncc(F)c(NCOCc2ccccc2)n1)c1ccc(F)cc1] | B | A | B | A | clear pale yellow oil | | 372 | 370 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 122 | 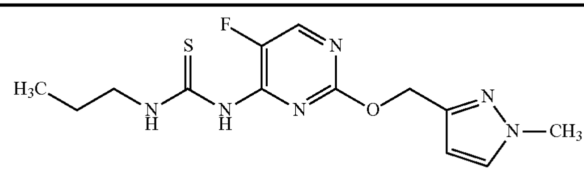 | C | A | D | B | white solid | 107-108 | 325 | | 323 |
| 123 | 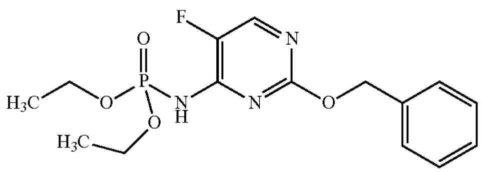 [SMILES: CCOP(=O)(Nc1nc(OCc2ccccc2)ncc1F)OCC] | C | A | D | C | clear yellow oil | | 356 | | 354 |
| 124 | 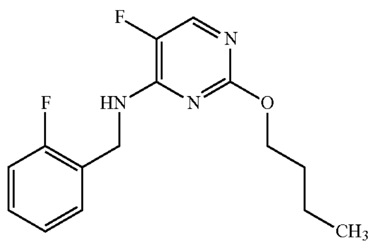 | E | E | E | E | Pale yellow liquid | | 294 | | |
| 125 | 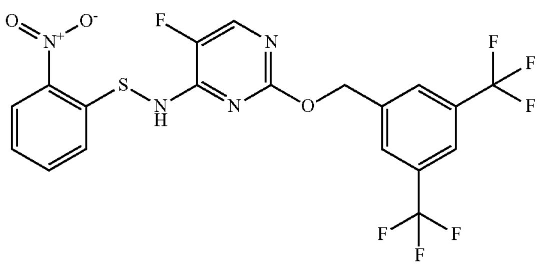 [SMILES: O=[N+]([O-])c1ccccc1SNc1nc(OCc2cc(C(F)(F)F)cc(C(F)(F)F)c2)ncc1F] | D | D | C | C | yellow solid | 175-180 | 509 | | 507 |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 126 | 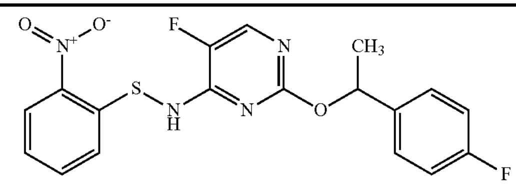 | A | A | A | A | brown oil | | 405 | 403 | |
| 127 | 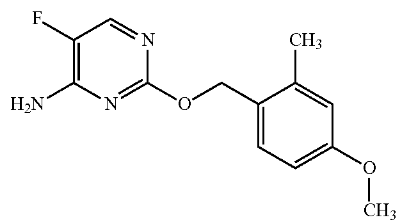 | A | A | A | A | white solid | 126 | 284 | 282 | |
| 128 | 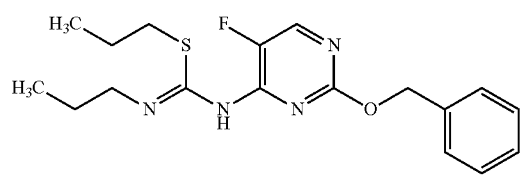 [SMILES: CCC/N=C(/Nc1nc(OCc2ccccc2)ncc1F)SCCC] | E | E | E | E | Off white solid | | 363 | | |
| 129 | 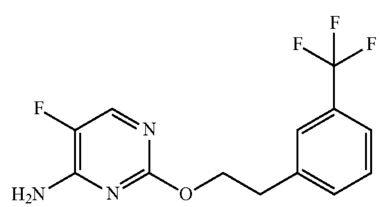 [SMILES: Nc1nc(OCCc2cccc(C(F)(F)F)c2)ncc1F] | A | A | C | A | white solid | 119-120 | 302 | 300 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 130 | 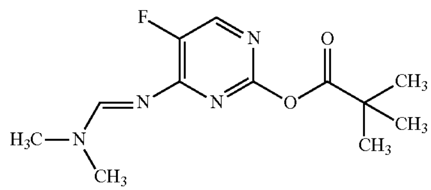 | A | A | A | A | white solid | 139-141 | 269 | | |
| 131 | 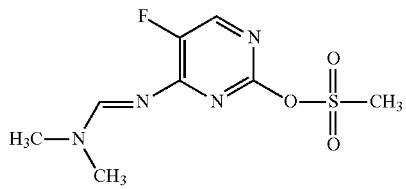 | C | A | C | B | white crystals | 133-134 | 263 | | |
| 132 | 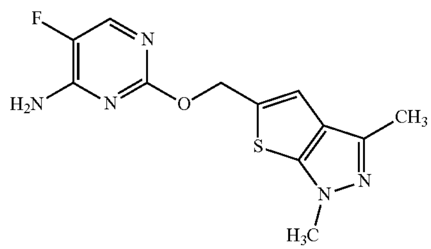 [SMILES: Cc1nn(C)c2sc(COc3ncc(F)c(N)n3)cc12] | A | A | A | A | beige solid | 171-173 | 316 (M + Na) | | |
| 133 | 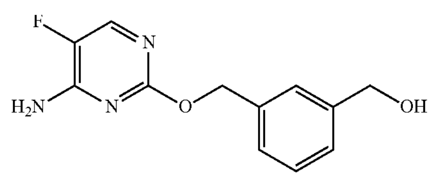 [SMILES: Nc1nc(OCc2cccc(CO)c2)ncc1F] | B | A | B | A | white solid | 120-123 | | 248 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 134 | 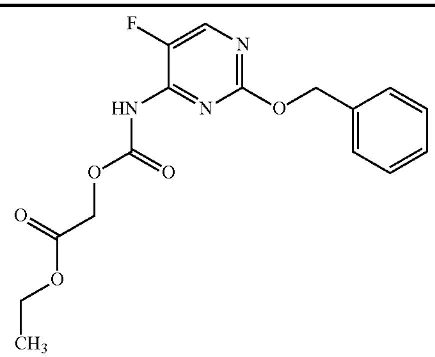 | B | A | D | B | | | 350 | 348 | |
| 135 | 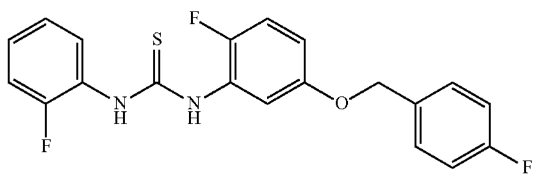 [SMILES: Fc1ccc(COc2ccc(F)c(NC(=S)Nc3ccccc3F)c2)cc1] | B | A | A | A | off-white solid | 144-146 | 391 | 389 | |
| 136 | 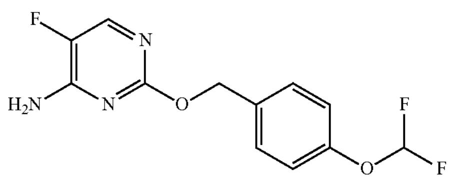 [SMILES: Nc1nc(OCc2ccc(OC(F)F)cc2)ncc1F] | A | A | A | A | off-white solid | 103-105 | 286 | 284 | |
| 137 | 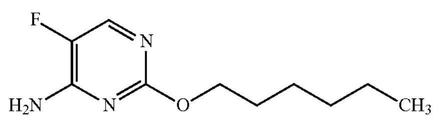 | C | A | C | A | white solid | 55-57 | 214 | 212 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 138 | 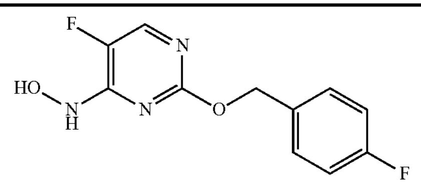 | A | A | A | A | off white solid | 111-116 | 254 | 252 | |
| 139 | 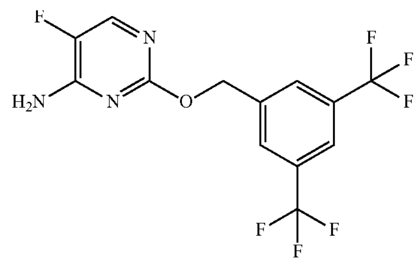 [SMILES: Nc1nc(OCc2cc(C(F)(F)F)cc(C(F)(F)F)c2)ncc1F] | D | C | C | B | white solid | 106 | 356 | 354 | |
| 140 | 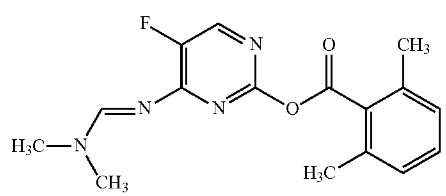 | A | A | A | A | white solid | 120-125 | 317 | | |
| 141 | 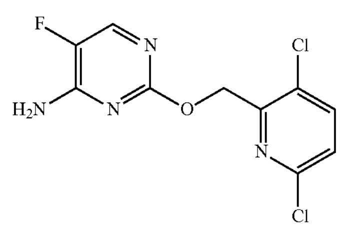 [SMILES: Nc1nc(OCc2nc(Cl)ccc2Cl)ncc1F] | B | C | D | A | beige solid | 175-176 | 290 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|------|-----------|---|---|---|---|---|---|---|---|---|
| 142 | 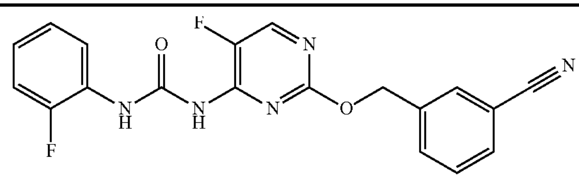 | D | D | D | D | off-white solid | 204-205 | 382 | 380 | |
| 143 | 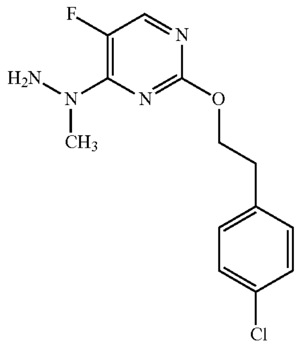 [SMILES: CN(N)c1nc(OCCc2ccc(Cl)cc2)ncc1F] | E | E | E | E | Off white solid | | 296 | | |
| 144 | 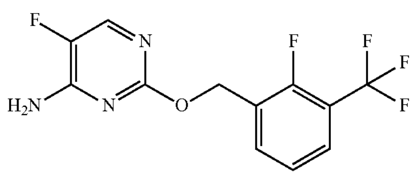 [SMILES: Nc1nc(OCc2cccc(C(F)(F)F)c2F)ncc1F] | A | A | A | A | white solid | 101 | 306 | 304 | |
| 145 | 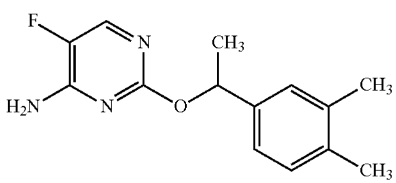 | A | A | A | A | clear oil | | | 260 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 146 | 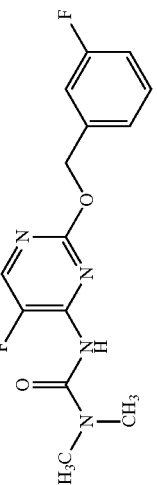 | A | A | A | A | white solid | | 295 | | |
| 147 | 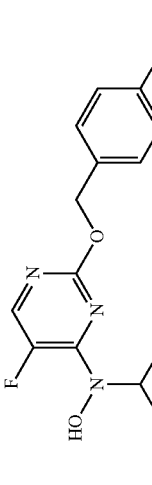 | C | C | D | B | off white solid | 146.8-149.4 | 297 | 294 | |
| 148 | 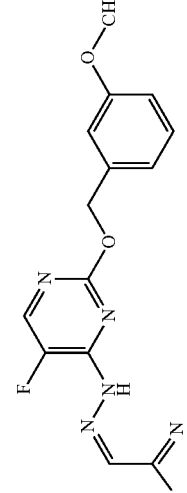 | D | D | B | B | yellow solid | 125-129 | 374 | 372 | |
| 149 | 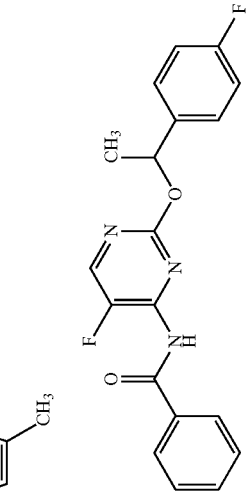 | D | B | C | A | yellow oil | | 356 | 354 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 150 | 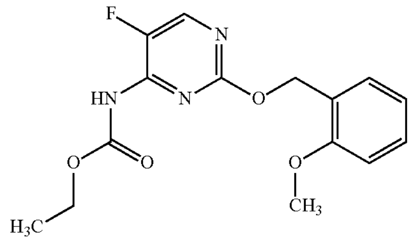 [SMILES: CCOC(=O)Nc1nc(OCc2ccccc2OC)ncc1F] | C | A | D | A | | | 322 | 320 | |
| 151 | 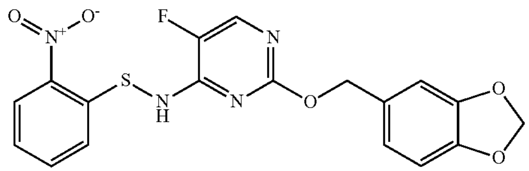 [SMILES: O=[N+]([O-])c1ccccc1SNc1nc(OCc2ccc3c(c2)OCO3)ncc1F] | C | C | D | D | yellow oil | | 417 | 415 | |
| 152 | 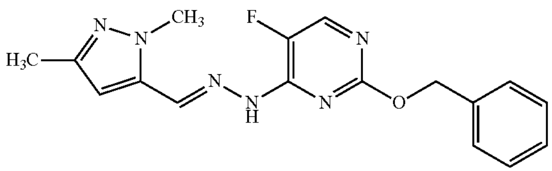 [SMILES: Cc1cc(/C=N/Nc2nc(OCc3ccccc3)ncc2F)n(C)n1] | C | A | C | A | white solid | 157-161 | 341 | 339 | |
| 153 | 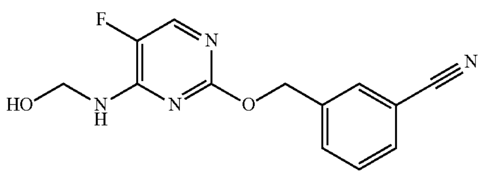 [SMILES: N#Cc1cccc(COc2ncc(F)c(NCO)n2)c1] | A | A | A | A | white solid | 144-145 | 275 | 273 | |
| 154 | 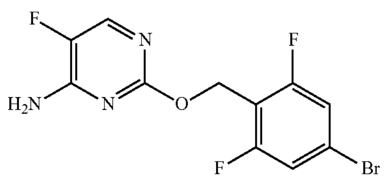 [SMILES: Nc1nc(OCc2c(F)cc(Br)cc2F)ncc1F] | A | A | A | A | white solid | 158 | 335 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 155 | 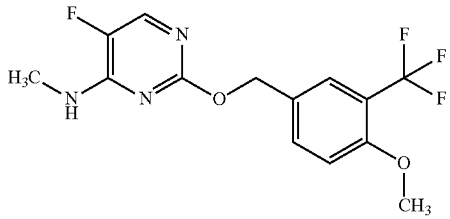 [SMILES: CNc1nc(OCc2ccc(OC)c(C(F)(F)F)c2)ncc1F] | A | A | B | A | white solid | 94-96 | | | 330 |
| 156 | 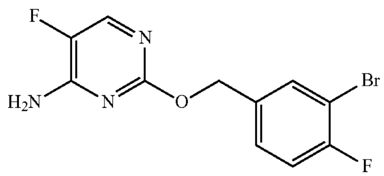 | A | A | A | A | white solid | 128-130 | 318 | 316 | |
| 157 | 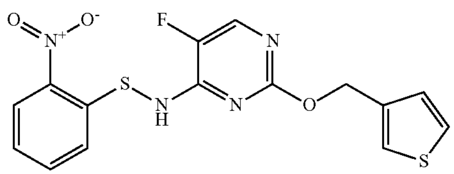 [SMILES: O=[N+]([O-])c1ccccc1SNc1nc(OCc2ccsc2)ncc1F] | C | C | C | A | yellow solid | 170-175 | 379 | 377 | |
| 158 | 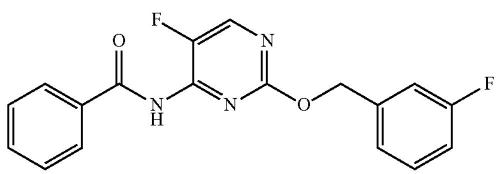 [SMILES: O=C(Nc1nc(OCc2cccc(F)c2)ncc1F)c1ccccc1] | A | A | A | A | white solid | 91-93 | 342 | 340 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 159 | 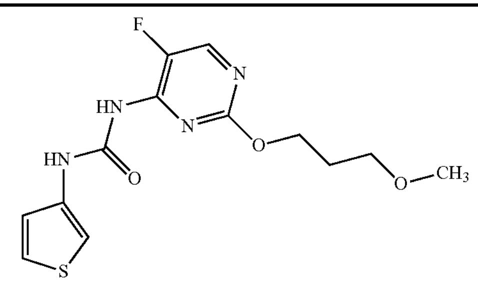 | C | D | D | D | off white solid | | 327 | | |
| 160 | 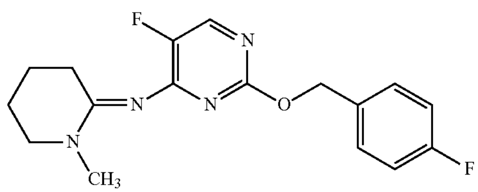 [SMILES: CN1CCCC/C1=N\c1nc(OCc2ccc(F)cc2)ncc1F] | A | A | A | A | clear yellow oil | | 333 | | |
| 161 | 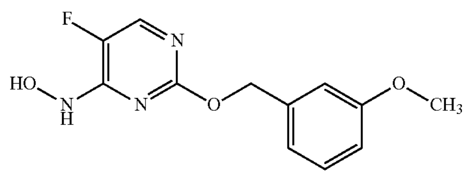 [SMILES: COc1cccc(COc2ncc(F)c(NO)n2)c1] | C | A | A | A | white solid | 121.5-125 | 267 | 264 | |
| 162 | 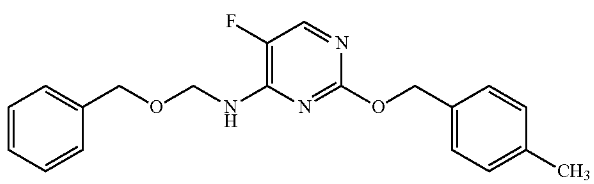 [SMILES: Cc1ccc(COc2ncc(F)c(NCOCc3ccccc3)n2)cc1] | D | D | C | A | white solid | 71-73 | 354 | 352 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 163 | 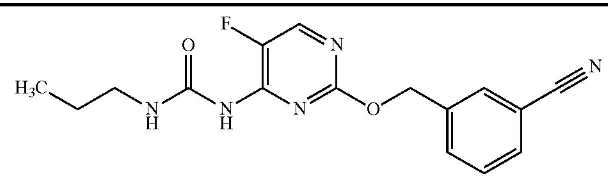 | D | D | D | D | off-white solid | 161-162 | 330 | 328 | |
| 164 | 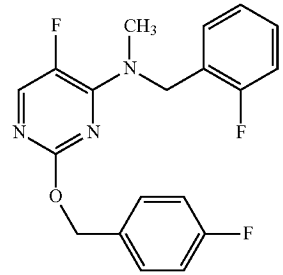 [SMILES: CN(Cc1ccccc1F)c1nc(OCc2ccc(F)cc2)ncc1F] | D | B | C | B | clear oil | | 360 | | |
| 165 | 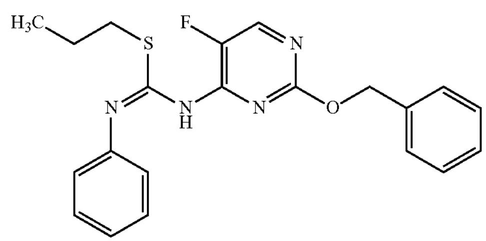 [SMILES: CCCS/C(=N/c1ccccc1)Nc1nc(OCc2ccccc2)ncc1F] | E | E | E | E | Off white solid | | 397 | | |
| 166 | 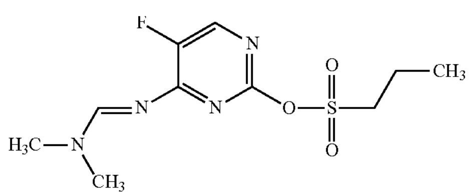 | A | A | A | A | brown semi-solid | | 391 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SEPTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 167 | 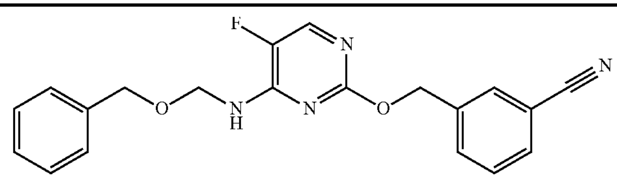 | D | D | D | C | white tacky solid | | 365 | 363 | |
| 168 | 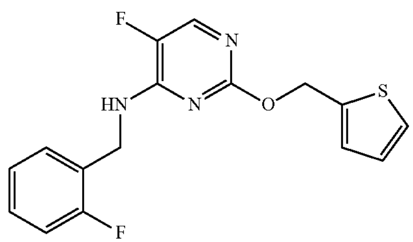 [SMILES: Fc1ccccc1CNc1nc(OCc2cccs2)ncc1F] | D | C | D | C | | | 334 | | |
| 169 | 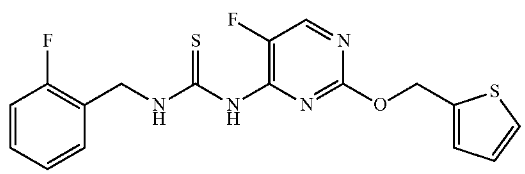 | D | D | B | A | off-white solid | 154-155 | 393 | 391 | |
| 170 | 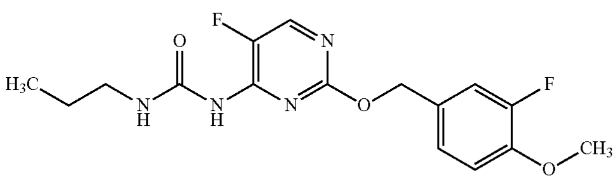 [SMILES: CCCNC(=O)Nc1nc(OCc2ccc(OC)c(F)c2)ncc1F] | D | D | D | D | off-white solid | 169-171 | 353 | 351 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 171 | 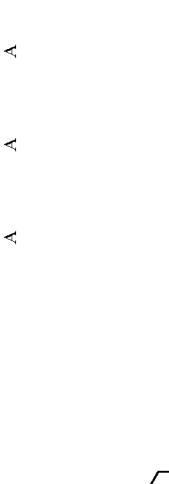 | A | A | A | A | off-white solid | 85-87 | 248 | | 246 |
| 172 | 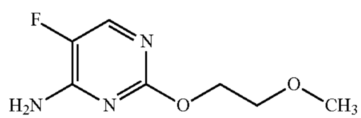 | D | D | D | D | white solid | 77-78 | 188 | | 186 |
| 173 | 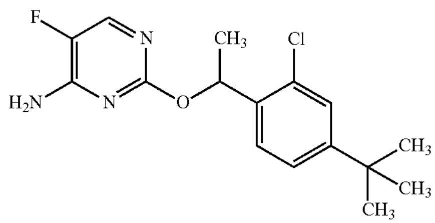 [SMILES: CC(Oc1ncc(F)c(N)n1)c1ccc(C(C)(C)C)cc1Cl] | D | B | B | A | white solid | 141-147 | | 322 | |
| 174 | 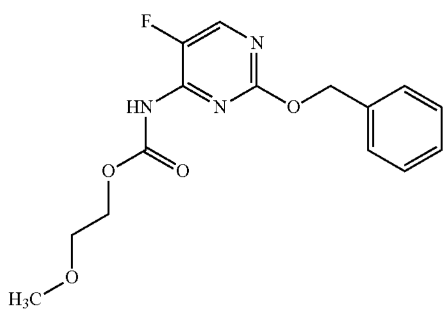 [SMILES: COCCOC(=O)Nc1nc(OCc2ccccc2)ncc1F] | A | A | A | A | | | 322 | | 320 |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 175 | 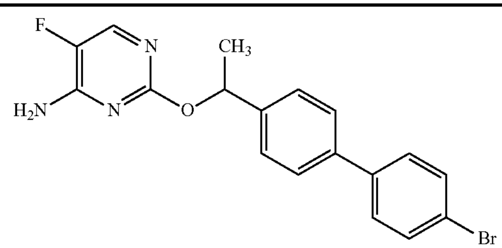 | D | D | A | A | yellow solid | 177-179 | | 388 | |
| 176 | 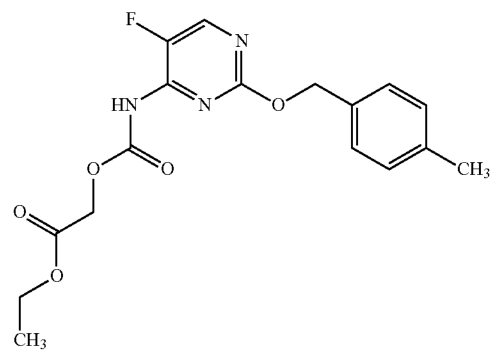 [SMILES: CCOC(=O)COC(=O)Nc1nc(OCc2ccc(C)cc2)ncc1F] | A | A | B | A | | | 362 | | |
| 177 | 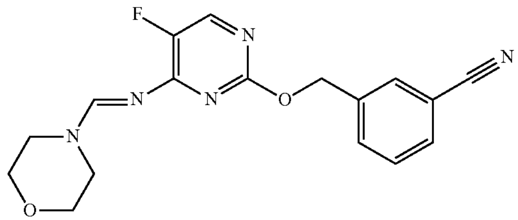 [SMILES: N#Cc1cccc(COc2ncc(F)c(/N=C/N3CCOCC3)n2)c1] | A | A | A | A | white solid | 119-120 | 342 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 178 | 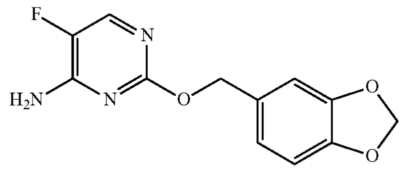 [SMILES: Nc1nc(OCc2ccc3c(c2)OCO3)ncc1F] | A | A | A | A | white solid | 153 | 264 | | 262 |
| 179 | 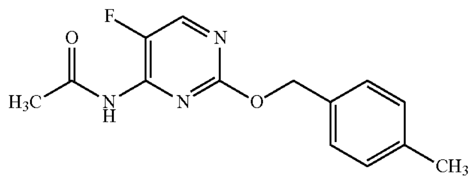 [SMILES: CC(=O)Nc1nc(OCc2ccc(C)cc2)ncc1F] | A | A | A | A | white solid | 155-156 | 276 | 274 | |
| 180 | 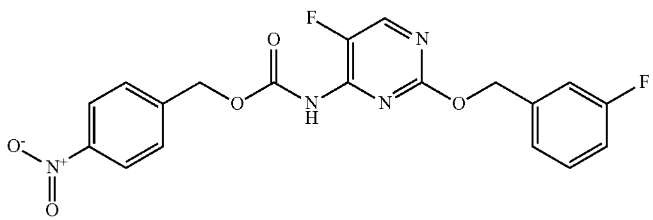 [SMILES: O=C(Nc1nc(OCc2cccc(F)c2)ncc1F)OCc1ccc([N+](=O)[O-])cc1] | D | D | D | B | white solid | 163-165 | 417 | 415 | |
| 181 | 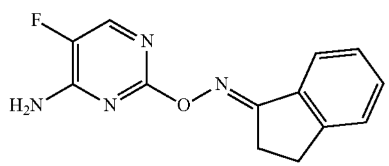 [SMILES: Nc1nc(O/N=C2\CCc3ccccc32)ncc1F] | A | A | A | A | white solid | 203-205 | 259 | 257 | |
| 182 | 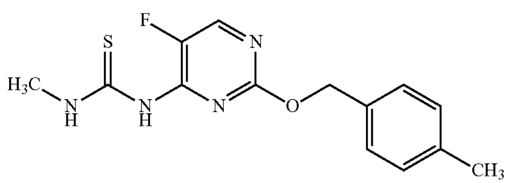 | A | A | A | A | white solid | 160-161 | 307 | 305 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 183 | 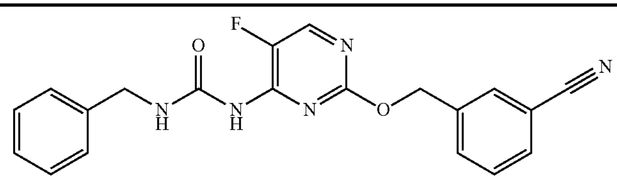 | D | D | D | D | white solid | 175-177 | 378 | 376 | |
| 184 | 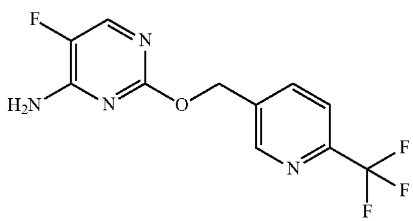 [SMILES: Nc1nc(OCc2ccc(C(F)(F)F)nc2)ncc1F] | B | A | A | A | white solid | 147-148 | 289 | | |
| 185 | 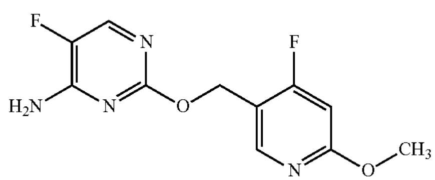 [SMILES: COc1cc(F)c(COc2ncc(F)c(N)n2)cn1] | A | A | A | A | pale yellow glass | | 268 | | |
| 186 | 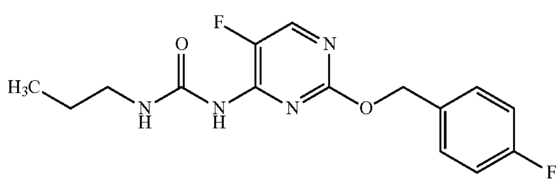 | D | D | B | B | fluffy white solid | 172-173 | 323 | 321 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 187 | 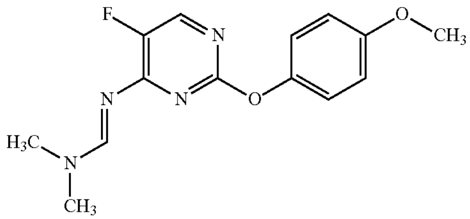 | D | B | D | D | light green solid | 90-92 | 291 | | |
| 188 | 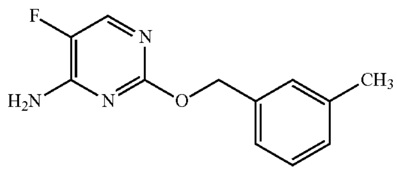 | A | A | A | A | white solid | 92-94 | 234 | 232 | |
| 189 | 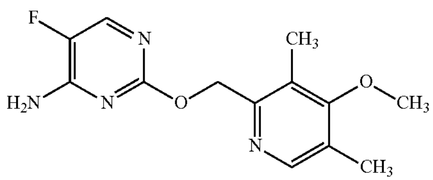 [SMILES: COc1c(C)cnc(COc2ncc(F)c(N)n2)c1C] | B | A | B | A | white solid | 163-164 | 279 | | |
| 190 | 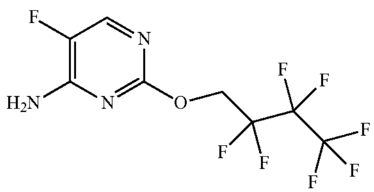 [SMILES: Nc1nc(OCC(F)(F)C(F)(F)C(F)(F)F)ncc1F] | D | D | D | D | white solid | 74-75 | 312 | 310 | |
| 191 | 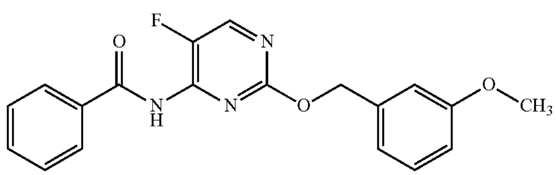 [SMILES: COc1cccc(COc2ncc(F)c(NC(=O)c3ccccc3)n2)c1] | A | A | A | A | viscous yellow oil | | 354 | 352 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 192 | Chiral; tetraacetyl glucopyranosyl-O-(4-amino-5-fluoropyrimidin-2-yl) | B | A | A | A | white solid foam | | | | |
| 193 | 4-amino-5-fluoro-2-(4-benzyloxybenzyloxy)pyrimidine | A | A | A | A | yellow solid | 120 | 326 | 324 | |
| 194 | 4-amino-5-fluoro-2-(2,4,6-trifluorobenzyloxy)pyrimidine | A | A | A | A | white solid | 154 | 274 | 272 | |
| 195 | 4-amino-5-fluoro-2-(4-butylbenzyloxy)pyrimidine | C | A | B | A | light yellow solid | 51-53 | 387 | 385 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 196 | 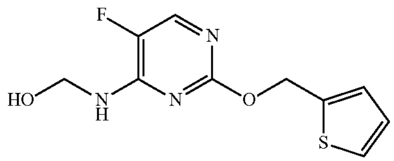 [SMILES: OCNc1nc(OCc2cccs2)ncc1F] | A | A | A | A | white solid | 93-95 | 256 | | 254 |
| 197 | 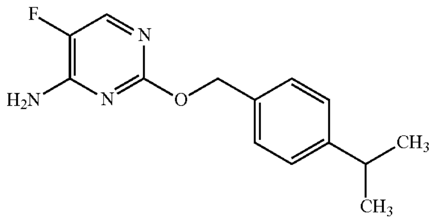 [SMILES: CC(C)c1ccc(COc2ncc(F)c(N)n2)cc1] | B | A | B | A | white solid | 65-66 | 262 | | 260 |
| 198 | 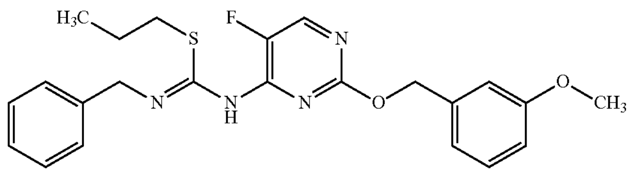 [SMILES: CCCS/C(=N\Cc1ccccc1)Nc1nc(OCc2cccc(OC)c2)ncc1F] | E | E | E | E | Pale yellow solid | | 441 | | |
| 199 | 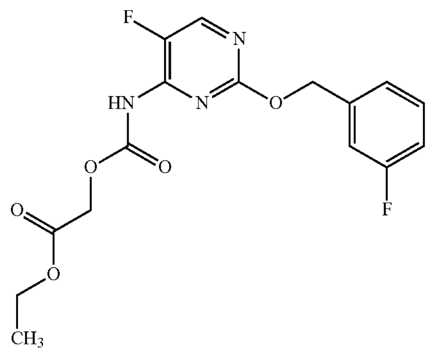 [SMILES: CCOC(=O)COC(=O)Nc1nc(OCc2cccc(F)c2)ncc1F] | B | A | D | A | | | 368 | | 366 |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 200 | 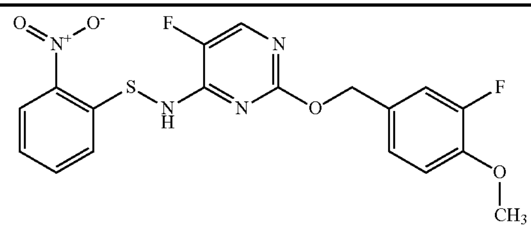 | D | D | D | C | yellow solid | 181-186 | 421 | 419 | |
| 201 | 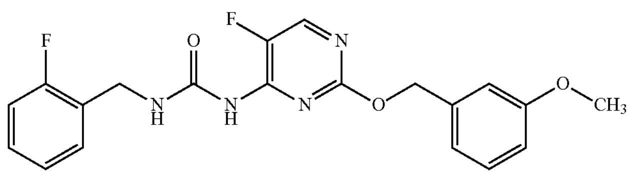 [SMILES: COc1cccc(COc2ncc(F)c(NC(=O)NCc3ccccc3F)n2)c1] | D | D | D | D | white solid | 161-162 | 401 | 399 | |
| 202 | 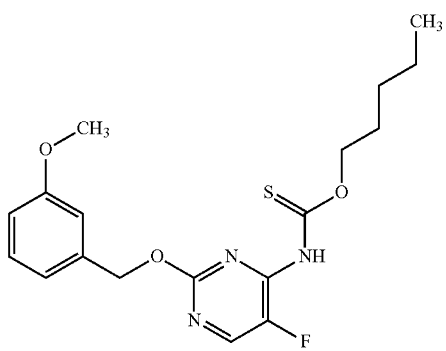 [SMILES: CCCCCOC(=S)Nc1nc(OCc2cccc(OC)c2)ncc1F] | E | E | E | E | Pale yellow solid | | 380 | | |
| 203 | 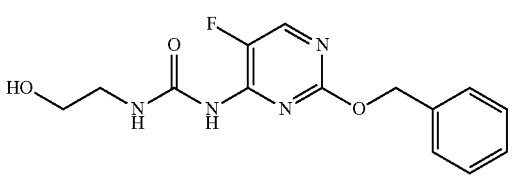 [SMILES: O=C(NCCO)Nc1nc(OCc2ccccc2)ncc1F] | D | B | D | D | white solid | 159-161 | — | 303 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 204 | 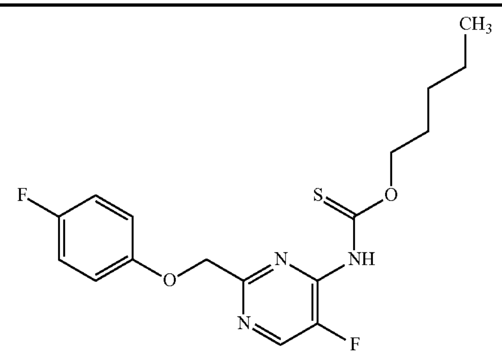 | E | E | E | E | Pale yellow solid | | 368 | | |
| 205 | 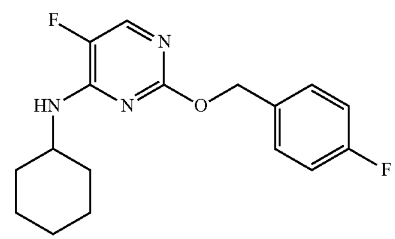 [SMILES: Fc1ccc(COc2ncc(F)c(NC3CCCCC3)n2)cc1] | D | B | D | D | pale yellow oil | | 321 | 318 | |
| 206 | 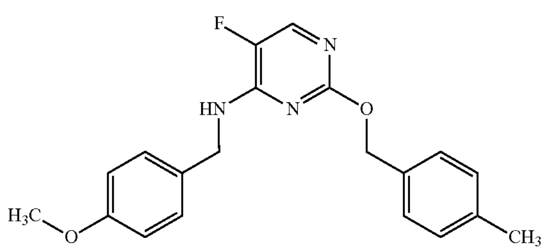 | E | E | E | E | Off white solid | | | 352 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 207 | 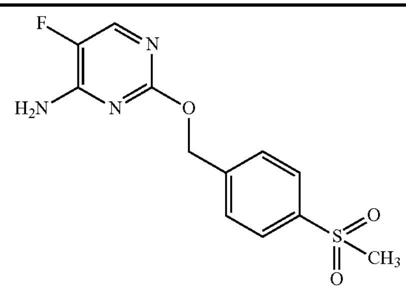 | D | D | D | C | tan solid | 142-147 | 298 | 296 | |
| 208 | 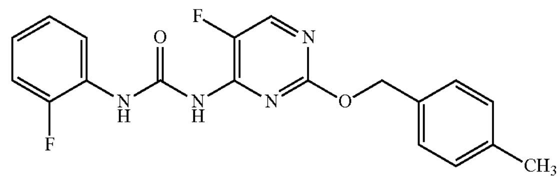 [SMILES: Cc1ccc(COc2ncc(F)c(NC(=O)Nc3ccccc3F)n2)cc1] | D | C | D | D | white solid | 196-198 | 371 | 369 | |
| 209 | 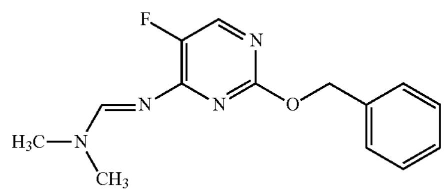 [SMILES: CN(C)/C=N/c1nc(OCc2ccccc2)ncc1F] | A | A | A | A | white solid | 84-85 | 275 | | |
| 210 | 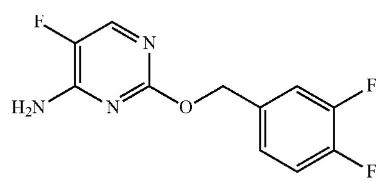 [SMILES: Nc1nc(OCc2ccc(F)c(F)c2)ncc1F] | A | A | A | A | white solid | 121-123 | 256 | 254 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 211 | 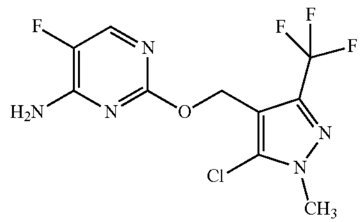 [SMILES: Cn1nc(C(F)(F)F)c(COc2ncc(F)c(N)n2)c1Cl] | A | A | A | A | off-white solid | 173-174 | 326 | 324 | |
| 212 | 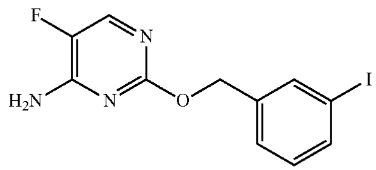 [SMILES: Nc1nc(OCc2cccc(I)c2)ncc1F] | A | A | A | A | off-white solid | 122-124 | 346 | 344 | |
| 213 | 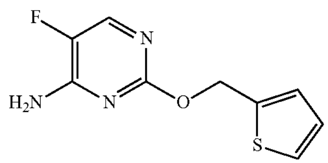 | A | A | A | A | White Solid | 90-92 | 226 | | |
| 214 | 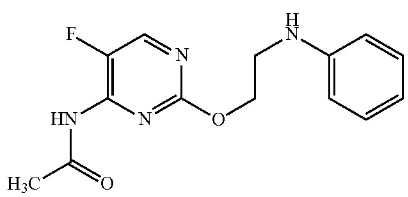 [SMILES: CC(=O)Nc1nc(OCCNc2ccccc2)ncc1F] | D | D | D | D | white solid | 110-113 | 291 | | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 215 | 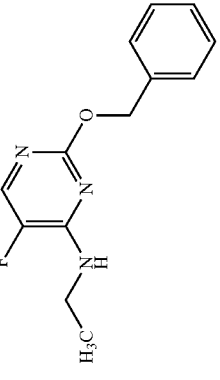 | E | E | E | E | Off white solid | | 248 | | |
| 216 | 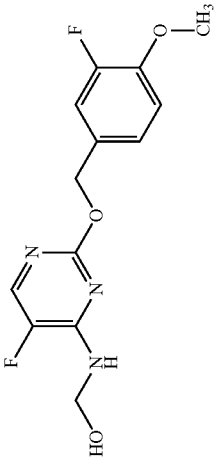 | B | A | A | A | white solid | 108-112 | 298 | 296 | |
| 217 | 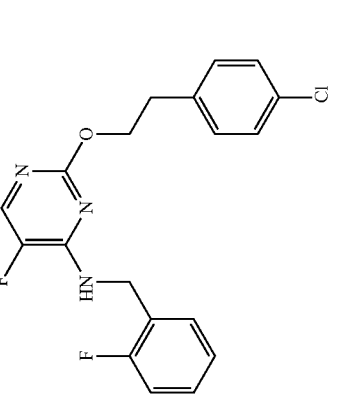 | E | E | E | E | Pale yellow liquid | | 376 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 218 | 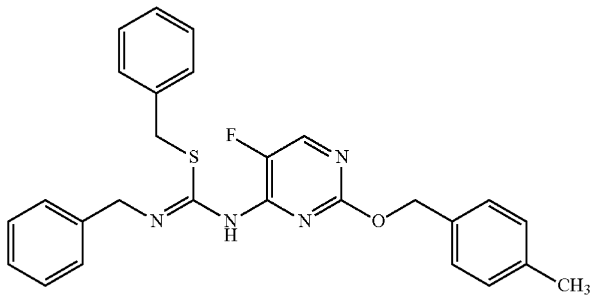 [SMILES: Cc1ccc(COc2ncc(F)c(N/C(=N/Cc3ccccc3)SCc3ccccc3)n2)cc1] | E | E | E | E | Pale yellow solid | | 473 | | |
| 219 | 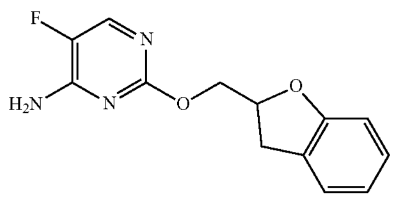 [SMILES: Nc1nc(OCC2Cc3ccccc3O2)ncc1F] | D | B | B | A | off-white solid | 141-143 | 262 | 260 | |
| 220 | 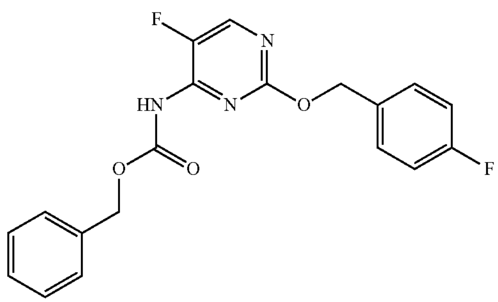 [SMILES: O=C(Nc1nc(OCc2ccc(F)cc2)ncc1F)OCc1ccccc1] | A | A | A | A | | | 372 | 370 | |
| 221 | 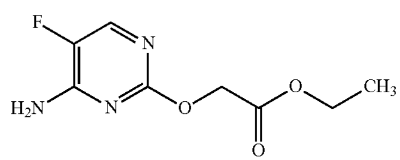 | E | E | E | E | white solid | 113-115 | 215 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 222 | 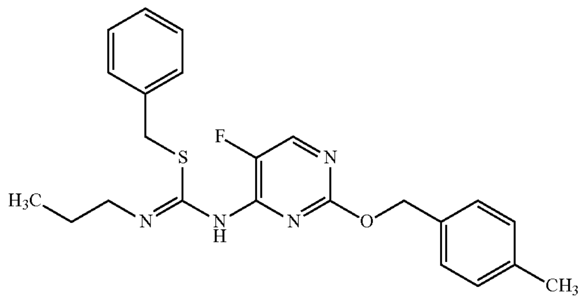 [SMILES: CCC/N=C(/Nc1nc(OCc2ccc(C)cc2)ncc1F)SCc1ccccc1] | E | E | E | E | Pale yellow viscous liquid | | | 423 | |
| 223 | 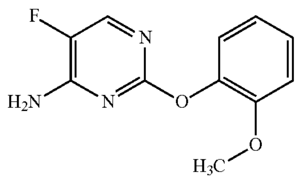 | A | A | A | A | white solid | 132-134 | 236 | 234 | |
| 224 | 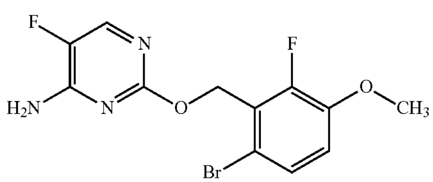 [SMILES: COc1ccc(Br)c(COc2ncc(F)c(N)n2)c1F] | D | C | C | A | white solid | 184 | 347 | 345 | |
| 225 | 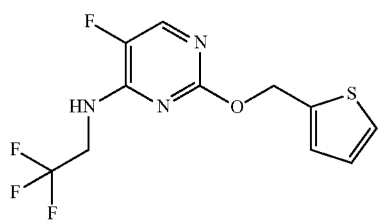 [SMILES: Fc1cnc(OCc2cccs2)nc1NCC(F)(F)F] | E | E | E | E | | | | 306 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 226 | 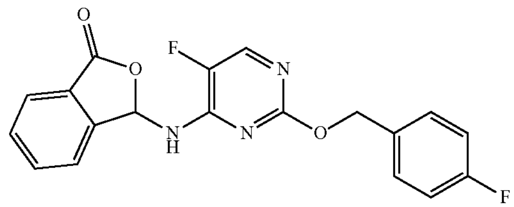 [SMILES: O=C1OC(Nc2nc(OCc3ccc(F)cc3)ncc2F)c2ccccc21] | A | A | A | A | white glassy solid | 68-77 | 370 | | |
| 227 | 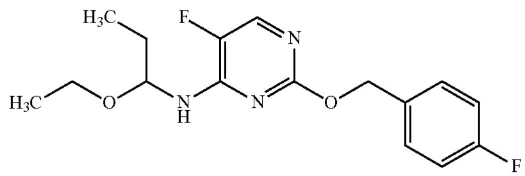 [SMILES: CCOC(CC)Nc1nc(OCc2ccc(F)cc2)ncc1F] | A | A | A | A | white solid | 56-57 | 324 | 322 | |
| 228 | 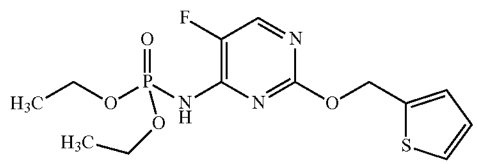 [SMILES: CCOP(=O)(Nc1nc(OCc2cccs2)ncc1F)OCC] | B | A | C | A | light yellow solid | | 362 | 360 | |
| 229 | 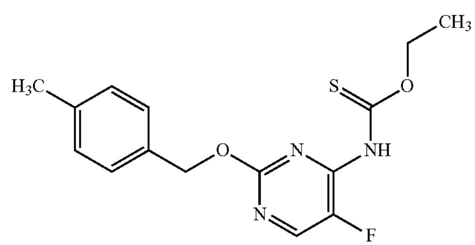 [SMILES: CCOC(=S)Nc1nc(OCc2ccc(C)cc2)ncc1F] | E | E | E | E | Off white solid | | 322 | | |
| 230 | 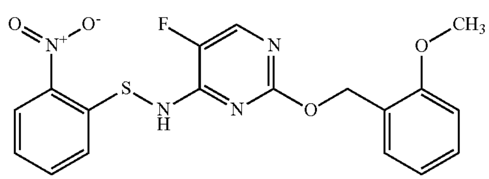 [SMILES: COc1ccccc1COc1ncc(F)c(NSc2ccccc2[N+](=O)[O-])n1] | D | D | A | A | yellow solid | 159-163 | 403 | 401 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 231 | 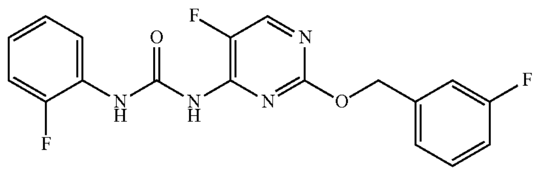 | D | D | D | D | white solid | 193-194 | 375 | 373 | |
| 232 | 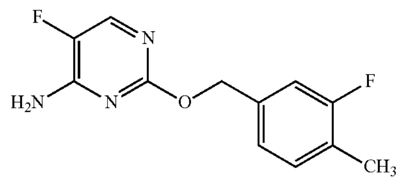 | A | A | A | A | white solid | 105-107 | 252 | 250 | |
| 233 | 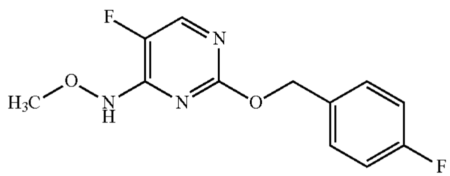 [SMILES: CONc1nc(OCc2ccc(F)cc2)ncc1F] | A | A | B | A | white solid | 114-115 | | | |
| 234 | 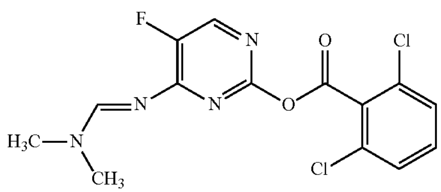 [SMILES: CN(C)/C=N/c1nc(OC(=O)c2c(Cl)cccc2Cl)ncc1F] | A | A | A | A | pale yellow solid | | 357 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 235 | 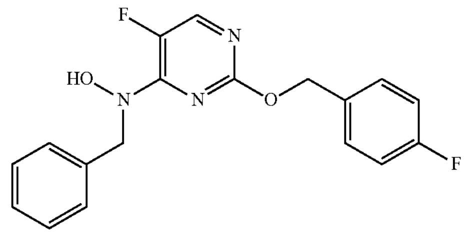 [SMILES: ON(Cc1ccccc1)c1nc(OCc2ccc(F)cc2)ncc1F] | B | A | A | A | viscous yellow oil | | 345 | 342 | |
| 236 | 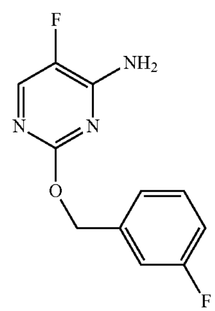 [SMILES: Nc1nc(OCc2cccc(F)c2)ncc1F] | A | A | A | A | white solid | 111-113 | 238 | | |
| 237 | 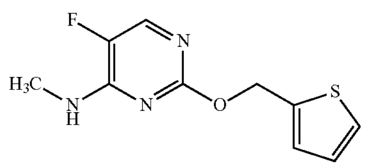 [SMILES: CNc1nc(OCc2cccs2)ncc1F] | D | D | D | D | white solid | 62-65 | 240 | 238 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 238 | 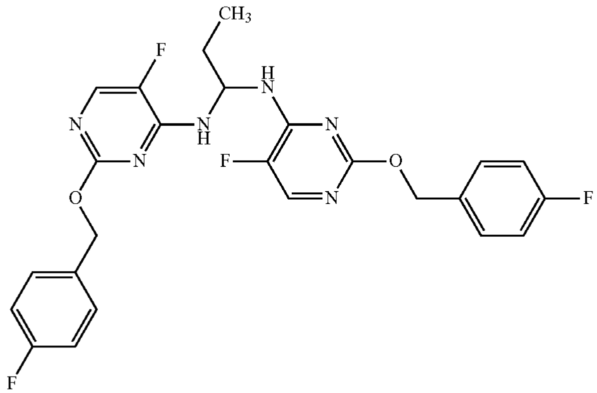 [SMILES: CCC(Nc1nc(OCc2ccc(F)cc2)ncc1F)Nc1nc(OCc2ccc(F)cc2)ncc1F] | D | C | D | B | clear colorless oil | | 515 | 513 | |
| 239 | 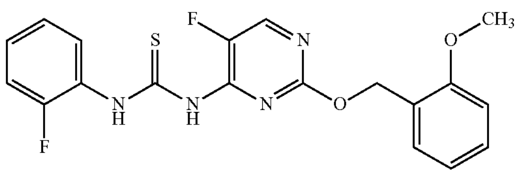 [SMILES: COc1ccccc1COc1ncc(F)c(NC(=S)Nc2ccccc2F)n1] | B | A | A | A | white solid | 165-166 | 403 | 401 | |
| 240 | 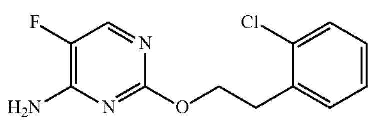 [SMILES: Nc1nc(OCCc2ccccc2Cl)ncc1F] | D | D | D | C | white solid | 86-87 | 268 | 266 | |
| 241 | 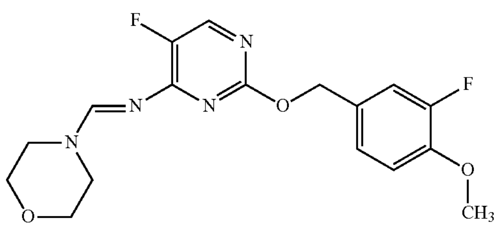 | A | B | A | A | white solid | 164-165 | 365 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 242 | 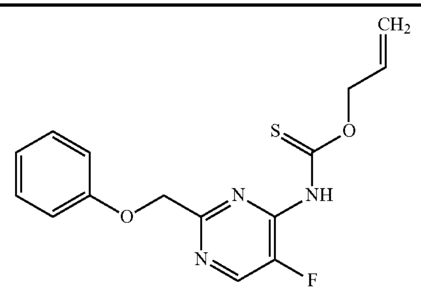 | E | E | E | E | Pale yellow solid | | 320 | | |
| 243 | 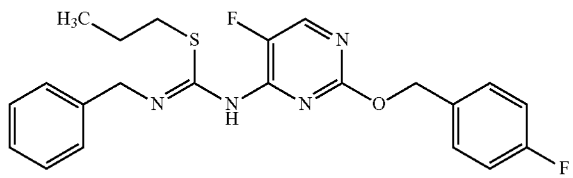 [SMILES: CCCS/C(=N\Cc1ccccc1)Nc1nc(OCc2ccc(F)cc2)ncc1F] | E | E | E | E | Pale yellow solid | | 429 | | |
| 244 | 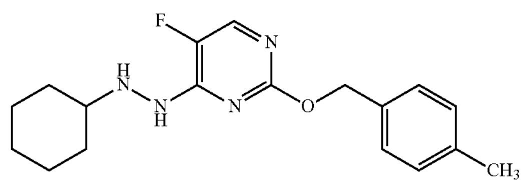 [SMILES: Cc1ccc(COc2ncc(F)c(NNC3CCCCC3)n2)cc1] | D | A | D | A | pale yellow solid | 138-142 | 332 | 329 | |
| 245 | 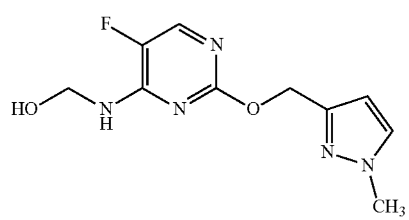 [SMILES: Cn1ccc(COc2ncc(F)c(NCO)n2)n1] | B | A | B | A | white solid | 145-148 | 254 | 252 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 246 | 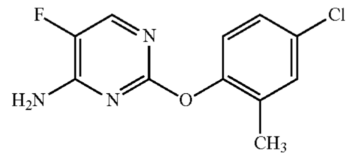 [SMILES: Cc1cc(Cl)ccc1Oc1ncc(F)c(N)n1] | E | E | D | D | white solid | 157-158 | 254 | 252 | |
| 247 | 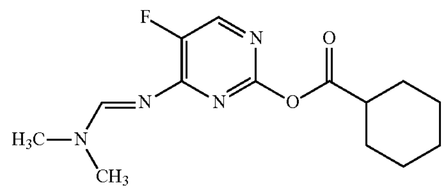 | A | A | A | A | off white solid | 94-95 | 295 | | |
| 248 | 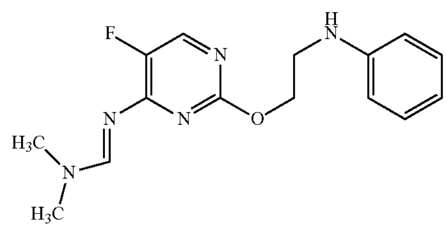 [SMILES: CN(C)/C=N/c1nc(OCCNc2ccccc2)ncc1F] | A | A | D | A | off white solid | 102-104 | 304 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 249 | 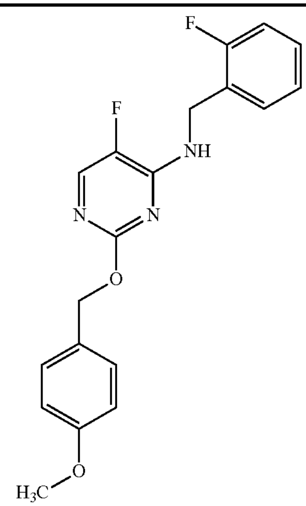 | C | B | C | A | off white solid | 92-93 | 358 | 356 | |
| 250 | 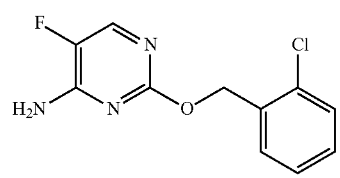 [SMILES: Nc1nc(OCc2ccccc2Cl)ncc1F] | E | E | E | E | white solid | 117-118 | 254 | 252 | |
| 251 | 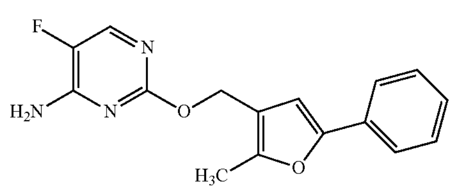 [SMILES: Cc1oc(-c2ccccc2)cc1COc1ncc(F)c(N)n1] | A | A | A | A | beige solid | 120-122 | 300 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 252 | 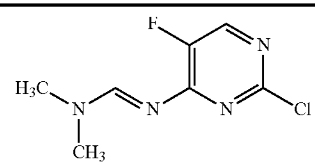 | D | D | C | C | white solid | 132-135 | | | |
| 253 | 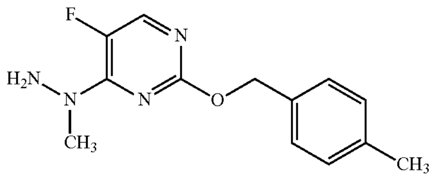 | B | A | C | A | yellow oil | | 263 | 261 | |
| 254 | 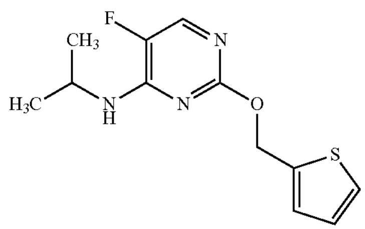 [SMILES: CC(C)Nc1nc(OCc2cccs2)ncc1F] | E | E | E | E | Gummy liquid | | 268 | | |
| 255 | 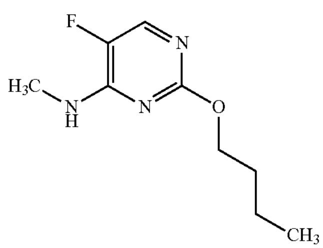 | E | E | E | E | Off white solid | | 200 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 256 | 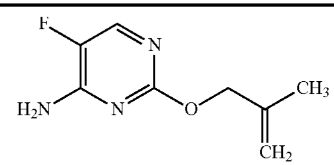 | D | C | D | D | white solid | 83-84 | 184 | | 182 |
| 257 | 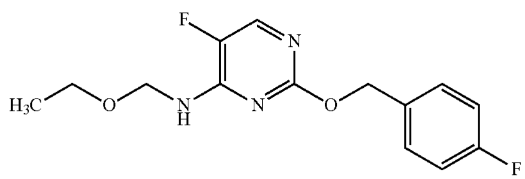 [SMILES: CCOCNc1nc(OCc2ccc(F)cc2)ncc1F] | B | A | B | A | white solid | 90-91 | 296 | 294 | |
| 258 | 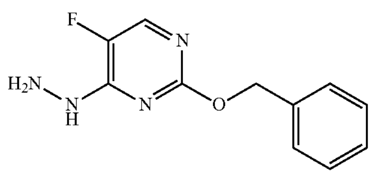 [SMILES: NNc1nc(OCc2ccccc2)ncc1F] | C | B | B | A | off white solid | 80-82 | 236 | 233 | |
| 259 | 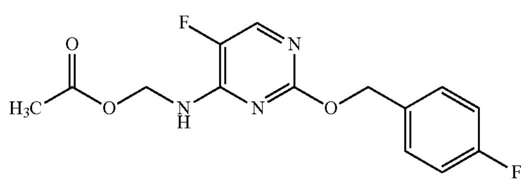 [SMILES: CC(=O)OCNc1nc(OCc2ccc(F)cc2)ncc1F] | A | A | B | A | white solid | 103-105 | 310 | | |
| 260 | 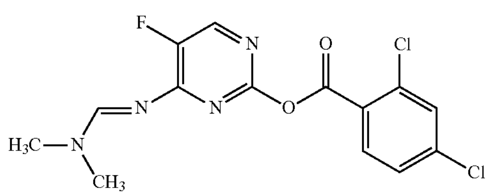 | A | A | A | A | off white slid | 95 (dec) | 357 | | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 261 | 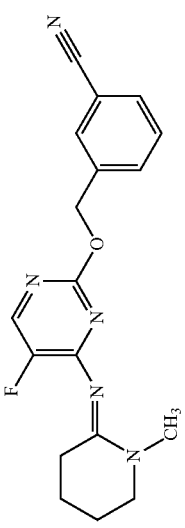 | B | A | B | A | pale amber oil | | 340 | | |
| 262 | 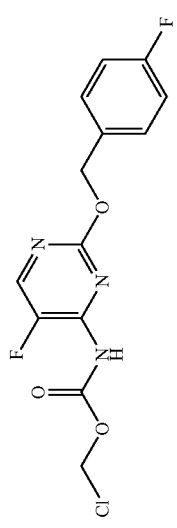 | A | A | B | A | white solid | 101-105 | | | |
| 263 | 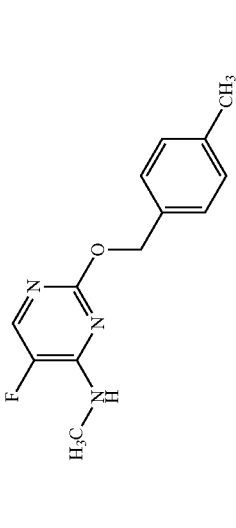 | E | E | E | E | Off white solid | | 270 M + Na | | |
| 264 | 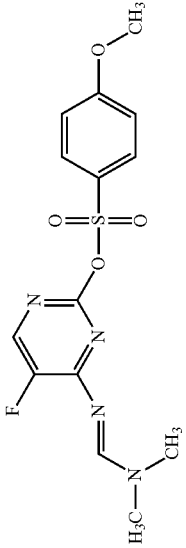 | A | A | B | A | white solid | 131-133 | 356 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 265 | 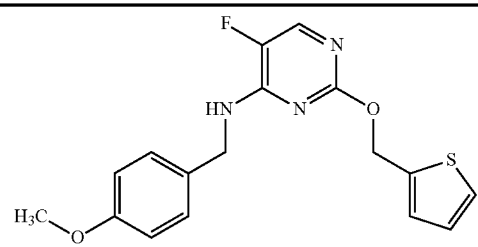 | E | E | E | E | Yellow solid | | | | 344 |
| 266 | 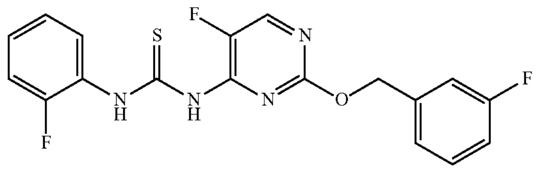 [SMILES: Fc1cccc(COc2ncc(F)c(NC(=S)Nc3ccccc3F)n2)c1] | D | A | A | A | white solid | 137-138 | 391 | 389 | |
| 267 | 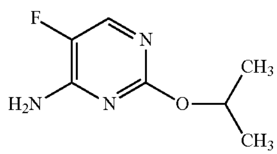 | D | D | D | D | white solid | 104-105 | 172 | 170 | |
| 268 | 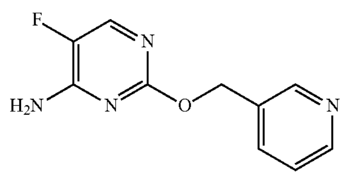 [SMILES: Nc1nc(OCc2cccnc2)ncc1F] | C | B | D | C | white solid | 126-127 | | 247 | |
| 269 | 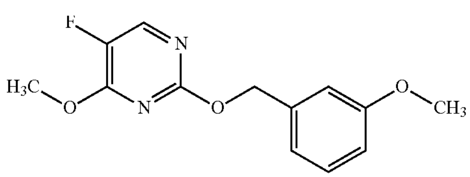 | D | D | D | D | pale green solid | 91-94 | 265 | 237 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 270 | 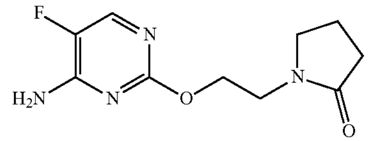 [SMILES: Nc1nc(OCCN2CCCC2=O)ncc1F] | D | D | D | D | white solid | 111-112 | | 239 | |
| 271 | 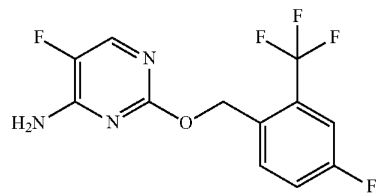 [SMILES: Nc1nc(OCc2ccc(F)cc2C(F)(F)F)ncc1F] | B | A | A | A | white solid | 119 | 306 | 304 | |
| 272 | 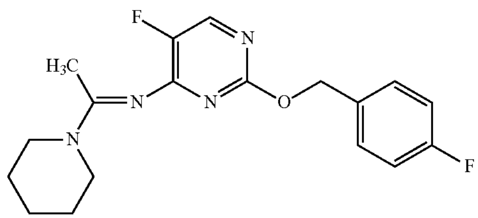 [SMILES: C/C(=N\c1nc(OCc2ccc(F)cc2)ncc1F)N1CCCCC1] | A | A | A | A | clear yellow oil | | 349 | | |
| 273 | 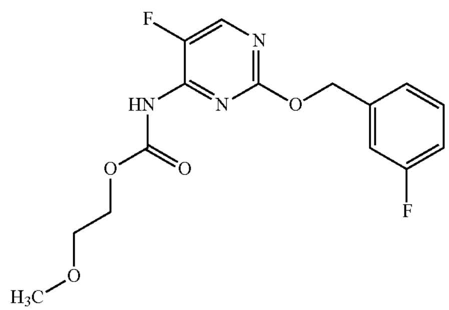 [SMILES: COCCOC(=O)Nc1nc(OCc2cccc(F)c2)ncc1F] | A | A | B | A | | | 340 | 338 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 274 | 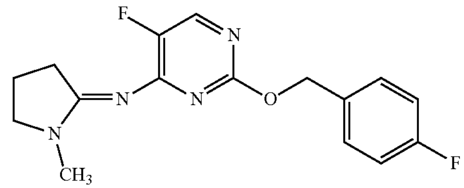 [SMILES: CN1CCC/C1=N\c1nc(OCc2ccc(F)cc2)ncc1F] | A | A | A | A | off white solid | 84-86 | 319 | | |
| 275 | 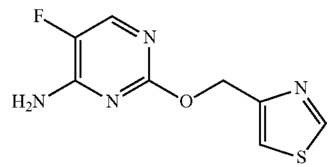 [SMILES: Nc1nc(OCc2cscn2)ncc1F] | A | A | A | A | beige solid | 136 | 227 | | |
| 276 | 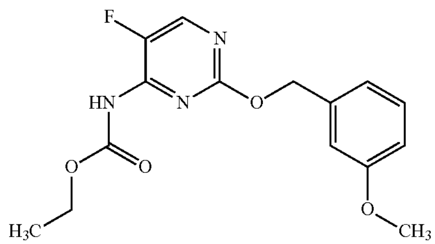 | A | A | A | A | | | 322 | 320 | |
| 277 | 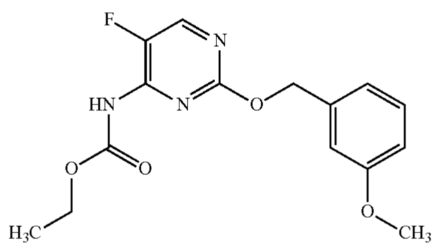 [SMILES: CCOC(=O)Nc1nc(OCc2cccc(OC)c2)ncc1F] | E | E | E | E | | | | 290 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 278 | 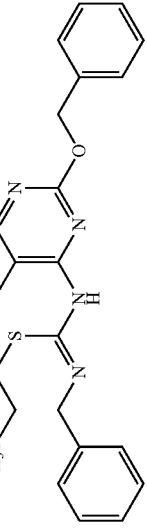 | E | E | E | E | Off white solid | | 411 | | |
| 279 | 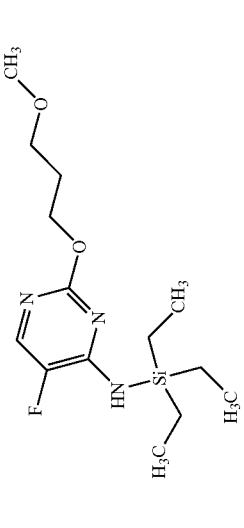 | A | A | B | A | yellow gummy solid | | 316 | | |
| 280 | 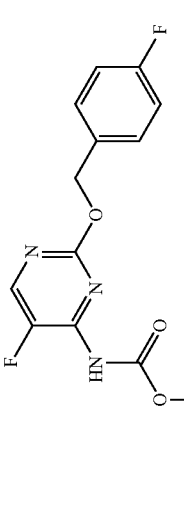 | A | A | A | A | | | 340 | 338 | |
| 281 | 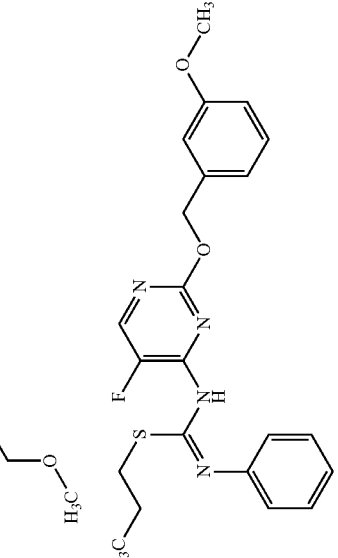 | E | E | E | E | Pale yellow solid | | 427 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 282 | 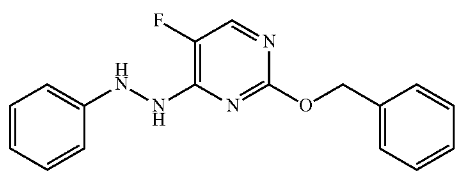 [SMILES: Fc1cnc(OCc2ccccc2)nc1NNc1ccccc1] | C | B | D | C | dark brown solid | 158-163 | 312 | 309 | |
| 283 | 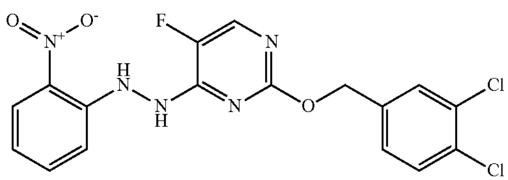 [SMILES: O=[N+]([O-])c1ccccc1NNc1nc(OCc2ccc(Cl)c(Cl)c2)ncc1F] | D | C | B | A | yellow solid | 166-176 | 441 | 439 | |
| 284 | 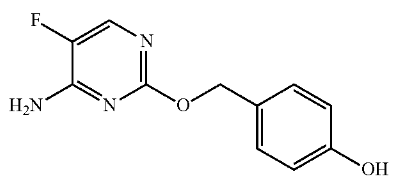 [SMILES: Nc1nc(OCc2ccc(O)cc2)ncc1F] | D | D | D | D | white solid | 196-198 | 236 | 234 | |
| 285 | 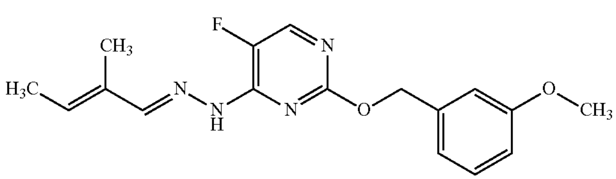 [SMILES: C/C=C(C)/C=N/Nc1nc(OCc2cccc(OC)c2)ncc1F] | C | C | B | A | pale brown solid | 118-120 | 331 | 329 | |
| 286 | 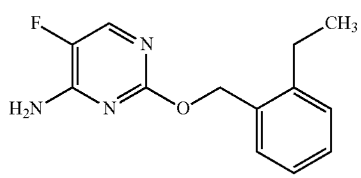 [SMILES: CCc1ccccc1COc1ncc(F)c(N)n1] | B | A | A | A | off-white solid | 121-123 | 248 | 246 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 287 | 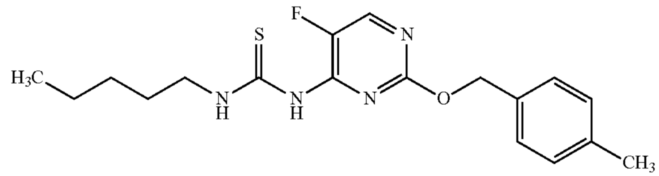 [SMILES: CCCCCNC(=S)Nc1nc(OCc2ccc(C)cc2)ncc1F] | A | A | A | A | white solid | 115-116 | 363 | 361 | |
| 288 | 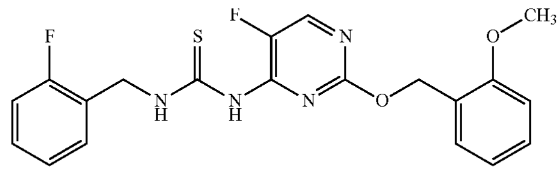 [SMILES: COc1ccccc1COc1ncc(F)c(NC(=S)NCc2ccccc2F)n1] | D | D | D | D | white solid | 188-190 | 401 | 399 | |
| 289 | 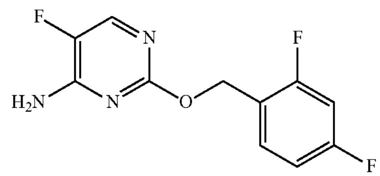 [SMILES: Nc1nc(OCc2ccc(F)cc2F)ncc1F] | A | A | A | A | white solid | 128 | | 254 | |
| 290 | 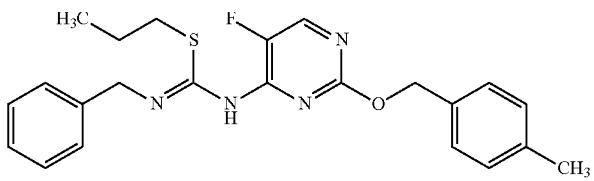 [SMILES: CCCS/C(=N\Cc1ccccc1)Nc1nc(OCc2ccc(C)cc2)ncc1F] | E | E | E | E | Pale yellow solid | | 425 | | |
| 291 | 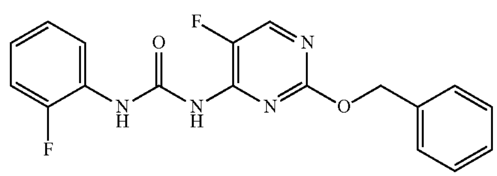 | D | C | D | D | off-white solid | 198-200 | 357 | 355 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 292 | 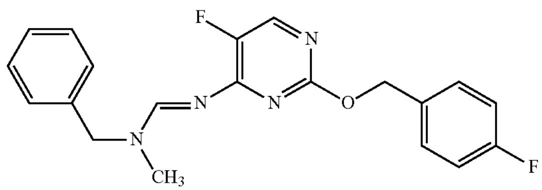 | A | A | A | A | colorless oil | | 369 | | |
| 293 | 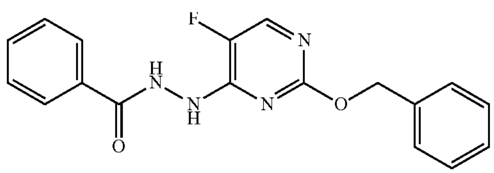 [SMILES: O=C(NNc1nc(OCc2ccccc2)ncc1F)c1ccccc1] | D | D | D | D | white solid | 200-202 | 340 | 337 | |
| 294 | 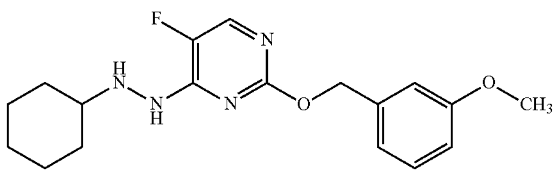 [SMILES: COc1cccc(COc2ncc(F)c(NNC3CCCCC3)n2)c1] | D | A | D | A | yellow oil | | 347 | | |
| 295 | 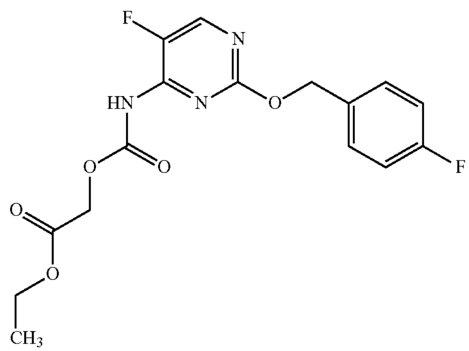 [SMILES: CCOC(=O)COC(=O)Nc1nc(OCc2ccc(F)cc2)ncc1F] | A | A | A | A | | | | 366 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 296 | 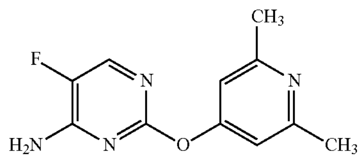 | D | C | D | D | white solid | | 235 | 233 | |
| 297 | 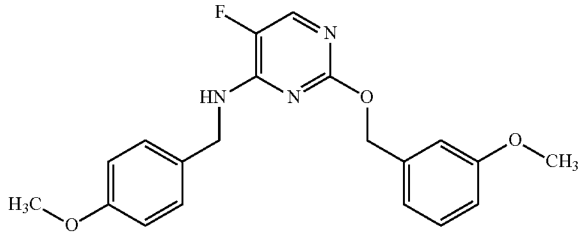 | E | E | E | E | Pale yellow liquid | | | 368 | |
| 298 | 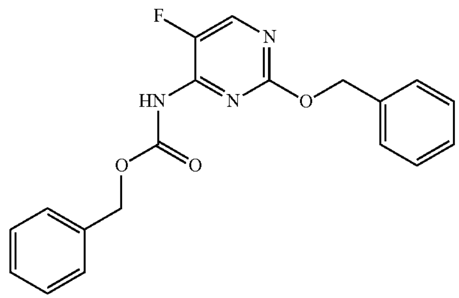 [SMILES: O=C(Nc1nc(OCc2ccccc2)ncc1F)OCc1ccccc1] | A | A | A | A | | | 354 | 352 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 299 | 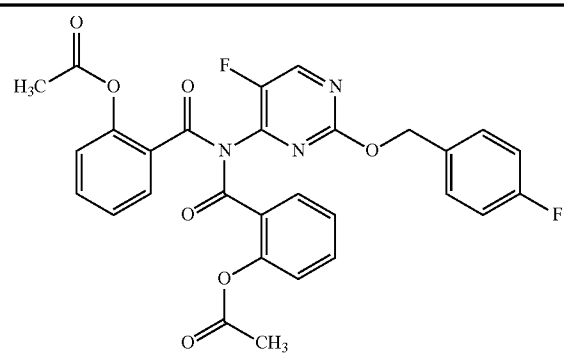 | E | E | E | E | off white solid | 83-88 | 562 | | |
| 300 | 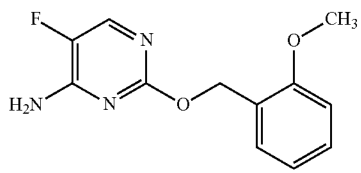 [SMILES: COc1ccccc1COc1ncc(F)c(N)n1] | A | A | A | A | white solid | 106-107 | 250 | 248 | |
| 301 | 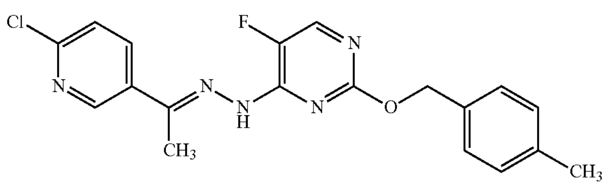 [SMILES: C/C(=N\Nc1nc(OCc2ccc(C)cc2)ncc1F)c1ccc(Cl)nc1] | B | A | C | C | tan solid | 136-139 | 386 | 384 | |
| 302 | 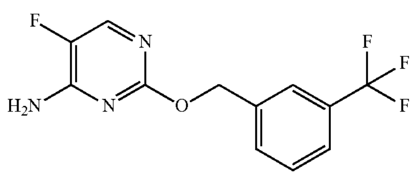 [SMILES: Nc1nc(OCc2cccc(C(F)(F)F)c2)ncc1F] | A | A | A | A | grey solid | 105-107 | | 386 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 303 | 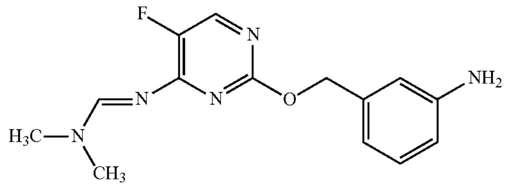 | B | A | C | A | thick oil | | 290 | | |
| 304 | 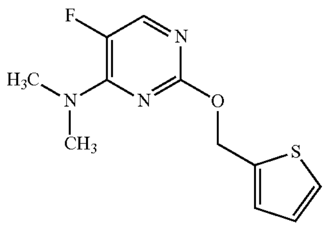 [SMILES: CN(C)c1nc(OCc2cccs2)ncc1F] | E | E | E | E | Yellow liquid | | 276 [M + Na] | | |
| 305 | 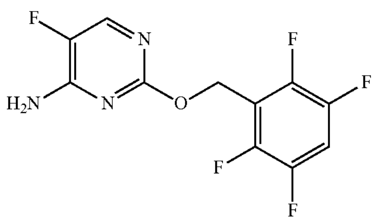 [SMILES: Nc1nc(OCc2c(F)c(F)cc(F)c2F)ncc1F] | E | E | E | E | white solid | | 292 | 290 | |
| 306 | 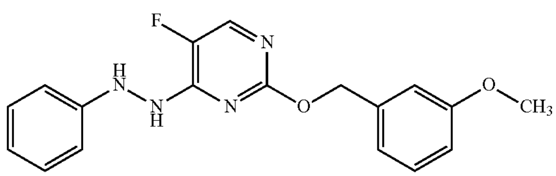 [SMILES: COc1cccc(COc2ncc(F)c(NNc3ccccc3)n2)c1] | C | C | D | A | brown solid | 108-112 | 341 | 339 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 307 | 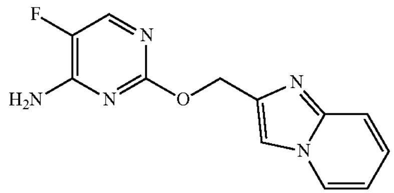 [SMILES: Nc1nc(OCc2cn3ccccc3n2)ncc1F] | A | A | A | A | white solid | 161-163 | 261 | 258 | |
| 308 | 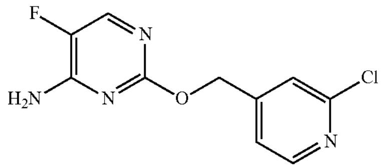 [SMILES: Nc1nc(OCc2ccnc(Cl)c2)ncc1F] | A | A | A | A | yellow solid | 182-183 | 256 | | |
| 309 | 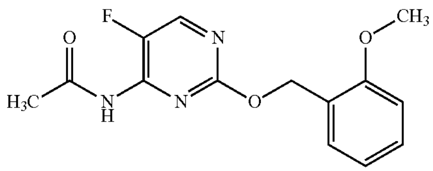 [SMILES: COc1ccccc1COc1ncc(F)c(NC(C)=O)n1] | A | A | A | A | white solid | | 292 | 290 | |
| 310 | 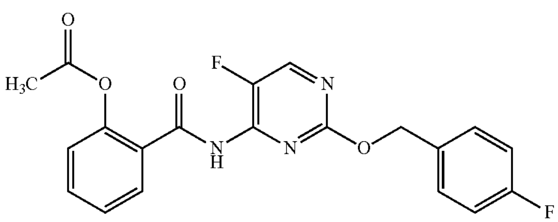 [SMILES: CC(=O)Oc1ccccc1C(=O)Nc1nc(OCc2ccc(F)cc2)ncc1F] | E | E | E | E | colorless oil | | 400 | 398 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 311 | 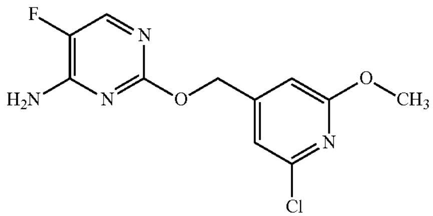 [SMILES: COc1cc(COc2ncc(F)c(N)n2)cc(Cl)n1] | A | A | A | A | white solid | 160-161 | 286 | | |
| 312 | 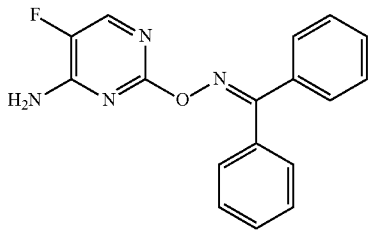 [SMILES: Nc1nc(ON=C(c2ccccc2)c2ccccc2)ncc1F] | A | A | A | A | white solid | 196-200 | 309 | 307 | |
| 313 | 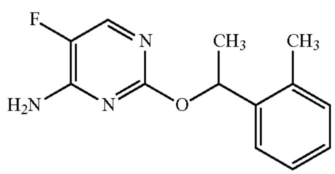 [SMILES: Cc1ccccc1C(C)Oc1ncc(F)c(N)n1] | A | A | A | A | white solid | 99-102 | | 246 | |
| 314 | 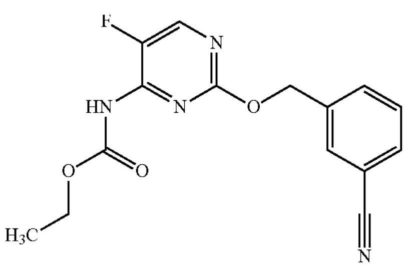 [SMILES: CCOC(=O)Nc1nc(OCc2cccc(C#N)c2)ncc1F] | A | A | A | A | | | 317 | 315 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 315 | 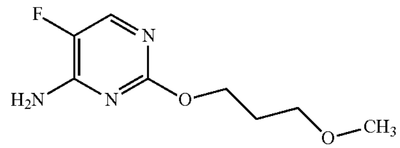 | A | A | B | A | white solid | 64-65 | 202 | 200 | |
| 316 | 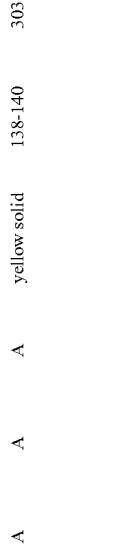 | A | A | A | A | yellow solid | 138-140 | 303 | | |
| 317 | 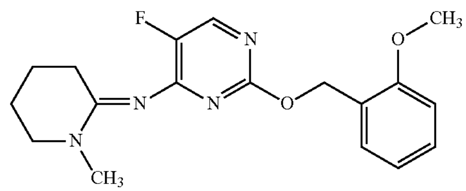 [SMILES: COc1ccccc1COc1ncc(F)c(/N=C2\CCCCN2C)n1] | C | A | B | A | pale amber oil | | 345 | | |
| 318 | 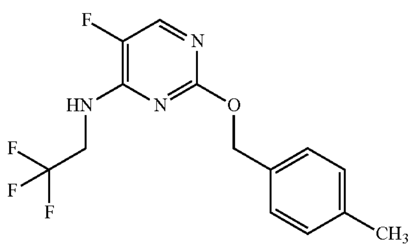 [SMILES: Cc1ccc(COc2ncc(F)c(NCC(F)(F)F)n2)cc1] | E | E | E | E | | | | 314 | |
| 319 | 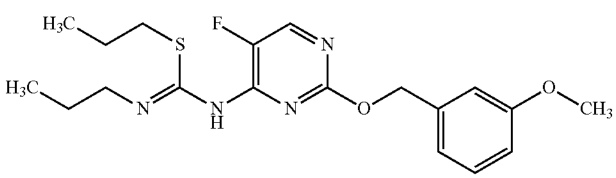 [SMILES: CCC/N=C(/Nc1nc(OCc2cccc(OC)c2)ncc1F)SCCC] | E | E | E | E | Pale yellow viscous liquid | | 393 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 320 | 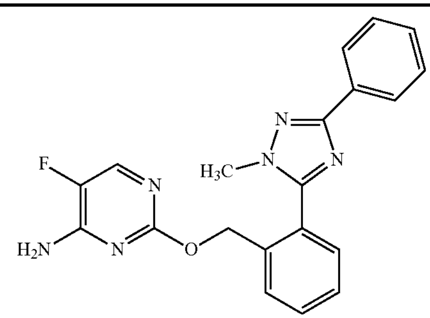 | C | C | D | D | yellow solid | 209 | | 377 | |
| 321 | 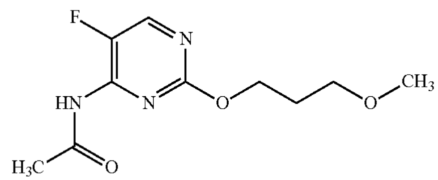 | A | A | A | A | LIGHT YELLOW SOLID | 112-114 | 244 | | |
| 322 | 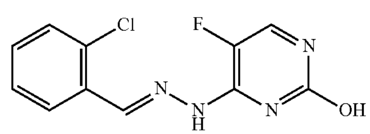 [SMILES: Oc1ncc(F)c(N/N=C/c2ccccc2Cl)n1] | D | D | D | D | yellow solid | 235-237 | 267 | 265 | |
| 323 | 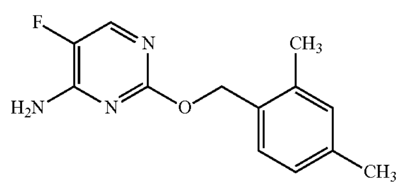 | A | A | A | A | white solid | 153 | 248 | 246 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 324 | 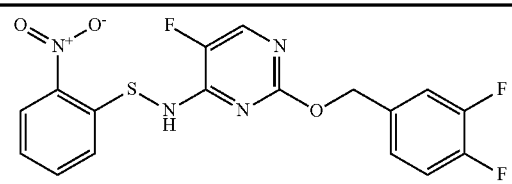 | D | C | A | A | yellow solid | 185-189 | 409 | 407 | |
| 325 | 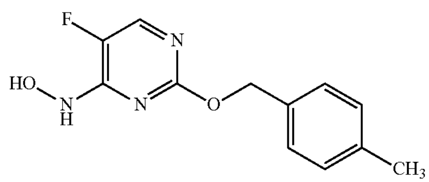 [SMILES: Cc1ccc(COc2ncc(F)c(NO)n2)cc1] | A | A | A | A | off white solid | 138-141 | 250 | 248 | |
| 326 | 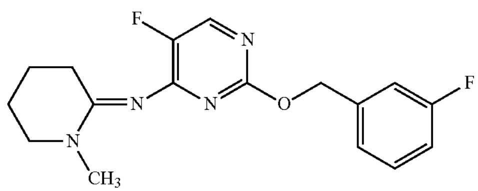 [SMILES: CN1CCCC/C1=N\c1nc(OCc2cccc(F)c2)ncc1F] | B | A | A | A | pale amber oil | | 333 | | |
| 327 | 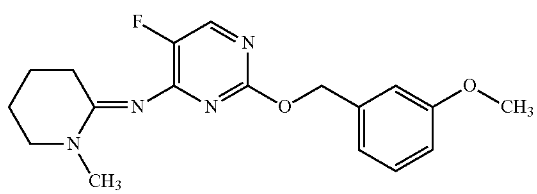 [SMILES: COc1cccc(COc2ncc(F)c(/N=C3\CCCCN3C)n2)c1] | B | A | B | A | pale amber oil | | 345 | | |
| 328 | 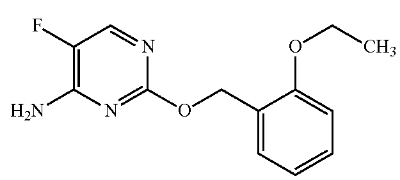 [SMILES: CCOc1ccccc1COc1ncc(F)c(N)n1] | A | A | A | A | off-white solid | 116-117 | 264 | 262 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 329 | 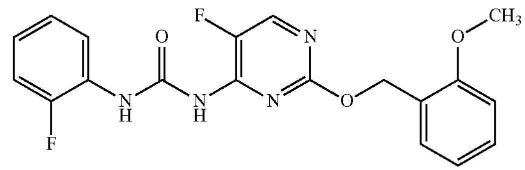 | D | D | D | D | white solid | 187-188 | 387 | 385 | |
| 330 | 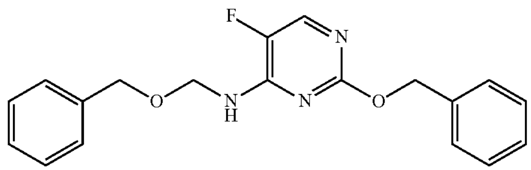 [SMILES: Fc1cnc(OCc2ccccc2)nc1NCOCc1ccccc1] | D | C | D | A | white solid | 75-77 | 340 | 338 | |
| 331 | 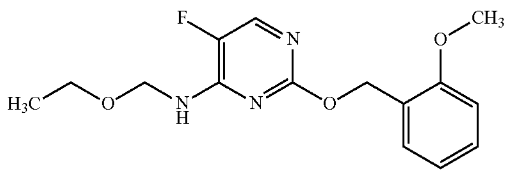 [SMILES: CCOCNc1nc(OCc2ccccc2OC)ncc1F] | A | A | A | A | clear colorless oil | | 308 | 306 | |
| 332 | 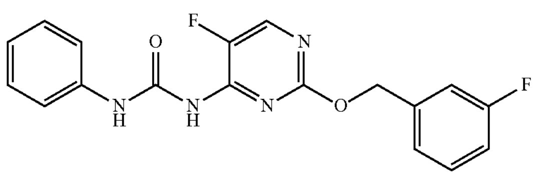 [SMILES: O=C(Nc1ccccc1)Nc1nc(OCc2cccc(F)c2)ncc1F] | B | C | A | A | yellow-white solid | 121-123 | 356 | 354 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 333 | 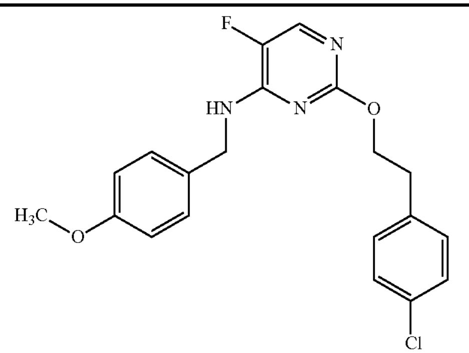 | E | E | E | E | Gummy liquid | | 388 | | |
| 334 | 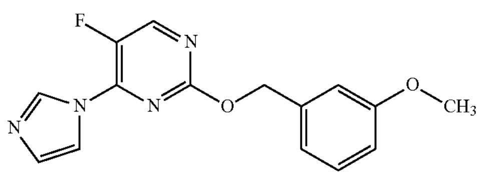 [SMILES: COc1cccc(COc2ncc(F)c(-n3ccnc3)n2)c1] | A | A | A | A | white solid | 79-80 | 301 | | |
| 335 | 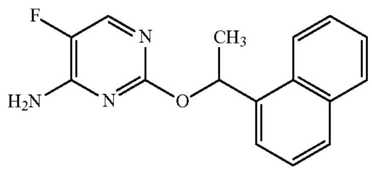 [SMILES: CC(Oc1ncc(F)c(N)n1)c1cccc2ccccc12] | A | A | A | A | orange oil | | | 282 | |
| 336 | 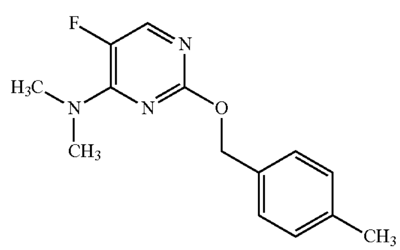 | E | E | E | E | Gummy liquid | | 262 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 337 | 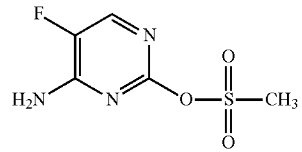 | C | C | C | A | white solid | 191-192 | 208 | 206 | |
| 338 | 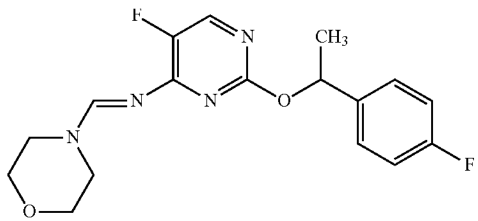 [SMILES: CC(Oc1ncc(F)c(/N=C/N2CCOCC2)n1)c1ccc(F)cc1] | A | A | A | A | white solid | 102-103 | 349 | | |
| 339 | 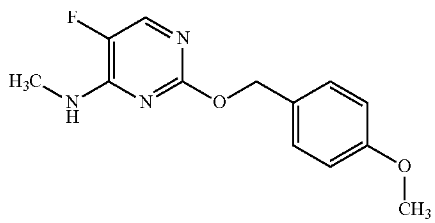 | C | B | D | C | white solid | 63-65 | 264 | 262 | |
| 340 | 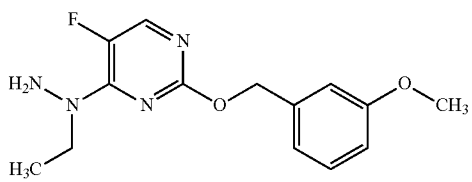 [SMILES: CCN(N)c1nc(OCc2cccc(OC)c2)ncc1F] | C | A | D | A | yellow oil | | 294 | 291 | |
| 341 | 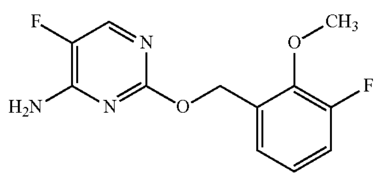 [SMILES: COc1c(F)cccc1COc1ncc(F)c(N)n1] | A | A | A | A | white solid | 129 | 268 | 266 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 342 | 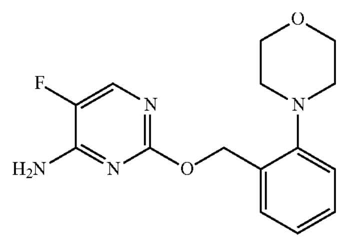 [SMILES: Nc1nc(OCc2ccccc2N2CCOCC2)ncc1F] | A | A | A | A | off-white crystals | 147-149 | 305 | 303 | |
| 343 | 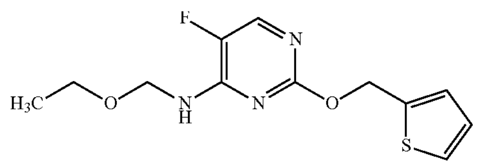 [SMILES: CCOCNc1nc(OCc2cccs2)ncc1F] | A | A | C | A | white solid | 55-57 | 284 | 282 | |
| 344 | 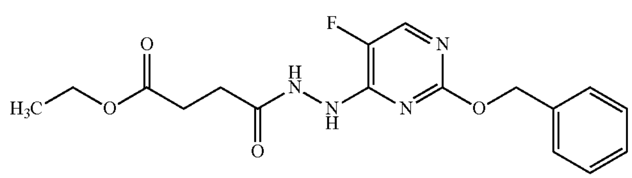 [SMILES: CCOC(=O)CCC(=O)NNc1nc(OCc2ccccc2)ncc1F] | D | C | C | C | off white solid | 117-121 | 363 | 361 | |
| 345 | 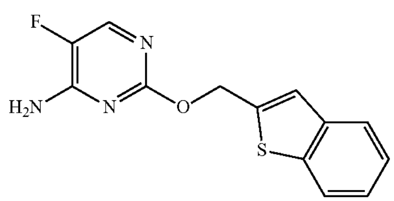 [SMILES: Nc1nc(OCc2cc3ccccc3s2)ncc1F] | A | A | A | A | white solid | 154-156 | 276 | | |
| 346 | 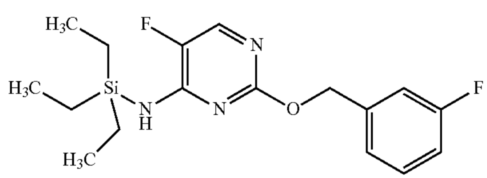 [SMILES: CC[Si](CC)(CC)Nc1nc(OCc2cccc(F)c2)ncc1F] | A | A | A | A | clear oil | | 352 | 350 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 347 | 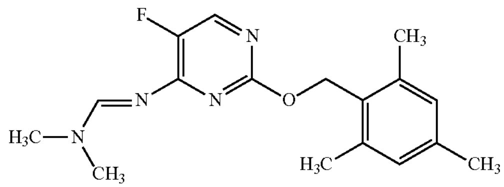 | A | A | A | A | white solid | 134-135 | 317 | | |
| 348 | 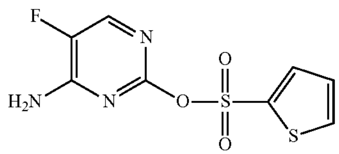 [SMILES: Nc1nc(OS(=O)(=O)c2cccs2)ncc1F] | A | A | A | A | white solid | 128-130 | | | |
| 349 | 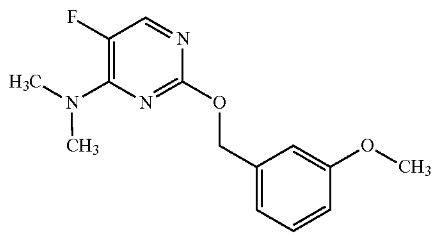 | E | E | E | E | Pale yellow liquid | | 278 | | |
| 350 | 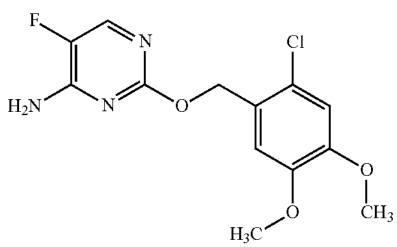 | A | A | A | A | white solid | 117 | 314 | 312 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 351 | 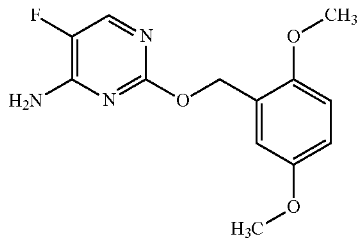 [SMILES: COc1ccc(OC)c(COc2ncc(F)c(N)n2)c1] | A | A | A | A | white solid | 151 | 280 | | 278 |
| 352 | 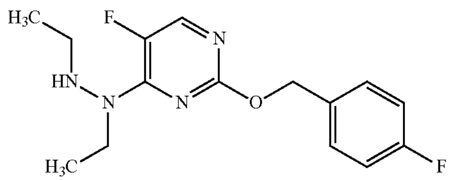 [SMILES: CCNN(CC)c1nc(OCc2ccc(F)cc2)ncc1F] | D | D | D | D | colorless liquid | | 310 | 307 | |
| 353 | 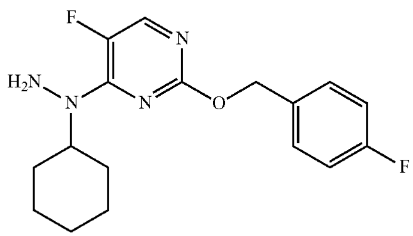 | D | D | D | D | white solid | 68-72 | 335 | 333 | |
| 354 | 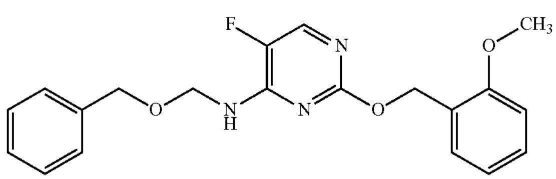 [SMILES: COc1ccccc1COc1ncc(F)c(NCOCc2ccccc2)n1] | C | A | B | A | clear pale yellow oil | | 370 | 368 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SEPTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 355 | 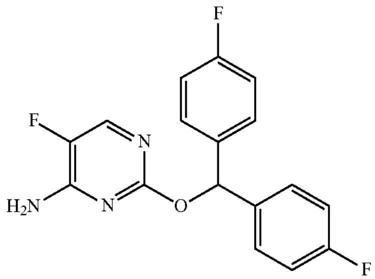 [SMILES: Nc1nc(OC(c2ccc(F)cc2)c2ccc(F)cc2)ncc1F] | A | A | A | A | white solid | 150-152 | | | 330 |
| 356 | 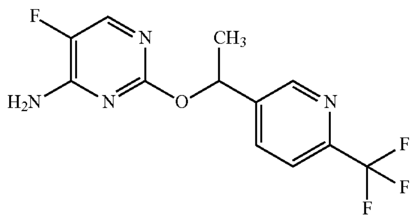 [SMILES: CC(Oc1ncc(F)c(N)n1)c1ccc(C(F)(F)F)nc1] | C | B | C | B | orange oil | | | 301 | |
| 357 | 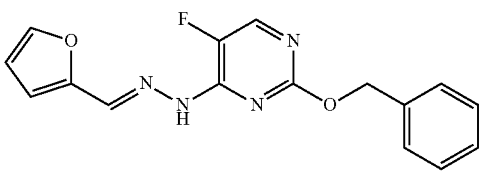 [SMILES: Fc1cnc(OCc2ccccc2)nc1N/N=C/c1ccco1] | D | B | C | C | off white solid | 173-177 | 313 | 311 | |
| 358 | 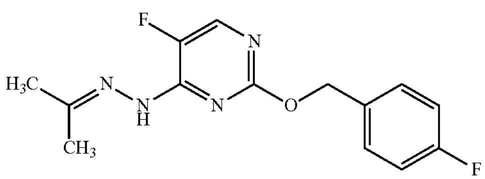 [SMILES: CC(C)=NNc1nc(OCc2ccc(F)cc2)ncc1F] | C | A | D | B | brown solid | 120-123 | 293 | 291 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 359 | 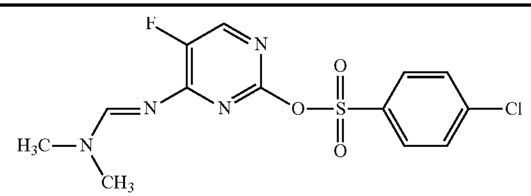 | A | A | A | A | white solid | 172-174 | 360 | | |
| 360 | 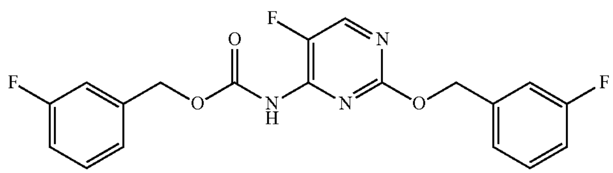 [SMILES: O=C(Nc1nc(OCc2cccc(F)c2)ncc1F)OCc1cccc(F)c1] | A | A | A | A | white solid | 105-106 | 390 | 388 | |
| 361 | 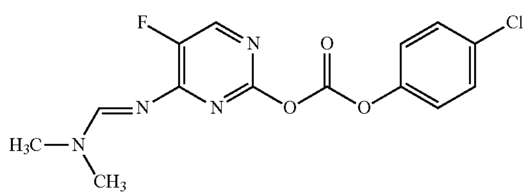 [SMILES: CN(C)/C=N/c1nc(OC(=O)Oc2ccc(Cl)cc2)ncc1F] | A | A | B | A | white solid | 150-153 | 339 | | |
| 362 | 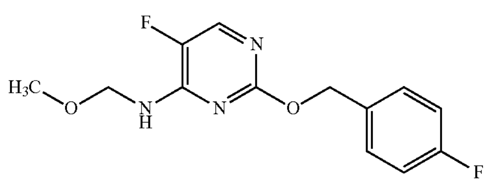 [SMILES: COCNc1nc(OCc2ccc(F)cc2)ncc1F] | B | A | B | A | white solid | 115-116 | 282 | 280 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 363 | 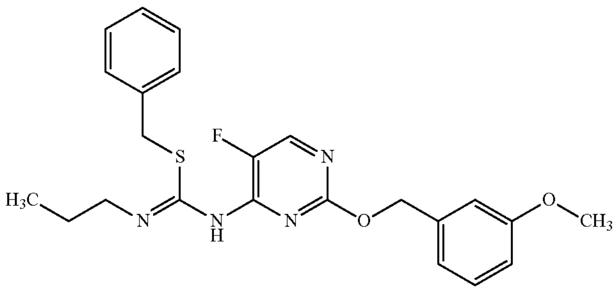 [SMILES: CCC/N=C(/Nc1nc(OCc2cccc(OC)c2)ncc1F)SCc1ccccc1] | E | E | E | E | Pale yellow viscous liquid | | 441 | | |
| 364 | 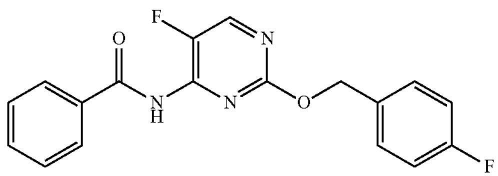 [SMILES: O=C(Nc1nc(OCc2ccc(F)cc2)ncc1F)c1ccccc1] | A | A | A | A | white solid | 114-115 | 342 | 340 | |
| 365 | 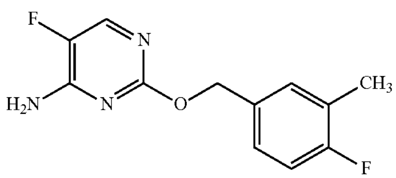 [SMILES: Cc1cc(COc2ncc(F)c(N)n2)ccc1F] | A | A | A | A | tacky yellow glass | | 252 | | |
| 366 | 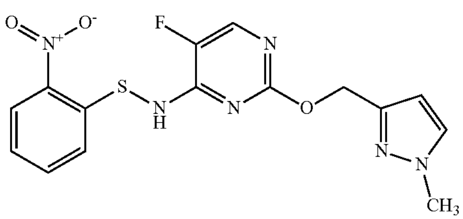 [SMILES: Cn1ccc(COc2ncc(F)c(NSc3ccccc3[N+](=O)[O-])n2)n1] | B | A | A | A | yellow solid | 186-192 | 377 | 375 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 367 | 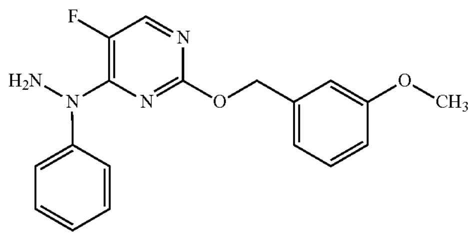 [SMILES: COc1cccc(COc2ncc(F)c(N(N)c3ccccc3)n2)c1] | D | D | D | D | off white solid | 94-97.5 | 341 | | |
| 368 | 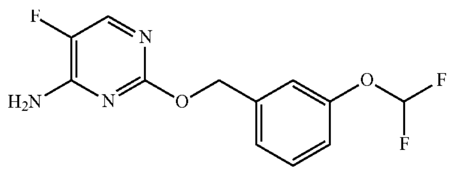 [SMILES: Nc1nc(OCc2cccc(OC(F)F)c2)ncc1F] | A | A | A | A | tan solid | 95-96 | 286 | 284 | |
| 369 | 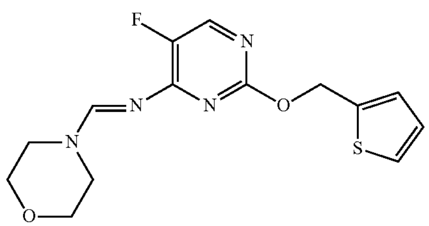 [SMILES: Fc1cnc(OCc2cccs2)nc1/N=C/N1CCOCC1] | A | A | A | A | white solid | 138-139 | 323 | | |
| 370 | 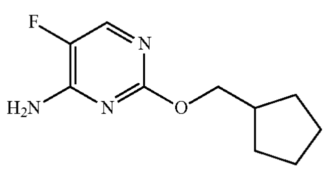 [SMILES: Nc1nc(OCC2CCCC2)ncc1F] | D | D | D | D | white solid | 93-94 | 212 | 210 | |
| 371 | 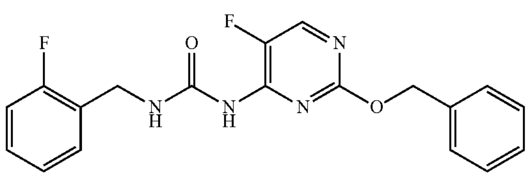 [SMILES: O=C(NCc1ccccc1F)Nc1nc(OCc2ccccc2)ncc1F] | D | D | D | D | white solid | 168-169 | 371 | 369 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 372 | 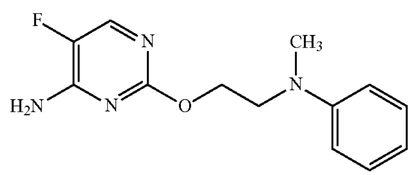 [SMILES: CN(CCOc1ncc(F)c(N)n1)c1ccccc1] | E | E | C | A | white solid | 138-139 | 263 | 261 | |
| 373 | 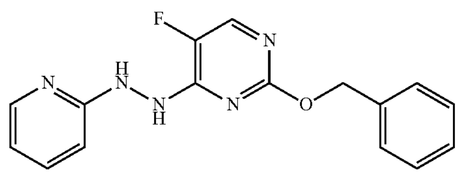 [SMILES: Fc1cnc(OCc2ccccc2)nc1NNc1ccccn1] | C | B | D | D | brown solid | 44-50 | 313 | 310 | |
| 374 | 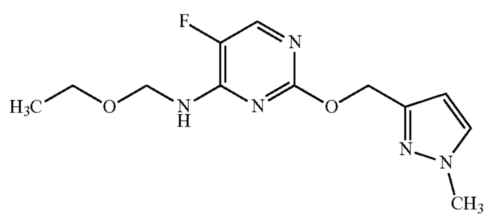 [SMILES: CCOCNc1nc(OCc2ccn(C)n2)ncc1F] | A | A | B | A | clear pale yellow oil | | 282 | 280 | |
| 375 | 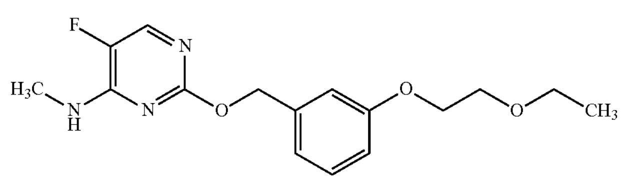 [SMILES: CCOCCOc1cccc(COc2ncc(F)c(NC)n2)c1] | C | A | D | D | yellow oil | | 322 | 320 | |
| 376 | 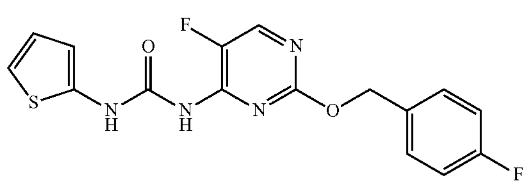 [SMILES: O=C(Nc1cccs1)Nc1nc(OCc2ccc(F)cc2)ncc1F] | D | C | D | D | lavender powder | 214-216 | 363 | 361 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 377 | 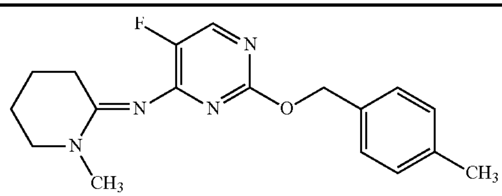 | B | A | A | A | pale amber oil | | 329 | | |
| 378 | 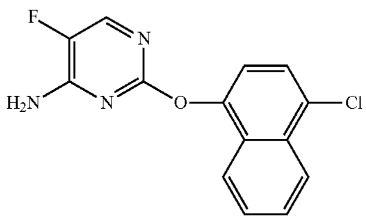 [SMILES: Nc1nc(Oc2ccc(Cl)c3ccccc23)ncc1F] | A | A | B | A | white solid | 177-179 | 290 | 288 | |
| 379 | 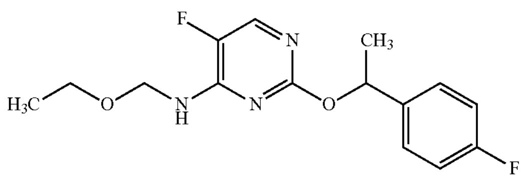 [SMILES: CCOCNc1nc(OC(C)c2ccc(F)cc2)ncc1F] | B | A | A | A | white solid | 84-85 | 310 | 308 | |
| 380 | 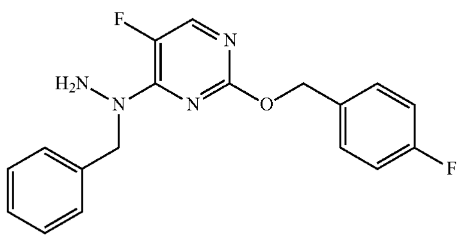 [SMILES: NN(Cc1ccccc1)c1nc(OCc2ccc(F)cc2)ncc1F] | D | A | A | A | off white solid | 73-76 | 343 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 381 | 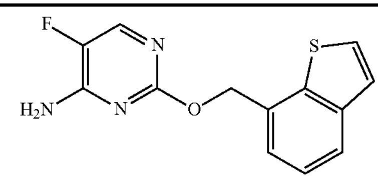 | A | A | A | A | light yellow solid | 173-175 | 276 | 274 | |
| 382 | 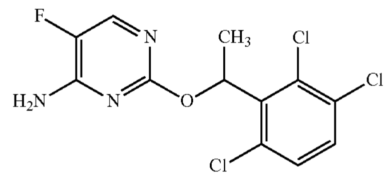 [SMILES: CC(Oc1ncc(F)c(N)n1)c1c(Cl)ccc(Cl)c1Cl] | D | A | A | A | white solid | 149-152 | | 336 | |
| 383 | 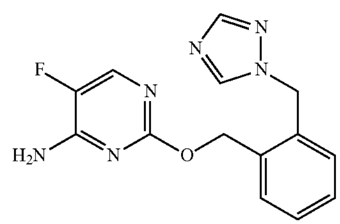 [SMILES: Nc1nc(OCc2ccccc2Cn2cncn2)ncc1F] | C | D | D | D | yellow solid | 118-120 | — | 299 | |
| 384 | 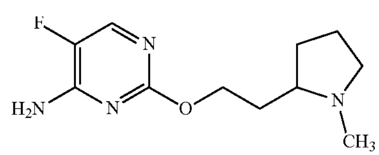 [SMILES: CN1CCCC1CCOc1ncc(F)c(N)n1] | C | A | B | A | dark oil | | 241 | 239 | |
| 385 | 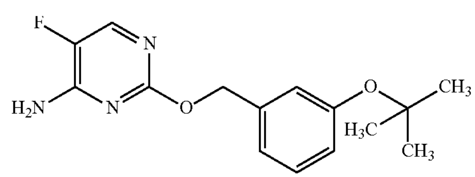 [SMILES: CC(C)(C)Oc1cccc(COc2ncc(F)c(N)n2)c1] | A | A | A | A | ivory solid | 104-105 | 292 | 290 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 386 | 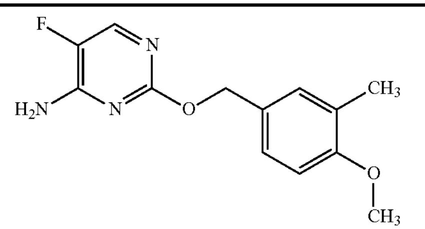 | A | A | A | A | white solid | 124 | 264 | | 262 |
| 387 | 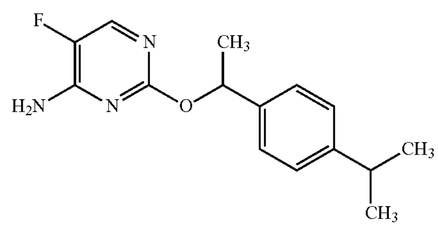 | A | A | A | A | orange oil | | | | 274 |
| 388 | 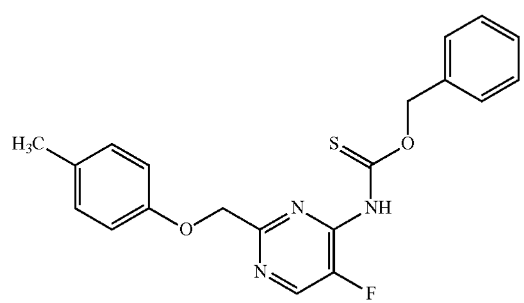 [SMILES: Cc1ccc(OCc2ncc(F)c(NC(=S)OCc3ccccc3)n2)cc1] | E | E | E | E | Pale yellow solid | | 384 | | |
| 389 | 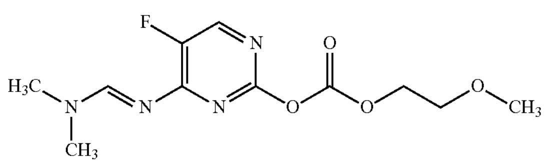 | A | A | A | A | light yellow solid | 88.5-89.5 | 308.8 (Na+) | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 390 | 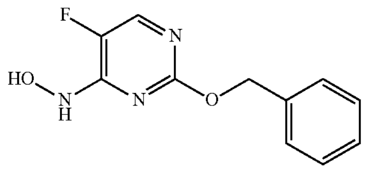 [SMILES: ONc1nc(OCc2ccccc2)ncc1F] | A | A | A | A | off-white solid | 96-100 | 236 | | 234 |
| 391 | 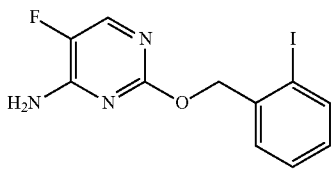 [SMILES: Nc1nc(OCc2ccccc2I)ncc1F] | C | A | B | A | off-white solid | 132-135 | 346 | | 344 |
| 392 | 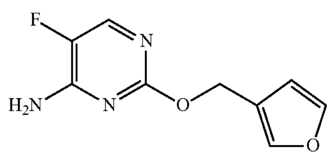 [SMILES: Nc1nc(OCc2ccoc2)ncc1F] | A | A | A | A | off-white solid | | 210 | | |
| 393 | 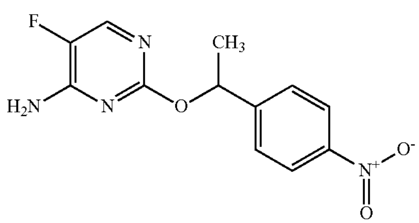 [SMILES: CC(Oc1ncc(F)c(N)n1)c1ccc([N+](=O)[O-])cc1] | C | A | C | A | clear oil | | | 277 | |
| 394 | 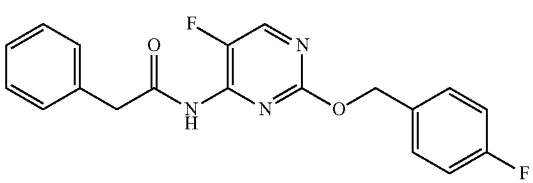 [SMILES: O=C(Cc1ccccc1)Nc1nc(OCc2ccc(F)cc2)ncc1F] | A | A | A | A | white solid | 177-179 | 356 | | 354 |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 395 | 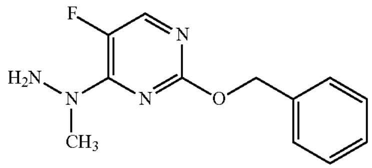 [SMILES: CN(N)c1nc(OCc2ccccc2)ncc1F] | C | B | D | D | yellow oil | | 249 | 247 | |
| 396 | 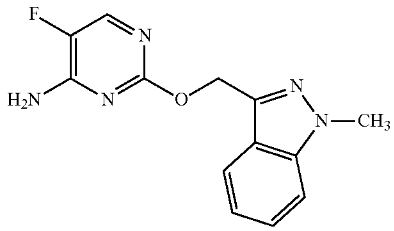 [SMILES: Cn1nc(COc2ncc(F)c(N)n2)c2ccccc21] | A | A | A | A | off-white solid | 181-183 | 274 | 272 | |
| 397 | 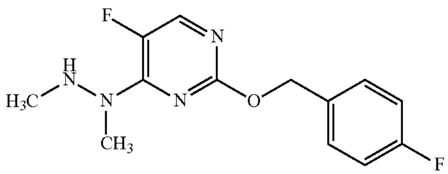 [SMILES: CNN(C)c1nc(OCc2ccc(F)cc2)ncc1F] | D | D | D | D | colorless oil | | 282 | 279 | |
| 398 | 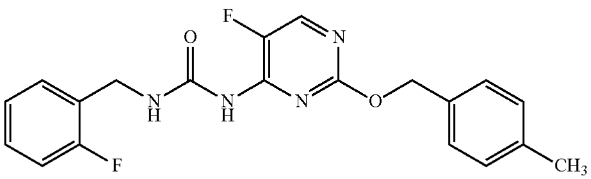 [SMILES: Cc1ccc(COc2ncc(F)c(NC(=O)NCc3ccccc3F)n2)cc1] | D | C | D | D | white solid | 176-178 | 385 | 383 | |
| 399 | 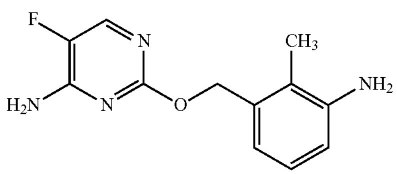 | A | A | B | A | white solid | 174 | 249 | 247 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 400 | 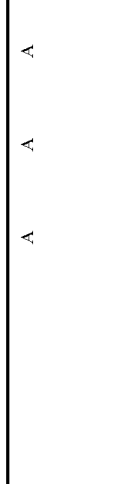 | A | A | A | A | off-white solid | 154-156 | 264 | 262 | |
| 401 | 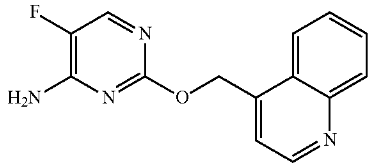 [SMILES: Nc1nc(OCc2ccnc3ccccc23)ncc1F] | A | A | A | A | off-white solid | | 271 | | |
| 402 | 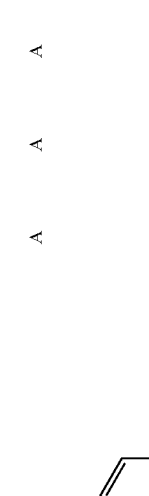 | A | A | A | A | white solid | 121-122 | 331 | | |
| 403 | 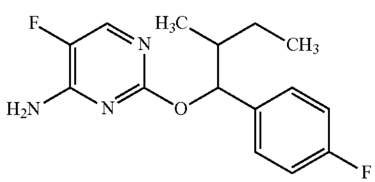 [SMILES: CCC(C)C(Oc1ncc(F)c(N)n1)c1ccc(F)cc1] | C | A | A | A | white solid | 93-94 | | 292 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 404 | 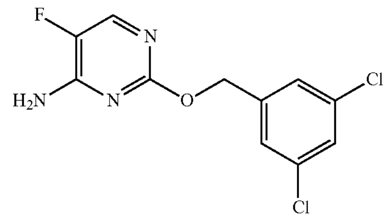 | A | A | A | A | white solid | | 289 | 287 | |
| 405 | 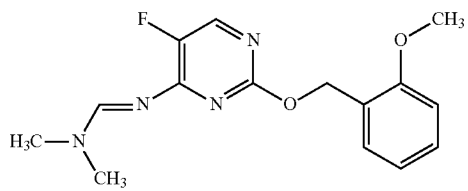 | A | A | A | A | clear pale yellow oil | | 305 | | |
| 406 | 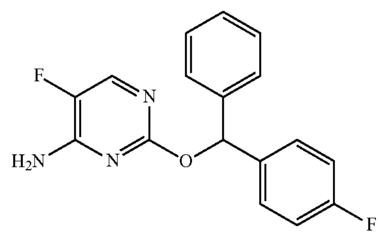 [SMILES: Nc1nc(OC(c2ccccc2)c2ccc(F)cc2)ncc1F] | A | A | A | A | white solid | 134-138 | | 312 | |
| 407 | 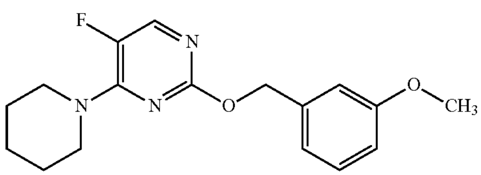 [SMILES: COc1cccc(COc2ncc(F)c(N3CCCCC3)n2)c1] | D | D | D | D | yellow oil | | 318 | | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 408 | 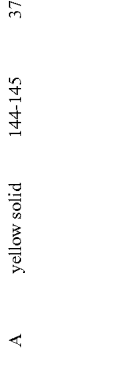 | D | A | D | A | yellow solid | 144-145 | 377 | 375 | |
| 409 | 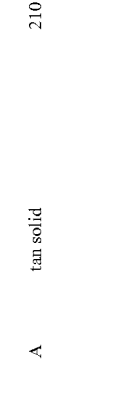 | A | A | A | A | tan solid | | 210 | | |
| 410 | 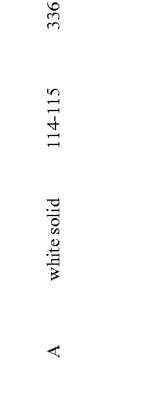 | B | A | B | A | white solid | 114-115 | 336 | | |
| 411 | 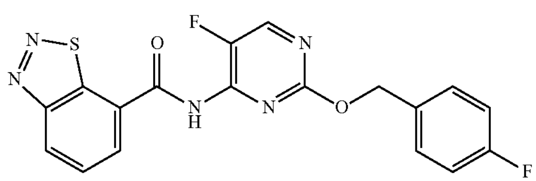 [SMILES: O=C(Nc1nc(OCc2ccc(F)cc2)ncc1F)c1cccc2nnsc12] | C | C | A | A | white solid | 138-142 | 400 | 398 | |
| 412 | 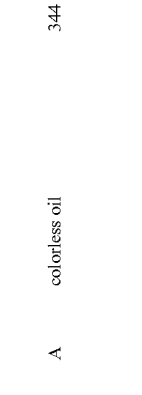 | D | B | D | A | colorless oil | | 344 | 342 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 413 | 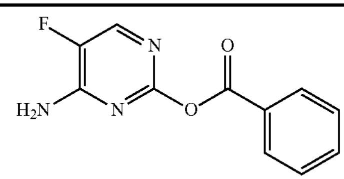 | A | A | A | A | white solid | 245-247 | 234 | 232 | |
| 414 | 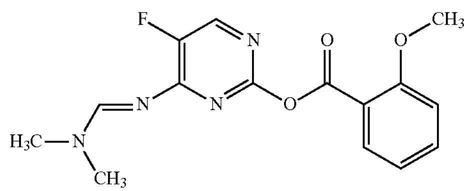 | E | E | E | E | white solid | 125 (dec) | 319 | | |
| 415 | 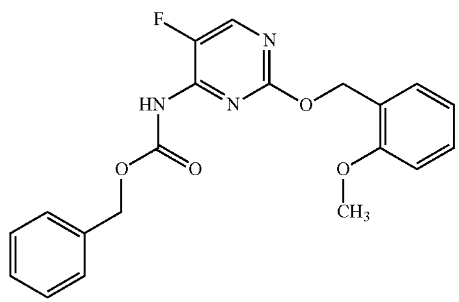 [SMILES: COc1ccccc1COc1ncc(F)c(NC(=O)OCc2ccccc2)n1] | A | A | B | A | | | 384 | 382 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 416 | 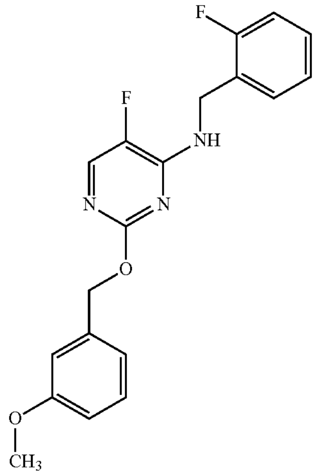 [SMILES: COc1cccc(COc2ncc(F)c(NCc3ccccc3F)n2)c1] | D | C | D | D | | | 358 | | |
| 417 | 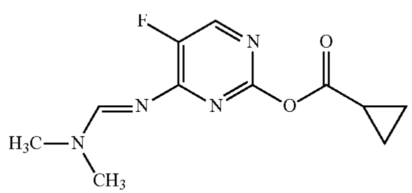 [SMILES: CN(C)/C=N/c1nc(OC(=O)C2CC2)ncc1F] | A | A | A | A | white solid | 105-115 (dec) | 253 | | |
| 418 | 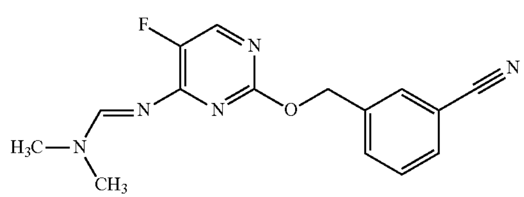 [SMILES: CN(C)/C=N/c1nc(OCc2cccc(C#N)c2)ncc1F] | A | A | A | A | brown oil | | 300 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 419 | 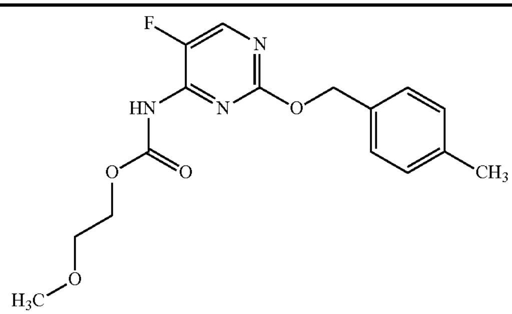 | A | A | A | A | | | 336 | 334 | |
| 420 | 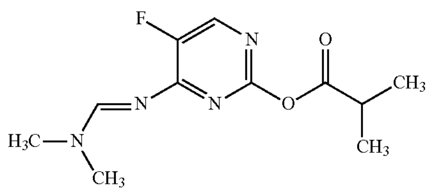 [SMILES: CC(C)C(=O)Oc1ncc(F)c(/N=C/N(C)C)n1] | A | A | A | A | white solid | 93-94 | 255 | | |
| 421 | 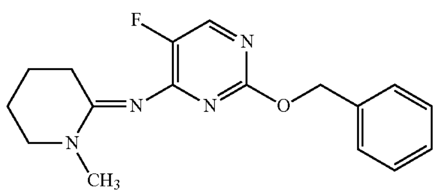 | A | A | A | A | pale amber oil | | 315 | | |
| 422 | 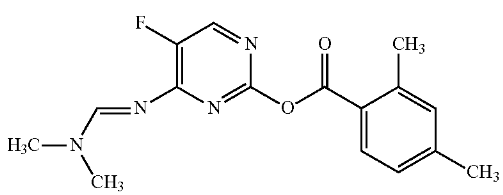 | A | A | A | A | white solid | 111-112 | 317 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 423 | 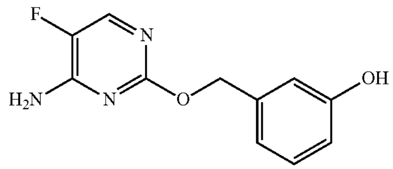 [SMILES: Nc1nc(OCc2cccc(O)c2)ncc1F] | D | D | D | D | white solid | | 236 | 234 | |
| 424 | 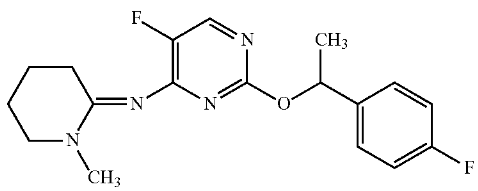 | B | A | B | A | pale amber solid | 93-100 | 347 | | |
| 425 | 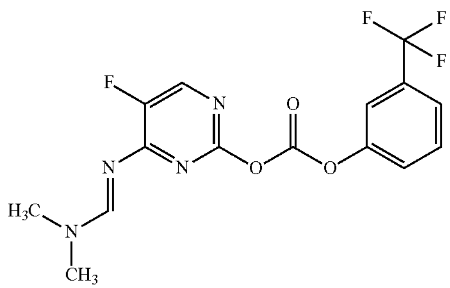 [SMILES: CN(C)/C=N/c1nc(OC(=O)Oc2cccc(C(F)(F)F)c2)ncc1F] | A | A | A | A | white solid | 95-99 | 372 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 426 | 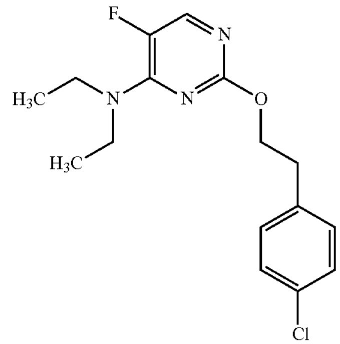 [SMILES: CCN(CC)c1nc(OCCc2ccc(Cl)cc2)ncc1F] | E | E | E | E | Colourless liquid | | 324 | | |
| 427 | 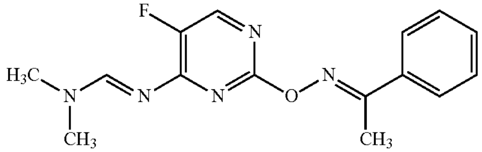 [SMILES: C/C(=N\Oc1ncc(F)c(/N=C/N(C)C)n1)c1ccccc1] | A | A | A | A | yellow white solid | 125-126 | 302 | | |
| 428 | 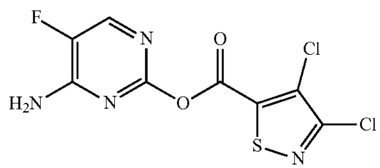 [SMILES: Nc1nc(OC(=O)c2snc(Cl)c2Cl)ncc1F] | C | A | B | B | light yellow solid | | 309 | 307 | |
| 429 | 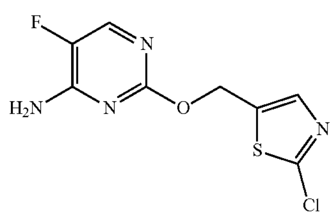 [SMILES: Nc1nc(OCc2cnc(Cl)s2)ncc1F] | A | A | A | A | beige solid | 168-169 | 261 | 259 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SEPTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 430 | 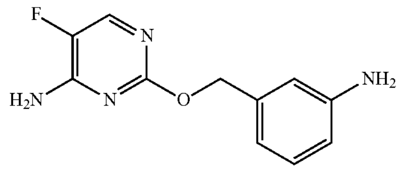 | A | A | A | A | dark brown solid | 128-130 | 235 | 233 | |
| 431 | 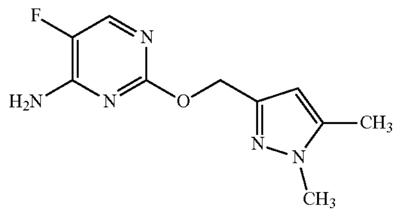 | A | A | A | A | clear yellow oil | | 238 | | |
| 432 | 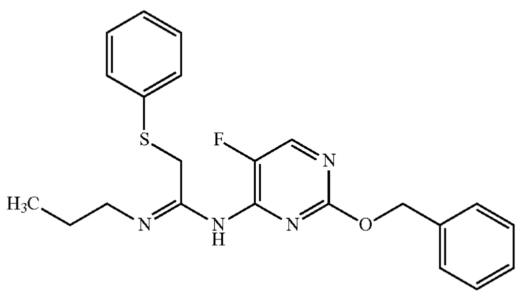 [SMILES: CCC/N=C(\CSc1ccccc1)Nc1nc(OCc2ccccc2)ncc1F] | E | E | E | E | Pale yellow solid | | 411 | | |
| 433 | 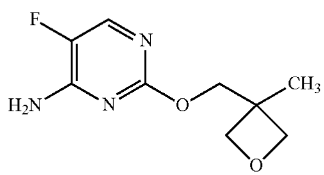 | D | D | D | D | yellow solid | | 214 | 212 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 434 | 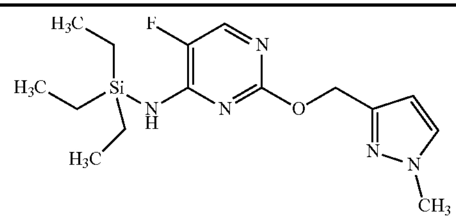 | A | A | A | A | clear oil | | 338 | | |
| 435 | 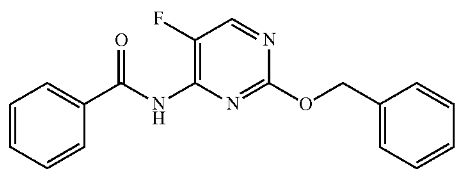 [SMILES: O=C(Nc1nc(OCc2ccccc2)ncc1F)c1ccccc1] | B | A | A | A | white solid | 115-117 | 324 | 322 | |
| 436 | 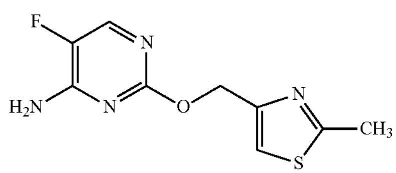 [SMILES: Cc1nc(COc2ncc(F)c(N)n2)cs1] | A | A | A | A | white solid | 115 | 241 | | |
| 437 | 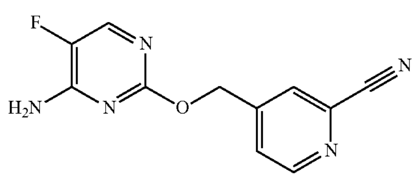 | D | B | D | B | brown solid | 182-183 | 246 | 244 | |
| 438 | 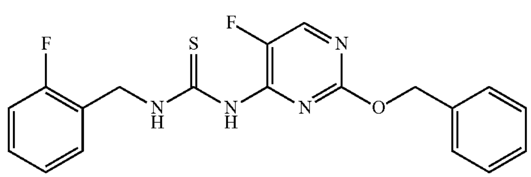 [SMILES: Fc1ccccc1CNC(=S)Nc1nc(OCc2ccccc2)ncc1F] | D | D | B | A | white solid | 162-164 | 387 | 385 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 439 | 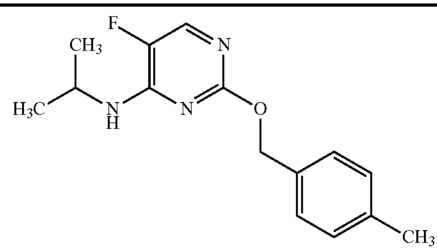 | E | E | E | E | Yellow solid | | 298 [M + Na] | | |
| 440 | 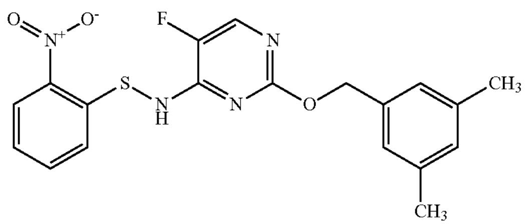 [SMILES: Cc1cc(C)cc(COc2ncc(F)c(NSc3ccccc3[N+](=O)[O-])n2)c1] | C | D | D | D | yellow solid | 172-179 | 401 | 399 | |
| 441 | 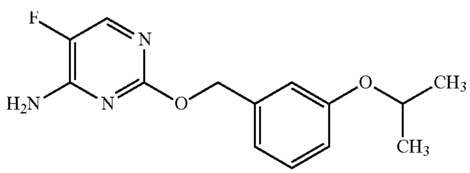 [SMILES: CC(C)Oc1cccc(COc2ncc(F)c(N)n2)c1] | A | A | A | A | light yellow solid | 61-62 | 278 | 276 | |
| 442 | 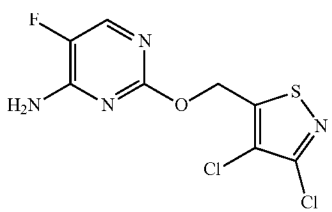 [SMILES: Nc1nc(OCc2snc(Cl)c2Cl)ncc1F] | A | A | A | A | fluffy off-white solid | 195-196 | 297 | 293 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 443 | 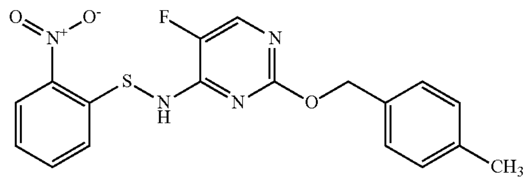 [SMILES: Cc1ccc(COc2ncc(F)c(NSc3ccccc3[N+](=O)[O-])n2)cc1] | C | C | A | A | yellow solid | 173-177 | 387 | 385 | |
| 444 | 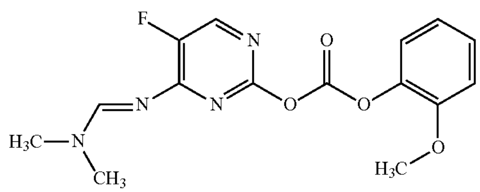 | A | A | A | A | white solid | 121-123 | 336 | | |
| 445 | 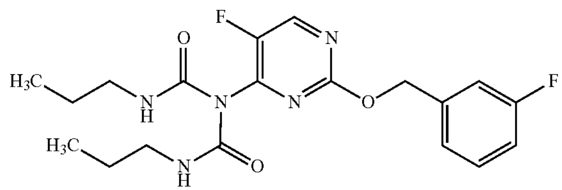 [SMILES: CCCNC(=O)N(C(=O)NCCC)c1nc(OCc2cccc(F)c2)ncc1F] | A | A | B | A | brown oil | | 408 | 406 | |
| 446 | 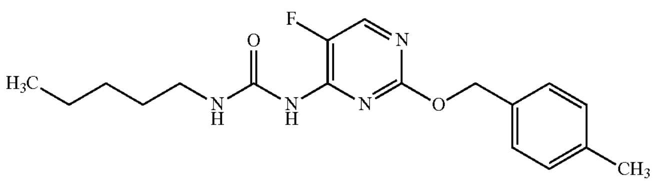 | E | E | E | E | white solid | 152-153 | 347 | 345 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 447 | 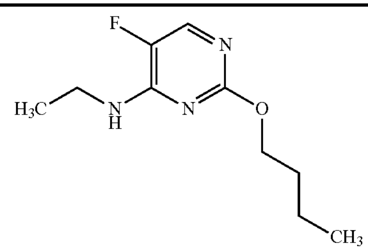 | E | E | E | E | Pale yellow liquid | | 214 | | |
| 448 | 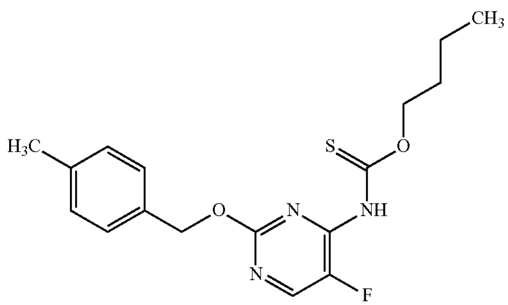 [SMILES: CCCCOC(=S)Nc1nc(OCc2ccc(C)cc2)ncc1F] | E | E | E | E | Pale yellow solid | | 364 | | |
| 449 | 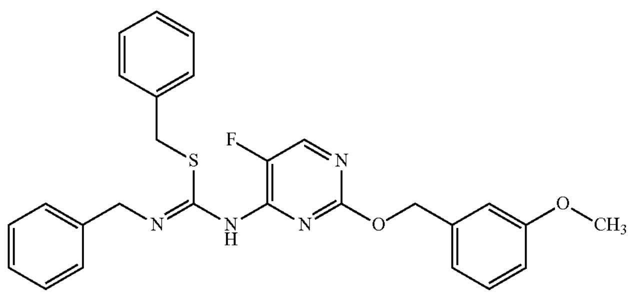 [SMILES: COc1cccc(COc2ncc(F)c(N/C(=N/Cc3ccccc3)SCc3ccccc3)n2)c1] | E | E | E | E | Off white solid | | 489 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 450 | 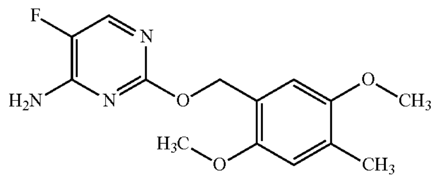 [SMILES: COc1cc(COc2ncc(F)c(N)n2)c(OC)cc1C] | A | B | A | A | white solid | 155 | 294 | 292 | |
| 451 | 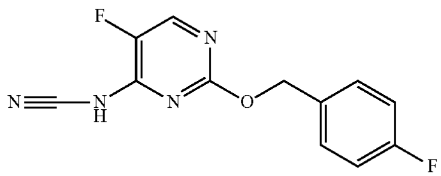 [SMILES: N#CNc1nc(OCc2ccc(F)cc2)ncc1F] | D | D | D | D | white solid | 158-160 | 263 | 261 | |
| 452 | 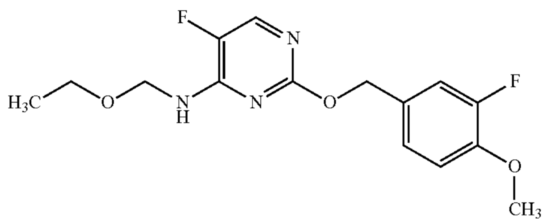 [SMILES: CCOCNc1nc(OCc2ccc(OC)c(F)c2)ncc1F] | A | A | A | A | white solid | 108-109 | 326 | 324 | |
| 453 | 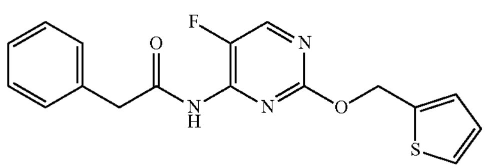 [SMILES: O=C(Cc1ccccc1)Nc1nc(OCc2cccs2)ncc1F] | B | A | A | A | light yellow glass | | 344 | 342 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 454 | 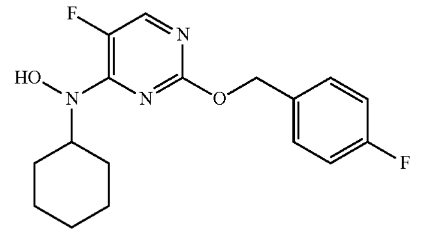 [SMILES: ON(c1nc(OCc2ccc(F)cc2)ncc1F)C1CCCCC1] | C | D | D | A | off white solid | 153.5-157.9 | 337 | | 334 |
| 455 | 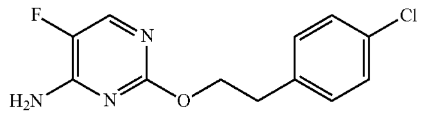 [SMILES: Nc1nc(OCCc2ccc(Cl)cc2)ncc1F] | C | A | B | A | white solid | 101-103 | 268 | 266 | |
| 456 | 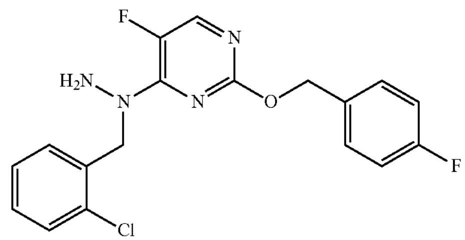 [SMILES: NN(Cc1ccccc1Cl)c1nc(OCc2ccc(F)cc2)ncc1F] | D | A | B | A | yellow oil | | 377 | | |
| 457 | 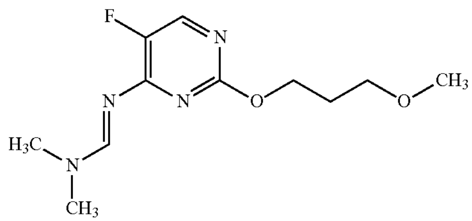 | B | A | B | A | LIGHT YELLOW SOLID | 53-55 | 257 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 458 | 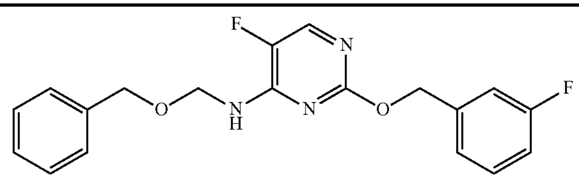 | D | D | D | B | white tacky solid | | 358 | 356 | |
| 459 | 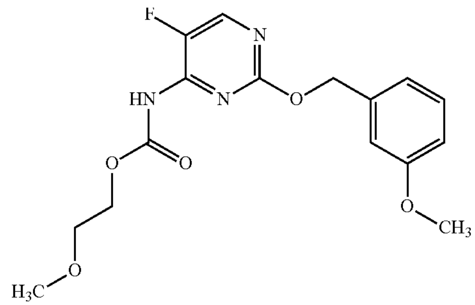 | A | A | B | A | | | 352 | 350 | |
| 460 | 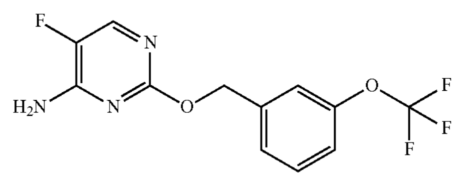 [SMILES: Nc1nc(OCc2cccc(OC(F)(F)F)c2)ncc1F] | A | A | A | A | white solid | | 304 | 302 | |
| 461 | 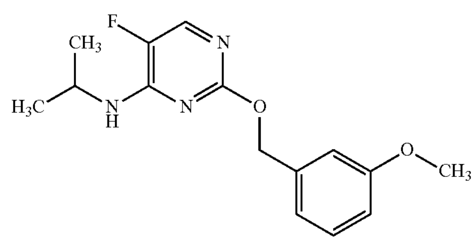 [SMILES: COc1cccc(COc2ncc(F)c(NC(C)C)n2)c1] | E | E | E | E | Gummy liquid | | | 290 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 462 | 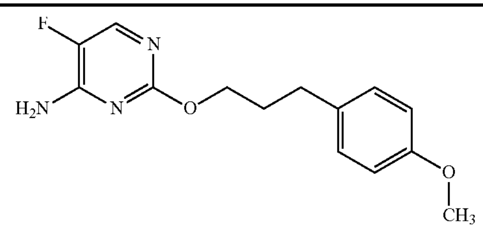 | B | C | B | A | white solid | 143-144 | 278 | 276 | |
| 463 | 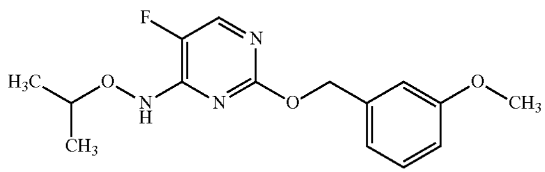 [SMILES: COc1cccc(COc2ncc(F)c(NOC(C)C)n2)c1] | C | B | D | B | colorless oil | | 308 | 306 | |
| 464 | 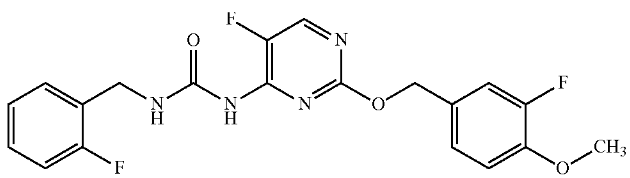 [SMILES: COc1ccc(COc2ncc(F)c(NC(=O)NCc3ccccc3F)n2)cc1F] | D | C | D | D | off-white solid | 171-174 | 419 | 417 | |
| 465 | 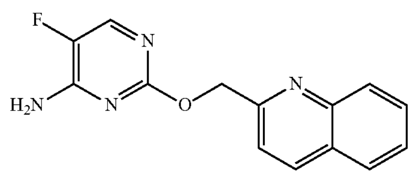 [SMILES: Nc1nc(OCc2ccc3ccccc3n2)ncc1F] | A | A | A | A | tan solid | 155-157 | 271 | 269 | |
| 466 | 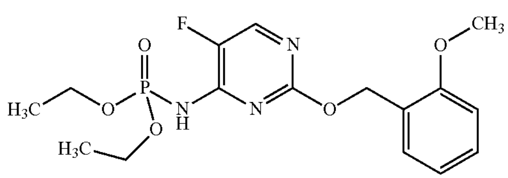 [SMILES: CCOP(=O)(Nc1nc(OCc2ccccc2OC)ncc1F)OCC] | D | D | D | D | light yellow glass | | 386 | 384 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 467 | 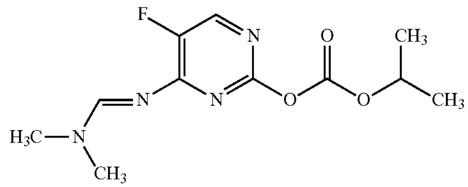 | A | A | A | A | white solid | 120-121 | 292.8 (Na+) | | |
| 468 | 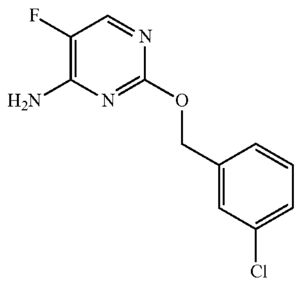 [SMILES: Nc1nc(OCc2cccc(Cl)c2)ncc1F] | A | A | A | A | white powder | 143-145 | 254 | | |
| 469 | 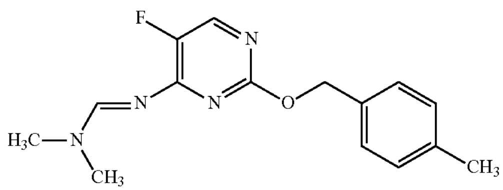 | A | A | A | A | white solid | 98-99 | 288 | | |
| 470 | 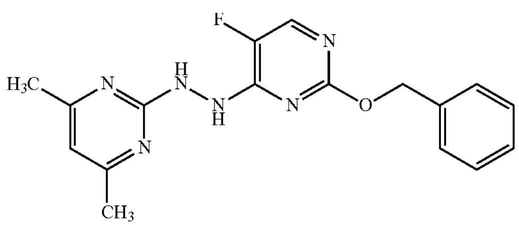 [SMILES: Cc1cc(C)nc(NNc2nc(OCc3ccccc3)ncc2F)n1] | C | C | D | D | pale pink solid | 154.4-157.2 | 342 | 340 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 471 | 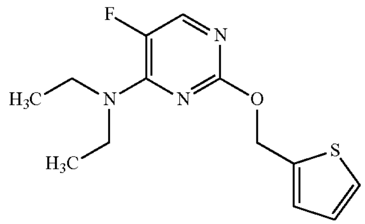 [SMILES: CCN(CC)c1nc(OCc2cccs2)ncc1F] | E | E | E | E | Gummy liquid | | 282 | | |
| 472 | 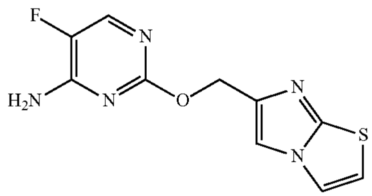 [SMILES: Nc1nc(OCc2cn3ccsc3n2)ncc1F] | A | A | A | A | yellow solid | 58-61 | 266 | 264 | |
| 473 | 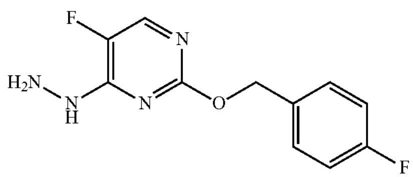 | C | A | C | A | fluffy white solid | 123-124 | 253 | 251 | |
| 474 | 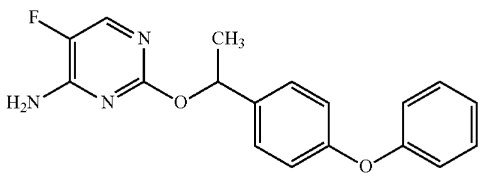 [SMILES: CC(Oc1ncc(F)c(N)n1)c1ccc(Oc2ccccc2)cc1] | A | A | A | A | clear oil | | | 324 | |
| 475 | 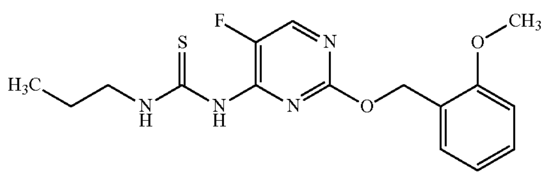 | B | A | B | A | white solid | 170-171 | 349 | 351 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 476 | 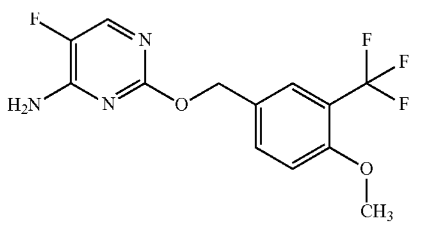 [SMILES: COc1ccc(COc2ncc(F)c(N)n2)cc1C(F)(F)F] | A | A | A | A | white solid | 123-125 | 318 | 316 | |
| 477 | 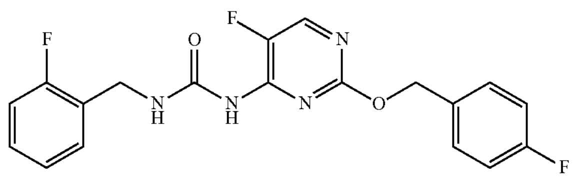 | D | B | D | D | white solid | 189-191 | 389 | 387 | |
| 478 | 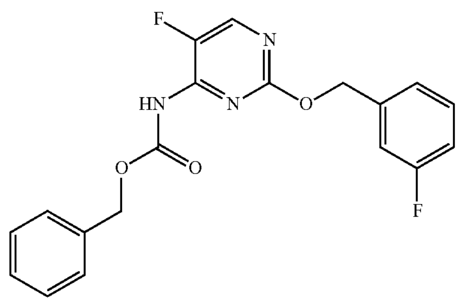 [SMILES: O=C(Nc1nc(OCc2cccc(F)c2)ncc1F)OCc1ccccc1] | A | A | B | A | | | 372 | 370 | |
| 479 | 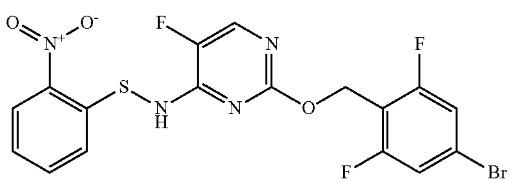 [SMILES: O=[N+]([O-])c1ccccc1SNc1nc(OCc2c(F)cc(Br)cc2F)ncc1F] | B | B | A | A | yellow solid | 143-150 | 488 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 480 | 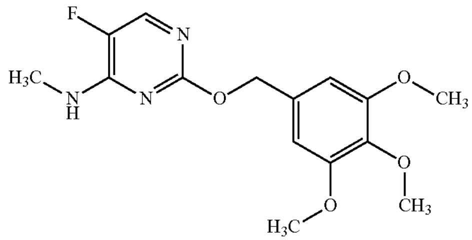 | D | D | D | D | pale yellow solid | 150-154 | 324 | 322 | |
| 481 | 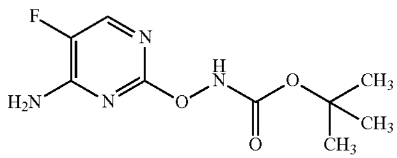 | A | A | A | A | white solid | 169-174 (dec) | | | |
| 482 | 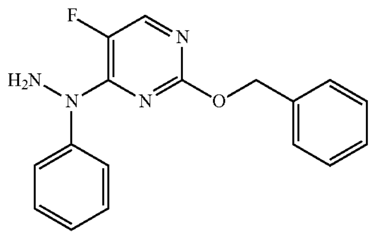 [SMILES: NN(c1ccccc1)c1nc(OCc2ccccc2)ncc1F] | D | C | D | D | off white solid | 111-115 | 312 | 309 | |
| 483 | 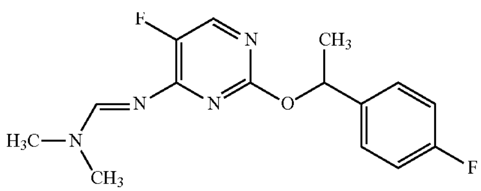 [SMILES: CC(Oc1ncc(F)c(/N=C/N(C)C)n1)c1ccc(F)cc1] | A | A | A | A | clear yellow oil | | 307 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 484 | 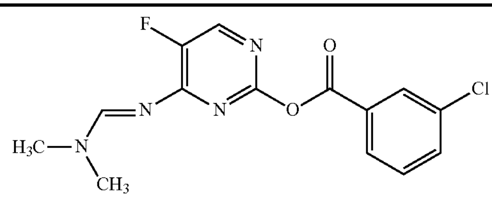 | A | A | A | A | yellow oil | | 323 | | |
| 485 | 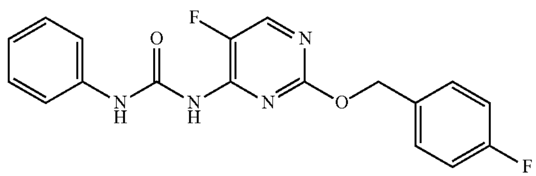 [SMILES: O=C(Nc1ccccc1)Nc1nc(OCc2ccc(F)cc2)ncc1F] | D | D | D | D | white solid | 206-207 | 357 | 355 | |
| 486 | 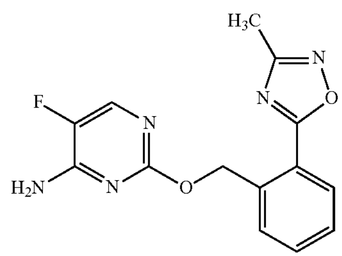 [SMILES: Cc1noc(-c2ccccc2COc2ncc(F)c(N)n2)n1] | C | C | D | D | ivory solid | 188-189 | 302 | 300 | |
| 487 | 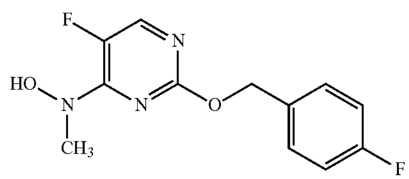 [SMILES: CN(O)c1nc(OCc2ccc(F)cc2)ncc1F] | D | A | D | A | white solid | 153.8-157.1 | 268 | 266 | |
| 488 | 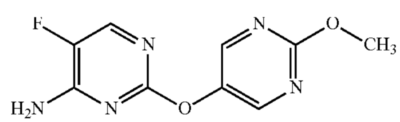 [SMILES: COc1ncc(Oc2ncc(F)c(N)n2)cn1] | D | D | D | D | white solid | 191-192 | 238 | 236 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 489 | 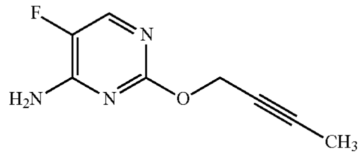 | A | A | D | B | white solid | 122-123 | 182 | 180 | |
| 490 | 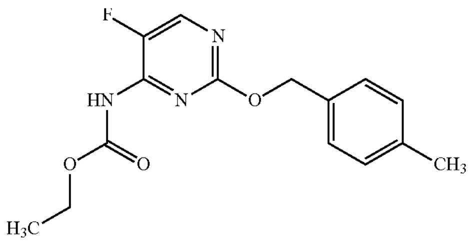 [SMILES: CCOC(=O)Nc1nc(OCc2ccc(C)cc2)ncc1F] | A | A | A | A | | | 306 | 304 | |
| 491 | 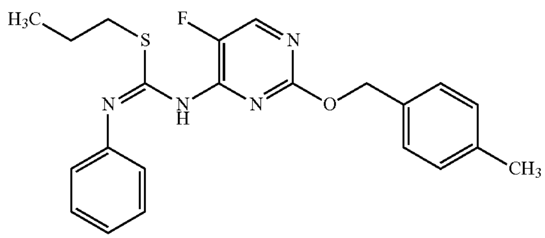 [SMILES: CCCS/C(=N/c1ccccc1)Nc1nc(OCc2ccc(C)cc2)ncc1F] | E | E | E | E | Pale yellow solid | | 411 | | |
| 492 | 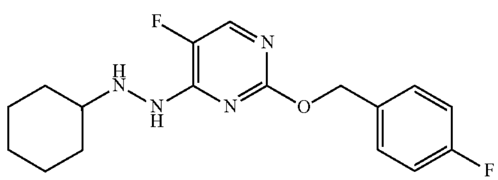 [SMILES: Fc1ccc(COc2ncc(F)c(NNC3CCCCC3)n2)cc1] | D | C | D | C | pale brown solid | 139-143 | 335 | 333 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 493 | 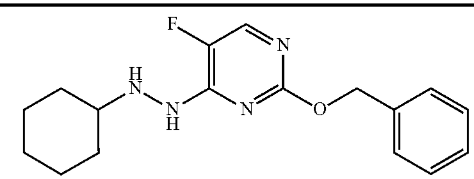 | D | D | D | C | pale yellow solid | 95-98 | 318 | 315 | |
| 494 | 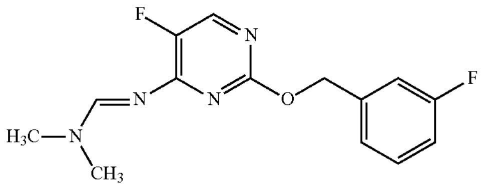 | A | A | A | A | off white solid | 77-78 | 293 | | |
| 495 | 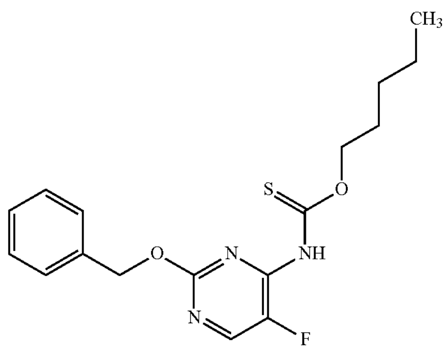 [SMILES: CCCCCOC(=S)Nc1nc(OCc2ccccc2)ncc1F] | E | E | E | E | Yellow solid | | 350 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 496 | 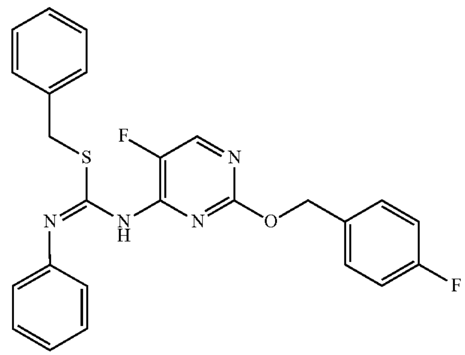 [SMILES: Fc1ccc(COc2ncc(F)c(N/C(=N\c3ccccc3)SCc3ccccc3)n2)cc1] | E | E | E | E | Pale yellow solid | | 463 | | |
| 497 | 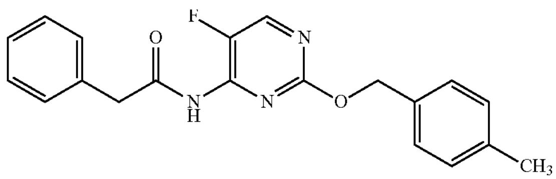 [SMILES: Cc1ccc(COc2ncc(F)c(NC(=O)Cc3ccccc3)n2)cc1] | D | C | B | A | white solid | 123-124 | 352 | 350 | |
| 498 | 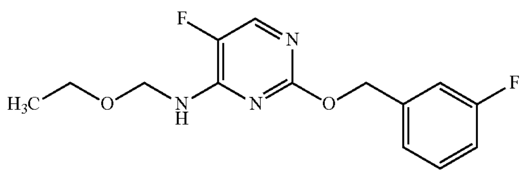 [SMILES: CCOCNc1nc(OCc2cccc(F)c2)ncc1F] | A | A | A | A | white solid | 56-58 | 296 | 294 | |
| 499 | 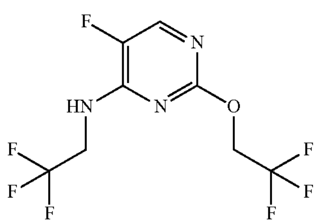 [SMILES: Fc1cnc(OCC(F)(F)F)nc1NCC(F)(F)F] | E | E | E | E | | | | 292 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 500 | 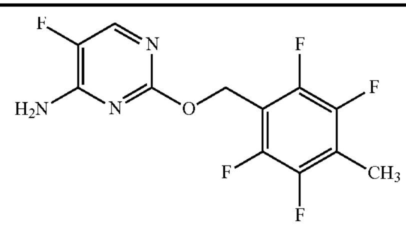 | A | A | A | A | white solid | 147-150 | 306 | 304 | |
| 501 | 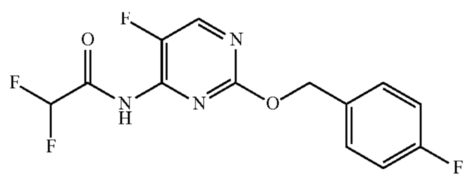 [SMILES: O=C(Nc1nc(OCc2ccc(F)cc2)ncc1F)C(F)F] | A | A | A | A | viscous semisolid | | 316 | 314 | |
| 502 | 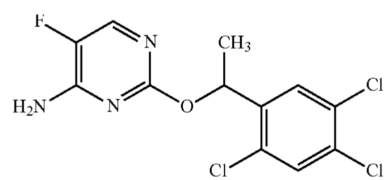 [SMILES: CC(Oc1ncc(F)c(N)n1)c1cc(Cl)c(Cl)cc1Cl] | D | D | D | D | white solid | 130-134 | | 336 | |
| 503 | 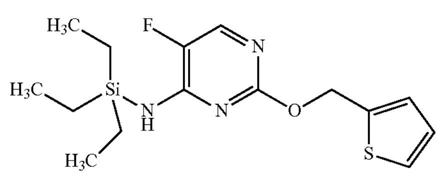 [SMILES: CC[Si](CC)(CC)Nc1nc(OCc2cccs2)ncc1F] | A | A | A | A | clear oil | | 341 | 339 | |
| 504 | 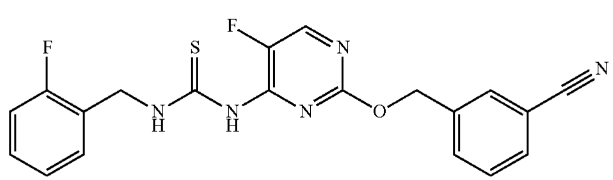 | D | D | D | B | off-white solid | 165-166 | 412 | 410 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 505 | 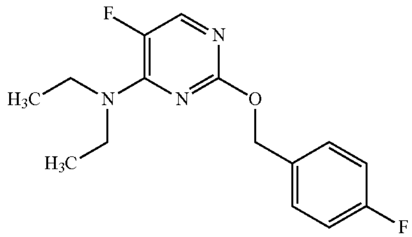 [SMILES: CCN(CC)c1nc(OCc2ccc(F)cc2)ncc1F] | E | E | E | E | Brown liquid | | 294 | | |
| 506 | 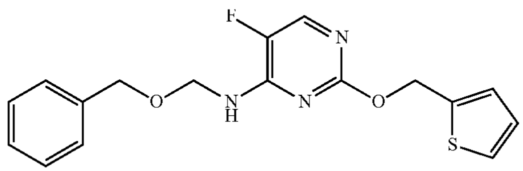 [SMILES: Fc1cnc(OCc2cccs2)nc1NCOCc1ccccc1] | D | D | C | A | white solid | 95-97 | 346 | 344 | |
| 507 | 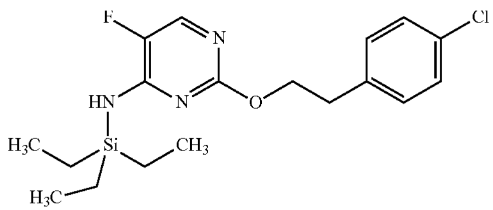 [SMILES: CC[Si](CC)(CC)Nc1nc(OCCc2ccc(Cl)cc2)ncc1F] | D | A | B | A | YELLOW GUMMY SOLID | | 382 | | |
| 508 | 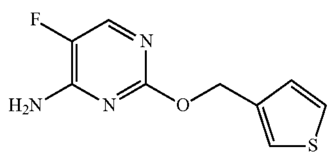 [SMILES: Nc1nc(OCc2ccsc2)ncc1F] | A | A | A | A | tan solid | | 226 | | |
| 509 | 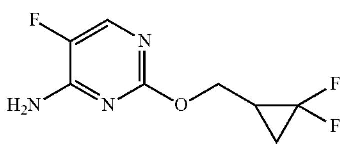 [SMILES: Nc1nc(OCC2CC2(F)F)ncc1F] | C | D | D | D | tan solid | 72-77 | 220 | 218 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 510 | 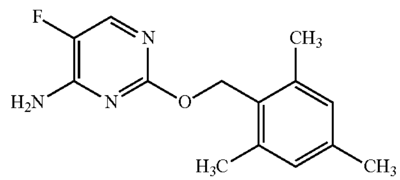 [SMILES: Cc1cc(C)c(COc2ncc(F)c(N)n2)c(C)c1] | B | A | B | A | white solid | 150 | 262 | | 260 |
| 511 | 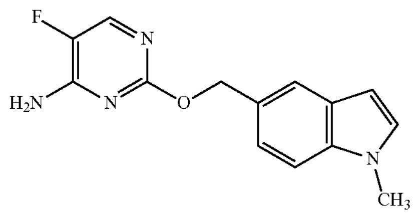 | C | C | B | B | yellow oil | | | 271 | |
| 512 | 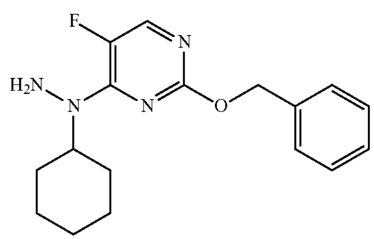 [SMILES: NN(c1nc(OCc2ccccc2)ncc1F)C1CCCCC1] | D | D | D | B | off white solid | 63-67 | 318 | | |
| 513 | 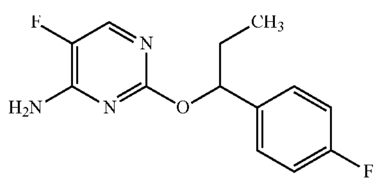 [SMILES: CCC(Oc1ncc(F)c(N)n1)c1ccc(F)cc1] | A | A | A | A | sticky solid | | | 264 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 514 | 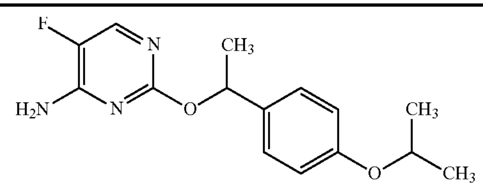 | A | A | A | A | yellow oil | | | | 288 |
| 515 | 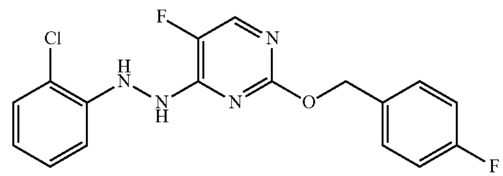 | D | D | D | A | brown solid | 123-129 | 363 | 361 | |
| 516 | 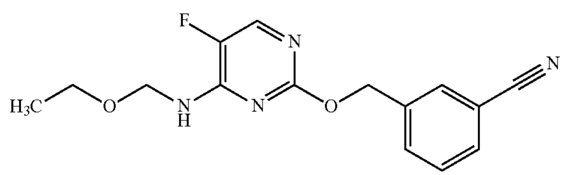 [SMILES: CCOCNc1nc(OCc2cccc(C#N)c2)ncc1F] | A | A | A | A | clear pale yellow oil | | 303 | 301 | |
| 517 | 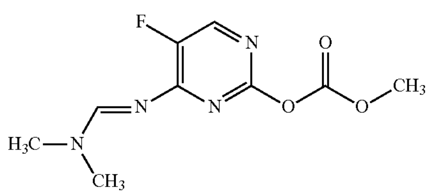 | A | A | A | A | white solid | 125-127 | 243 | | |
| 518 | 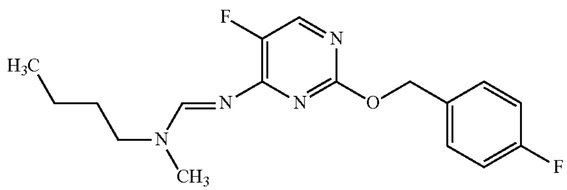 | A | A | A | A | tan oil | | 335 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 519 | 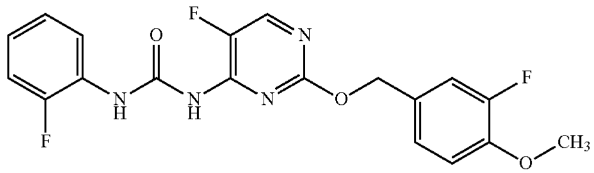 | D | D | D | D | white solid | 208-211 | 405 | 403 | |
| 520 | 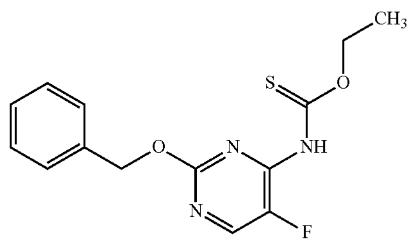 [SMILES: CCOC(=S)Nc1nc(OCc2ccccc2)ncc1F] | E | E | E | E | Pale yellow solid | | 308 | | |
| 521 | 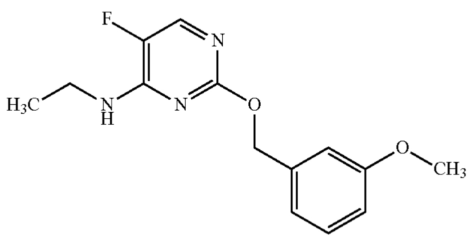 [SMILES: CCNc1nc(OCc2cccc(OC)c2)ncc1F] | E | E | E | E | Pale yellow solid | | 278 | | |
| 522 | 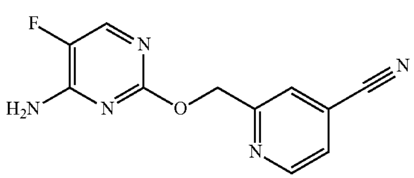 [SMILES: N#Cc1ccnc(COc2ncc(F)c(N)n2)c1] | D | D | D | C | rust solid | 188-189 | 246 | 244 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 523 | 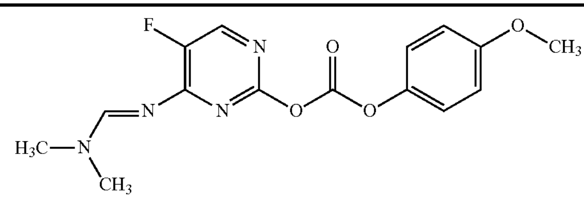 | A | A | A | A | white solid | 127-130 | 356.8 (Na+) | | |
| 524 | 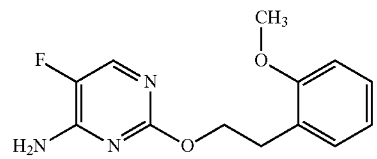 | D | B | D | B | white solid | 100-101 | 264 | 262 | |
| 525 | 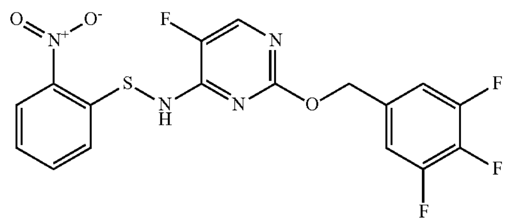 [SMILES: O=[N+]([O-])c1ccccc1SNc1nc(OCc2cc(F)c(F)c(F)c2)ncc1F] | A | A | A | A | yellow solid | 154-160 | 427 | 425 | |
| 526 | 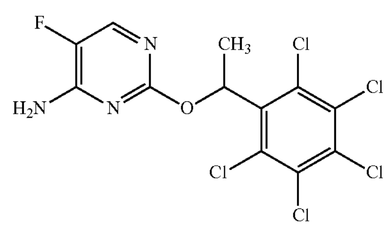 [SMILES: CC(Oc1ncc(F)c(N)n1)c1c(Cl)c(Cl)c(Cl)c(Cl)c1Cl] | D | D | D | B | yellow solid | 216-218 | | 404 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 527 | 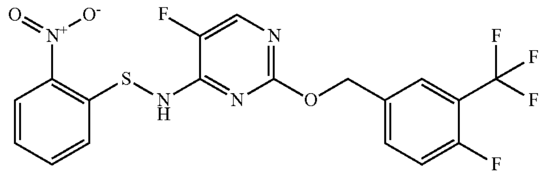 [SMILES: O=[N+]([O-])c1ccccc1SNc1nc(OCc2ccc(F)c(C(F)(F)F)c2)ncc1F] | D | D | B | A | yellow solid | 178-182 | 459 | 457 | |
| 528 | 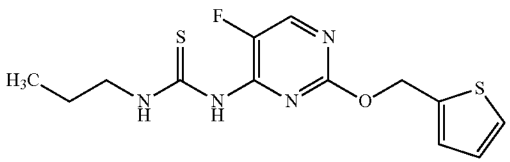 [SMILES: CCCNC(=S)Nc1nc(OCc2cccs2)ncc1F] | D | B | A | A | tan solid | 121-124 | 327 | 325 | |
| 529 | 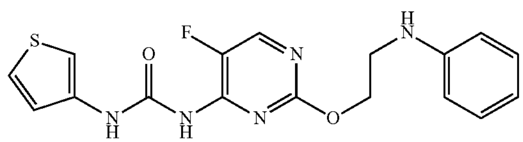 [SMILES: O=C(Nc1ccsc1)Nc1nc(OCCNc2ccccc2)ncc1F] | D | D | D | D | OFF WHITE SOLID | 188-190 | | | |
| 530 | 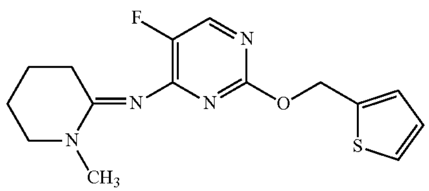 | B | A | A | A | pale amber oil | | 321 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 531 | 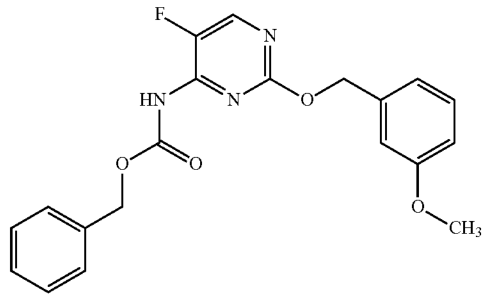 [SMILES: COc1cccc(COc2ncc(F)c(NC(=O)OCc3ccccc3)n2)c1] | A | A | A | A | | | 384 | 382 | |
| 532 | 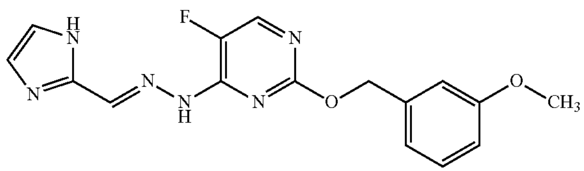 [SMILES: COc1cccc(COc2ncc(F)c(N/N=C/c3ncc[nH]3)n2)c1] | D | C | C | B | off white solid | 157-162 | 343 | 341 | |
| 533 | 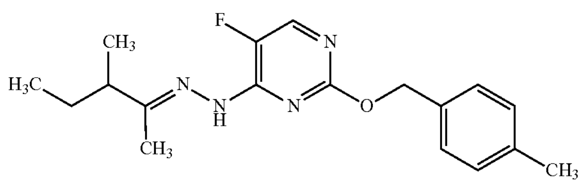 [SMILES: CCC(C)/C(C)=N/Nc1nc(OCc2ccc(C)cc2)ncc1F] | D | C | B | B | white solid | 120-123 | 331 | 329 | |
| 534 | 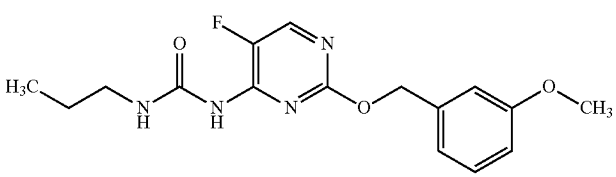 [SMILES: CCCNC(=O)Nc1nc(OCc2cccc(OC)c2)ncc1F] | D | C | D | C | white solid | 147-148 | 335 | 333 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 535 | 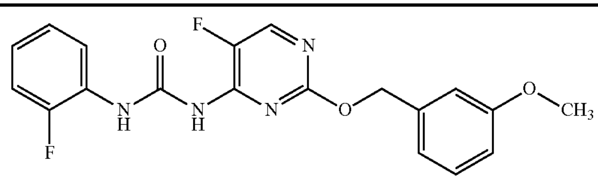 | D | D | D | D | white solid | 182-183 | 387 | 385 | |
| 536 | 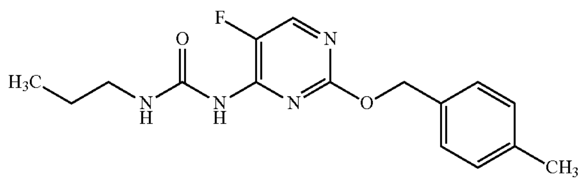 [SMILES: CCCNC(=O)Nc1nc(OCc2ccc(C)cc2)ncc1F] | C | C | D | D | white solid | 171-172 | 319 | 317 | |
| 537 | 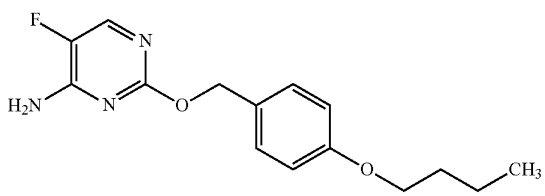 [SMILES: CCCCOc1ccc(COc2ncc(F)c(N)n2)cc1] | A | A | A | A | off-white solid | 112-113 | 292 | 290 | |
| 538 | 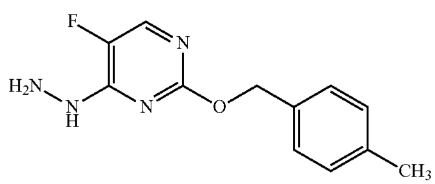 | B | A | C | B | pale biege solid | 103-107 | 250 | 247 | |
| 539 | 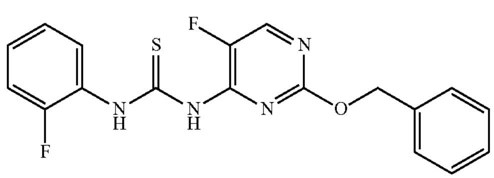 [SMILES: Fc1ccccc1NC(=S)Nc1nc(OCc2ccccc2)ncc1F] | D | D | A | A | white solid | 142-144 | 373 | 371 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 540 | 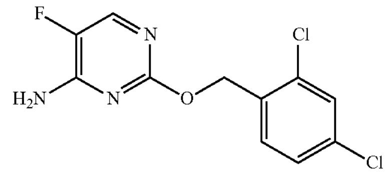 [SMILES: Nc1nc(OCc2ccc(Cl)cc2Cl)ncc1F] | A | A | A | A | white solid | 185 | 289 | 287 | |
| 541 | 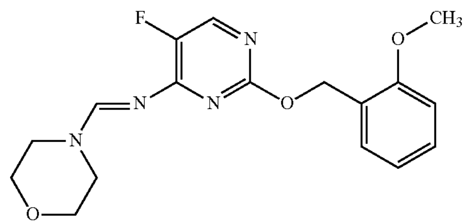 [SMILES: COc1ccccc1COc1ncc(F)c(/N=C/N2CCOCC2)n1] | A | A | A | A | white solid | 99-100 | 347 | | |
| 542 | 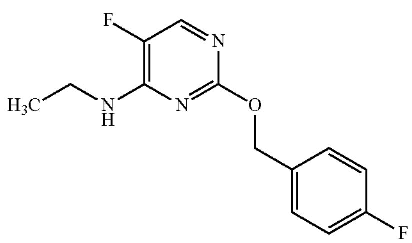 [SMILES: CCNc1nc(OCc2ccc(F)cc2)ncc1F] | E | E | E | E | Off white solid | | 266 | | |
| 543 | 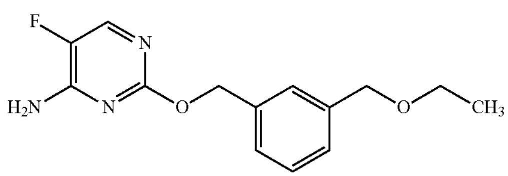 [SMILES: CCOCc1cccc(COc2ncc(F)c(N)n2)c1] | A | A | A | A | colorless oil | | | 276 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 544 | 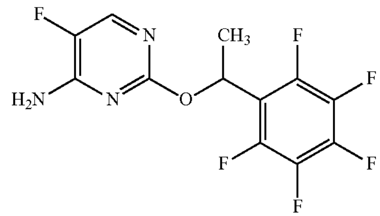 [SMILES: CC(Oc1ncc(F)c(N)n1)c1c(F)c(F)c(F)c(F)c1F] | D | D | D | C | white solid | 134-140 | | | 322 |
| 545 | 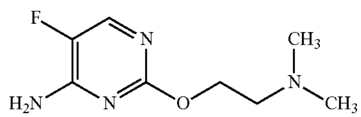 | D | B | D | C | white solid | 134-135 | | 199 | |
| 546 | 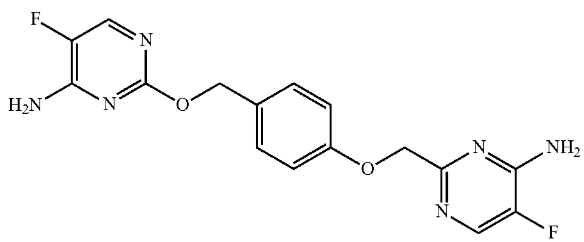 [SMILES: Nc1nc(COc2ccc(COc3ncc(F)c(N)n3)cc2)ncc1F] | B | D | B | B | white solid | 235-238 | | 360 | |
| 547 | 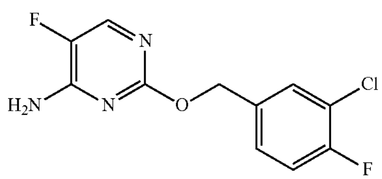 | A | A | A | A | white solid | 130-132 | 273 | 271 | |
| 548 | 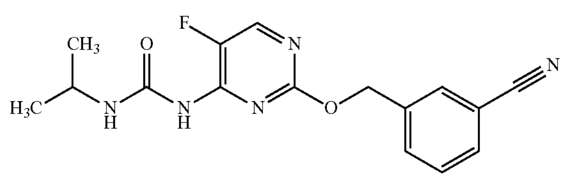 [SMILES: CC(C)NC(=O)Nc1nc(OCc2cccc(C#N)c2)ncc1F] | D | D | D | D | white solid | 196-198 | 330 | 328 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 549 | 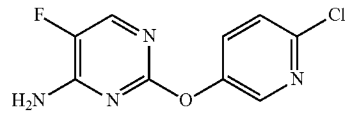 | D | D | C | D | white solid | 187-188 | 241 | 239 | |
| 550 | 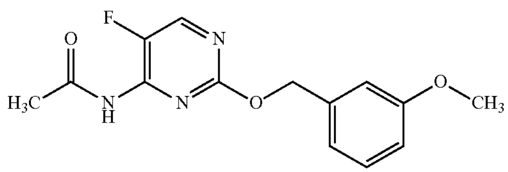 | A | A | A | A | white solid | 105-106 | 292 | 290 | |
| 551 | 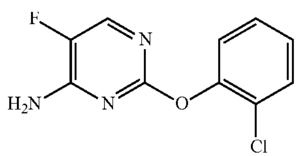 [SMILES: Nc1nc(Oc2ccccc2Cl)ncc1F] | E | E | D | C | white solid | 155-156 | 240 | 238 | |
| 552 | 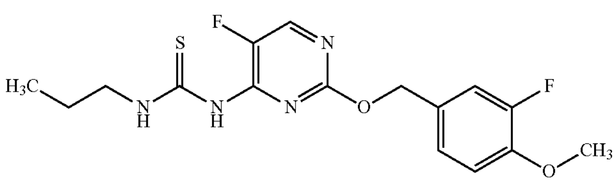 | D | A | D | A | off-white solid | 148-149 | 369 | 367 | |
| 553 | 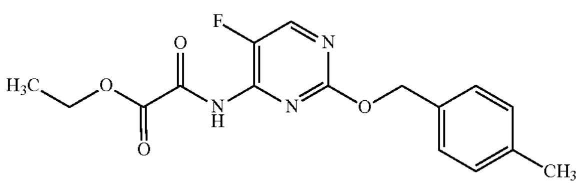 [SMILES: CCOC(=O)C(=O)Nc1nc(OCc2ccc(C)cc2)ncc1F] | A | A | A | A | clear oil | | 334 | 332 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 554 | 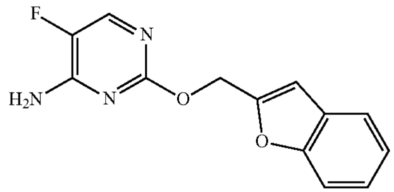 | C | A | C | A | white solid | 123-124 | 260 | 258 | |
| 555 | 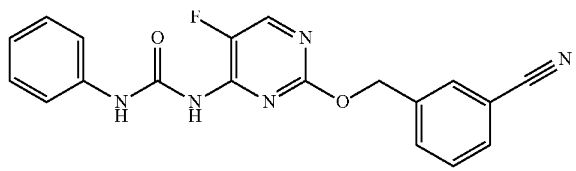 [SMILES: N#Cc1cccc(COc2ncc(F)c(NC(=O)Nc3ccccc3)n2)c1] | D | D | D | D | white solid | 203-205 (dec) | 364 | 362 | |
| 556 | 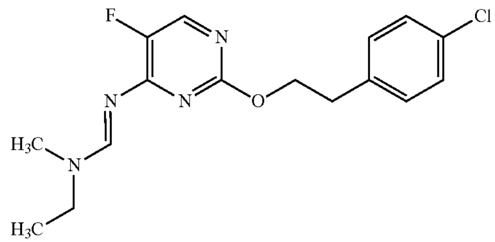 [SMILES: CCN(C)/C=N/c1nc(OCCc2ccc(Cl)cc2)ncc1F] | D | A | C | A | WHITE SOLID | 100-103 | 323 | | |
| 557 | 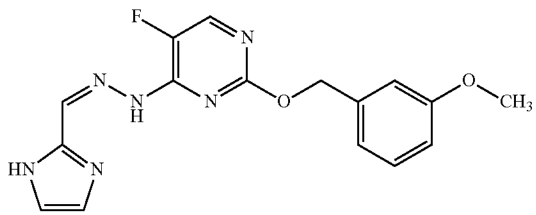 [SMILES: COc1cccc(COc2ncc(F)c(N/N=C\c3ncc[nH]3)n2)c1] | D | D | C | D | white solid | 208-210 | 343 | 341 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 558 | 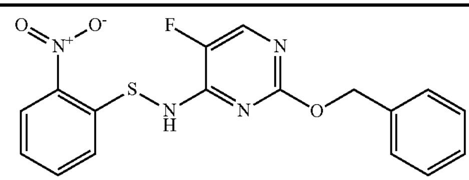 | C | C | A | A | yellow solid | 167-171 | 373 | 371 | |
| 559 | 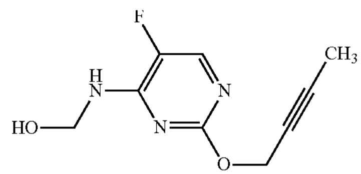 | A | A | B | A | PALE YELLOW SOLID | | 212 | | |
| 560 | 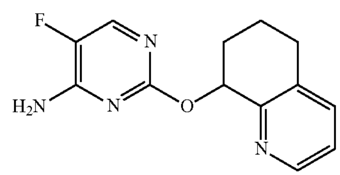 [SMILES: Nc1nc(OC2CCCc3cccnc32)ncc1F] | D | A | D | C | yellow solid | | 261 | 259 | |
| 561 | 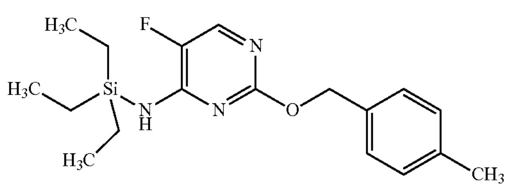 | A | A | A | A | clear oil | | 349 | | |
| 562 | 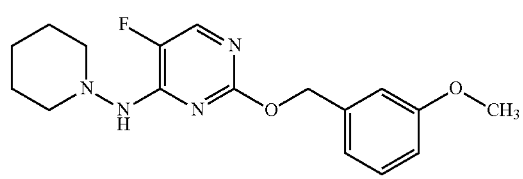 [SMILES: COc1cccc(COc2ncc(F)c(NN3CCCCC3)n2)c1] | D | C | D | D | yellow oil | | 333 | 331 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SEPTTR 1DP 25 ppm | SEPTTR 1DP 100 ppm | Phys. App. | MP | Mass Spec. (ES+) | Mass Spec. (ES-) | GCMS |
|---|---|---|---|---|---|---|---|---|---|---|
| 563 | 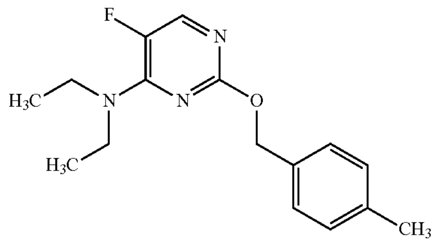 | E | E | E | E | Colourless liquid | | 290 | | |
| 564 | 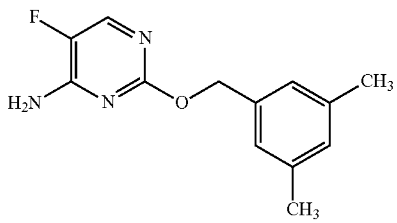 | C | A | B | A | white solid | 109 | 248 | 246 | |
| 565 | 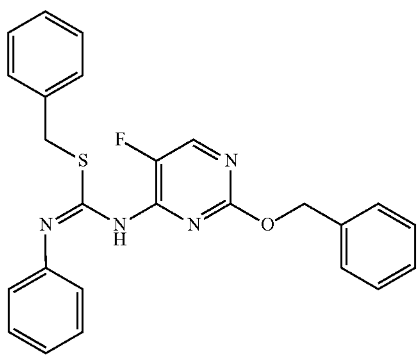 [SMILES: Fc1cnc(OCc2ccccc2)nc1N/C(=N\c1ccccc1)SCc1ccccc1] | E | E | E | E | White solid | | 445 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 566 | 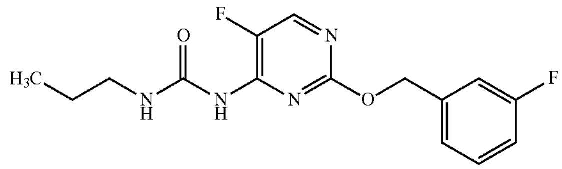 [SMILES: CCCNC(=O)Nc1nc(OCc2cccc(F)c2)ncc1F] | D | D | D | D | white solid | 158-159 | 323 | 321 | |
| 567 | 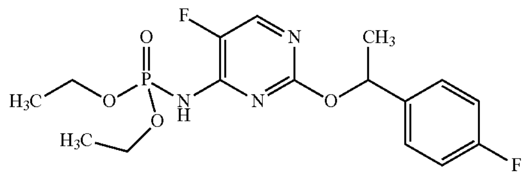 [SMILES: CCOP(=O)(Nc1nc(OC(C)c2ccc(F)cc2)ncc1F)OCC] | C | A | C | B | clear yellow oil | | 388 | 386 | |
| 568 | 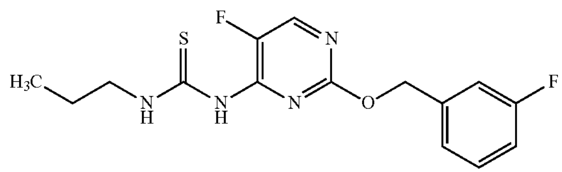 [SMILES: CCCNC(=S)Nc1nc(OCc2cccc(F)c2)ncc1F] | A | A | B | A | off-white solid | 125-126 | 339 | 337 | |
| 569 | 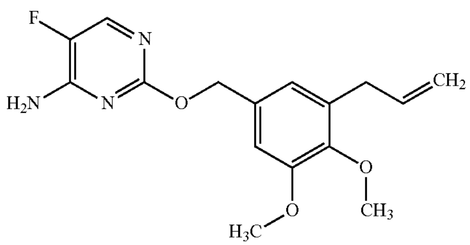 [SMILES: C=CCc1cc(COc2ncc(F)c(N)n2)cc(OC)c1OC] | B | A | A | A | white solid | 90 | 320 | 318 | |
| 570 | 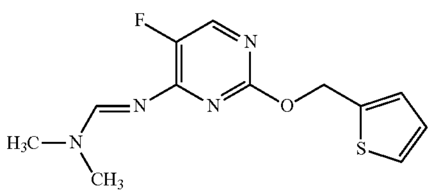 | A | A | A | A | off white solid | 101-102 | 281 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 571 | 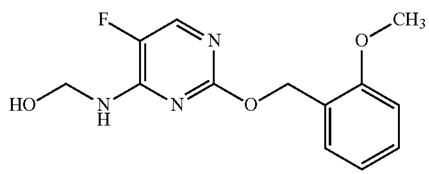 [SMILES: COc1ccccc1COc1ncc(F)c(NCO)n1] | A | A | A | A | white solid | 132-133 | 280 | 278 | |
| 572 | 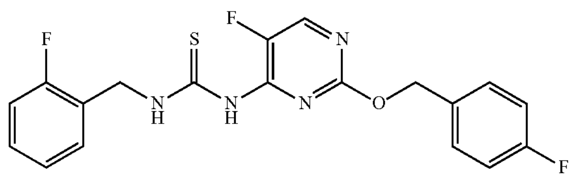 | C | B | C | A | off-white solid | 178-179 | 405 | 403 | |
| 573 | 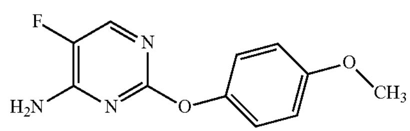 [SMILES: COc1ccc(Oc2ncc(F)c(N)n2)cc1] | D | D | C | B | white solid | 201-202 | 236 | 234 | |
| 574 | 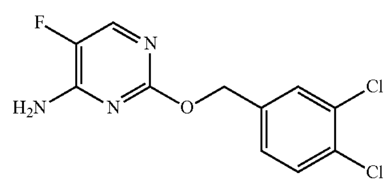 | A | A | A | A | white solid | 131 | 289 | 287 | |
| 575 | 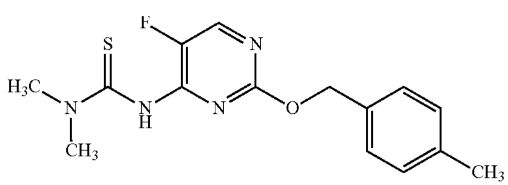 | E | E | E | E | yellow oil | | 321 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SEPTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 576 | 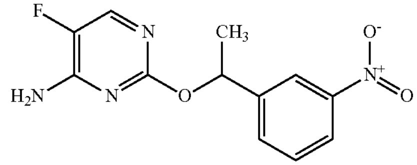 [SMILES: CC(Oc1ncc(F)c(N)n1)c1cccc([N+](=O)[O-])c1] | C | A | C | A | white solid | 117-122 | | 277 | |
| 577 | 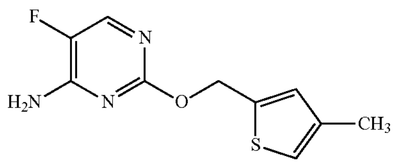 [SMILES: Cc1csc(COc2ncc(F)c(N)n2)c1] | A | A | A | A | off-white solid | 86-88 | 240 | | |
| 578 | 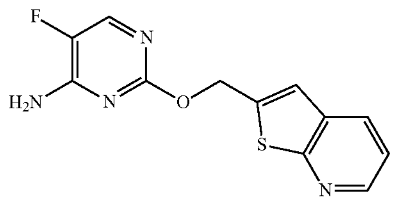 [SMILES: Nc1nc(OCc2cc3cccnc3s2)ncc1F] | A | A | A | A | pale yellow solid | 140-142 | 277 | | |
| 579 | 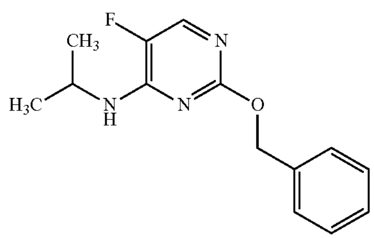 [SMILES: CC(C)Nc1nc(OCc2ccccc2)ncc1F] | E | E | E | E | Pale yellow solid | | 262 | | |
| 580 | 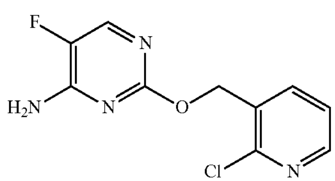 [SMILES: Nc1nc(OCc2cccnc2Cl)ncc1F] | D | B | B | A | white solid | 185-187 | 256 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 581 | 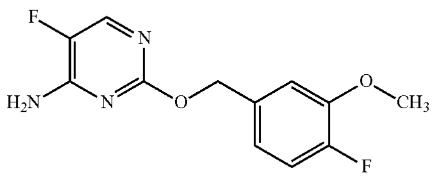 [SMILES: COc1cc(COc2ncc(F)c(N)n2)ccc1F] | A | A | A | A | white solid | 120 | 268 | 266 | |
| 582 | 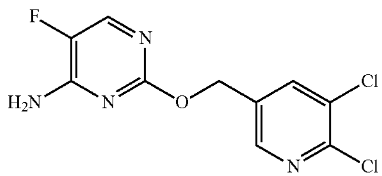 [SMILES: Nc1nc(OCc2cnc(Cl)c(Cl)c2)ncc1F] | A | A | A | A | off-white solid | 162 | 290 | 288 | |
| 583 | 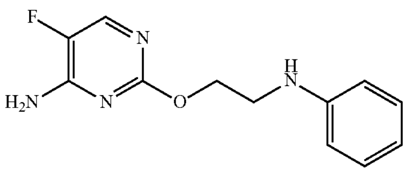 [SMILES: Nc1nc(OCCNc2ccccc2)ncc1F] | A | A | D | A | white solid | 108-109 | 249 | 247 | |
| 584 | 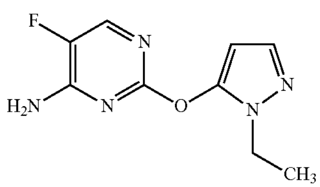 | D | A | D | A | off white solid | 153-154 | 224 | 222 | |
| 585 | 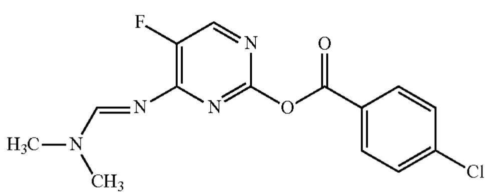 [SMILES: CN(C)/C=N/c1nc(OC(=O)c2ccc(Cl)cc2)ncc1F] | A | A | A | A | white solid | 125 (dec) | 323 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 586 | 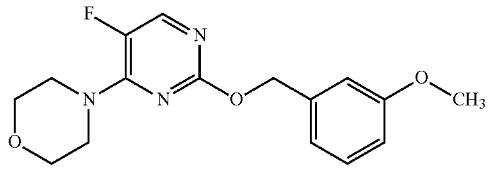 [SMILES: COc1cccc(COc2ncc(F)c(N3CCOCC3)n2)c1] | D | D | D | D | colorless oil | | 320 | | |
| 587 | 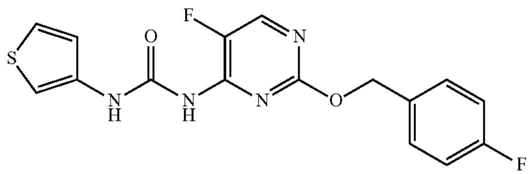 [SMILES: O=C(Nc1ccsc1)Nc1nc(OCc2ccc(F)cc2)ncc1F] | C | A | D | D | white solid | 200-201 | 363 | 361 | |
| 588 | 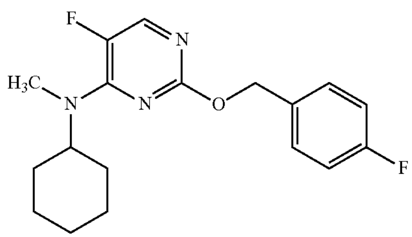 [SMILES: CN(c1nc(OCc2ccc(F)cc2)ncc1F)C1CCCCC1] | D | D | D | D | white solid | 86.3-89.8 | 335 | | |
| 589 | 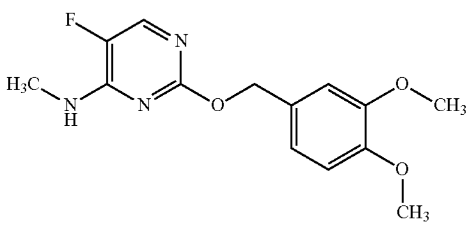 | D | D | D | D | white solid | >200 | 294 | 292 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 590 | 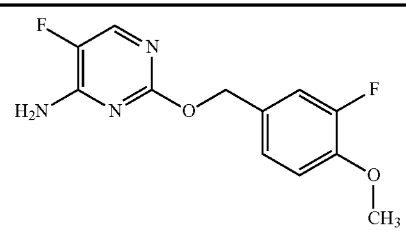 | A | A | A | A | white solid | 154 | 268 | | 266 |
| 591 | 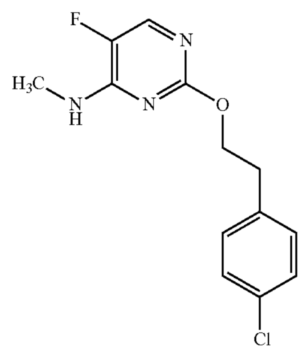 [SMILES: CNc1nc(OCCc2ccc(Cl)cc2)ncc1F] | E | E | E | E | Off white solid | | 282 | | |
| 592 | 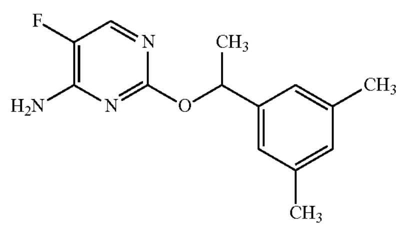 [SMILES: Cc1cc(C)cc(C(C)Oc2ncc(F)c(N)n2)c1] | A | A | A | A | yellow oil | | | 260 | |
| 593 | 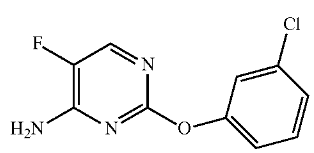 [SMILES: Nc1nc(Oc2cccc(Cl)c2)ncc1F] | E | E | D | B | white solid | 134-135 | 240 | 238 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 594 | 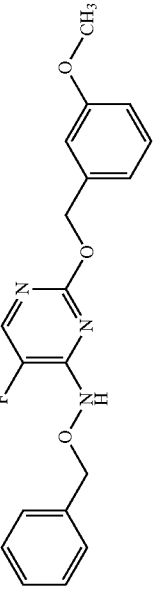 | D | C | D | B | white solid | 104.4-107 | 356 | 354 | |
| 595 | 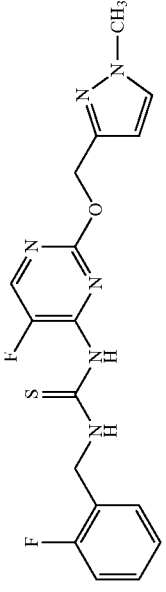 | D | D | C | A | off-white solid | 160-161 | 391 | 389 | |
| 596 | 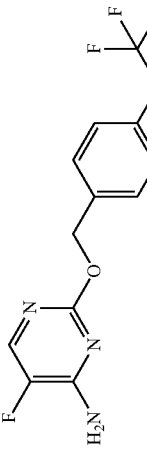 | A | A | A | A | off-white solid | 105-107 | 305 | 302 | |
| 597 | 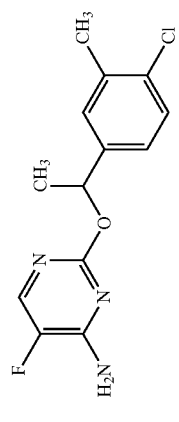 | A | A | A | A | clear oil | | | 280 | |
| 598 | 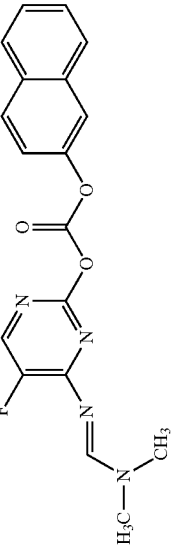 | A | A | B | A | white solid | 156-160 | 356 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 599 | 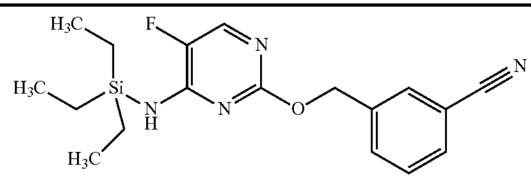 | A | A | B | A | clear oil | | 359 | 357 | |
| 600 | 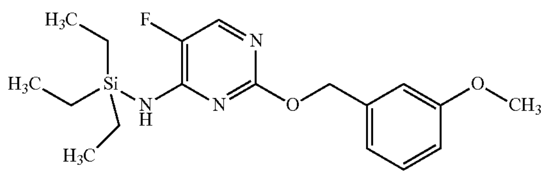 [SMILES: CC[Si](CC)(CC)Nc1nc(OCc2cccc(OC)c2)ncc1F] | A | A | A | A | clear oil | | 365 | | |
| 601 | 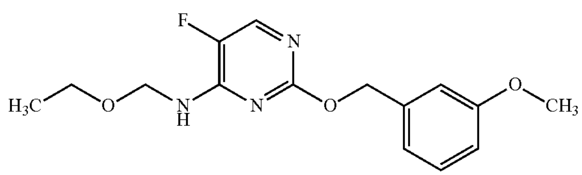 [SMILES: CCOCNc1nc(OCc2cccc(OC)c2)ncc1F] | A | A | A | A | white solid | 53-54 | 308 | 306 | |
| 602 | 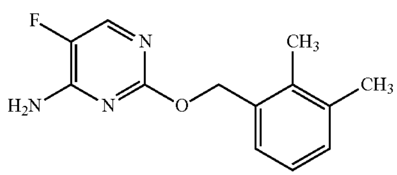 | D | D | D | B | white solid | 144 | | 247 | |
| 603 | 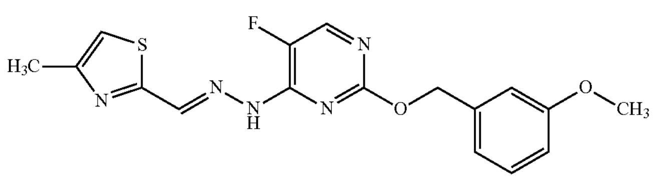 | D | D | C | A | off white solid | 173-176 | 374 | 372 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 604 | 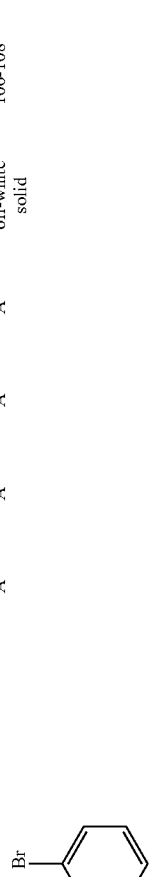 | A | A | A | A | off-white solid | 106-108 | #### | #### | |
| 605 | 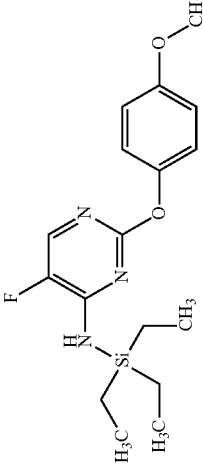 | D | A | B | A | WHITE SOLID | 64-67 | 350 | | |
| 606 | 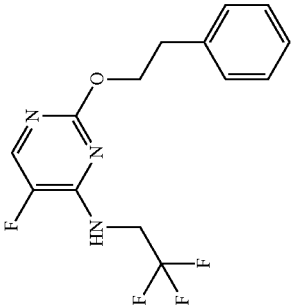 | E | E | E | E | | | 316 | | |
| 607 | 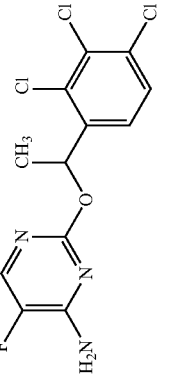 | D | C | D | D | white solid | 112-113 | | 334 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 608 | 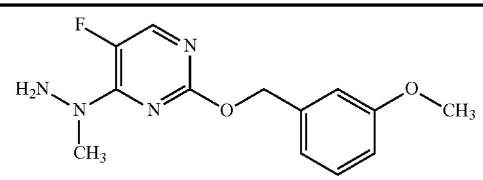 | B | A | B | A | dark red oil | | 279 | 262 | |
| 609 | 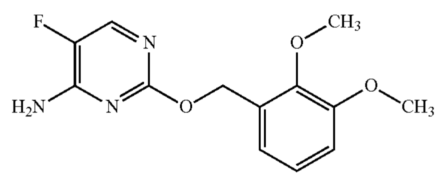 [SMILES: COc1cccc(COc2ncc(F)c(N)n2)c1OC] | A | A | A | A | white solid | 112 | 280 | 278 | |
| 610 | 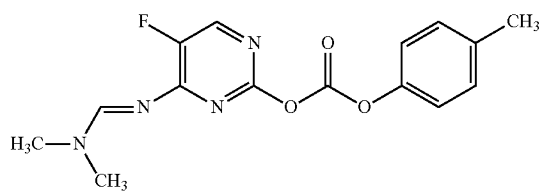 | C | B | B | A | white solid | 157-159 | 319 | | |
| 611 | 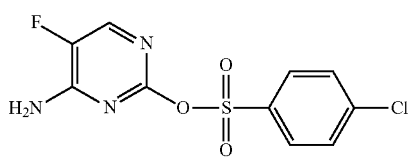 [SMILES: Nc1nc(OS(=O)(=O)c2ccc(Cl)cc2)ncc1F] | A | A | A | A | white solid | | | | |
| 612 | 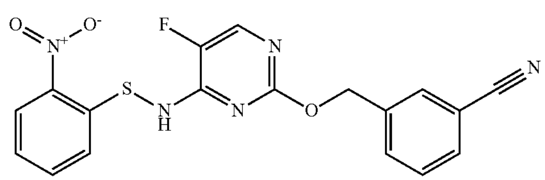 [SMILES: N#Cc1cccc(COc2ncc(F)c(NSc3ccccc3[N+](=O)[O-])n2)c1] | A | A | A | A | yellow solid | 398 | 396 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 613 | 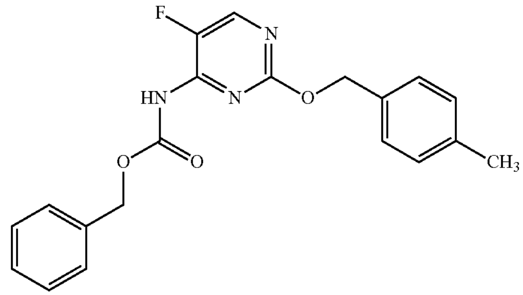 [SMILES: Cc1ccc(COc2ncc(F)c(NC(=O)OCc3ccccc3)n2)cc1] | A | A | A | A | | 368 | 366 | | |
| 614 | 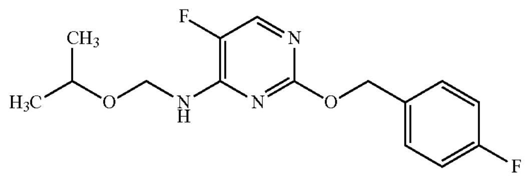 [SMILES: CC(C)OCNc1nc(OCc2ccc(F)cc2)ncc1F] | A | A | A | A | white solid | 75-76 | 310 | 308 | |
| 615 | 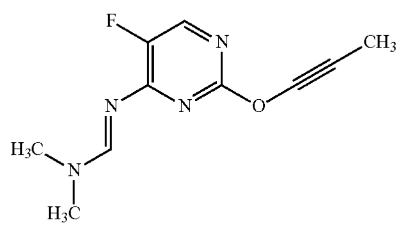 [SMILES: CC#COc1ncc(F)c(/N=C/N(C)C)n1] | A | A | C | A | YELLOW SOLID | 58-60 | 237 | | |
| 616 | 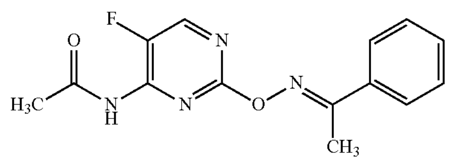 [SMILES: CC(=O)Nc1nc(O/N=C(\C)c2ccccc2)ncc1F] | A | A | A | A | white solid | 149-151 | | 287 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 617 | 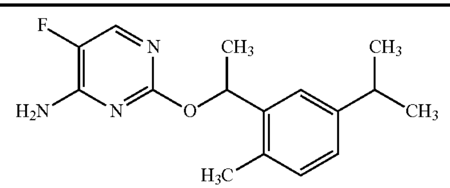 | A | A | A | A | clear oil | | | 288 | |
| 618 | 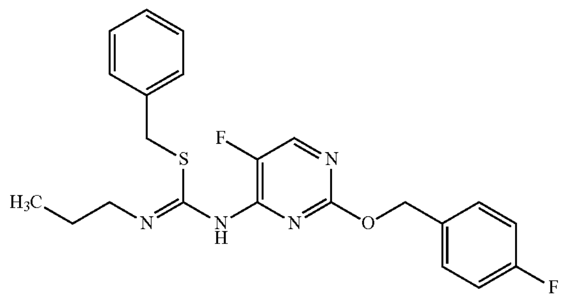 [SMILES: CCC/N=C(/Nc1nc(OCc2ccc(F)cc2)ncc1F)SCc1ccccc1] | E | E | E | E | Off white solid | | 429 | | |
| 619 | 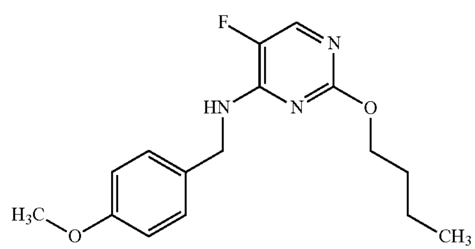 | E | E | E | E | Gummy liquid | | 306 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 620 | 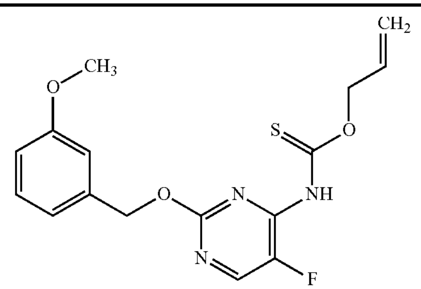 | E | E | E | E | Pale yellow solid | | 350 | | |
| 621 | 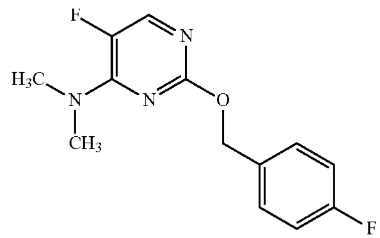 [SMILES: CN(C)c1nc(OCc2ccc(F)cc2)ncc1F] | E | E | E | E | Off white solid | | 266 | | |
| 622 | 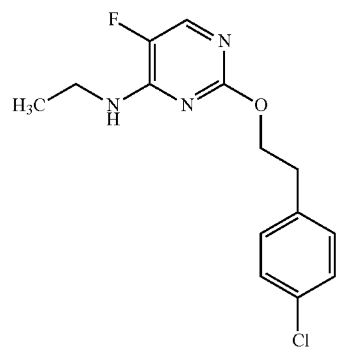 [SMILES: CCNc1nc(OCCc2ccc(Cl)cc2)ncc1F] | E | E | E | E | Pale yellow liquid | | 296 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 623 | 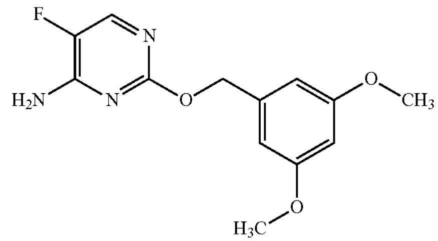 [SMILES: COc1cc(COc2ncc(F)c(N)n2)cc(OC)c1] | B | A | A | A | white solid | 112 | 280 | | 278 |
| 624 | 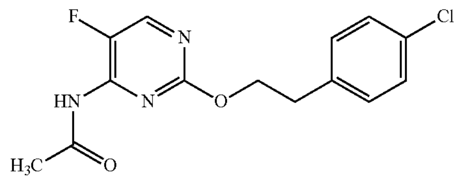 [SMILES: CC(=O)Nc1nc(OCCc2ccc(Cl)cc2)ncc1F] | B | A | B | A | LIGHT BROWN SOLID | 128-130 | 310 | | |
| 625 | 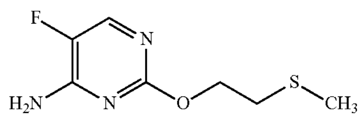 | D | C | D | C | white solid | 114-115 | | 202 | |
| 626 | 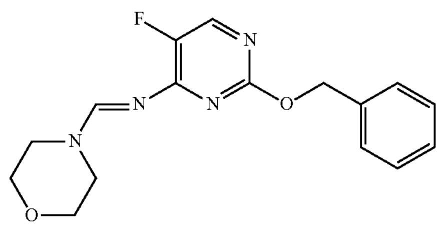 [SMILES: Fc1cnc(OCc2ccccc2)nc1/N=C/N1CCOCC1] | A | A | A | A | white solid | 130-131 | 317 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 627 | 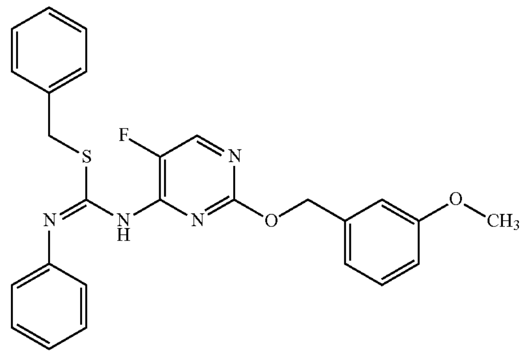 [SMILES: COc1cccc(COc2ncc(F)c(N/C(=N\c3ccccc3)SCc3ccccc3)n2)c1] | E | E | E | E | Pale yellow solid | | 475 | | |
| 628 | 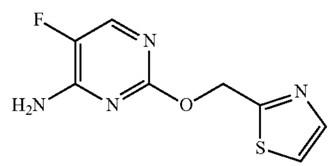 [SMILES: Nc1nc(OCc2nccs2)ncc1F] | B | A | C | A | beige solid | 101-103 | 227 | | |
| 629 | 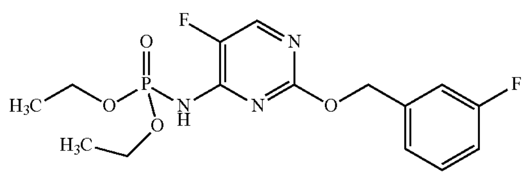 [SMILES: CCOP(=O)(Nc1nc(OCc2cccc(F)c2)ncc1F)OCC] | D | B | D | B | light yellow solid | | 374 | 372 | |
| 630 | 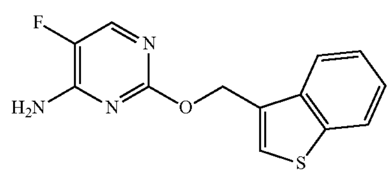 [SMILES: Nc1nc(OCc2csc3ccccc23)ncc1F] | A | A | A | A | white solid | 167-169 | 276 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 631 | 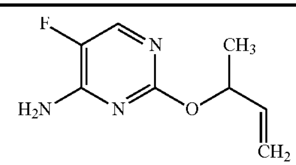 | D | D | D | D | clear yellow oil | | 184 | | 182 |
| 632 | 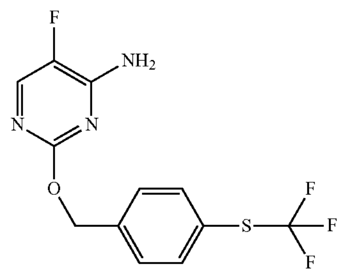 [SMILES: Nc1nc(OCc2ccc(SC(F)(F)F)cc2)ncc1F] | A | A | A | A | white solid | 128-131 | 320 | 318 | |
| 633 | 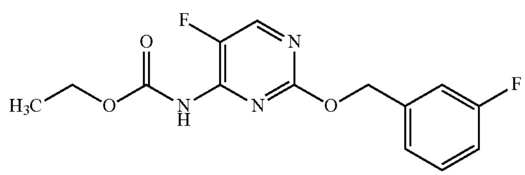 [SMILES: CCOC(=O)Nc1nc(OCc2cccc(F)c2)ncc1F] | A | A | A | A | white solid | | | 308 | |
| 634 | 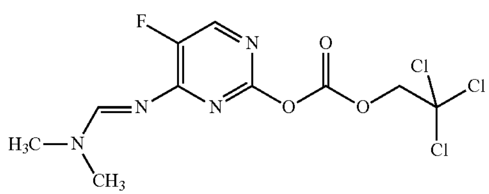 | A | A | A | A | white solid | 130-133 | 359 | | |
| 635 | 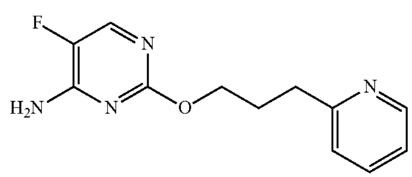 [SMILES: Nc1nc(OCCCc2ccccn2)ncc1F] | D | A | C | A | white solid | 117-118 | | 247 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 636 | 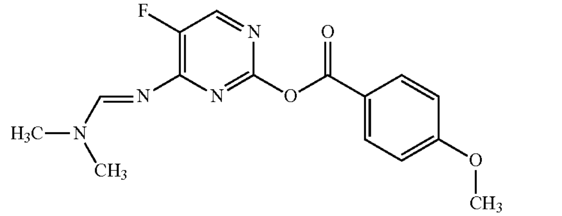 | A | A | A | A | white solid | 132-135 | 319 | | |
| 637 | 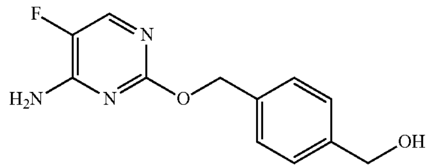 [SMILES: Nc1nc(OCc2ccc(CO)cc2)ncc1F] | A | A | A | A | white solid | 158-160 | | 249 | |
| 638 | 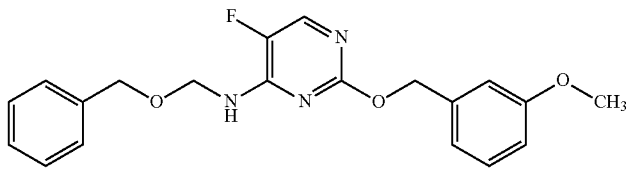 [SMILES: COc1cccc(COc2ncc(F)c(NCOCc3ccccc3)n2)c1] | D | B | B | A | white solid | 77-78 | 370 | 368 | |
| 639 | 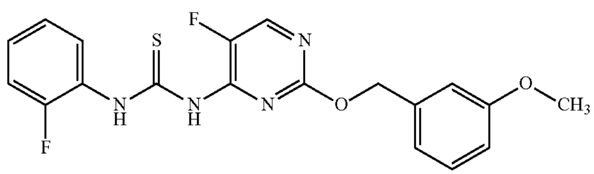 | B | A | A | A | white solid | 136-137 | 403 | 401 | |
| 640 | 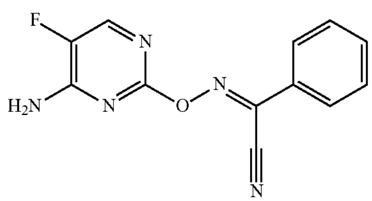 [SMILES: N#C/C(=N\Oc1ncc(F)c(N)n1)c1ccccc1] | A | A | A | A | yellow white solid | 218-220 | 258 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SEPTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 641 | 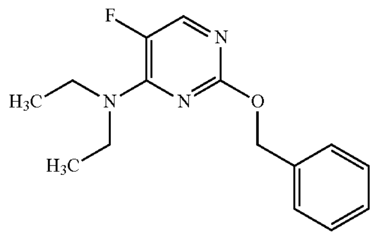 [SMILES: CCN(CC)c1nc(OCc2ccccc2)ncc1F] | E | E | E | E | Pale yellow liquid | | 276 | | |
| 642 | 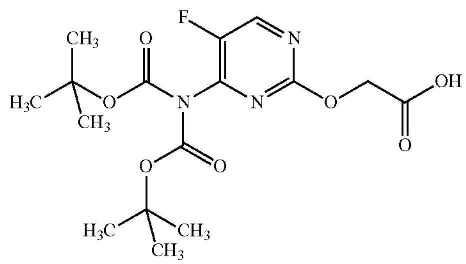 [SMILES: CC(C)(C)OC(=O)N(C(=O)OC(C)(C)C)c1nc(OCC(=O)O)ncc1F] | E | E | E | E | white foam | 61-65 | 410 (M + Na) | | |
| 643 | 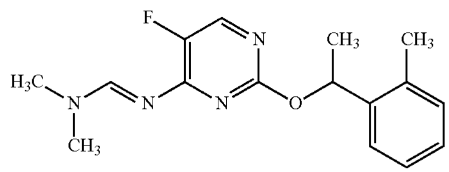 [SMILES: Cc1ccccc1C(C)Oc1ncc(F)c(/N=C/N(C)C)n1] | A | A | A | A | pasty off-white solid | | | | |
| 644 | 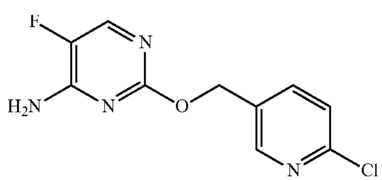 [SMILES: Nc1nc(OCc2ccc(Cl)nc2)ncc1F] | A | A | A | A | white solid | 164-166 | 255 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 645 | 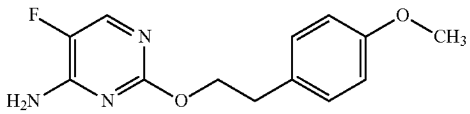 | D | B | C | A | white solid | 117-118 | 264 | 262 | |
| 646 | 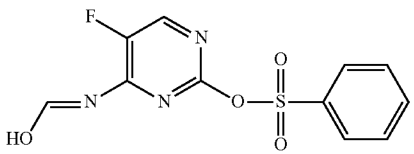 [SMILES: O=S(=O)(Oc1ncc(F)c(/N=C/O)n1)c1ccccc1] | A | A | B | A | white solid | 185-187 | 298 | 296 | |
| 647 | 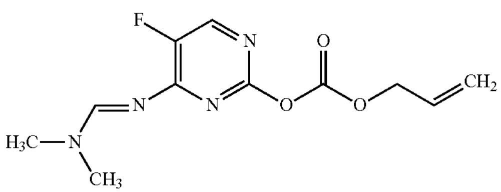 [SMILES: C=CCOC(=O)Oc1ncc(F)c(/N=C/N(C)C)n1] | A | A | A | A | white solid | 89-90 | 290.8 (Na+) | | |
| 648 | 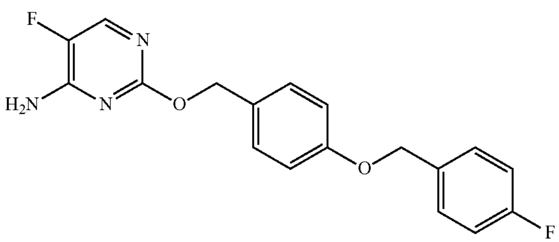 [SMILES: Nc1nc(OCc2ccc(OCc3ccc(F)cc3)cc2)ncc1F] | A | A | A | A | white solid | 132 | 344 | 342 | |
| 649 | 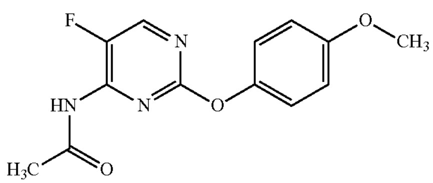 [SMILES: COc1ccc(Oc2ncc(F)c(NC(C)=O)n2)cc1] | D | A | D | C | LIGHT YELLOW SOLID | 130-132 | 278 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 650 | 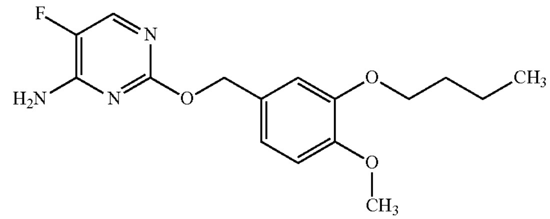 [SMILES: CCCCOc1cc(COc2ncc(F)c(N)n2)ccc1OC] | A | A | A | A | yellow solid | 108 | 322 | | 320 |
| 651 | 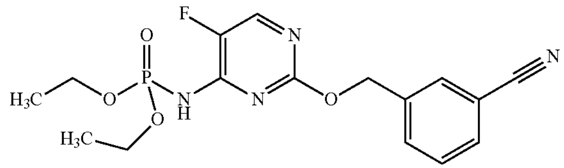 [SMILES: CCOP(=O)(Nc1nc(OCc2cccc(C#N)c2)ncc1F)OCC] | D | B | D | D | white solid | | 381 | 379 | |
| 652 | 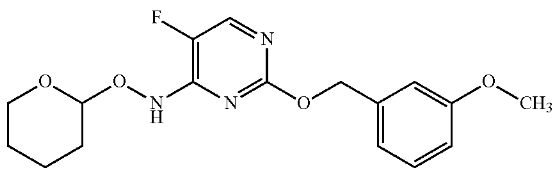 [SMILES: COc1cccc(COc2ncc(F)c(NOC3CCCCO3)n2)c1] | D | A | D | B | yellow oil | | 350 | 348 | |
| 653 | 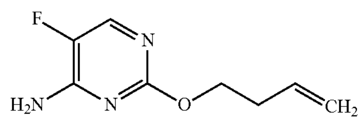 | C | A | D | D | white solid | 58-59 | 184 | | |
| 654 | 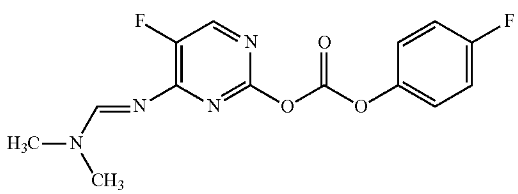 [SMILES: CN(C)/C=N/c1nc(OC(=O)Oc2ccc(F)cc2)ncc1F] | A | A | A | A | white solid | 118-121 | 324 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 655 | 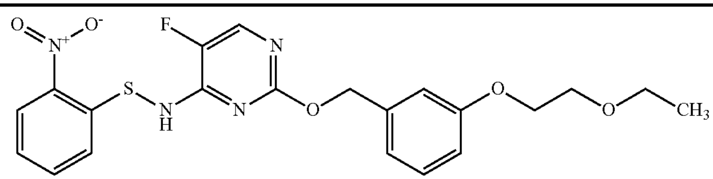 | B | C | B | A | yellow solid | 144-146 | 461 | 459 | |
| 656 | 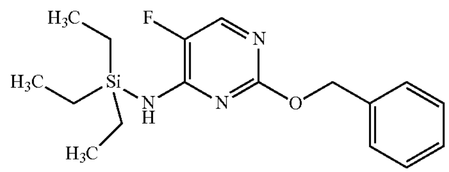 [SMILES: CC[Si](CC)(CC)Nc1nc(OCc2ccccc2)ncc1F] | A | A | A | A | clear oil | | 334 | | |
| 657 | 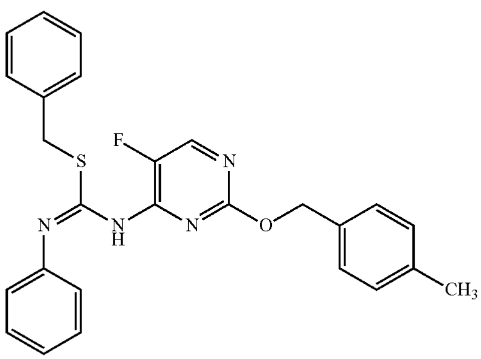 [SMILES: Cc1ccc(COc2ncc(F)c(N/C(=N\c3ccccc3)SCc3ccccc3)n2)cc1] | E | E | E | E | Off white solid | | 459 | | |
| 658 | 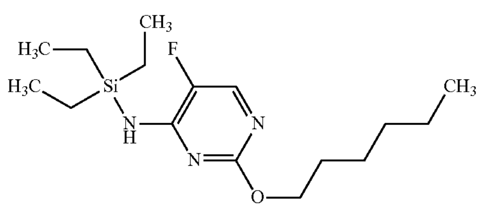 [SMILES: CCCCCCOc1ncc(F)c(N[Si](CC)(CC)CC)n1] | D | B | D | B | YELLOW GUMMY SOLID | | | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 659 | 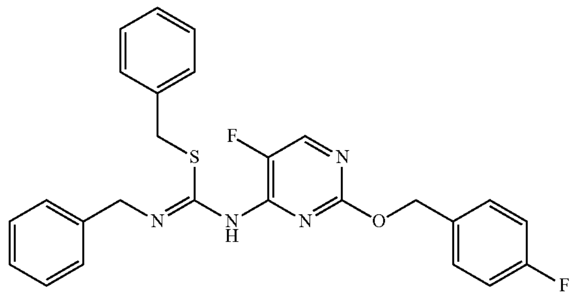 [SMILES: Fc1ccc(COc2ncc(F)c(N/C(=N/Cc3ccccc3)SCc3ccccc3)n2)cc1] | E | E | E | E | Pale yellow solid | | 477 | | |
| 660 | 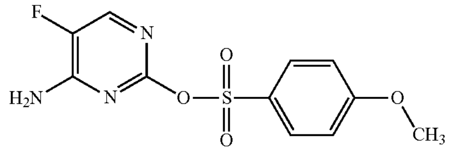 [SMILES: COc1ccc(S(=O)(=O)Oc2ncc(F)c(N)n2)cc1] | C | D | A | A | white solid | 160-161 | | | |
| 661 | 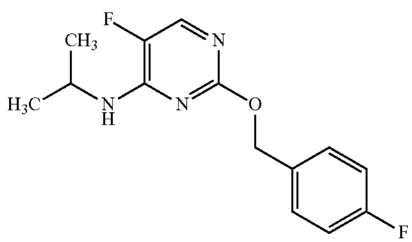 [SMILES: CC(C)Nc1nc(OCc2ccc(F)cc2)ncc1F] | E | E | E | E | Off white solid | | 280 | | |
| 662 | 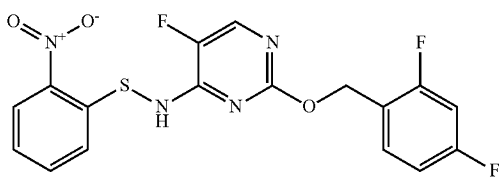 [SMILES: O=[N+]([O-])c1ccccc1SNc1nc(OCc2ccc(F)cc2F)ncc1F] | C | C | D | A | yellow solid | 176 | 409 | 407 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 663 | 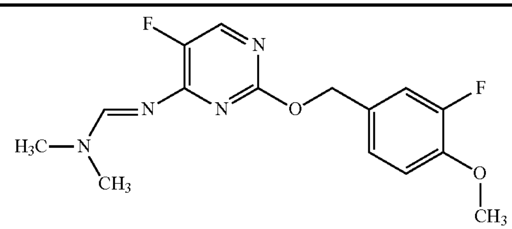 | A | A | A | A | yellow solid | 123-124 | 323 | | |
| 664 | 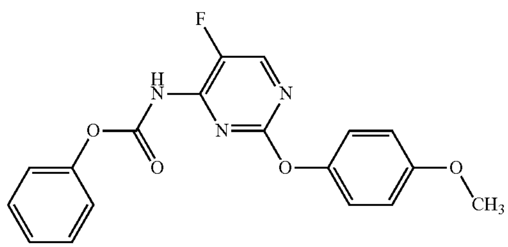 [SMILES: COc1ccc(Oc2ncc(F)c(NC(=O)Oc3ccccc3)n2)cc1] | D | D | D | C | OFF WHITE SOLID | 125-127 | 356 | | |
| 665 | 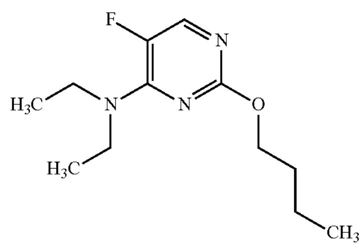 [SMILES: CCCCOc1ncc(F)c(N(CC)CC)n1] | E | E | E | E | Colourless liquid | | 242 | | |
| 666 | 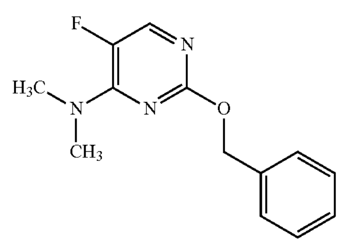 [SMILES: CN(C)c1nc(OCc2ccccc2)ncc1F] | E | E | E | E | Yellow solid | | 248 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 667 | 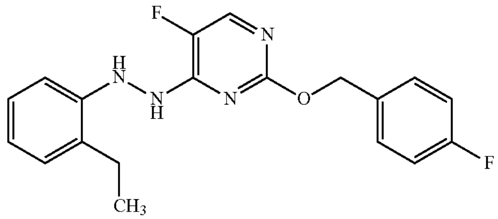 [SMILES: CCc1ccccc1NNc1nc(OCc2ccc(F)cc2)ncc1F] | D | A | D | A | brown solid | 108-111 | 357 | 355 | |
| 668 | 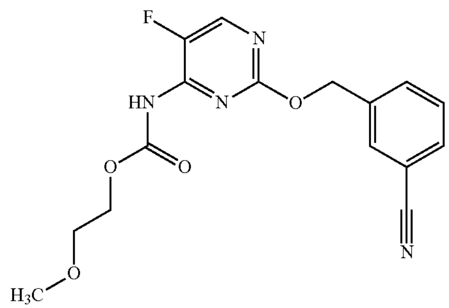 [SMILES: COCCOC(=O)Nc1nc(OCc2cccc(C#N)c2)ncc1F] | A | A | C | A | | | 347 | 345 | |
| 669 | 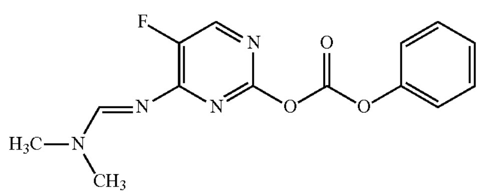 | A | A | A | A | white solid | 135-136 | 305 | | |
| 670 | 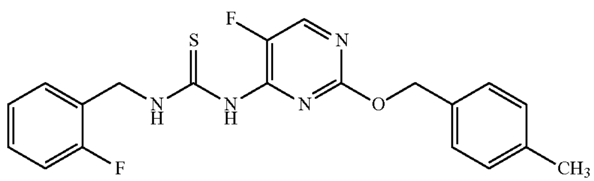 | B | A | B | A | off-white solid | 188-190 | 401 | 399 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 671 | 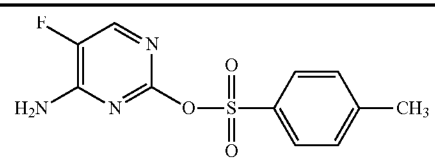 | A | A | A | A | white solid | 153-154 | | | |
| 672 | 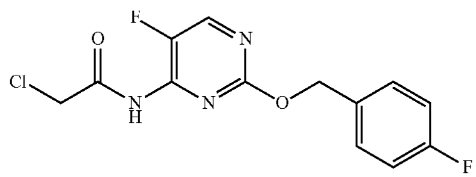 [SMILES: O=C(CCl)Nc1nc(OCc2ccc(F)cc2)ncc1F] | A | A | A | A | off-white solid | 127-129 | 314 | | |
| 673 | 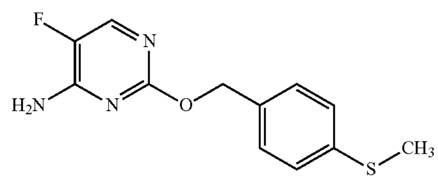 [SMILES: CSc1ccc(COc2ncc(F)c(N)n2)cc1] | A | A | A | A | off-white solid | 94-95 | 266 | 264 | |
| 674 | 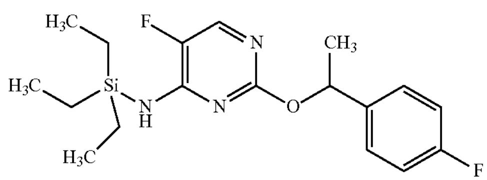 [SMILES: CC[Si](CC)(CC)Nc1nc(OC(C)c2ccc(F)cc2)ncc1F] | A | A | A | A | clear oil | | 366 | 364 | |
| 675 | 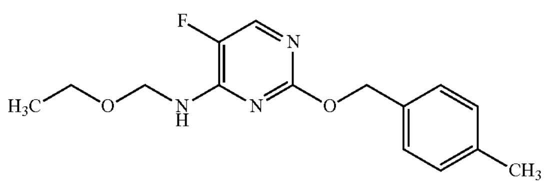 [SMILES: CCOCNc1nc(OCc2ccc(C)cc2)ncc1F] | A | A | A | A | light tan waxy solid | | 292 | 290 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 676 | 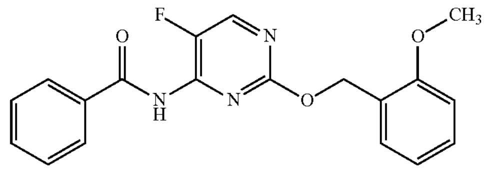 [SMILES: COc1ccccc1COc1ncc(F)c(NC(=O)c2ccccc2)n1] | D | D | C | A | yellow oil | | 354 | 352 | |
| 677 | 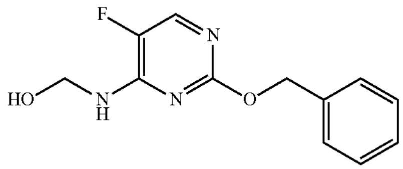 [SMILES: OCNc1nc(OCc2ccccc2)ncc1F] | A | A | A | A | white solid | 113-114 | 250 | 248 | |
| 678 | 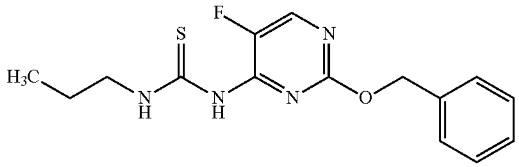 [SMILES: CCCNC(=S)Nc1nc(OCc2ccccc2)ncc1F] | C | A | D | A | off-white crystals | 128-129 | 321 | 319 | |
| 679 | 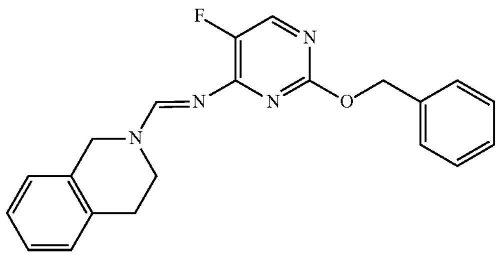 [SMILES: Fc1cnc(OCc2ccccc2)nc1/N=C/N1CCc2ccccc2C1] | A | A | A | A | off white solid | 98-99 | 363 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 680 | 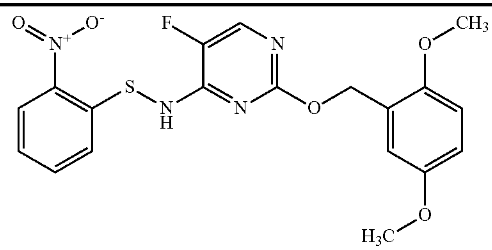 | C | C | D | D | yellow solid | 175-182 | 433 | 431 | |
| 681 | 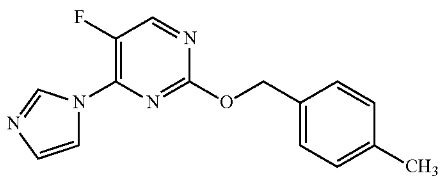 | A | A | A | A | white solid | 86-88 | 285 | | |
| 682 | 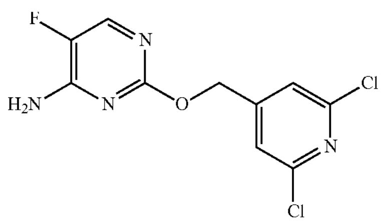 [SMILES: Nc1nc(OCc2cc(Cl)nc(Cl)c2)ncc1F] | A | A | A | A | off-white solid | 153-155 | 290 | | |
| 683 | 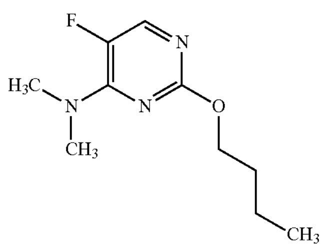 | E | E | E | E | Colourless liquid | | 236 [M + Na] | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 684 | 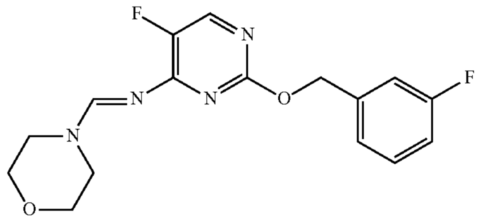 [SMILES: Fc1cccc(COc2ncc(F)c(/N=C/N3CCOCC3)n2)c1] | A | A | A | A | white solid | 94-95 | 335 | | |
| 685 | 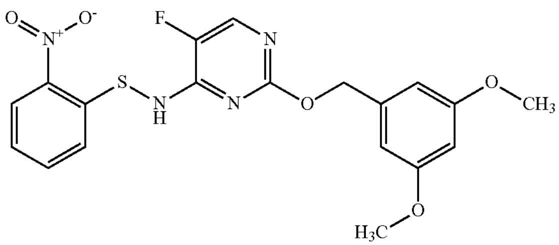 [SMILES: COc1cc(COc2ncc(F)c(NSc3ccccc3[N+](=O)[O-])n2)cc(OC)c1] | D | D | D | A | yellow solid | 175-183 | 433 | 431 | |
| 686 | 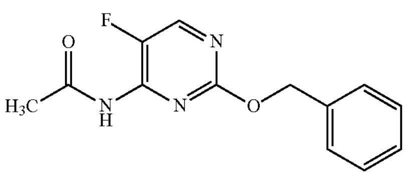 [SMILES: CC(=O)Nc1nc(OCc2ccccc2)ncc1F] | E | E | E | E | white solid | 160-161 | 262 | 260 | |
| 687 | 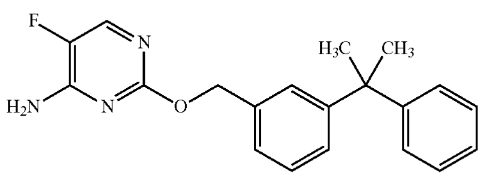 [SMILES: CC(C)(c1ccccc1)c1cccc(COc2ncc(F)c(N)n2)c1] | D | D | C | A | yellow solid | 122 | 338 | 336 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 688 | 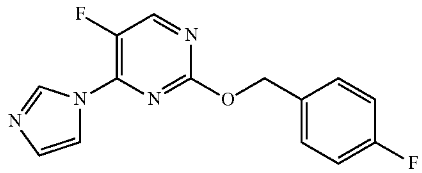 [SMILES: Fc1ccc(COc2ncc(F)c(-n3ccnc3)n2)cc1] | A | A | A | A | white solid | 93-95 | 289 | | |
| 689 | 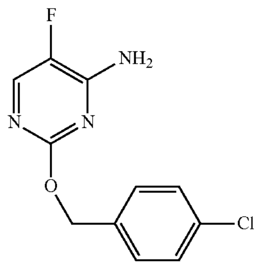 [SMILES: Nc1nc(OCc2ccc(Cl)cc2)ncc1F] | A | A | A | A | white solid | 126-128 | 254 | 252 | |
| 690 | 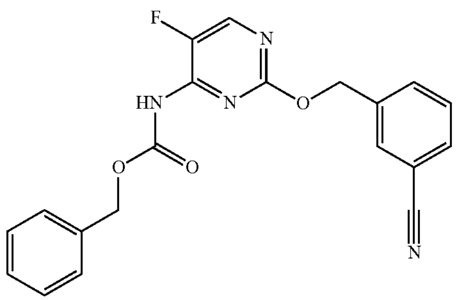 [SMILES: N#Cc1cccc(COc2ncc(F)c(NC(=O)OCc3ccccc3)n2)c1] | A | A | B | A | | | 379 | 377 | |
| 691 | 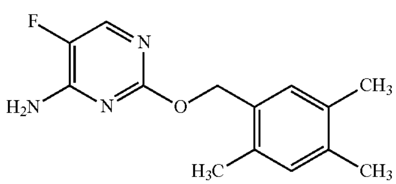 | B | A | B | A | yellow solid | 162 | 262 | 260 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 692 | 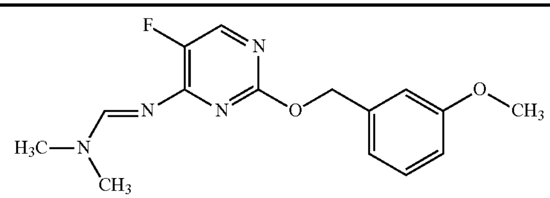 | A | A | A | A | clear yellow oil | | 305 | | |
| 693 | 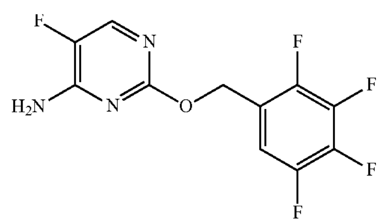 [SMILES: Nc1nc(OCc2cc(F)c(F)c(F)c2F)ncc1F] | A | A | A | A | white solid | 127-130 | 292 | 290 | |
| 694 | 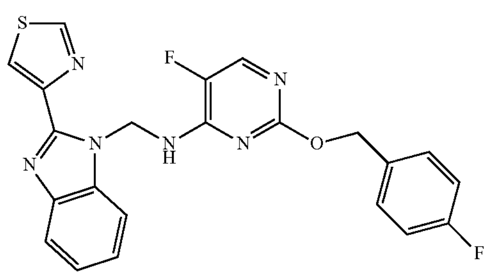 [SMILES: Fc1ccc(COc2ncc(F)c(NCn3c(-c4cscn4)nc4ccccc43)n2)cc1] | D | C | D | C | white solid | 181-183 | 451 | 449 | |
| 695 | 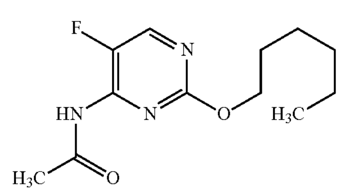 | D | C | D | A | WHITE SOLID | 100-102 | 256 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 696 | 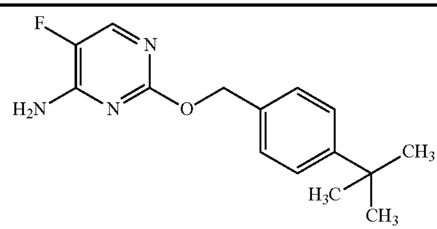 | B | A | A | A | off-white solid | 98-102 | 276 | 274 | |
| 697 | 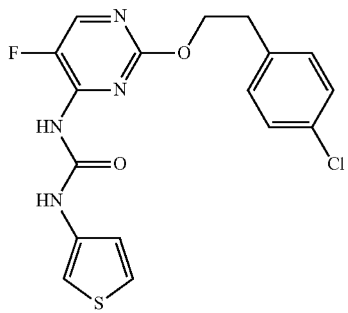 [SMILES: O=C(Nc1ccsc1)Nc1nc(OCCc2ccc(Cl)cc2)ncc1F] | C | C | D | D | LIGHT YELLOW SOLID | | 393 | | |
| 698 | 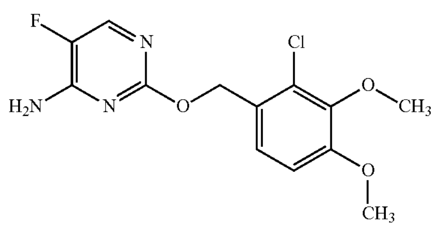 [SMILES: COc1ccc(COc2ncc(F)c(N)n2)c(Cl)c1OC] | A | A | A | A | white solid | 117 | 314 | 312 | |
| 699 | 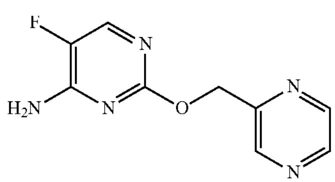 [SMILES: Nc1nc(OCc2cnccn2)ncc1F] | B | A | A | A | tannish solid | | 222 | | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 700 | 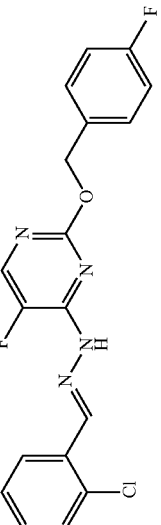 | C | A | D | B | tan solid | 185-187 | 375 | 373 | |
| 701 | 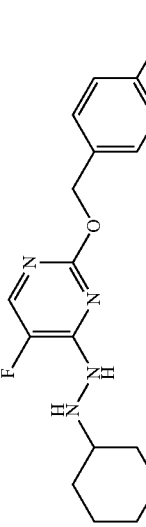 | D | A | D | A | pale yellow solid | 138-142 | 332 | 329 | |
| 702 | 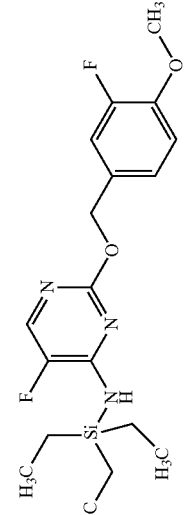 | A | A | A | A | clear oil | | 382 | 380 | |
| 703 | 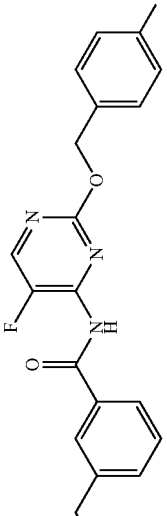 | D | D | D | C | white solid | 116-117 | 435 | 433 | |
| 704 | 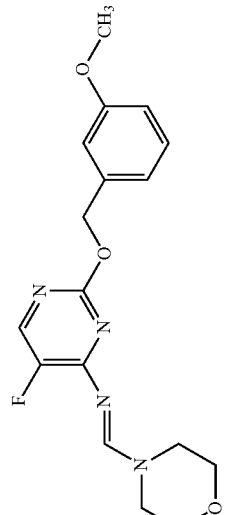 | A | A | A | A | white solid | 76-77 | 347 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 705 | 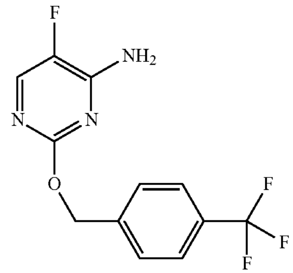 [SMILES: Nc1nc(OCc2ccc(C(F)(F)F)cc2)ncc1F] | B | A | A | A | white solid | 117-119 | 288 | 286 | |
| 706 | 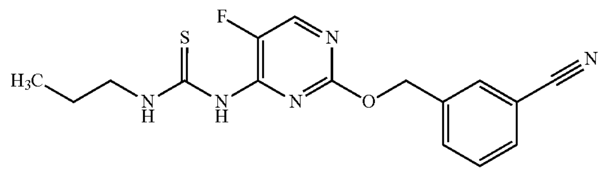 [SMILES: CCCNC(=S)Nc1nc(OCc2cccc(C#N)c2)ncc1F] | D | B | D | A | light yellow solid | 163-165 | 346 | 344 | |
| 707 | 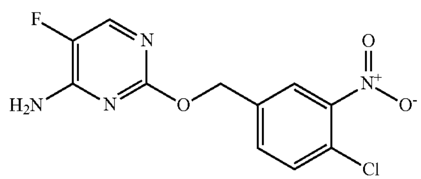 [SMILES: Nc1nc(OCc2ccc(Cl)c([N+](=O)[O-])c2)ncc1F] | A | A | A | A | orange solid | 156 | 299 | 297 | |
| 708 | 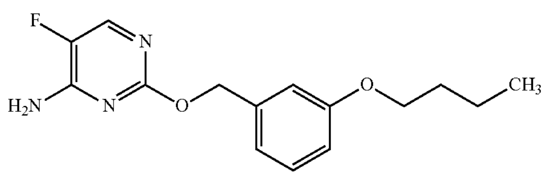 [SMILES: CCCCOc1cccc(COc2ncc(F)c(N)n2)c1] | A | A | A | A | white solid | 89-90 | 292 | 290 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 709 | 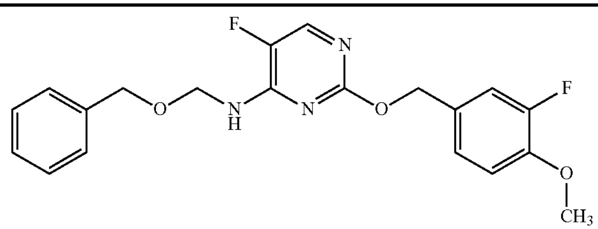 | D | B | D | A | clear colorless oil | | 388 | 386 | |
| 710 | 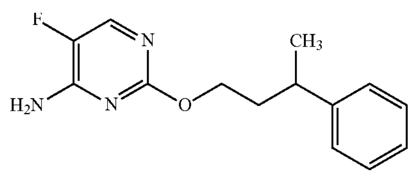 [SMILES: CC(CCOc1ncc(F)c(N)n1)c1ccccc1] | B | A | B | A | colorless oil | | 262 | 260 | |
| 711 | 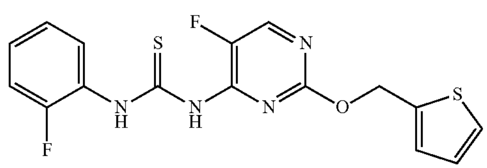 [SMILES: Fc1ccccc1NC(=S)Nc1nc(OCc2cccs2)ncc1F] | C | A | B | A | white solid | 138-139 | 379 | 377 | |
| 712 | 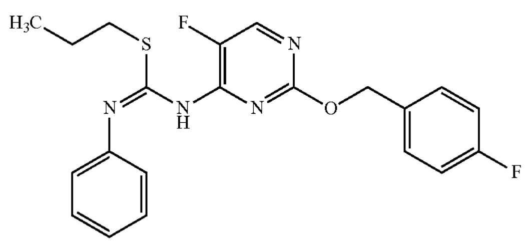 [SMILES: CCCS/C(=N/c1ccccc1)Nc1nc(OCc2ccc(F)cc2)ncc1F] | E | E | E | E | Off white solid | | 415 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 713 | 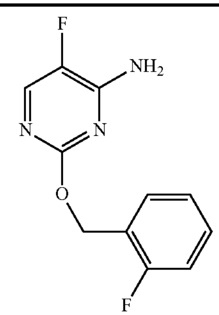 | B | A | A | A | brown solid | 95-98 | 238 | | |
| 714 | 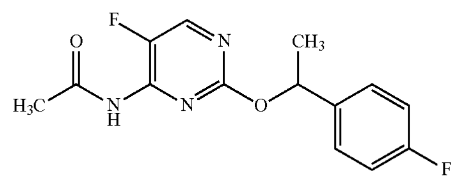 [SMILES: CC(=O)Nc1nc(OC(C)c2ccc(F)cc2)ncc1F] | A | A | A | A | yellow oil | | 294 | 292 | |
| 715 | 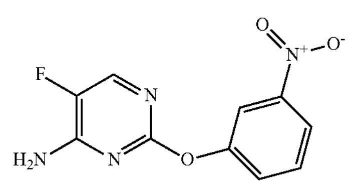 [SMILES: Nc1nc(Oc2cccc([N+](=O)[O-])c2)ncc1F] | D | D | C | B | white solid | 198-201 | 251 | 249 | |
| 716 | 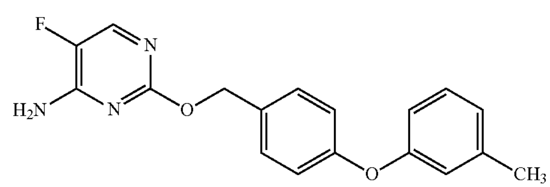 [SMILES: Cc1cccc(Oc2ccc(COc3ncc(F)c(N)n3)cc2)c1] | A | A | A | A | yellow solid | 93 | 326 | 324 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 717 | 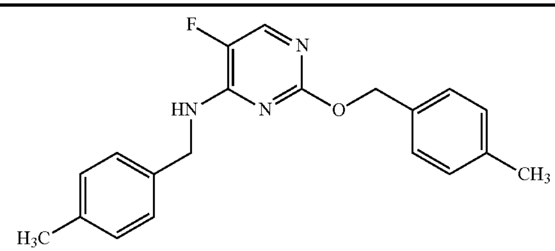 | A | A | B | A | | | 338 | | |
| 718 | 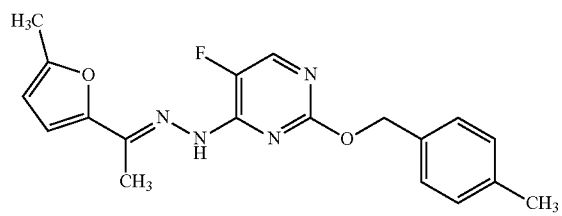 [SMILES: C/C(=N\Nc1nc(OCc2ccc(C)cc2)ncc1F)c1ccc(C)o1] | C | C | C | A | pale yellow solid | 135-139 | 356 | 353 | |
| 719 | 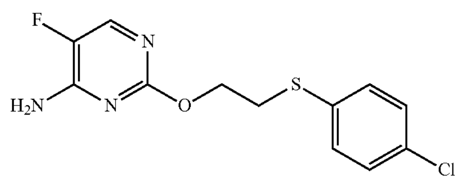 [SMILES: Nc1nc(OCCSc2ccc(Cl)cc2)ncc1F] | E | E | D | B | white solid | 103-104 | 300 | 298 | |
| 720 | 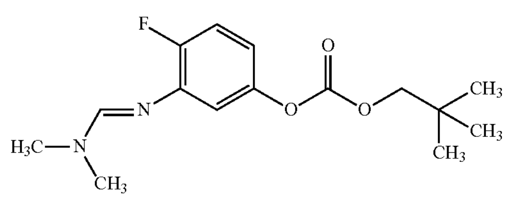 [SMILES: CN(C)/C=N/c1cc(OC(=O)OCC(C)(C)C)ccc1F] | A | A | A | A | white solid | 115 | 299 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 721 | 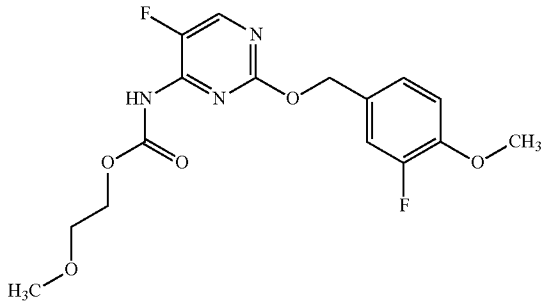 | E | E | E | E | | | 370 | | 368 |
| 722 | 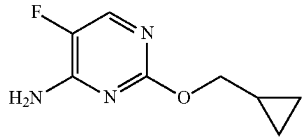 [SMILES: Nc1nc(OCC2CC2)ncc1F] | D | C | D | D | light yellow solid | 58-59 | 184 | 182 | |
| 723 | 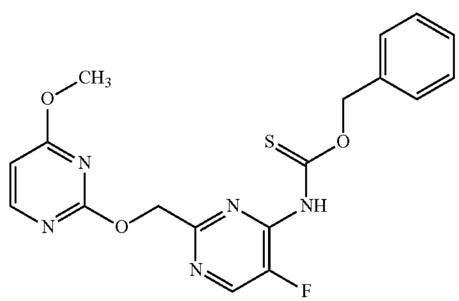 [SMILES: COc1ccnc(OCc2ncc(F)c(NC(=S)OCc3ccccc3)n2)n1] | E | E | E | E | Pale yellow solid | | 400 | | |
| 724 | 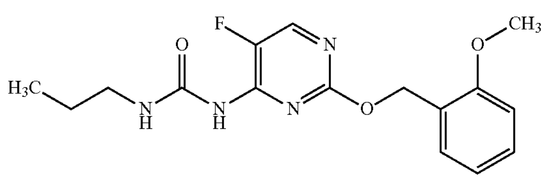 [SMILES: CCCNC(=O)Nc1nc(OCc2ccccc2OC)ncc1F] | D | D | D | C | white solid | 170-171 | 335 | 333 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 725 | 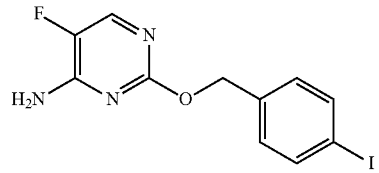 [SMILES: Nc1nc(OCc2ccc(I)cc2)ncc1F] | A | A | A | A | yellow solid | 146-147 | 346 | 344 | |
| 726 | 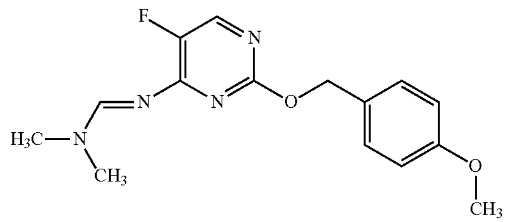 | A | A | A | A | white solid | 109-110 | 305 | | |
| 727 | 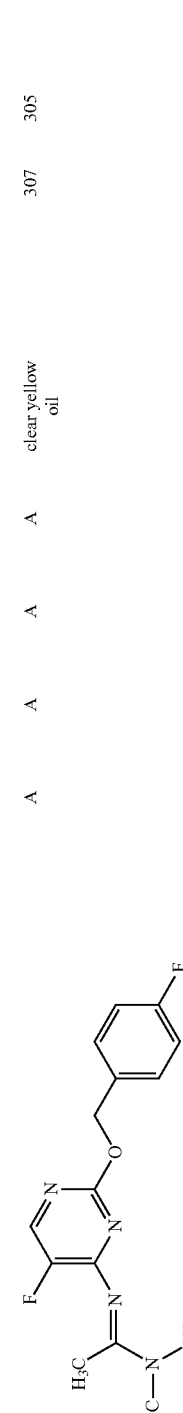 | A | A | A | A | clear yellow oil | | 307 | 305 | |
| 728 | 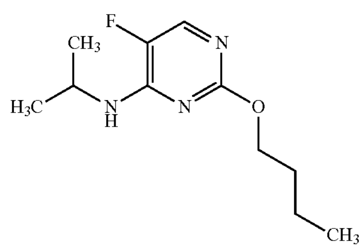 | E | E | E | E | Brown liquid | | 228 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 729 | 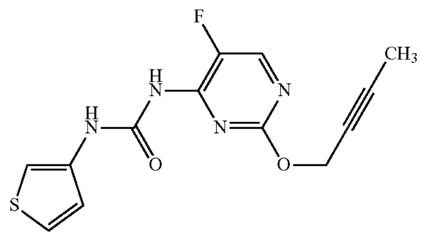 [SMILES: CC#CCOc1ncc(F)c(NC(=O)Nc2ccsc2)n1] | B | B | B | C | light yellow solid | 178-180 | 307 | | |
| 730 | 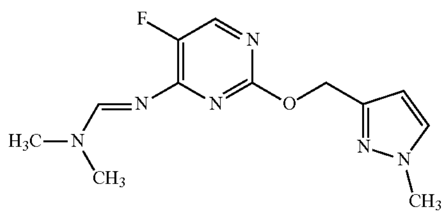 | A | A | A | A | clear yellow oil | | 279 | | |
| 731 | 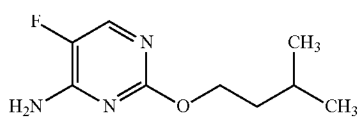 | D | D | D | D | white solid | 84-85 | 200 | 198 | |
| 732 | 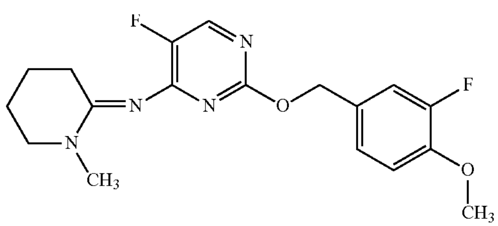 [SMILES: COc1ccc(COc2ncc(F)c(/N=C3\CCCCN3C)n2)cc1F] | B | A | A | A | pale amber oil | | 362 | | |
| 733 | 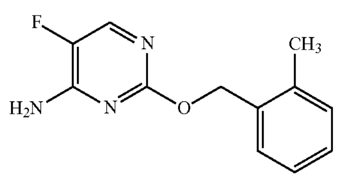 | A | A | A | A | white solid | 96-98 | 234 | 232 | |

TABLE I-continued
Three day curative (3DC) and one day protectant (1DP) Activity of Compounds on SEPTTR at 25 and 100 ppm
| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 734 | 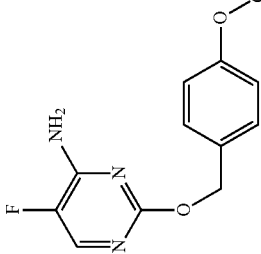 | A | A | A | A | White solid | 110-111 | 250 | 248 | |
| 735 | 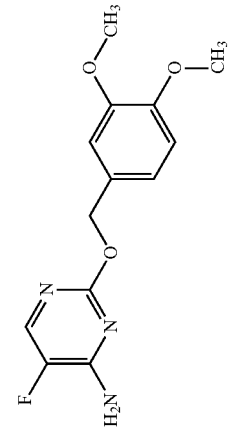 | A | A | A | A | white solid | | | 378 | |
| 736 | 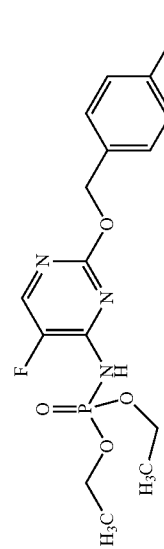 | D | D | D | D | white solid | | 370 | 368 | |
| 737 | 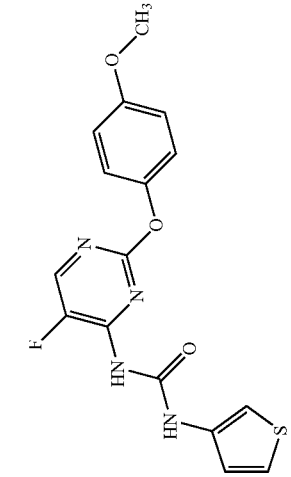 | D | D | D | D | YELLOW SOLID | | 361 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 738 | 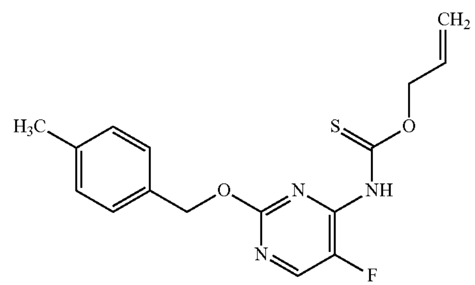 [SMILES: C=CCOC(=S)Nc1nc(OCc2ccc(C)cc2)ncc1F] | E | E | E | E | Pale yellow solid | | 334 | | |
| 739 | 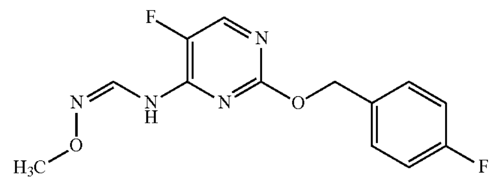 [SMILES: CO/N=C\Nc1nc(OCc2ccc(F)cc2)ncc1F] | A | A | A | A | white solid | 87-88 | 295 | 293 | |
| 740 | 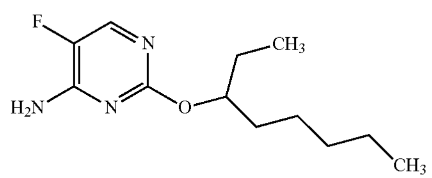 | E | E | D | D | yellow oil | | 242 | 240 | |
| 741 | 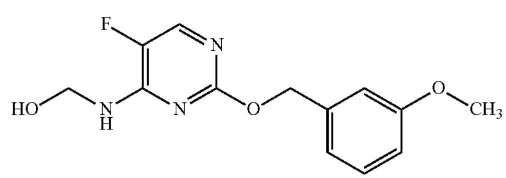 [SMILES: COc1cccc(COc2ncc(F)c(NCO)n2)c1] | A | A | C | A | clear colorless oil | | 280 | 278 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 742 | 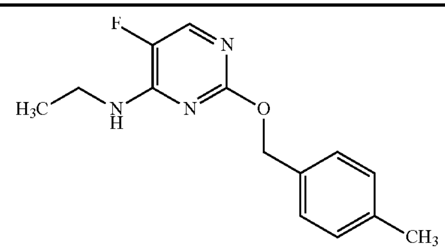 | E | E | E | E | Pale yellow solid | | 284 [M + Na] | | |
| 743 | 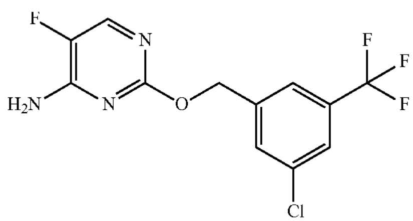 [SMILES: Nc1nc(OCc2cc(Cl)cc(C(F)(F)F)c2)ncc1F] | A | A | A | A | yellow solid | 93 | | 320 | |
| 744 | 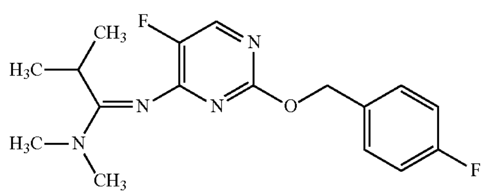 [SMILES: CC(C)/C(=N\c1nc(OCc2ccc(F)cc2)ncc1F)N(C)C] | A | A | A | A | tan oil | | 335 | | |
| 745 | 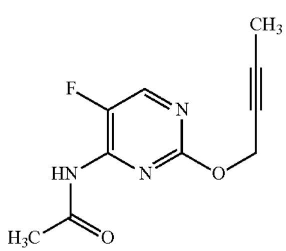 | A | A | A | A | WHITE SOLID | 158-160 | 224 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 746 | 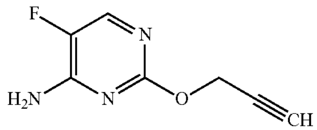 | D | A | D | D | orange solid | 106-108 | 168 | | 166 |
| 747 | 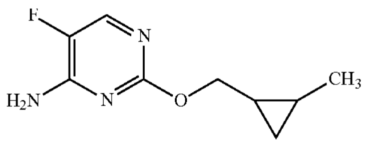 | B | A | D | A | tan oil | | — | | 196 |
| 748 | 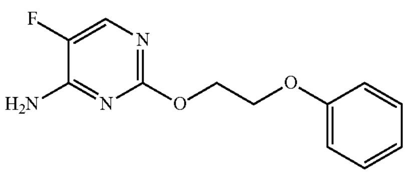 [SMILES: Nc1nc(OCCOc2ccccc2)ncc1F] | E | E | D | D | white solid | 112-113 | 250 | | 248 |
| 749 | 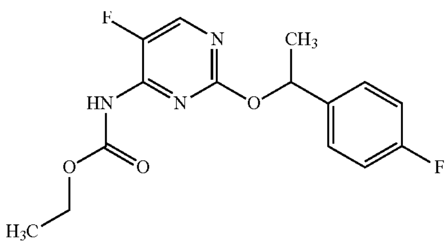 [SMILES: CCOC(=O)Nc1nc(OC(C)c2ccc(F)cc2)ncc1F] | A | A | A | A | | | 324 | | 322 |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 750 | 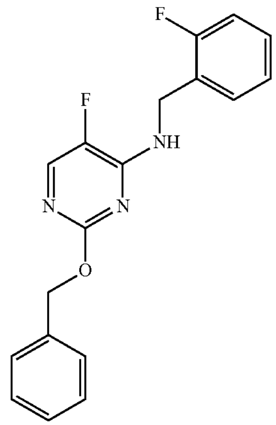 [SMILES: Fc1ccccc1CNc1nc(OCc2ccccc2)ncc1F] | C | B | C | A | | | 328 | | |
| 751 | 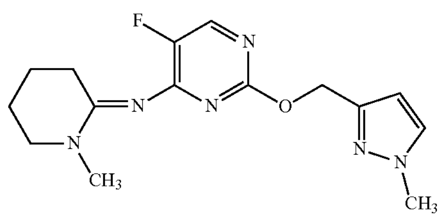 [SMILES: CN1CCCC/C1=N\c1nc(OCc2ccn(C)n2)ncc1F] | C | A | B | A | pale amber oil | | 319 | | |
| 752 | 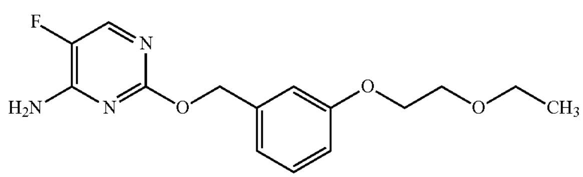 [SMILES: CCOCCOc1cccc(COc2ncc(F)c(N)n2)c1] | A | A | A | A | colorless oil | | 308 | 306 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 753 | 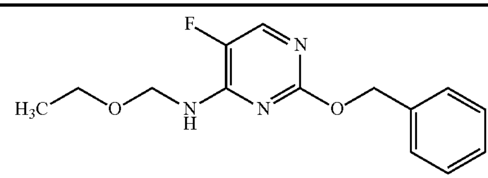 | A | A | A | A | clear pale yellow oil | | 278 | | 276 |
| 754 | 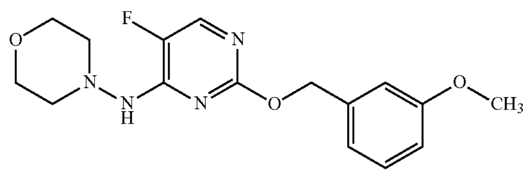 [SMILES: COc1cccc(COc2ncc(F)c(NN3CCOCC3)n2)c1] | D | C | D | D | colorless oil | | 336 | 333 | |
| 755 | 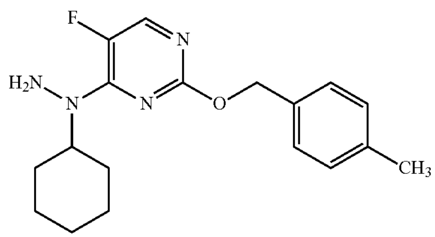 [SMILES: Cc1ccc(COc2ncc(F)c(N(N)C3CCCCC3)n2)cc1] | D | D | C | C | pale yellow oil | | 331 | | |
| 756 | 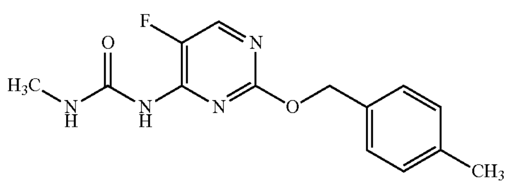 | C | D | D | D | white solid | 199-200 | 348 | 346 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 757 | 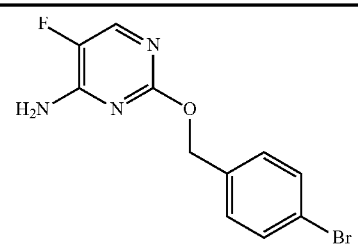 | A | A | A | A | light yellow needles | 127-129 | 299 | 297 | |
| 758 | 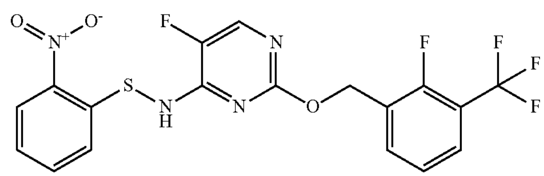 [SMILES: O=[N+]([O-])c1ccccc1SNc1nc(OCc2cccc(C(F)(F)F)c2F)ncc1F] | C | B | C | A | yellow solid | 163-170 | 459 | 457 | |
| 759 | 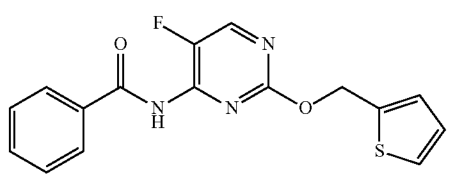 [SMILES: O=C(Nc1nc(OCc2cccs2)ncc1F)c1ccccc1] | C | A | B | A | yellow oil | | 330 | 328 | |
| 760 | 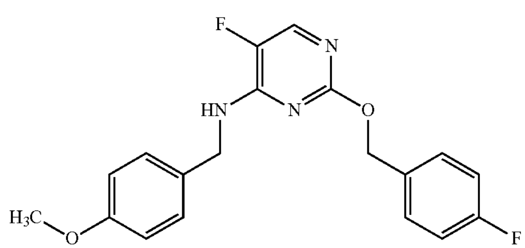 [SMILES: COc1ccc(CNc2nc(OCc3ccc(F)cc3)ncc2F)cc1] | E | E | E | E | Off white solid | | | 356 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 761 | 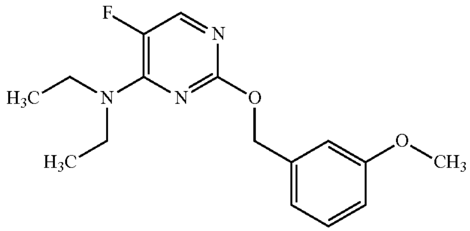 [SMILES: CCN(CC)c1nc(OCc2cccc(OC)c2)ncc1F] | E | E | E | E | Brown liquid | | 306 | | |
| 762 | 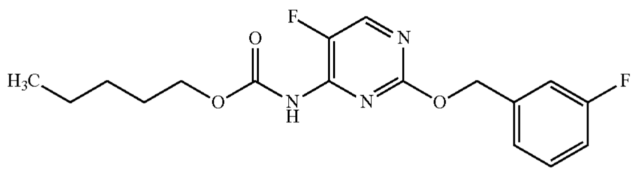 [SMILES: CCCCCOC(=O)Nc1nc(OCc2cccc(F)c2)ncc1F] | A | A | A | A | white solid | 61-62 | 352 | 350 | |
| 763 | 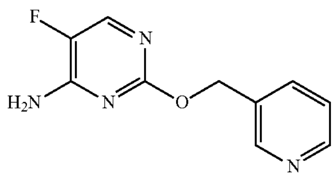 [SMILES: Nc1nc(OCc2cccnc2)ncc1F] | A | A | A | A | off-white solid | | 221 | | |
| 764 | 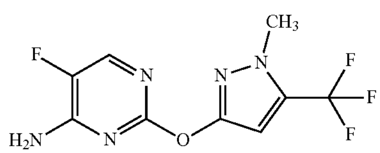 | D | D | D | D | white solid | 145-146 | 278 | 276 | |
| 765 | 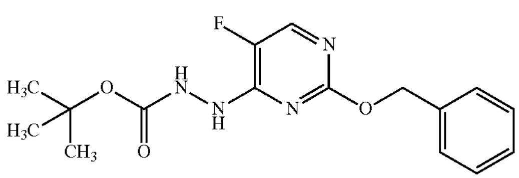 [SMILES: CC(C)(C)OC(=O)NNc1nc(OCc2ccccc2)ncc1F] | D | D | D | C | white solid | 44-49 | 335 | 333 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 766 | 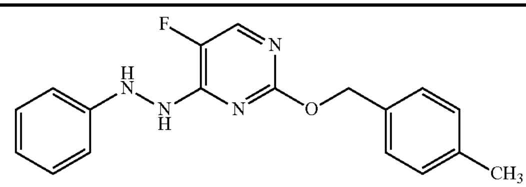 | D | C | D | B | dark brown solid | 132-140 | 325 | 323 | |
| 767 | 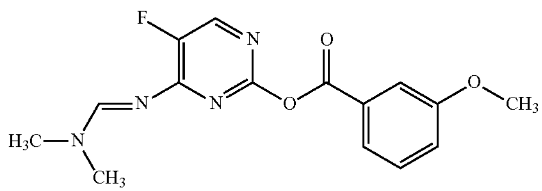 | A | A | A | A | white solid | 110 (dec) | 319 | | |
| 768 | 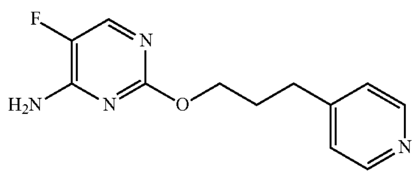 [SMILES: Nc1nc(OCCCc2ccncc2)ncc1F] | D | C | D | C | white solid | 183-184 | 249 | 247 | |
| 769 | 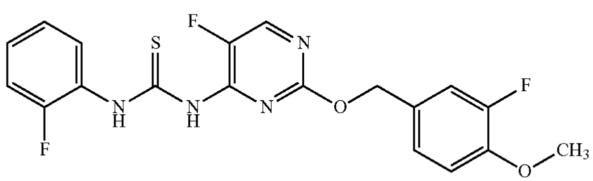 [SMILES: COc1ccc(COc2ncc(F)c(NC(=S)Nc3ccccc3F)n2)cc1F] | D | A | B | A | off-white solid | 150-152 | 421 | 419 | |
| 770 | 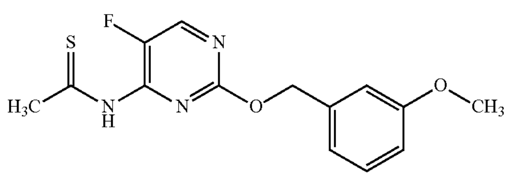 [SMILES: COc1cccc(COc2ncc(F)c(NC(C)=S)n2)c1] | A | A | A | A | yellow oil | | | 306 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 771 | 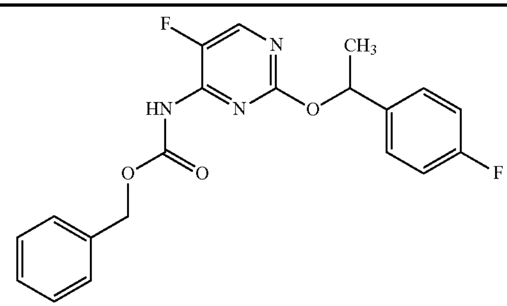 | A | A | A | A | | | 386 | 384 | |
| 772 | 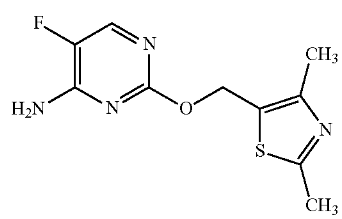 [SMILES: Cc1nc(C)c(COc2ncc(F)c(N)n2)s1] | A | A | A | A | yellow solid | 180-181 | 255 | | |
| 773 | 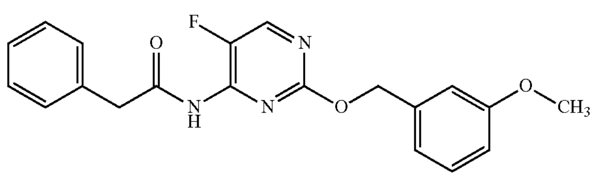 [SMILES: COc1cccc(COc2ncc(F)c(NC(=O)Cc3ccccc3)n2)c1] | D | D | C | A | white solid | 132-134 | 368 | 366 | |
| 774 | 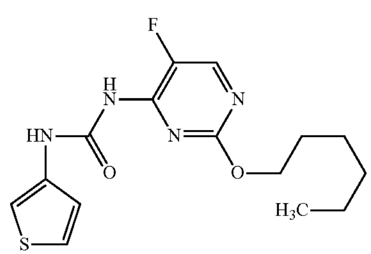 [SMILES: CCCCCCOc1ncc(F)c(NC(=O)Nc2ccsc2)n1] | D | D | D | D | LIGHT YELLOW SOLID | | 339 | | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 775 | 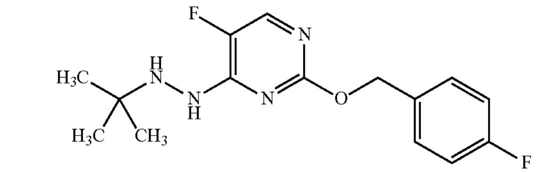 [SMILES: CC(C)(C)NNc1nc(OCc2ccc(F)cc2)ncc1F] | D | D | D | D | white solid | 77-80 | 310 | 307 | |
| 776 | 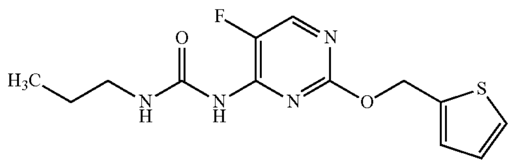 | D | D | D | D | white solid | 157-158 | 311 | 309 | |
| 777 | 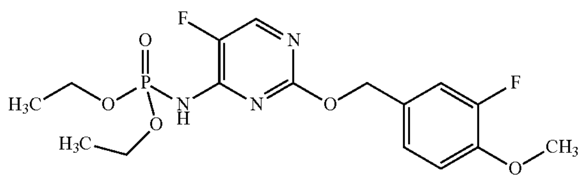 [SMILES: CCOP(=O)(Nc1nc(OCc2ccc(OC)c(F)c2)ncc1F)OCC] | D | C | D | D | white solid | | 404 | 402 | |
| 778 | 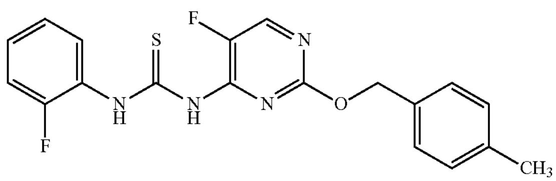 | A | A | A | A | white solid | 146-147 | 387 | 385 | |
| 779 | 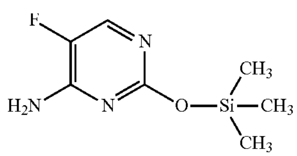 | A | A | A | A | white solid | 118-120 | | | 201 |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 780 | 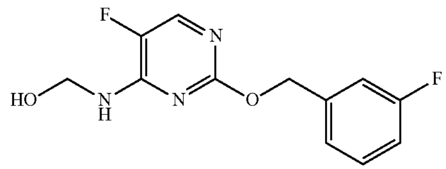 [SMILES: OCNc1nc(OCc2cccc(F)c2)ncc1F] | A | A | A | A | white solid | 107-108 | 268 | 266 | |
| 781 | 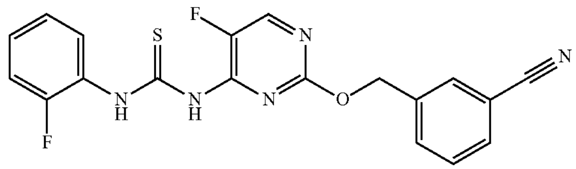 [SMILES: N#Cc1cccc(COc2ncc(F)c(NC(=S)Nc3ccccc3F)n2)c1] | D | C | D | B | light yellow solid | 160-162 | 398 | 396 | |
| 782 | 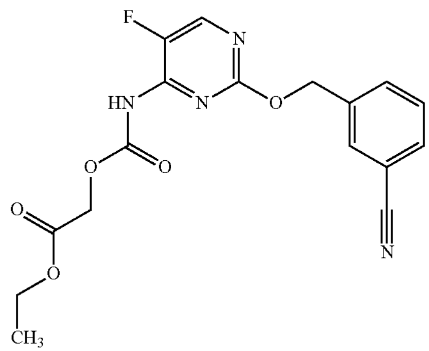 [SMILES: CCOC(=O)COC(=O)Nc1nc(OCc2cccc(C#N)c2)ncc1F] | C | A | D | C | | | 375 | 373 | |
| 783 | 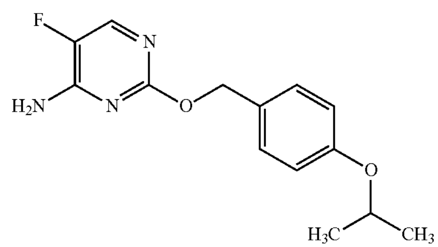 | A | A | A | A | off-white solid | 51-54 | 278 | 276 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 784 | 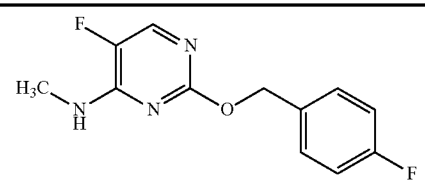 | D | D | D | D | white solid | 112-115 | | | 250 |
| 785 | 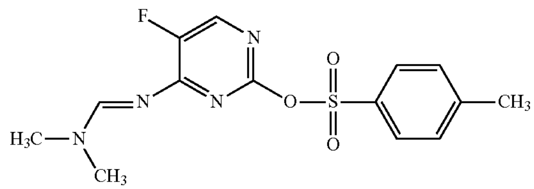 | A | A | A | A | white solid | 163-164 | 340 | | |
| 786 | 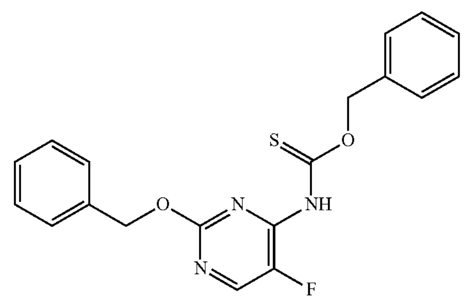 [SMILES: Fc1cnc(OCc2ccccc2)nc1NC(=S)OCc1ccccc1] | E | E | E | E | Pale yellow semi solid | | 370 | | |
| 787 | 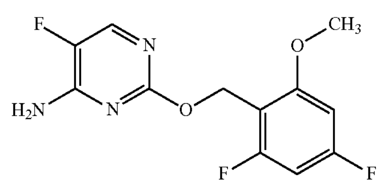 [SMILES: COc1cc(F)cc(F)c1COc1ncc(F)c(N)n1] | A | A | A | A | white solid | 171 | 286 | 284 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 788 | 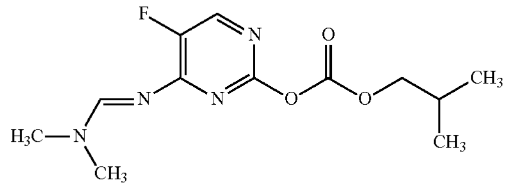 | A | A | A | A | white solid | 59-60 | 285 | | |
| 789 | 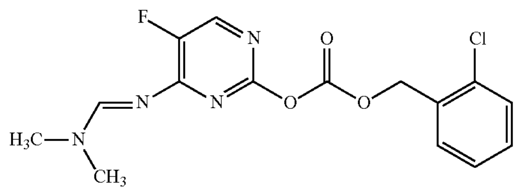 [SMILES: CN(C)/C=N/c1nc(OC(=O)OCc2ccccc2Cl)ncc1F] | A | A | A | A | white solid | 134-141 | 353 | | |
| 790 | 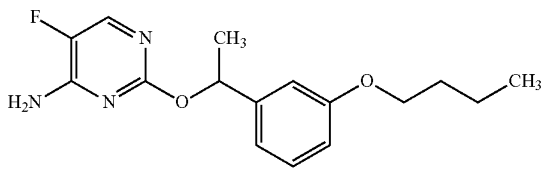 [SMILES: CCCCOc1cccc(C(C)Oc2ncc(F)c(N)n2)c1] | A | A | A | A | clear oil | | | 304 | |
| 791 | 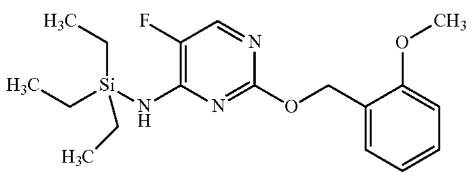 [SMILES: CC[Si](CC)(CC)Nc1nc(OCc2ccccc2OC)ncc1F] | E | E | E | E | clear oil | | 365 | | |
| 792 | 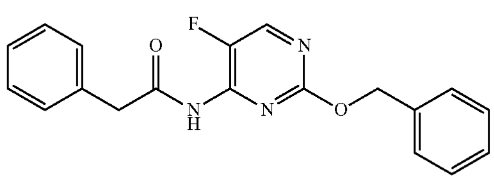 [SMILES: O=C(Cc1ccccc1)Nc1nc(OCc2ccccc2)ncc1F] | C | B | A | A | white solid | 123-125 | 338 | 336 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 793 | 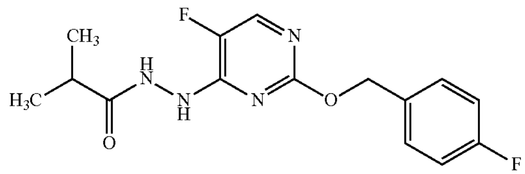 [SMILES: CC(C)C(=O)NNc1nc(OCc2ccc(F)cc2)ncc1F] | D | D | D | D | off-white solid | 158-166 | 323 | 321 | |
| 794 | 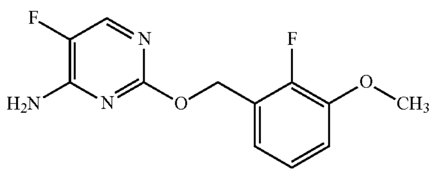 [SMILES: COc1cccc(COc2ncc(F)c(N)n2)c1F] | A | A | A | A | white solid | 108 | | 266 | |
| 795 | 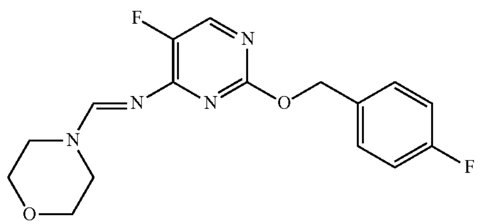 [SMILES: Fc1ccc(COc2ncc(F)c(/N=C/N3CCOCC3)n2)cc1] | A | A | A | A | white solid | 124-125 | 335 | | |
| 796 | 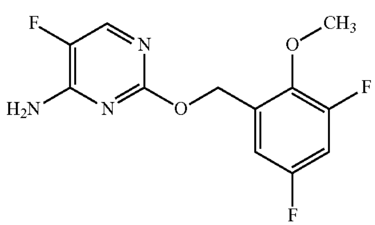 [SMILES: COc1c(F)cc(F)cc1COc1ncc(F)c(N)n1] | A | A | A | A | white solid | 149 | 286 | 284 | |
| 797 | 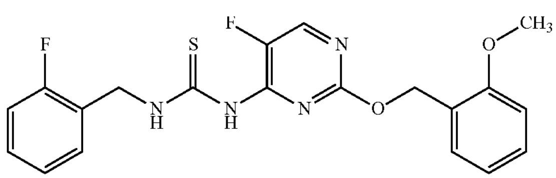 [SMILES: COc1ccccc1COc1ncc(F)c(NC(=S)NCc2ccccc2F)n1] | C | A | B | A | off-white solid | 167-168 | 417 | 415 | |

TABLE I-continued

Three day curative (3DC) and one day protectant (1DP) Activity of Compounds on SEPTTR at 25 and 100 ppm

| Cmpd | Structure | SEPTTR 3DC 25 ppm | SEPTTR 3DC 100 ppm | SETTTR 1DP 25 ppm | SEPTTR 1DP 100 ppm | Phys. App. | MP | Mass Spec. (ES+) | Mass Spec. (ES−) | GCMS |
|---|---|---|---|---|---|---|---|---|---|---|
| 798 | 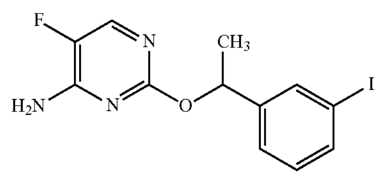 [SMILES: CC(Oc1ncc(F)c(N)n1)c1cccc(I)c1] | A | A | A | A | clear oil | | | 358 | |
| 799 | 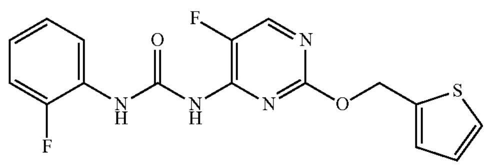 [SMILES: O=C(Nc1ccccc1F)Nc1nc(OCc2cccs2)ncc1F] | D | D | D | D | white solid | 200-202 | 363 | 361 | |
| 800 | 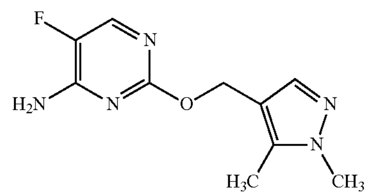 [SMILES: Cc1c(COc2ncc(F)c(N)n2)cnn1C] | A | A | A | A | tan solid | | 238 | | |
| 801 | 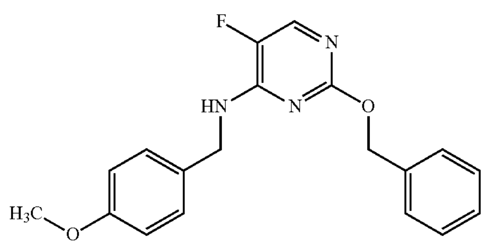 [SMILES: COc1ccc(CNc2nc(OCc3ccccc3)ncc2F)cc1] | E | E | E | E | Off white solid | | | 338 | |
| 802 | 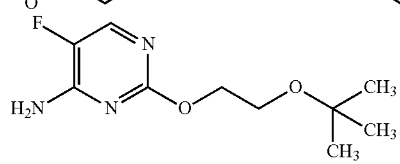 | D | D | D | D | white solid | 98-99 | 230 | 228 | |

TABLE II

| | | 1 DP Activity of Compounds on SEPTTR at 50 and 200 ppm | | | | | | |
|---|---|---|---|---|---|---|---|---|
| Cmpd | Structure | SEPTTR 1DP 50 ppm | SEPTTR 1DP 200 ppm | Phys. App. | MP | Mass Spec. (ES+) | Mass Spec. (ES−) | GCMS |
| 803 | | D | B | | | 320 | | |
| 804 | | C | B | | | 360 | | |
| 805 | | B | A | | | 342 | | |
| 806 | | E | A | | | 384 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|------|-----------|-------------------|---------------------|-----------|-----|------------------|------------------|------|
| 807 | 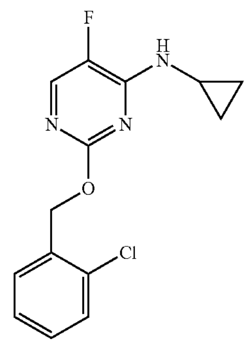 [SMILES: Fc1cnc(OCc2ccccc2Cl)nc1NC1CC1] | E | A | | | 294 | | |
| 808 | 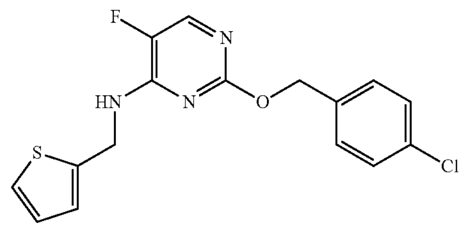 [SMILES: Fc1cnc(OCc2ccc(Cl)cc2)nc1NCc1cccs1] | A | A | | | 350 | | |
| 809 | 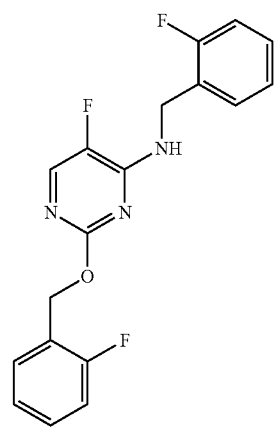 [SMILES: Fc1ccccc1CNc1nc(OCc2ccccc2F)ncc1F] | B | A | | | 346 | | |
| 810 | 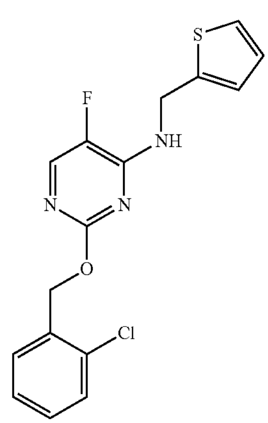 [SMILES: Fc1cnc(OCc2ccccc2Cl)nc1NCc1cccs1] | E | A | | | 350 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 811 | 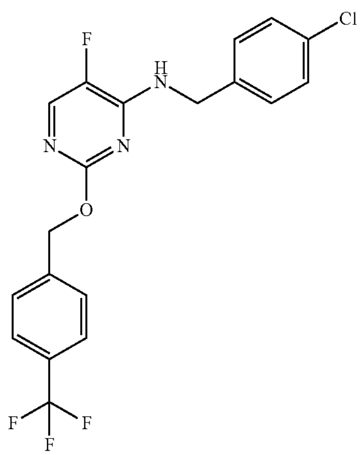 [SMILES: Fc1cnc(OCc2ccc(C(F)(F)F)cc2)nc1NCc1ccc(Cl)cc1] | A | A | | | 412 | | |
| 812 | 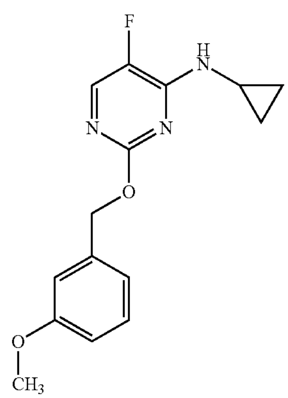 [SMILES: COc1cccc(COc2ncc(F)c(NC3CC3)n2)c1] | E | A | | | 290 | | |
| 813 | 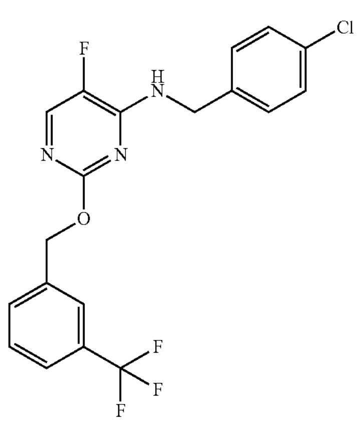 [SMILES: Fc1cnc(OCc2cccc(C(F)(F)F)c2)nc1NCc1ccc(Cl)cc1] | A | A | | | 412 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 814 | 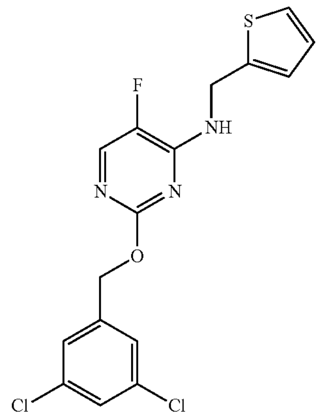 [SMILES: Fc1cnc(OCc2cc(Cl)cc(Cl)c2)nc1NCc1cccs1] | E | A | | | 384 | | |
| 815 | 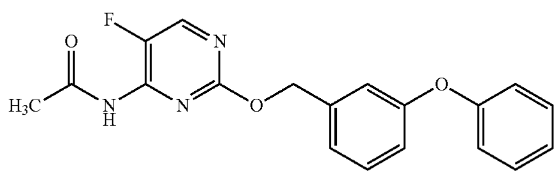 [SMILES: CC(=O)Nc1nc(OCc2cccc(Oc3ccccc3)c2)ncc1F] | A | A | white solid | 115-118 | 354 | 352 | |
| 816 | 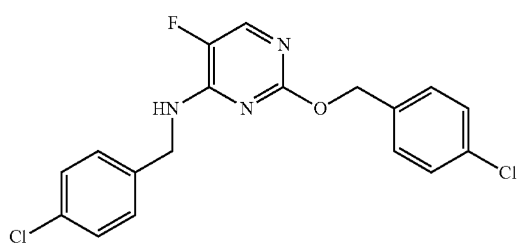 [SMILES: Fc1cnc(OCc2ccc(Cl)cc2)nc1NCc1ccc(Cl)cc1] | A | A | | | 378 | | |
| 817 | 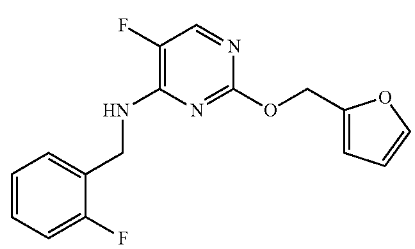 [SMILES: Fc1ccccc1CNc1nc(OCc2ccco2)ncc1F] | C | A | | | 318 | | |
| 818 | 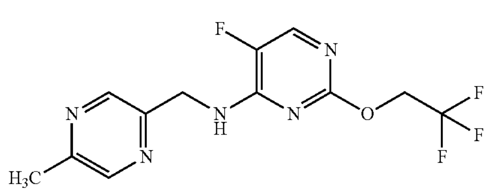 [SMILES: Cc1cnc(CNc2nc(OCC(F)(F)F)ncc2F)cn1] | D | D | | | 317 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 819 | 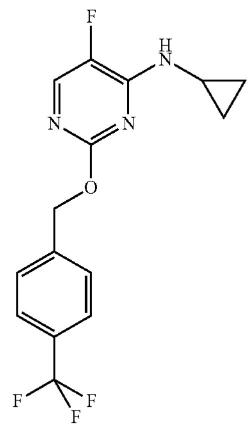 [SMILES: Fc1cnc(OCc2ccc(C(F)(F)F)cc2)nc1NC1CC1] | E | A | off white solid | | 328 | | |
| 820 | 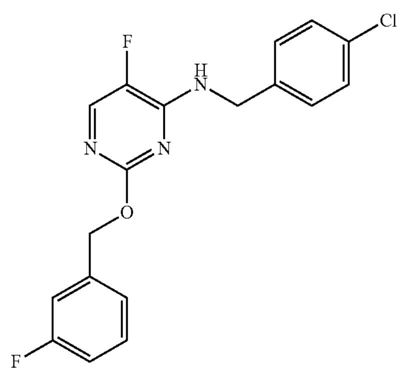 [SMILES: Fc1cccc(COc2ncc(F)c(NCc3ccc(Cl)cc3)n2)c1] | C | A | | | 362 | | |
| 821 | 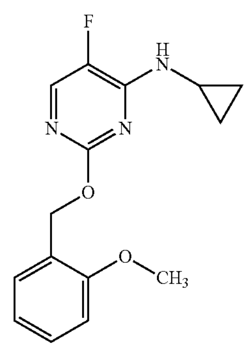 [SMILES: COc1ccccc1COc1ncc(F)c(NC2CC2)n1] | E | A | | | 290 | | |
| 822 | 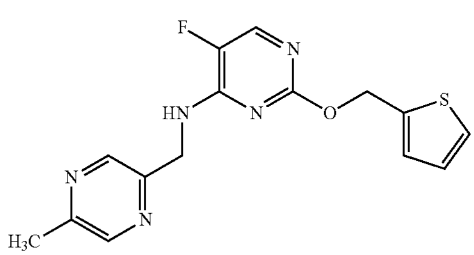 | C | A | | | 332 | | |

TABLE II-continued
1 DP Activity of Compounds on SEPTTR at 50 and 200 ppm
| Cmpd | Structure | SEPTTR 1DP 50 ppm | SEPTTR 1DP 200 ppm | Phys. App. | MP | Mass Spec. (ES+) | Mass Spec. (ES−) | GCMS |
|------|-----------|-------------------|---------------------|------------|----|----|----|------|
| 823 | 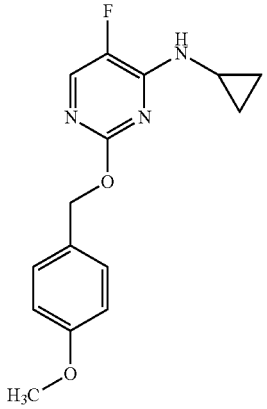 [SMILES: COc1ccc(COc2ncc(F)c(NC3CC3)n2)cc1] | E | A | | | | | 290 |
| 824 | 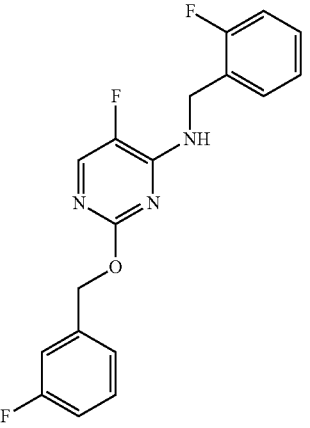 [SMILES: Fc1cccc(COc2ncc(F)c(NCc3ccccc3F)n2)c1] | A | A | | | | | 346 |
| 825 | 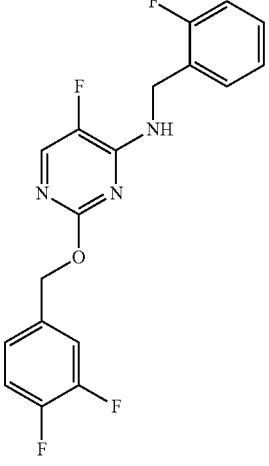 | B | A | | | | | 364 |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 826 | 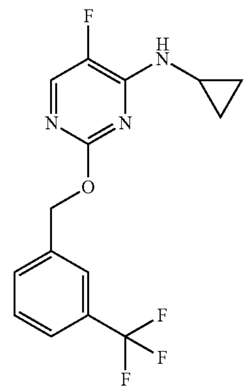 [SMILES: Fc1cnc(OCc2cccc(C(F)(F)F)c2)nc1NC1CC1] | E | A | | | 328 | | |
| 827 | 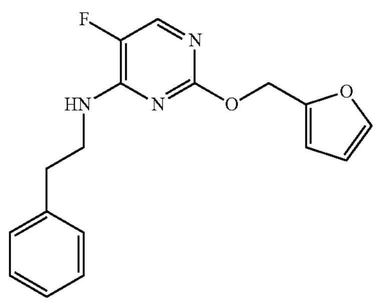 [SMILES: Fc1cnc(OCc2ccco2)nc1NCCc1ccccc1] | D | C | | | 314 | | |
| 828 | 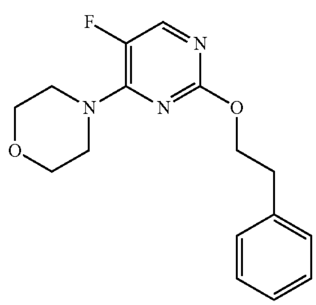 [SMILES: Fc1cnc(OCCc2ccccc2)nc1N1CCOCC1] | D | D | | | 304 | | |
| 829 | 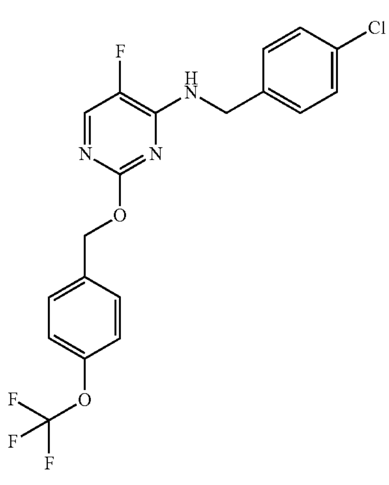 [SMILES: Fc1cnc(OCc2ccc(OC(F)(F)F)cc2)nc1NCc1ccc(Cl)cc1] | C | A | | | 428 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 830 | 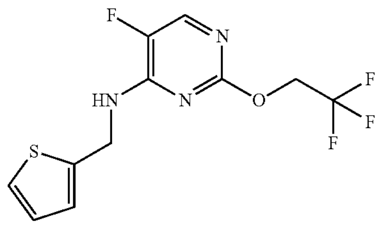 [SMILES: Fc1cnc(OCC(F)(F)F)nc1NCc1cccs1] | D | D | | | 308 | | |
| 831 | 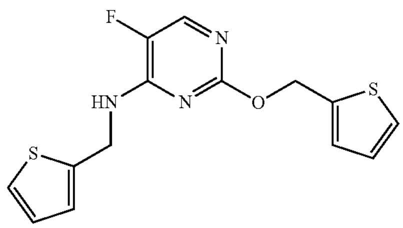 | B | A | | | 322 | | |
| 832 | 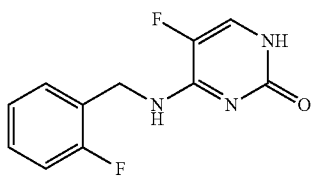 [SMILES: O=c1nc(NCc2ccccc2F)c(F)c[nH]1] | D | D | white solid | 167-169 | 238 | 236 | |
| 833 | 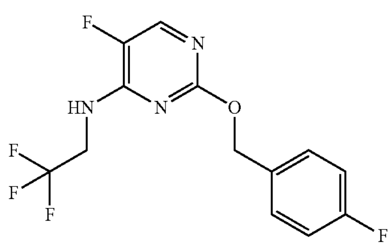 [SMILES: Fc1ccc(COc2ncc(F)c(NCC(F)(F)F)n2)cc1] | C | B | | | 318 | | |
| 834 | 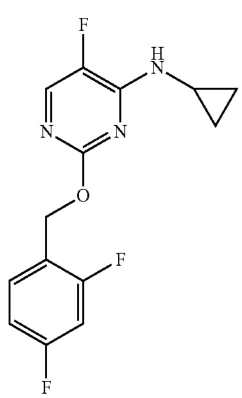 [SMILES: Fc1ccc(COc2ncc(F)c(NC3CC3)n2)c(F)c1] | E | A | | | 296 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 835 | 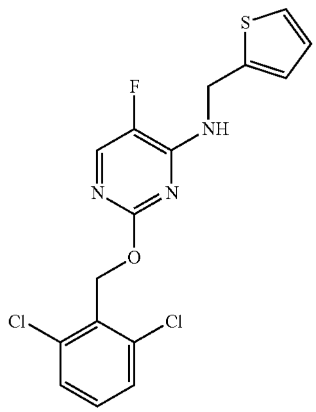 [SMILES: Fc1cnc(OCc2c(Cl)cccc2Cl)nc1NCc1cccs1] | E | A | | | 384 | | |
| 836 | 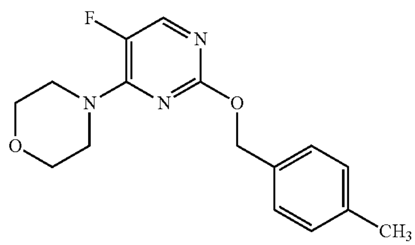 [SMILES: Cc1ccc(COc2ncc(F)c(N3CCOCC3)n2)cc1] | B | A | | | 304 | | |
| 837 | 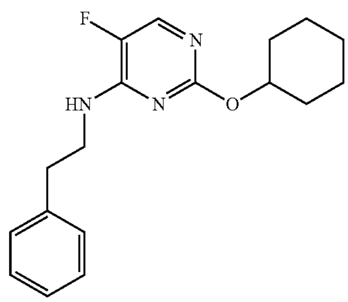 [SMILES: Fc1cnc(OC2CCCCC2)nc1NCCc1ccccc1] | D | D | | | 316 | | |
| 838 | 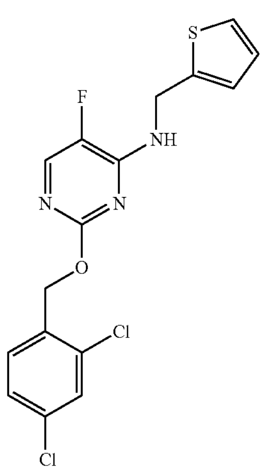 [SMILES: Fc1cnc(OCc2ccc(Cl)cc2Cl)nc1NCc1cccs1] | E | A | | | 384 | | |

TABLE II-continued
1 DP Activity of Compounds on SEPTTR at 50 and 200 ppm
| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 839 | 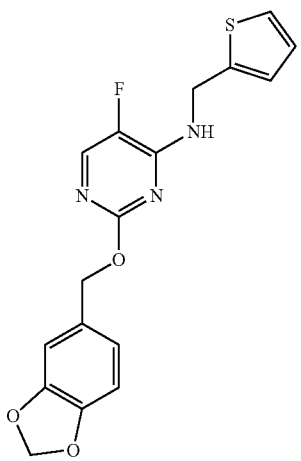 [SMILES: Fc1cnc(OCc2ccc3c(c2)OCO3)nc1NCc1cccs1] | E | A | | | 360 | | |
| 840 | 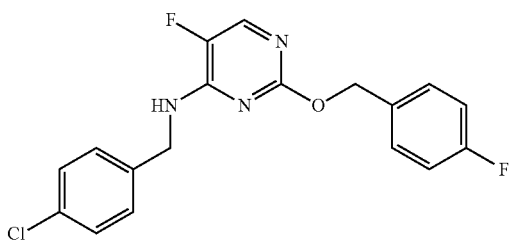 [SMILES: Fc1ccc(COc2ncc(F)c(NCc3ccc(Cl)cc3)n2)cc1] | B | A | | | 362 | | |
| 841 | 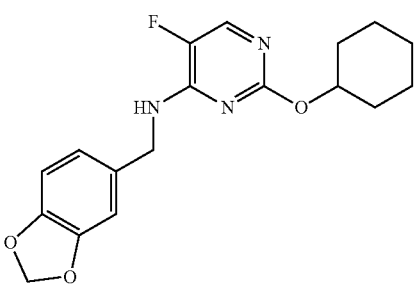 [SMILES: Fc1cnc(OC2CCCCC2)nc1NCc1ccc2c(c1)OCO2] | B | A | | | 346 | | |
| 842 | 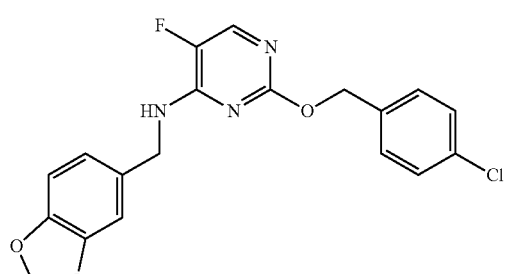 | A | A | | | 388 | | |
| 843 | 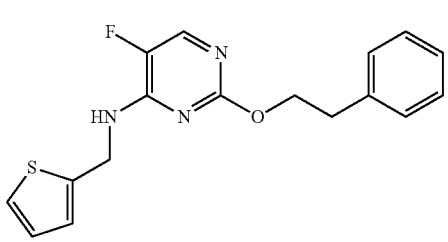 [SMILES: Fc1cnc(OCCc2ccccc2)nc1NCc1cccs1] | C | A | | | 330 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 844 | 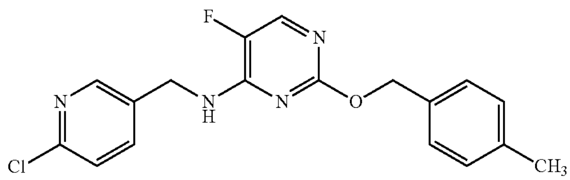 [SMILES: Cc1ccc(COc2ncc(F)c(NCc3ccc(Cl)nc3)n2)cc1] | A | A | | | | 357 | |
| 845 | 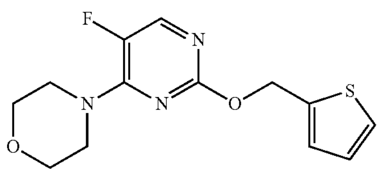 [SMILES: Fc1cnc(OCc2cccs2)nc1N1CCOCC1] | A | A | | | 296 | | |
| 846 | 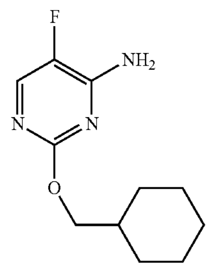 [SMILES: Nc1nc(OCC2CCCCC2)ncc1F] | D | C | white solid | 108-110 | 226 | 224 | |
| 847 | 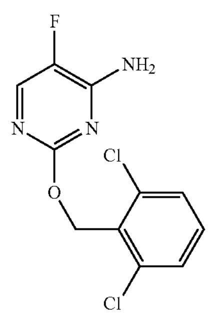 [SMILES: Nc1nc(OCc2c(Cl)cccc2Cl)ncc1F] | A | E | white solid | 155-157 | 288 | 286 | |
| 848 | 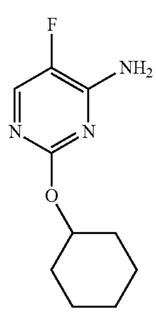 [SMILES: Nc1nc(OC2CCCCC2)ncc1F] | D | D | white solid | | 212 | 210 | |
| 849 | 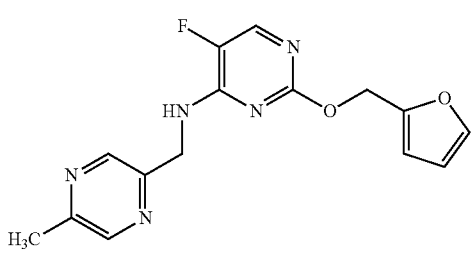 [SMILES: Cc1cnc(CNc2nc(OCc3ccco3)ncc2F)cn1] | A | A | | | 316 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 850 | 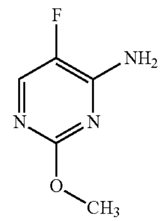 | D | B | yellow-white solid | 189-191 | 144 | | |
| 851 | 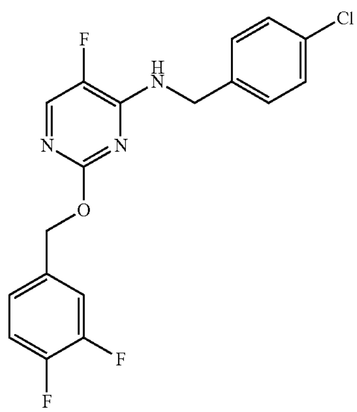 [SMILES: Fc1ccc(COc2ncc(F)c(NCc3ccc(Cl)cc3)n2)cc1F] | A | A | | | 380 | | |
| 852 | 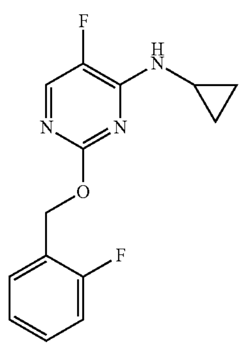 [SMILES: Fc1ccccc1COc1ncc(F)c(NC2CC2)n1] | B | A | | | 278 | | |
| 853 | 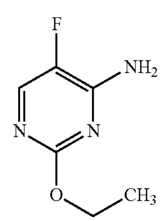 | D | D | white solid | 112-114 | 158 | | |
| 854 | 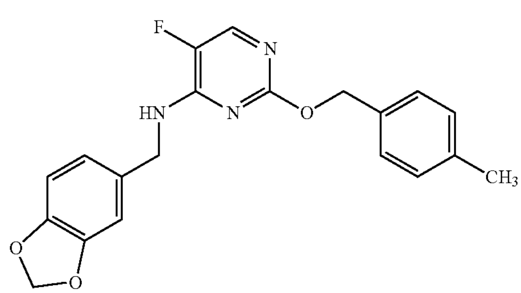 [SMILES: Cc1ccc(COc2ncc(F)c(NCc3ccc4c(c3)OCO4)n2)cc1] | B | A | | | 368 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 855 | 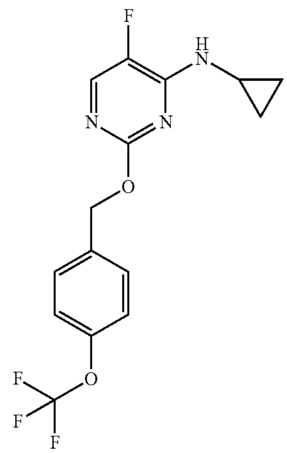 [SMILES: Fc1cnc(OCc2ccc(OC(F)(F)F)cc2)nc1NC1CC1] | E | A | | | 344 | | |
| 856 | 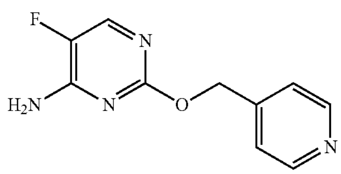 [SMILES: Nc1nc(OCc2ccncc2)ncc1F] | E | A | off-white solid | | 221 | | |
| 857 | 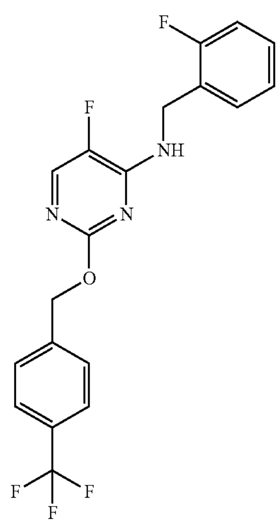 [SMILES: Fc1ccccc1CNc1nc(OCc2ccc(C(F)(F)F)cc2)ncc1F] | B | A | | | 397 | | |
| 858 | 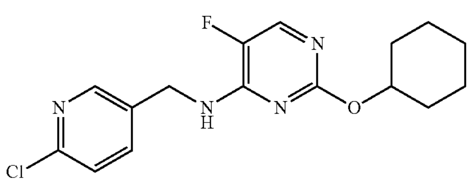 [SMILES: Fc1cnc(OC2CCCCC2)nc1NCc1ccc(Cl)nc1] | D | C | | | 335 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 859 | 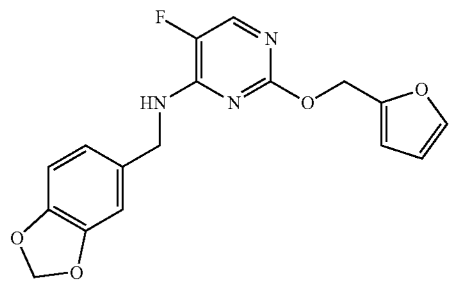 [SMILES: Fc1cnc(OCc2ccco2)nc1NCc1ccc2c(c1)OCO2] | A | A | | | 344 | | |
| 860 | 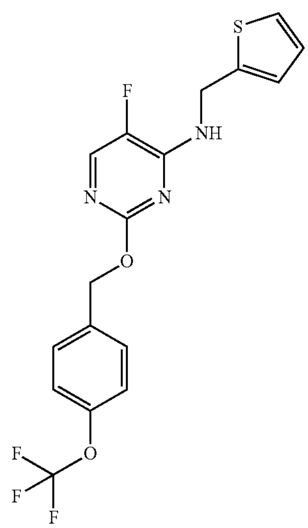 [SMILES: Fc1cnc(OCc2ccc(OC(F)(F)F)cc2)nc1NCc1cccs1] | E | A | | | 400 | | |
| 861 | 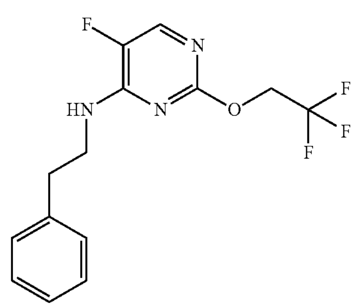 [SMILES: Fc1cnc(OCC(F)(F)F)nc1NCCc1ccccc1] | D | C | | | 316 | | |
| 862 | 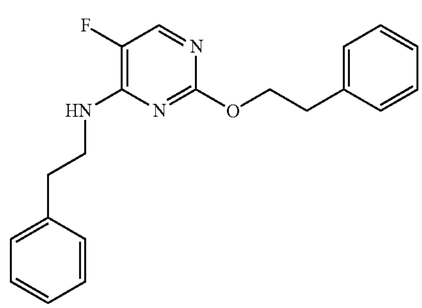 [SMILES: Fc1cnc(OCCc2ccccc2)nc1NCCc1ccccc1] | B | A | | | 338 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 863 | 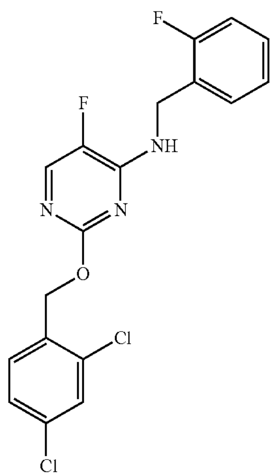 [SMILES: Fc1ccccc1CNc1nc(OCc2ccc(Cl)cc2Cl)ncc1F] | A | A | | | 398 | | |
| 864 | 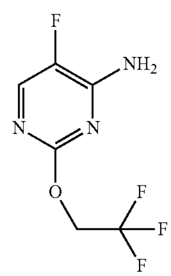 [SMILES: Nc1nc(OCC(F)(F)F)ncc1F] | D | C | white solid | 115-117 | 212 | 210 | |
| 865 | 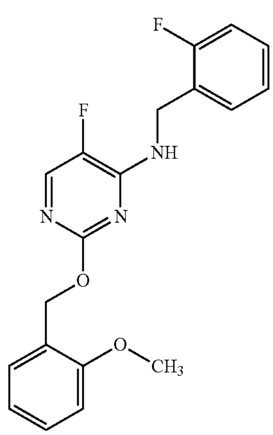 [SMILES: COc1ccccc1COc1ncc(F)c(NCc2ccccc2F)n1] | C | A | | | 358 | | |
| 866 | 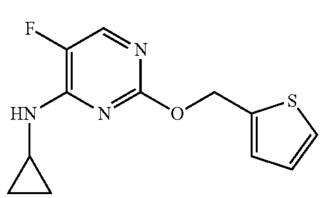 [SMILES: Fc1cnc(OCc2cccs2)nc1NC1CC1] | D | A | | | 266 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 867 | 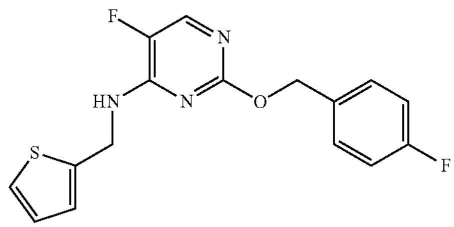 [SMILES: Fc1ccc(COc2ncc(F)c(NCc3cccs3)n2)cc1] | A | A | | | 334 | | |
| 868 | 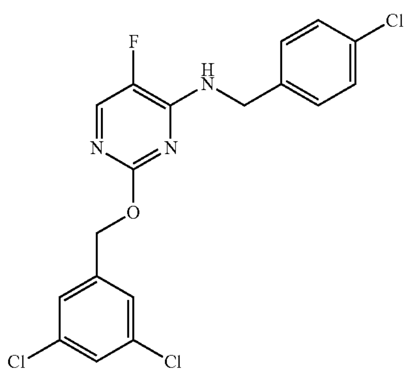 [SMILES: Fc1cnc(OCc2cc(Cl)cc(Cl)c2)nc1NCc1ccc(Cl)cc1] | B | A | | | 414 | | |
| 869 | 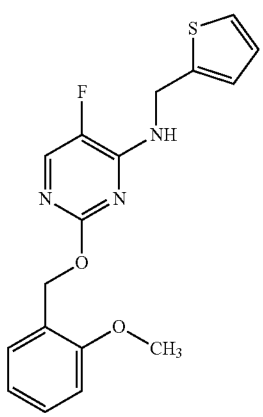 [SMILES: COc1ccccc1COc1ncc(F)c(NCc2cccs2)n1] | E | A | | | 346 | | |
| 870 | 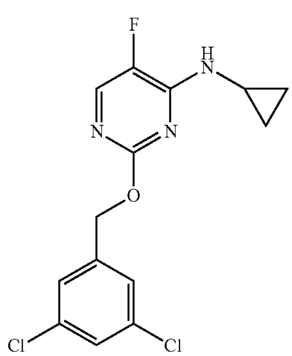 [SMILES: Fc1cnc(OCc2cc(Cl)cc(Cl)c2)nc1NC1CC1] | E | A | | | 330 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 871 | 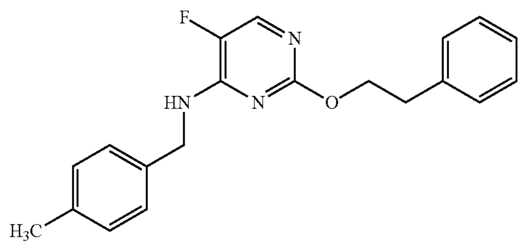 [SMILES: Cc1ccc(CNc2nc(OCCc3ccccc3)ncc2F)cc1] | D | C | | | 338 | | |
| 872 | 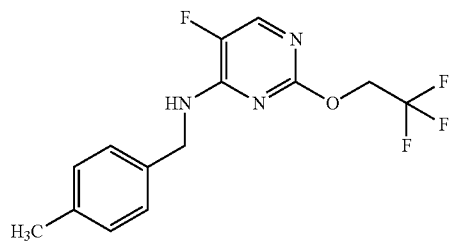 [SMILES: Cc1ccc(CNc2nc(OCC(F)(F)F)ncc2F)cc1] | C | B | | | 316 | | |
| 873 | 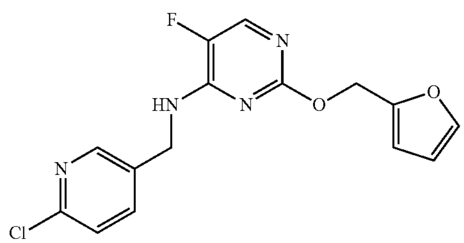 [SMILES: Fc1cnc(OCc2ccco2)nc1NCc1ccc(Cl)nc1] | D | D | | | 335 | | |
| 874 | 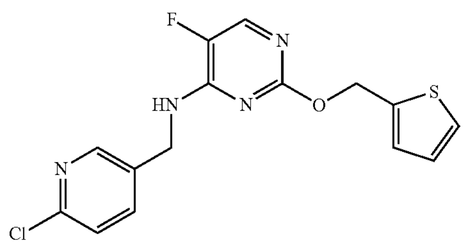 [SMILES: Fc1cnc(OCc2cccs2)nc1NCc1ccc(Cl)nc1] | D | D | | | 351 | | |
| 875 | 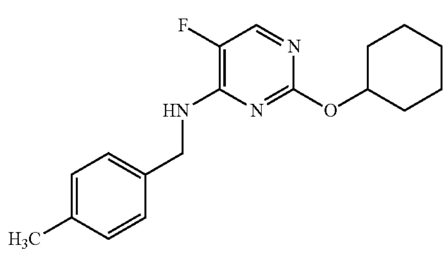 [SMILES: Cc1ccc(CNc2nc(OC3CCCCC3)ncc2F)cc1] | D | A | | | 316 | | |
| 876 | 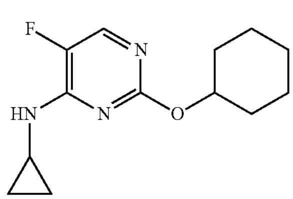 [SMILES: Fc1cnc(OC2CCCCC2)nc1NC1CC1] | D | D | | | 249 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 877 | 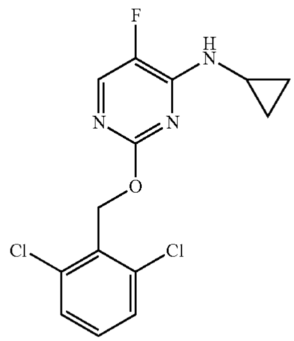 [SMILES: Fc1cnc(OCc2c(Cl)cccc2Cl)nc1NC1CC1] | E | A | | | 330 | | |
| 878 | 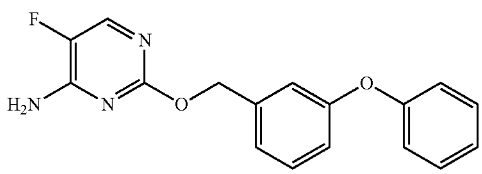 [SMILES: Nc1nc(OCc2cccc(Oc3ccccc3)c2)ncc1F] | A | A | yellow gummy solid | | 312 | 310 | |
| 879 | 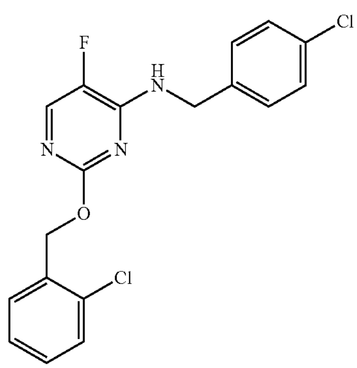 [SMILES: Fc1cnc(OCc2ccccc2Cl)nc1NCc1ccc(Cl)cc1] | A | A | | | 380 | | |
| 880 | 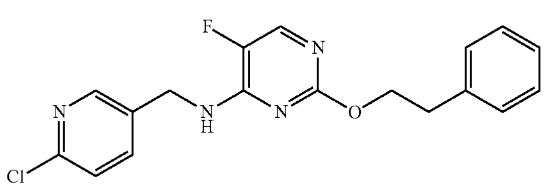 [SMILES: Fc1cnc(OCCc2ccccc2)nc1NCc1ccc(Cl)nc1] | D | C | | | 359 | | |
| 881 | 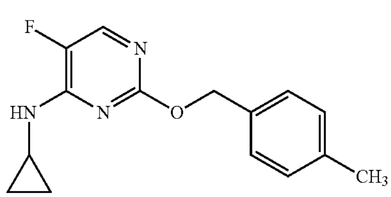 [SMILES: Cc1ccc(COc2ncc(F)c(NC3CC3)n2)cc1] | A | A | | | 274 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 882 | 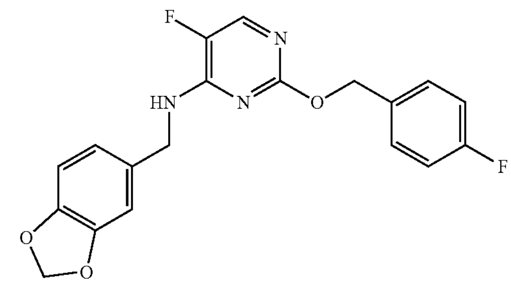 [SMILES: Fc1ccc(COc2ncc(F)c(NCc3ccc4c(c3)OCO4)n2)cc1] | A | A | | | 372 | | |
| 883 | 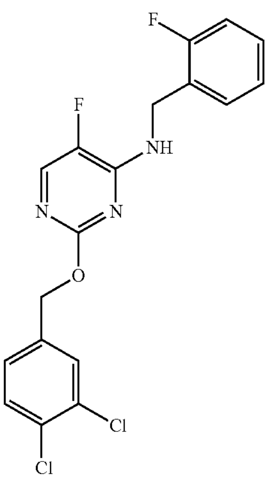 [SMILES: Fc1ccccc1CNc1nc(OCc2ccc(Cl)c(Cl)c2)ncc1F] | A | A | | | 398 | | |
| 884 | 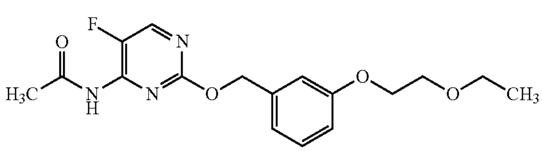 [SMILES: CCOCCOc1cccc(COc2ncc(F)c(NC(C)=O)n2)c1] | A | A | orange oil | | 350 | 348 | |
| 885 | 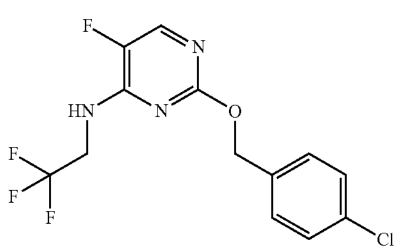 [SMILES: Fc1cnc(OCc2ccc(Cl)cc2)nc1NCC(F)(F)F] | C | B | | | 334 | | |
| 886 | 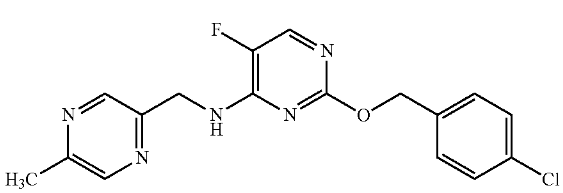 [SMILES: Cc1cnc(CNc2nc(OCc3ccc(Cl)cc3)ncc2F)cn1] | A | A | | | 360 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 887 | 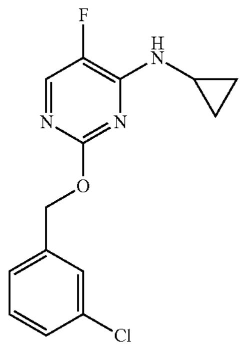 [SMILES: Fc1cnc(OCc2cccc(Cl)c2)nc1NC1CC1] | E | A | | | 294 | | |
| 888 | 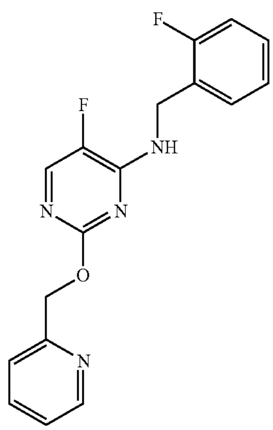 [SMILES: Fc1ccccc1CNc1nc(OCc2ccccn2)ncc1F] | D | B | | | 329 | | |
| 889 | 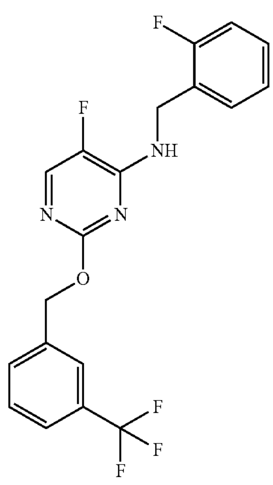 [SMILES: Fc1ccccc1CNc1nc(OCc2cccc(C(F)(F)F)c2)ncc1F] | A | A | | | 397 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 890 | 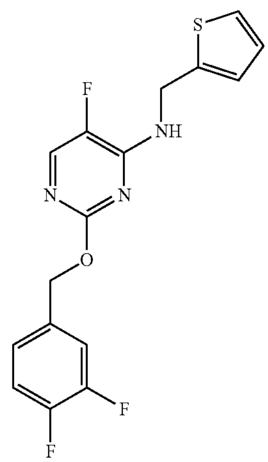 [SMILES: Fc1ccc(COc2ncc(F)c(NCc3cccs3)n2)cc1F] | E | A | | | 352 | | |
| 891 | 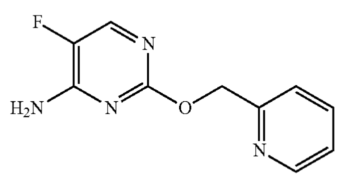 [SMILES: Nc1nc(OCc2ccccn2)ncc1F] | A | A | yellowish solid | | 221 | | |
| 892 | 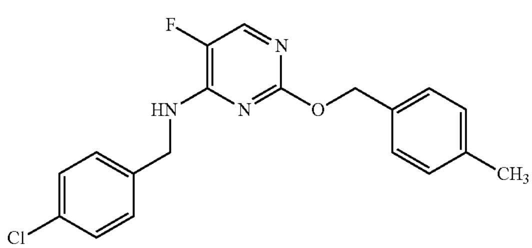 [SMILES: Cc1ccc(COc2ncc(F)c(NCc3ccc(Cl)cc3)n2)cc1] | B | A | | | 358 | | |
| 893 | 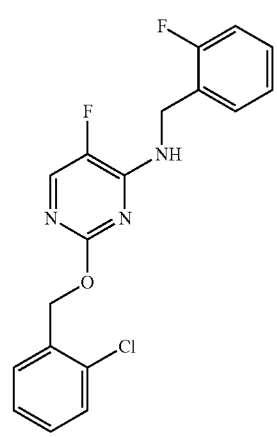 [SMILES: Fc1ccccc1CNc1nc(OCc2ccccc2Cl)ncc1F] | A | A | | | 362 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 894 | 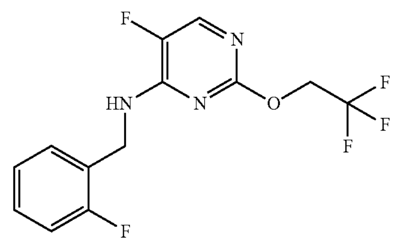 [SMILES: Fc1ccccc1CNc1nc(OCC(F)(F)F)ncc1F] | D | D | | | 320 | | |
| 895 | 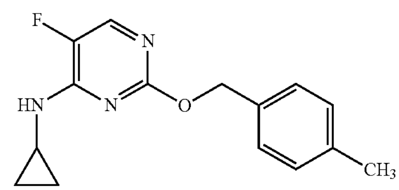 [SMILES: Cc1ccc(COc2ncc(F)c(NC3CC3)n2)cc1] | A | A | | | 294 | | |
| 896 | 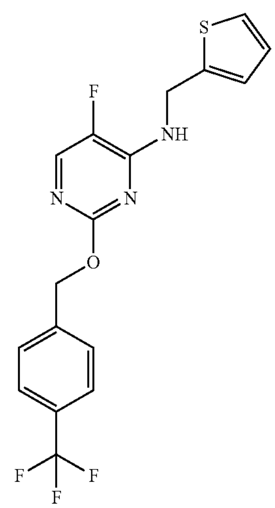 [SMILES: Fc1cnc(OCc2ccc(C(F)(F)F)cc2)nc1NCc1cccs1] | E | A | | | 384 | | |
| 897 | 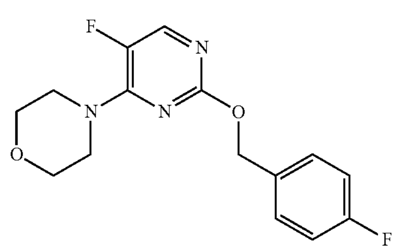 [SMILES: Fc1ccc(COc2ncc(F)c(N3CCOCC3)n2)cc1] | D | B | | | 308 | | |
| 898 | 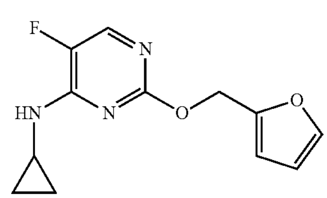 | D | D | | | 250 | | |

TABLE II-continued
1 DP Activity of Compounds on SEPTTR at 50 and 200 ppm
| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 899 | 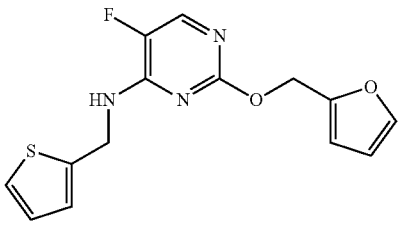 [SMILES: Fc1cnc(OCc2ccco2)nc1NCc1cccs1] | C | A | | | 306 | | |
| 900 | 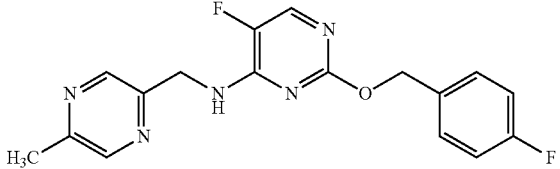 [SMILES: Cc1cnc(CNc2nc(OCc3ccc(F)cc3)ncc2F)cn1] | B | A | | | 344 | | |
| 901 | 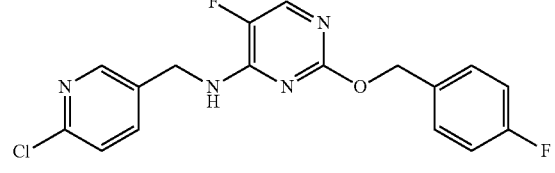 | B | A | | | 363 | | |
| 902 | 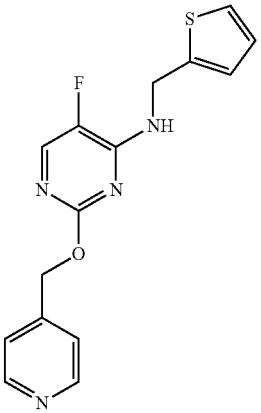 [SMILES: Fc1cnc(OCc2ccncc2)nc1NCc1cccs1] | E | A | | | 317 | | |
| 903 | 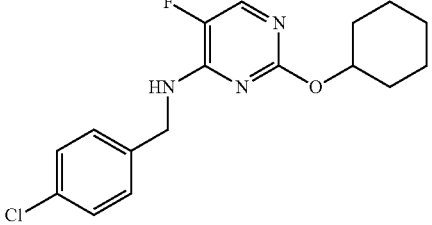 | D | A | | | 336 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 904 | 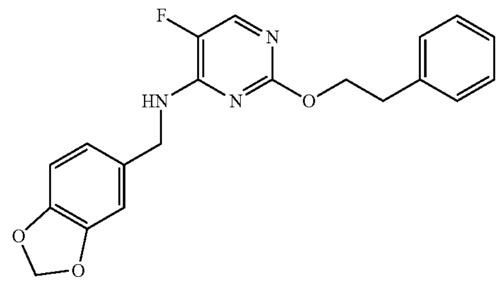 [SMILES: Fc1cnc(OCCc2ccccc2)nc1NCc1ccc2c(c1)OCO2] | D | C | | | 368 | | |
| 905 | 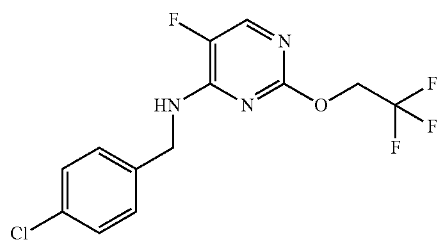 [SMILES: Fc1cnc(OCC(F)(F)F)nc1NCc1ccc(Cl)cc1] | C | B | | | 336 | | |
| 906 | 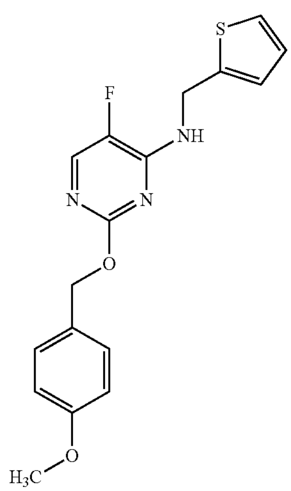 [SMILES: COc1ccc(COc2ncc(F)c(NCc3cccs3)n2)cc1] | E | A | | | 346 | | |
| 907 | 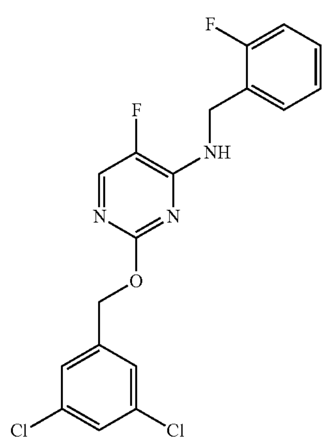 [SMILES: Fc1ccccc1CNc1nc(OCc2cc(Cl)cc(Cl)c2)ncc1F] | B | A | | | 398 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 908 | 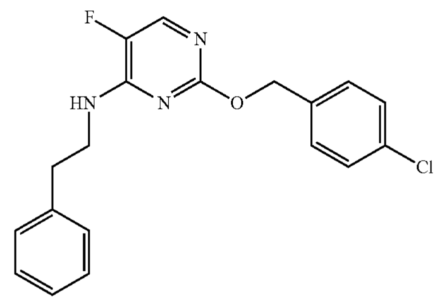 [SMILES: Fc1cnc(OCc2ccc(Cl)cc2)nc1NCCc1ccccc1] | A | A | | | 358 | | |
| 909 | 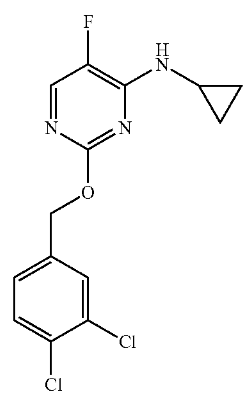 [SMILES: Fc1cnc(OCc2ccc(Cl)c(Cl)c2)nc1NC1CC1] | E | A | | | 328 | | |
| 910 | 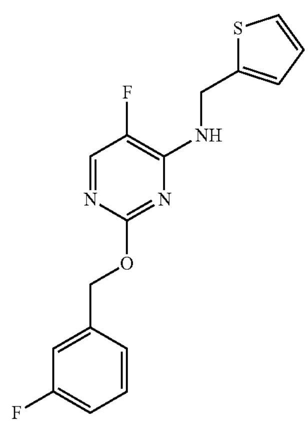 [SMILES: Fc1cccc(COc2ncc(F)c(NCc3cccs3)n2)c1] | E | A | | | 334 | | |
| 911 | 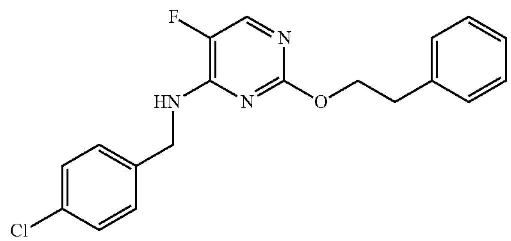 [SMILES: Fc1cnc(OCCc2ccccc2)nc1NCc1ccc(Cl)cc1] | D | D | | | 358 | | |

TABLE II-continued
1 DP Activity of Compounds on SEPTTR at 50 and 200 ppm
| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 912 | 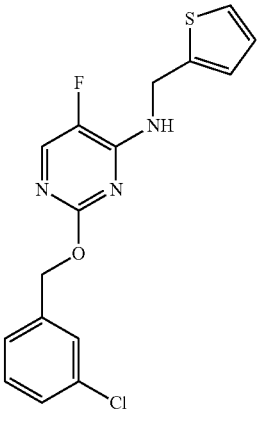 [SMILES: Fc1cnc(OCc2cccc(Cl)c2)nc1NCc1cccs1] | E | A | | | 350 | | |
| 913 | 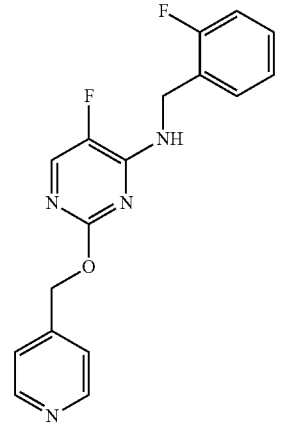 [SMILES: Fc1ccccc1CNc1nc(OCc2ccncc2)ncc1F] | A | A | | | 329 | | |
| 914 | 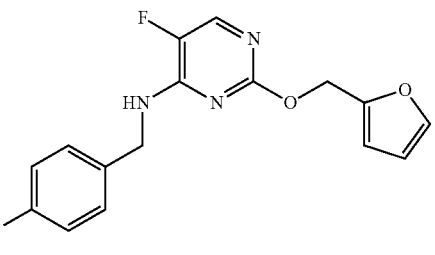 | D | A | | | 314 | | |
| 915 | 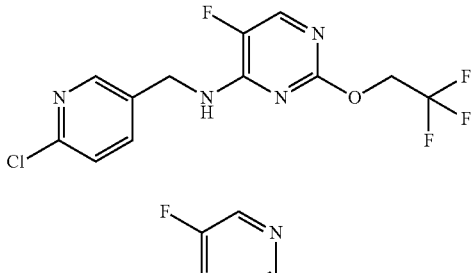 | D | D | | | 337 | | |
| 916 | 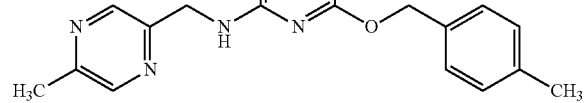 | A | A | | | 340 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 917 | 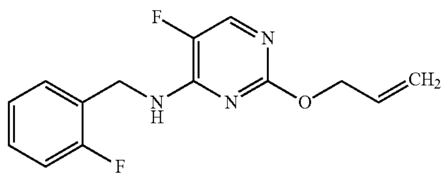 [SMILES: C=CCOc1ncc(F)c(NCc2ccccc2F)n1] | D | B | yellow-white solid | 54-56 | 278 | 276 | |
| 918 | 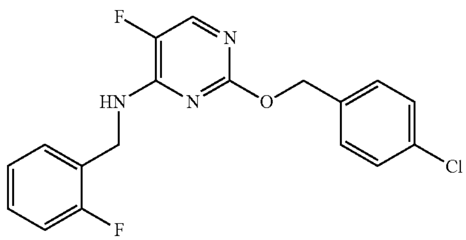 [SMILES: Fc1ccccc1CNc1nc(OCc2ccc(Cl)cc2)ncc1F] | A | A | | | 362 | | |
| 919 | 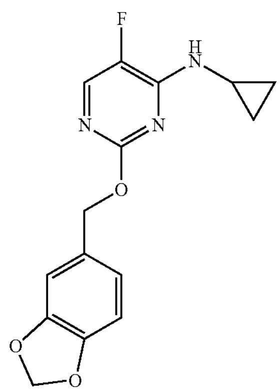 [SMILES: Fc1cnc(OCc2ccc3c(c2)OCO3)nc1NC1CC1] | E | A | | | 304 | | |
| 920 | 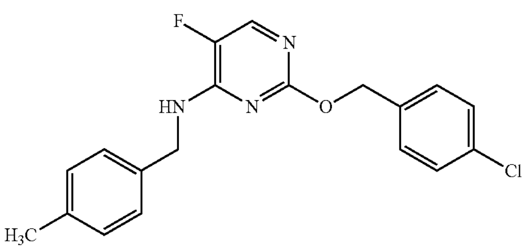 [SMILES: Cc1ccc(CNc2nc(OCc3ccc(Cl)cc3)ncc2F)cc1] | A | A | | | 359 | | |
| 921 | 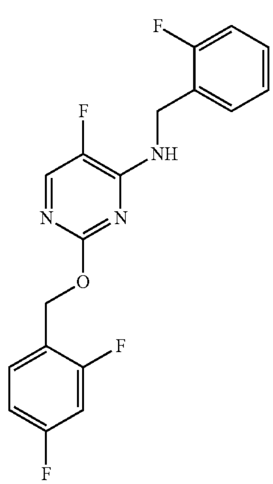 [SMILES: Fc1ccc(COc2ncc(F)c(NCc3ccccc3F)n2)c(F)c1] | A | A | | | 364 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 922 | 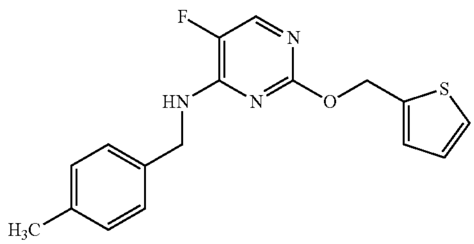 [SMILES: Cc1ccc(CNc2nc(OCc3cccs3)ncc2F)cc1] | B | C | | | 330 | | |
| 923 | 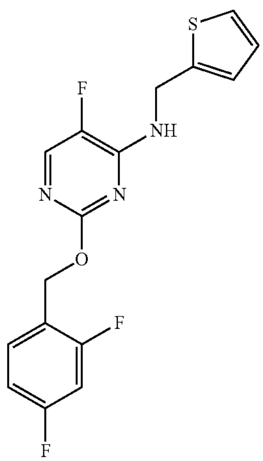 [SMILES: Fc1ccc(COc2ncc(F)c(NCc3cccs3)n2)c(F)c1] | E | A | | | 352 | | |
| 924 | 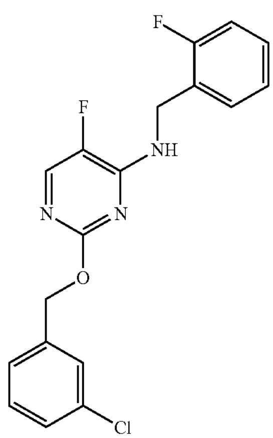 [SMILES: Fc1ccccc1CNc1nc(OCc2cccc(Cl)c2)ncc1F] | A | A | | | 362 | | |
| 925 | 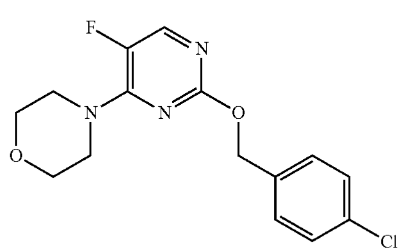 [SMILES: Fc1cnc(OCc2ccc(Cl)cc2)nc1N1CCOCC1] | D | D | | | 324 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 926 | 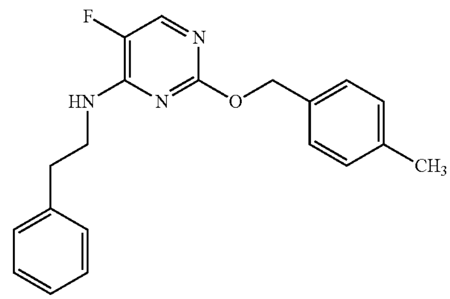 [SMILES: Cc1ccc(COc2ncc(F)c(NCCc3ccccc3)n2)cc1] | A | A | | | 338 | | |
| 927 | 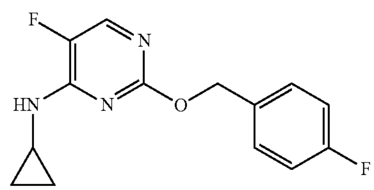 [SMILES: Fc1ccc(COc2ncc(F)c(NC3CC3)n2)cc1] | B | A | | | 278 | | |
| 928 | 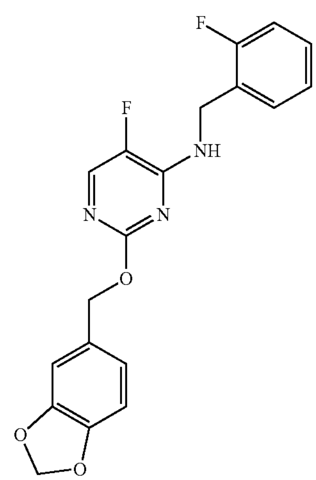 [SMILES: Fc1ccccc1CNc1nc(OCc2ccc3c(c2)OCO3)ncc1F] | A | A | | | 372 | | |
| 929 | 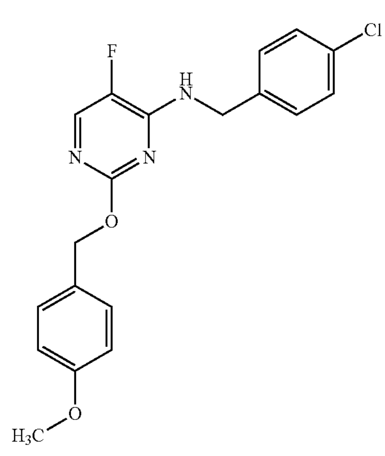 [SMILES: COc1ccc(COc2ncc(F)c(NCc3ccc(Cl)cc3)n2)cc1] | B | A | | | 374 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 930 | 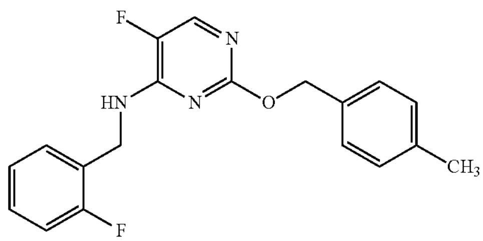 [SMILES: Cc1ccc(COc2ncc(F)c(NCc3ccccc3F)n2)cc1] | D | A | | | 342 | | |
| 931 | 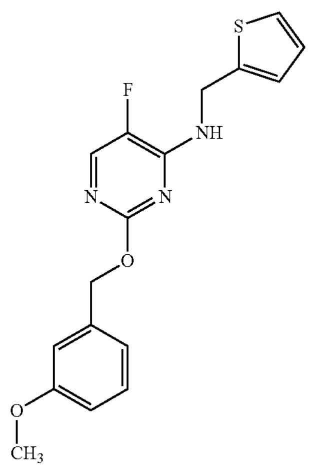 [SMILES: COc1cccc(COc2ncc(F)c(NCc3cccs3)n2)c1] | E | A | | | 346 | | |
| 932 | 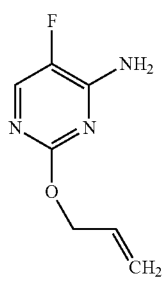 | A | A | white solid | 49-51 | 170 | 168 | |
| 933 | 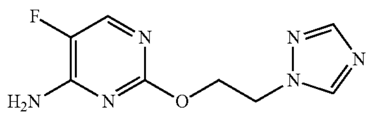 [SMILES: Nc1nc(OCCn2cncn2)ncc1F] | C | B | white solid | 145-149 | | 223 | |
| 934 | 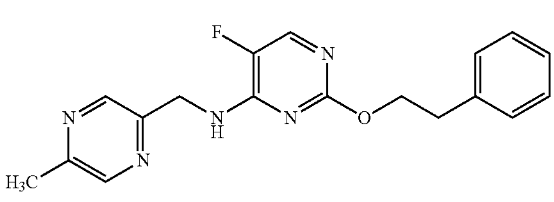 [SMILES: Cc1cnc(CNc2nc(OCCc3ccccc3)ncc2F)cn1] | D | C | | | 340 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 935 | 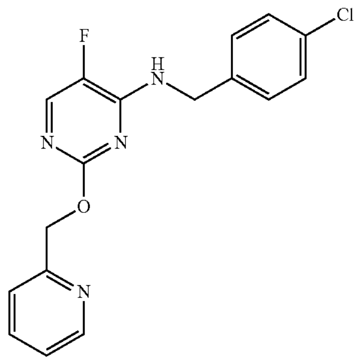 [SMILES: Fc1cnc(OCc2ccccn2)nc1NCc1ccc(Cl)cc1] | C | A | | | 345 | | |
| 936 | 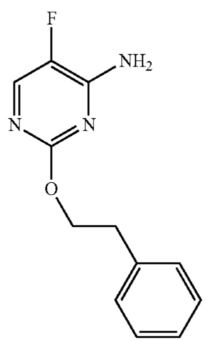 [SMILES: Nc1nc(OCCc2ccccc2)ncc1F] | A | A | white solid | 88-91 | 234 | 232 | |
| 937 | 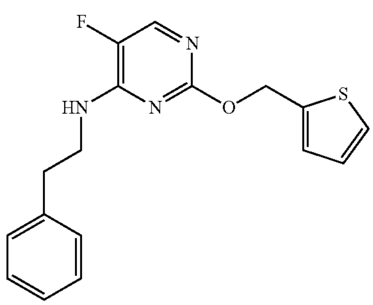 [SMILES: Fc1cnc(OCc2cccs2)nc1NCCc1ccccc1] | A | A | | | 330 | | |
| 938 | 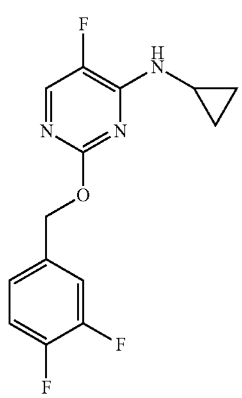 [SMILES: Fc1ccc(COc2ncc(F)c(NC3CC3)n2)cc1F] | E | A | | | 296 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 939 | 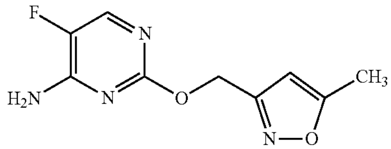 [SMILES: Cc1cc(COc2ncc(F)c(N)n2)no1] | D | A | off-white solid | | 225 | | |
| 940 | 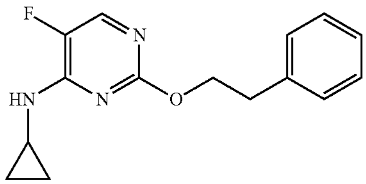 [SMILES: Fc1cnc(OCCc2ccccc2)nc1NC1CC1] | D | D | | | 274 | | |
| 941 | 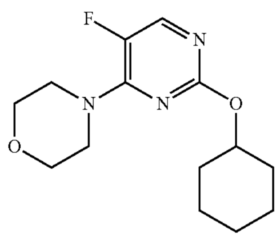 [SMILES: Fc1cnc(OC2CCCCC2)nc1N1CCOCC1] | D | D | | | 282 | | |
| 942 | 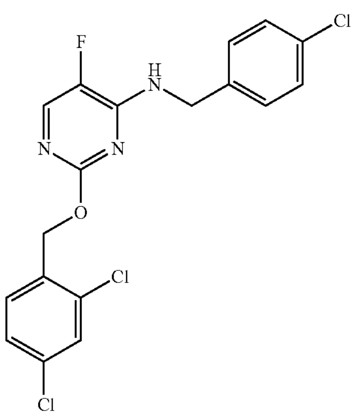 [SMILES: Fc1cnc(OCc2ccc(Cl)cc2Cl)nc1NCc1ccc(Cl)cc1] | A | A | | | 414 | | |
| 943 | 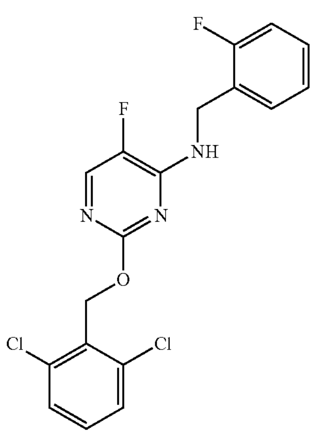 [SMILES: Fc1ccccc1CNc1nc(OCc2c(Cl)cccc2Cl)ncc1F] | B | A | | | 398 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|------|-----------|-------------------|---------------------|------------|-----|------------------|------------------|------|
| 944 | 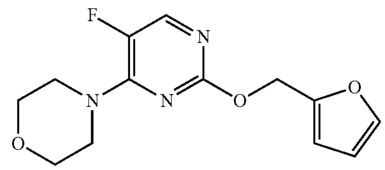 [SMILES: Fc1cnc(OCc2ccco2)nc1N1CCOCC1] | D | D | | | 280 | | |
| 945 | 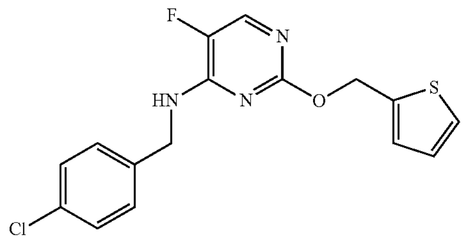 [SMILES: Fc1cnc(OCc2cccs2)nc1NCc1ccc(Cl)cc1] | A | A | | | 350 | | |
| 946 | 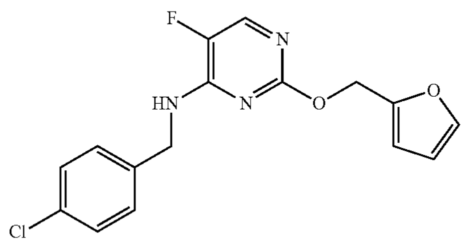 [SMILES: Fc1cnc(OCc2ccco2)nc1NCc1ccc(Cl)cc1] | B | A | | | 334 | | |
| 947 | 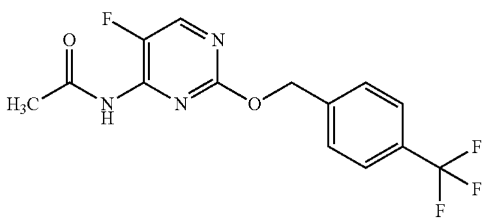 [SMILES: CC(=O)Nc1nc(OCc2ccc(C(F)(F)F)cc2)ncc1F] | A | A | white solid | 144-146 | 330 | 328 | |
| 948 | 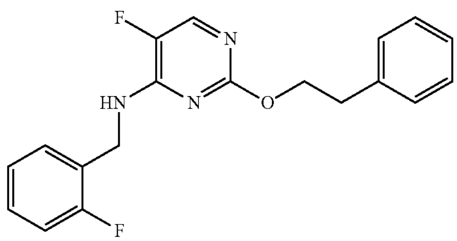 [SMILES: Fc1ccccc1CNc1nc(OCCc2ccccc2)ncc1F] | D | D | | | 342 | | |
| 949 | 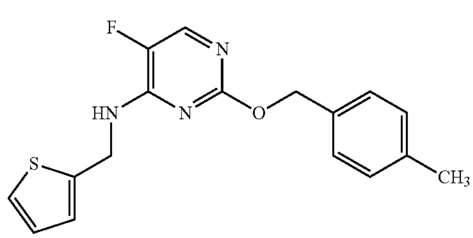 [SMILES: Cc1ccc(COc2ncc(F)c(NCc3cccs3)n2)cc1] | B | A | | | 330 | | |

TABLE II-continued

1 DP Activity of Compounds on SEPTTR at 50 and 200 ppm

| Cmpd | Structure | SEPTTR 1DP 50 ppm | SEPTTR 1DP 200 ppm | Phys. App. | MP | Mass Spec. (ES+) | Mass Spec. (ES−) | GCMS |
|---|---|---|---|---|---|---|---|---|
| 950 | 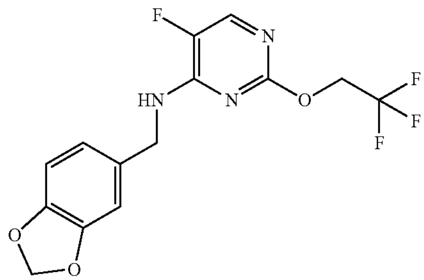 [SMILES: Fc1cnc(OCC(F)(F)F)nc1NCc1ccc2c(c1)OCO2] | D | D | | | 346 | | |
| 951 | 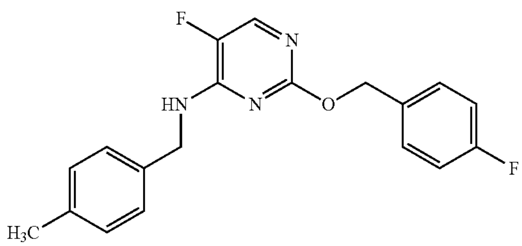 [SMILES: Cc1ccc(CNc2nc(OCc3ccc(F)cc3)ncc2F)cc1] | B | A | | | 342 | | |
| 952 | 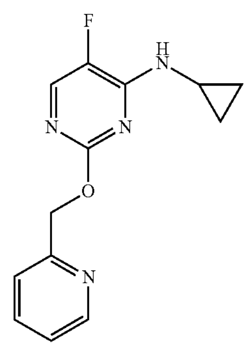 [SMILES: Fc1cnc(OCc2ccccn2)nc1NC1CC1] | E | C | | | 261 | | |
| 953 | 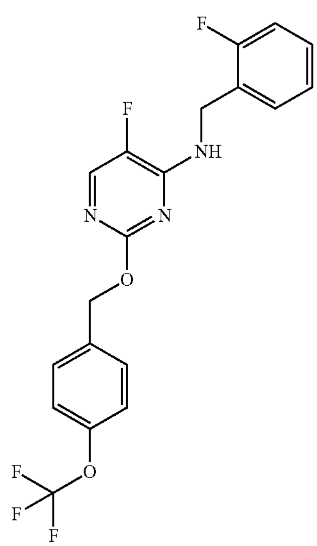 [SMILES: Fc1ccccc1CNc1nc(OCc2ccc(OC(F)(F)F)cc2)ncc1F] | C | A | | | 412 | | |

TABLE III

| | 1 DP Activity of Compounds on CERCBE, VENTIN, and MYCOFI | | | | | |
|---|---|---|---|---|---|---|
| Cmpd # | CERCBE 1 DP 25 ppm | CERCBE 1 DP 75 ppm | VENTIN 1 DP 25 ppm | VENTIN 1 DP 75 ppm | MYCOFI 1 DP 50 ppm | MYCOFI 1 DP 200 ppm |
| 1 | C | C | A | A | C | B |
| 3 | E | E | D | A | E | E |
| 4 | A | A | A | A | E | E |
| 5 | E | E | A | A | E | E |
| 7 | B | B | A | A | E | E |
| 9 | D | D | A | C | E | E |
| 10 | D | D | B | A | E | E |
| 11 | D | D | A | A | E | E |
| 14 | D | D | A | A | E | E |
| 15 | E | E | A | A | E | E |
| 20 | E | E | B | A | E | E |
| 23 | D | B | B | A | E | E |
| 24 | D | D | C | A | E | E |
| 35 | E | E | A | A | E | E |
| 36 | B | B | B | A | E | E |
| 46 | E | E | A | A | E | E |
| 61 | D | D | A | B | E | E |
| 68 | B | B | B | A | E | E |
| 69 | D | C | B | A | E | E |
| 79 | D | C | C | C | E | E |
| 121 | D | D | A | C | E | E |
| 122 | C | C | A | A | E | E |
| 125 | C | C | C | A | E | E |
| 135 | C | C | B | B | E | E |
| 137 | D | D | D | A | E | E |
| 141 | D | D | D | C | E | E |
| 155 | D | D | C | D | E | E |
| 158 | D | D | B | B | E | E |
| 163 | D | D | D | C | E | E |
| 164 | D | D | C | B | E | E |
| 169 | D | D | B | C | E | E |
| 180 | D | C | C | D | E | E |
| 187 | D | C | B | C | E | E |
| 189 | C | D | B | B | E | E |
| 190 | C | C | C | C | E | E |
| 207 | D | D | D | C | E | E |
| 209 | E | E | B | A | E | E |
| 211 | D | D | C | B | E | E |
| 214 | B | B | A | A | E | E |
| 221 | C | B | D | C | E | E |
| 226 | D | C | C | A | E | E |
| 233 | D | D | D | B | E | E |
| 236 | E | E | A | A | E | E |
| 248 | D | D | D | B | E | E |
| 251 | D | B | A | A | E | E |
| 260 | A | B | A | A | E | E |
| 270 | C | C | D | C | E | E |
| 271 | C | C | C | B | E | E |
| 288 | D | C | B | C | E | E |
| 311 | C | C | C | C | E | E |
| 313 | E | E | C | B | E | E |
| 316 | B | A | A | A | E | E |
| 335 | C | A | A | A | E | E |
| 337 | B | A | B | A | E | E |
| 341 | D | D | C | D | E | E |
| 342 | C | A | A | A | E | E |
| 343 | A | A | A | B | E | E |
| 345 | E | E | B | A | E | E |
| 347 | E | E | A | C | E | E |
| 352 | D | D | D | C | E | E |
| 353 | C | C | C | A | E | E |
| 356 | B | D | B | C | E | E |
| 370 | C | C | C | C | E | E |
| 373 | D | D | D | C | E | E |
| 384 | D | D | B | D | E | E |
| 410 | C | C | C | B | E | E |
| 411 | C | C | B | B | E | E |
| 418 | D | D | B | B | E | E |
| 436 | B | C | A | A | E | E |
| 452 | D | D | D | C | E | E |
| 469 | E | E | B | A | E | E |
| 481 | C | A | A | A | E | E |
| 483 | D | D | C | A | E | E |
| 488 | D | D | C | C | E | E |
| 510 | E | E | A | A | E | E |

TABLE III-continued

| | 1 DP Activity of Compounds on CERCBE, VENTIN, and MYCOFI | | | | | |
|---|---|---|---|---|---|---|
| Cmpd # | CERCBE 1 DP 25 ppm | CERCBE 1 DP 75 ppm | VENTIN 1 DP 25 ppm | VENTIN 1 DP 75 ppm | MYCOFI 1 DP 50 ppm | MYCOFI 1 DP 200 ppm |
| 524 | D | D | B | B | E | E |
| 538 | D | D | C | B | E | E |
| 554 | D | B | A | A | E | E |
| 560 | D | C | D | A | E | E |
| 569 | C | A | A | A | E | E |
| 570 | D | C | C | A | E | E |
| 582 | B | B | A | A | E | E |
| 584 | C | C | C | C | E | E |
| 593 | C | B | A | A | E | E |
| 626 | D | D | C | A | E | E |
| 630 | D | D | B | A | E | E |
| 631 | D | D | D | C | E | E |
| 635 | C | C | C | A | E | E |
| 649 | D | D | C | C | E | E |
| 651 | C | C | D | D | E | E |
| 687 | D | D | C | B | E | E |
| 694 | C | C | C | B | E | E |
| 707 | B | C | B | B | E | E |
| 710 | D | D | C | C | E | E |
| 719 | D | C | B | B | E | E |
| 720 | D | B | B | A | E | E |
| 730 | C | C | B | B | E | E |
| 732 | C | A | C | A | E | E |
| 734 | E | E | A | A | E | E |
| 739 | D | D | C | B | E | E |
| 741 | D | D | B | A | E | E |
| 764 | C | D | C | C | E | E |
| 800 | A | A | A | A | E | E |
| 804 | D | D | D | D | E | E |
| 845 | D | D | C | C | E | E |
| 849 | C | C | A | B | E | E |
| 858 | C | C | C | D | E | E |
| 860 | D | C | C | B | E | E |
| 894 | D | D | D | C | E | E |
| 933 | C | C | D | C | E | E |
| 941 | D | D | B | C | E | E |
| 952 | D | D | D | D | E | E |

TABLE IV

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 954 | | C | B | C | C | white solid | 247-250 | | 276.96 | |
| 955 | | D | D | D | D | white solid | 120-122 | 386.3 | | |
| 956 | | D | D | D | D | off-white solid | 221-223 | | 267.9 | |
| 957 | | C | C | D | D | White Solid | 175-178 | 235 [M + 2] | 232 | |
| 958 | | C | C | D | D | red crystalline solid | 123-125 | 377 | | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 959 | | D | D | D | D | pale yellow solid | 181-185 | 303 | 301 | |
| 960 | | D | D | D | D | yellow solid | 202-208 | 263 | 261 | |
| 961 | | A | A | A | A | white solid | 153-157 | 248 | 246 | |
| 962 | | A | A | A | A | white solid | 101-104 | 256 | 254 | |
| 963 | | C | D | D | D | Pale brown solid | 150-152 dec. | 245 | | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 964 | | D | C | D | D | Off white solid | 150-152 dec. | 278 | | |
| 965 | | C | C | C | A | tan solid | 236-238 | 269 | 267 | |
| 966 | | B | B | C | B | white solid | 249-251 | | 280.88 | |
| 967 | | B | B | C | C | white solid | 255-257 | | 246.93 | |
| 968 | | B | B | B | B | white solid | 255-257 | | 260.93 | |
| 969 | | C | B | C | C | white solid | 244-246 | | 260.93 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 970 | | C | C | C | B | white solid | 257-259 | | 278.91 | |
| 971 | | B | A | C | C | white solid | 289-293 | | 213 | |
| 972 | | B | B | B | A | white solid | 255-260 | | 242.2 | |
| 973 | | A | B | C | C | white solid | 290-295 | | 240.34 | |
| 974 | | B | C | B | A | white solid | 218-220 | 260 | 258 | |
| 975 | | D | D | D | D | white solid | 270-280 | | 228.2 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 976 | | D | D | D | D | white solid | 218-222 | | 256.9 | |
| 977 | | D | A | D | B | off white solid | 234-235 | 252 | 250 | |
| 978 | | D | D | D | D | white solid | 244-245 | 272 | 270 | |
| 979 | | D | B | D | C | white solid | 243-234 | 240 | 238 | |
| 980 | | D | D | D | D | white solid | 230-240 | | 213 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 981 | | D | D | D | D | white solid | 224-230 | | | 250.89 |
| 982 | | A | A | A | A | Off white solid | 60.4-63 | | 332 | |
| 983 | | A | A | A | A | Pale yellow solid | 83.3-85.8 | | 302 | |
| 984 | | A | A | A | A | Off white solid | 63.2-65.5 | | 350 | |
| 985 | | A | A | A | A | Off white solid | 60.8-62.9 | | 320 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 986 | | A | A | A | A | Off white solid | 62.3-65.9 | | 346 | |
| 987 | | A | A | A | A | Off white solid | 88.2-89.2 | | 316 | |
| 988 | | A | A | A | A | Pale yellow liquid | NA | | 362 | |
| 989 | | B | A | A | A | Pale yellow liquid | NA | 334 | | |
| 990 | | D | D | D | D | colorless oil | | 438 | | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 991 | | D | D | D | D | red oil | | 309 | | |
| 992 | | D | C | D | D | red oil | | 323 | | |
| 993 | | D | B | D | C | red solid | 95-98 | 310 | | |
| 994 | | D | D | D | C | white solid | 155-157 | 353 | 372.2 | |
| 995 | | D | D | D | C | red solid | 104-108 | 353 | 351 | |

TABLE IV-continued
Three day curative (3DC) and one day protectant (1DP) Activity of Compounds on SEPTTR at 25 and 100 ppm
| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 996 | 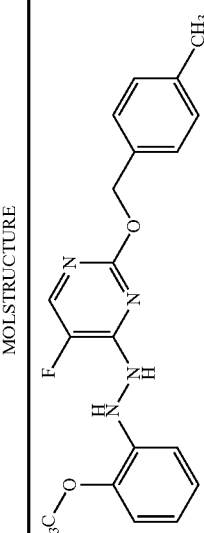 | C | B | C | B | brown semi-solid | | 354 | 353 | |
| 997 | 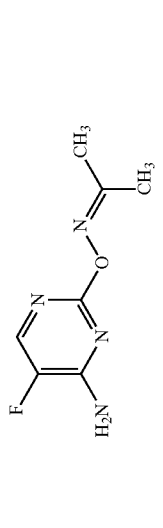 | A | A | A | A | white solid | 151-152 | 185 | | |
| 998 | 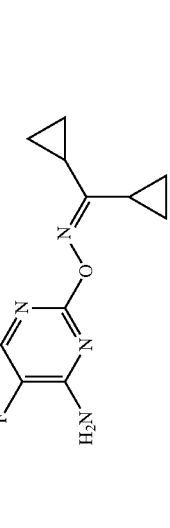 | A | A | A | A | yellow solid | 160-161 | 237 | 235 | |
| 999 | 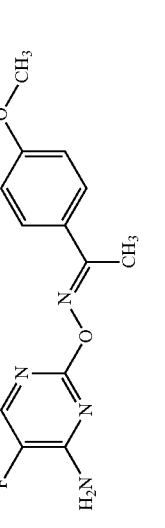 | A | A | A | A | tan solid | 168-169 | | 275 | |
| 1000 | 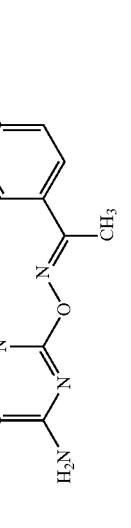 | A | A | A | A | tan solid | 183-184 | | 279 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1001 | | C | A | C | A | tan solid | 181-182 | 347 | 345 | |
| 1002 | | C | B | B | A | tan solid | 185-186 | 354 | 352 | |
| 1003 | | D | B | D | D | off-white solid | 134-137 | | 313.87 | |
| 1004 | | D | C | D | D | white solid | 152-155 | | 341.94 | |
| 1005 | | D | D | D | D | white solid | 147-150 | | 375.96 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1006 | | D | D | D | D | white solid | 129-131 | | 324.2 | |
| 1007 | | D | D | D | D | white solid | 150-153 | | 336.2 | |
| 1008 | | D | D | D | D | white solid | 134-136 | | 295.9 | |
| 1009 | | D | D | D | D | white solid | 139-142 | | 323.92 | |
| 1010 | | D | D | D | D | white solid | 150-153 | | 357.92 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1011 | | D | D | D | D | white solid | 117-119 | | | 325.92 |
| 1012 | | D | D | D | D | white solid | 120-122 | | | 353.97 |
| 1013 | | D | D | D | D | white solid | 129-131 | | | 387.93 |
| 1014 | | D | A | D | D | red solid | 114-118 | 361 | | |
| 1015 | | C | A | D | D | white solid | 141-144 | | 473.92 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1016 | | B | B | D | D | off-white solid | 158-160 (dec) | | | 436.88 |
| 1017 | | D | B | D | C | pale yellow solid | 109-115 | | 289 | |
| 1018 | | D | D | D | D | off white solid | 88-92 | 240 | 239 | |
| 1019 | | D | D | C | C | yellow solid | 161-165 | | 299 | |
| 1020 | | C | D | D | D | off white solid | 173-177 | | 263 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1021 | H₃C-CH(CH₂CH₃)-CH=N-NH-[4-F-2-OMe-pyrimidin-4-yl] | C | C | D | C | white solid | 132-135 | 241 | 239 | |
| 1022 | cyclopropyl-CH=N-NH-[4-F-2-OMe-pyrimidin-4-yl] | D | C | D | D | pale yellow solid | 129-134 | 210 | 209 | |
| 1023 | 2-furyl-CH=N-NH-[4-F-2-OMe-pyrimidin-4-yl] | D | D | D | D | yellow solid | 196-202 | 236 | 235 | |
| 1024 | 2-thienyl-CH=N-NH-[4-F-2-OMe-pyrimidin-4-yl] | D | D | D | D | yellow solid | 220-226 | 235 | 251 | |
| 1025 | 2,5-dimethylthiazol-4-yl-C(CH₃)=N-NH-[4-F-2-OMe-pyrimidin-4-yl] | C | D | D | D | yellow solid | 104-108 | | 294 | |
| 1026 | 4-F-C₆H₄-C(CH₃)=N-NH-[4-F-2-OMe-pyrimidin-4-yl] | D | C | C | C | yellow solid | 110-114 | 279 | 277 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1027 | | D | D | D | D | white solid | 162-166 | | | 456.1 |
| 1028 | | D | D | D | D | brown solid | 115-119 | 329 | 327 | |
| 1029 | | D | D | D | D | brown oil | | 379 | 377 | |
| 1030 | | D | D | D | D | brown solid | 143-147 | 403 | 403 | |
| 1031 | | D | D | D | D | brown solid | 126-130 | 253 | 251 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES-) | GCMS |
|---|---|---|---|---|---|---|---|---|---|---|
| 1032 | | D | D | C | C | white solid | 165-170 | 371 | 369 | |
| 1033 | | D | C | D | D | off white solid | 151-155 | 224 | 223 | |
| 1034 | | D | D | D | D | off white solid | 136-139 | | 267 | |
| 1035 | | D | D | D | D | brown solid | 122-127 | 391 | 389 | |
| 1036 | | D | D | D | D | brown oil | | 339 | 337 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1037 | | D | D | D | C | brown oil | | 379 | | |
| 1038 | | D | D | D | D | brown solid | 105-109 | 381 | 379 | |
| 1039 | | D | D | D | D | red solid | 119-124 | 343 | 341 | |
| 1040 | | D | D | D | D | brown oil | | 361 | 359 | |
| 1041 | | D | D | D | D | dark red solid | 102-108 | 394 | 393 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1042 | | D | C | D | D | red solid | 112-118 | 347 | 345 | |
| 1043 | | D | D | D | D | brown solid | 110-116 | 400 | 397 | |
| 1044 | | D | D | D | D | brown oil | | 386 | 384 | |
| 1045 | | D | D | D | D | red solid | 140-143 | 412 | 409 | |
| 1046 | | D | D | D | D | purple oil | | 398 | 396 | |

TABLE IV-continued
Three day curative (3DC) and one day protectant (1DP) Activity of Compounds on SEPTTR at 25 and 100 ppm
| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1047 |  | C | C | D | D | brown solid | 194-197 | 348 | 346 | |
| 1048 | 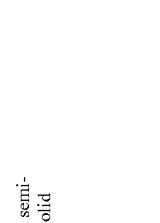 | D | D | D | D | red semi-solid | | | 269 | |
| 1049 |  | C | C | D | D | red oil | | 305 | 303 | |
| 1050 |  | D | C | D | D | red solid | 71-76 | 236 | 234 | |
| 1051 | 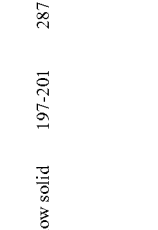 | C | D | D | D | yellow solid | 197-201 | 287 | 285 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1052 | (structure) | D | D | D | D | off white solid | 120-123 | 264 | 263 | |
| 1053 | (structure) | D | D | D | D | white semi-solid | | 239 | 238 | |
| 1054 | (structure) | D | D | D | D | yellow oil | | | 283 | |
| 1055 | (structure) | D | D | D | D | off white solid | 136-139 | 305 | | |
| 1056 | (structure) | C | C | D | D | pale yellow oil | | 187 | | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1057 | | D | D | D | D | white solid | 152-155 | 215 | 213 | |
| 1058 | | D | D | D | D | white solid | 80-85 | 174 | 172 | |
| 1059 | | D | C | D | D | peach colored solid | 115-120 | 185 | 183 | |
| 1060 | | D | D | D | D | yellow solid | 83-88 | 304 | 303 | |
| 1061 | | D | D | C | D | yellow solid | 118-123 | 327 | 325 | |
| 1062 | | D | D | D | D | yellow solid | 104-107 | 237 | 235 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1063 | | D | D | D | D | brown solid | 102-107 | 251 | 249 | |
| 1064 | | D | D | D | D | brown solid | 179-182 | 262 | 261 | |
| 1065 | | D | D | D | D | pale brown oil | | 250 | | |
| 1066 | | D | D | D | D | pale yellow oil | | 174 | 172 | |
| 1067 | | D | D | D | D | pale yellow oil | | 201 | 200 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1068 | 4-fluoro-3-(N-methyl-N-(4-chlorobenzyl)amino)-2-hydroxypyrimidine | D | D | D | D | White Solid | 218-222 | 269 [M + 2] | 266 | |
| 1069 | 4-fluoro-3-(N-methyl-N-(4-methylbenzyl)amino)-2-hydroxypyrimidine | B | B | D | D | White Solid | 200-203 | 249 [M + 2] | 246 | |
| 1070 | 4-fluoro-3-(N-methyl-N-(2-methoxybenzyl)amino)-2-hydroxypyrimidine | D | D | C | D | White Solid | 206-209 | 264 | 262 | |
| 1071 | 4-fluoro-3-(N-methyl-N-(4-trifluoromethylbenzyl)amino)-2-hydroxypyrimidine | C | C | D | C | White Solid | 258-261 (dec) | 303 [M + 2] | 300 | |
| 1072 | 5-fluoro-2-(allyloxy)-4-(N-(2-methoxyethoxy)amino)pyrimidine | D | D | D | D | off white solid | 64-67 | 214 | 212 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1073 | | D | D | C | D | peach colored solid | 146-150 | 295 | 293 | |
| 1074 | | D | C | D | D | brown solid | 151-155 | 289 | 287 | |
| 1075 | | D | D | D | D | brown oil | | 299 | 298 | |
| 1076 | | D | C | D | D | beige solid | 110 | 279 | 278 | |
| 1077 | | D | C | D | D | brown solid | 86-89 | 278 | 277 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1078 | | C | D | D | D | brown solid | 130-133 | 341 | 339 | |
| 1079 | | D | D | D | D | yellow oil | | 275 | 272 | |
| 1080 | | C | C | D | D | pale yellow solid | 79-83 | | 248 | |
| 1081 | | D | D | D | D | off white solid | 70-75 | | 277 | |
| 1082 | | D | D | D | D | white gum | | 250.1 | 248.1 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1083 | | A | A | A | A | white solid | 71-3 | 257 | | |
| 1084 | | A | A | A | A | white solid | 62-4 | 311 | | |
| 1085 | | A | A | A | A | white solid | 110-2 | 319 | | |
| 1086 | | D | D | D | D | brown oil | | 280 | 278 | |
| 1087 | | D | D | D | D | tacky brown solid | | 276 | 274 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1088 | | D | D | D | C | yellow oil | | 276 | 274 | |
| 1089 | | C | C | D | D | red solid | 114-118 | 351 | | |
| 1090 | | C | C | D | D | red solid | 84-89 | 395 | | |
| 1091 | | C | C | D | D | brown solid | 72-75 | 265 | 263 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1092 | ![structure] | D | C | D | C | off white solid | 201-206 | 201 | 199 | |
| 1093 | ![structure] | D | D | D | D | brown oil | | 235 | 233 | |
| 1094 | ![structure] | C | C | D | D | brown solid | 164-169 | 236 | 234 | |
| 1095 | ![structure] | D | D | D | D | off white solid | 146-150 | 236 | 234 | |
| 1096 | ![structure] | D | A | D | D | off white solid | 180-190 | 174 | 172 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1097 | | D | C | D | D | dark red solid | 110-113 | 301 | | |
| 1098 | | D | D | D | D | grey solid | 209-213 | 255 | 253 | |
| 1099 | | D | D | D | D | red oil | | 277 | | |
| 1100 | | C | C | D | D | red solid | 68-71 | 339 | 337 | |
| 1101 | | D | D | D | D | white solid | 215-217 | | 205.97 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1102 | | C | C | D | D | white solid | 216-218 | | 297.88 | |
| 1103 | | D | D | D | D | white solid | 236-239 | | 301.85 | |
| 1104 | | D | D | D | D | off-white solid | 203-205 | | 231.91 | |
| 1105 | | D | D | D | D | white solid | 157-159 | | 219.96 | |
| 1106 | | D | D | D | D | off-white solid | 209-211 | | 369.89 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1107 | | D | D | D | D | light tan solid | 124-128 (dec) | | | 363.95 |
| 1108 | | D | D | D | D | brown solid | 248-251 | 327 | 323 | |
| 1109 | | D | D | D | D | red solid | 35-37 | 287 | | |
| 1110 | | D | D | D | D | red solid | 92-95 | 267 | 267 | |
| 1111 | | D | D | D | D | yellow solid | 242-246 | 267 | 265 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1112 | | D | C | D | D | brown solid | 216-218 | 223 | 221 | |
| 1113 | | A | A | A | A | white solid | 116-121 | | 270 | |
| 1114 | | C | A | D | D | light yellow solid | 173-175 | 239 | 237 | |
| 1115 | | C | A | C | A | grey solid | | 188.1 | 186.2 | |
| 1116 | | E | E | E | E | White solid | | 292.64 | | |
| 1117 | | E | E | E | E | White solid | | 277.57 | | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1118 | | D | D | D | D | yellow solid | 235-237 | 267 | 265 | |
| 1119 | | A | A | A | A | white solid | 106-110 | 244 | 242 | |
| 1120 | | D | D | D | D | off white solid | 158-160 | 277 | 275 | |
| 1121 | | D | D | D | D | white solid | 209-212 | 297 | 295 | |
| 1122 | | D | D | D | D | white solid | 194-197 | 379 | 377 | |
| 1123 | | D | D | D | D | brown solid | 143-146 | 267 | 265 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1124 | | D | D | D | D | off white solid | 164-171 | 290 | 288 | |
| 1125 | | A | A | A | A | white solid | 138-141 | 252 | 228 | |
| 1126 | | A | A | A | A | white solid | 76-79 | 306 | 282 | |
| 1127 | | A | A | D | A | white solid | 83-87 | 267 | 183 | |
| 1128 | | D | D | D | D | off white solid | 131-135 | 435 | 433 | |

TABLE IV-continued

Three day curative (3DC) and one day protectant (1DP) Activity of Compounds on SEPTTR at 25 and 100 ppm

| Cmpd # | MOLSTRUCTURE | SEPTTR 3DC 25 ppm | SEPTTR 3DC 100 ppm | SETTTR 1DP 25 ppm | SETTTR 1DP 25 ppm | Appearance | MP | Mass Spec. (ES+) | Mass Spec. (ES−) | GCMS |
|---|---|---|---|---|---|---|---|---|---|---|
| 1129 | | D | D | D | D | white solid | 83-89 | 269 | 267 | |
| 1130 | | C | D | D | D | Pale brown solid | 119-122 dec. | 259 | | |
| 1131 | | A | A | A | A | pale yellow solid | 190-191 | 213 | 211 | |
| 1132 | | A | A | B | B | white solid | 220-230 | 284 | 282 | |

TABLE V

Percent SEPTTR control delivered by compound 15 (Table 1) treated Yuma seeds

| Rate g/100 kg seeds | Pot 1 | Pot 2 | Pot 3 | Pot 4 | Pot 5 | Pot 6 | Pot 7 | Pot 8 | % Control |
|---|---|---|---|---|---|---|---|---|---|
| 120 | 0 | 0 | 0 | 0 | 0 | 0 | 0 | 0 | A |
| 40 | 0 | 1 | 1 | 1 | 0 | 0 | 0 | 0 | A |
| 13.3 | 0 | 1 | 0 | 1 | 1 | 1 | 0 | 0 | A |
| 4.44 | 0 | 0 | 1 | 1 | 0 | 1 | 0 | 0 | A |
| 1.48 | 3 | 3 | 1 | 1 | 0 | 3 | 0 | 0 | A |
| 0 | 100 | 100 | 95 | 100 | 100 | 95 | 100 | 95 | 0 |

What is claimed is:

1. A compound of formula I

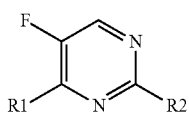

wherein $R^1$ is —$N(R^3)R^4$;
$R^2$ is —$OR^{21}$;
$R^3$ is:
H;
$C_1$-$C_6$ alkyl optionally substituted with 1- to 3 $R^5$;
$C_2$-$C_6$ alkenyl optionally substituted with 1-3 $R^5$;
a 5- or 6-membered heteroaromatic ring selected from the group consisting of furanyl, pyridinyl, pyridinyl-N-oxide, pyrimidinyl, pyridazinyl, pyrazinyl, thiazolyl, triazinyl, thiadiazolyl, oxazolyl, isoxazolyl, triazolyl, each heteroaromatic ring being optionally substituted with 1-3 $R^{30}$;
imidazole fused with an aromatic or heteroaromatic ring selected from the group consisting of benzene, oxazole, isoxazole, furan, thiazole, pyrimidine, pyridine, pyrrole, pyrazine, thiophene, each aromatic or heteroaromatic ring being optionally substituted with 1 to 3 $R^{30}$;
benzo[1,3]dioxolyl;
3H-isobenzofuran-1-onyl;
cyano;
$C_3$-$C_6$ alkynyl optionally substituted with 1-3 $R^5$;
—$C(=O)R^6$;
—$C(=O)OCH_2C(=O)R^8$;
—$C(=S)R^6$;
—$C(=S)NHR^8$;
—$C(=O)N(R^8)R^{10}$;
—$OR^7$;
—$P(O)(OR15)_2$;
—$S(O)_2R^8$;
—$SR^8$;
—$Si(R^8)_3$;
—$N(R^9)R^{10}$;
—$N=C(R^{15})R^{16}$;
—$(CHR^{22})_mR^{37}$;
—$(CHR^{24})OR^{29}$; or
—$C(=NR^{16})SR^{16}$; or
—$C(=NR^{27})NR^{13}R^{28}$;
wherein m is an integer from 1-3;
$R^4$ is:
H;
hydroxyl;
amino;
$C_1$-$C_6$ alkyl, optionally substituted with 1-3 $R^5$;
—$C(=O)R^6$; or
—$C(=O)N(R^8)R^{10}$;
alternatively $R^3$ and $R^4$ may be taken together to form:
a 5- or 6-membered saturated or unsaturated ring containing 1-3 heteroatoms wherein each ring may be optionally substituted with 1-3 $R^{11}$;
=$C(R^{12})N(R^{13})R^{14}$;
=$C(R^{13})(R^{14})$;
=$C(R^{15})OR^{15}$;
=$S(R^{34})_2$; or
=$NR^{35}$;
$R^5$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, —OH, N-methyl piperazine or $C_3$-$C_6$ trialkylsilyl;
$R^6$ is independently H, $C_1$-$C_6$ alkyl, $C_2$-$C_6$ alkenyl optionally substituted with 1-3 $R^{30}$, $C_1$-$C_5$ haloalkyl, $C_1$-$C_5$ alkoxy, $C_1$-$C_5$ haloalkoxy $C_2$-$C_6$ alkoxycarbonyl, $C_1$-$C_4$ alkoxyalkoxy, $C_2$-$C_6$ alkylaminocarbonyl; 1-benzo[1,2,3]thiadiazol-7-yl, thiazolyl, benzyl, phenyl, phenoxy, or benzyloxy wherein the thiazolyl, benzyl, phenyl, phenoxy, or benzyloxy may be optionally substituted with 1-3 $R^{20}$, or a 5- or 6-membered saturated or unsaturated ring containing 1-3 heteroatoms wherein each ring may be optionally substituted with 1-3 $R^{11}$;
$R^7$ is H, $C_1$-$C_6$ alkyl, $C_2$-$C_6$ alkenyl, $C_1$-$C_5$ halo alkyl, benzyl which may be optionally substituted with 1-5 $R^{20}$, —$CHR^{18}C(O)OR^{19}$, —$(CHR^{27})R^{28}$, —$Si(R^8)_3$, or a 5- or 6-membered saturated or unsaturated ring containing 1-3 heteroatoms wherein each ring may be optionally substituted with 1-3 $R^{11}$;
$R^8$ is independently $C_1$-$C_6$ alkyl, $C_1$-$C_6$ haloalkyl, amino, $C_1$-$C_6$ alkylamino, $C_2$-$C_6$ dialkylamino, methylene-2-furanyl, —$CHR^{15}C(O)OR^{19}$, benzyl optionally substituted with 1-3 $R^{30}$, phenyl optionally substituted with 1-3 $R^{30}$, or a 5- or 6-membered saturated or unsaturated ring containing 1-3 heteroatoms wherein each ring may be optionally substituted with 1-3 $R^{11}$;
$R^9$ is H, $C_1$-$C_6$ alkyl $C_1$-$C_6$ haloalkyl, —$C(=O)R^{17}$, benzothiazoyl, quinazolinyl, or phenyl optionally substituted with 1-3 $R^{20}$, or a 5- or 6-membered saturated or unsaturated ring containing 1-3 heteroatoms wherein each ring may be optionally substituted with 1-3 $R^{11}$;
$R^{10}$ is H or $C_1$-$C_6$ alkyl, $C_1$-$C_6$ haloalkyl, or phenyl optionally substituted with 1-3 $R^{20}$;
$R^{11}$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, amino, $C_1$-$C_6$ alkylamino, $C_2$-$C_6$ dialkylamino, $C_2$-$C_6$ alkoxycarbonyl, or $C_2$-$C_6$ alkylcarbonyl;
$R^{12}$ is H or $C_1$-$C_4$ alkyl;
$R^{13}$ and $R^{14}$ are independently H, cyano, —OH, $C_1$-$C_4$ alkyl, $C_1$-$C_6$ alkoxy, $C_2$-$C_6$, alkylcarbonyl, phenyl, or benzyl wherein the phenyl or benzyl may be optionally substituted with 1-3 $R^{20}$;
alternatively $R^{13}$ and $R^{14}$ may be taken together to form:
a 5- or 6-membered saturated or unsaturated ring containing 1-3 heteroatoms wherein each ring may be optionally substituted with 1-3 $R^{11}$, or 3,4-dihydro-1H-isoquinolin-2-yl;
alternatively $R^{12}$ and $R^{13}$ may be taken together to form:
a 5- or 6-membered saturated or unsaturated ring containing 1-3 heteroatoms wherein each ring may be optionally substituted with 1-3 $R^{11}$;

$R^{15}$ is H or $C_1$-$C_6$ alkyl, $C_2$-$C_6$ alkenyl, 2-benzofuranyl, or a 5- or 6-membered saturated or unsaturated ring containing 1-3 heteroatoms wherein each ring may be optionally substituted with 1-3 $R^{11}$;

$R^{16}$ is H, $C_1$-$C_6$ alkyl, or phenyl optionally substituted with 1-3 $R^{20}$;

alternatively $R^{15}$ and $R^{16}$ may be taken together as —(CH$_2$)$_4$— or —(CH$_2$)$_5$—;

$R^{17}$ is H, $C_1$-$C_6$ alkyl, $C_2$-$C_6$ alkenyl, $C_1$-$C_6$ haloalkyl, $C_1$-$C_6$ alkoxy, benzyl, phenyl, phenoxy, or benzyloxy wherein each ring may be optionally substituted with 1-3 $R^{20}$, a 5- or 6-membered saturated or unsaturated ring containing 1-3 heteroatoms wherein each ring may be optionally substituted with 1-3 $R^{11}$;

$R^{18}$ is H, $C_1$-$C_6$ alkyl, or $C_1$-$C_6$ haloalkyl;

$R^{19}$ is H, $C_1$-$C_6$ alkyl, $C_1$-$C_6$ haloalkyl, or benzyl;

$R^{20}$ is independently halogen, cyano, nitro, amino, $C_1$-$C_6$ alkoxyalkoxy, $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ haloalkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$—CS dialkylamino, $C_3$-$C_8$ dialkylaminocarbonyl, $C_2$-$C_6$ alkoxycarbonyl, $C_2$-$C_6$ alkylcarbonyl, $C_3$-$C_6$ trialkylsilyl, 2-[(E)-methoxyimino]-N-methyl-acetamidyl, phenyl, benzyl, benzyloxy, phenoxy, or a 5- or 6-membered heteroaromatic ring wherein each phenyl, benzyl, benzyloxy, phenoxy, or 5- or 6-membered heteroaromatic ring may be optionally substituted with 1-3 substitutents independently selected from $R^{31}$;

$R^{21}$ is:
H;
$C_1$-$C_4$ alkyl;
$C_1$-$C_6$ haloalkyl;
$C_2$-$C_4$ alkenyl;
$C_2$-$C_4$ haloalkenyl;
$C_3$-$C_4$ alkynyl;
$C_3$-$C_4$ haloalkynyl;
phenyl, naphthyl, or tetrahydroquinolinyl each optionally substituted with 1-3 $R^{20}$;
—(CHR$^{22}$)$_m$R$^{23}$;
—(CHR$^{24}$)$_m$C(O)OR$^{25}$;
—(CHR$^{24}$)$_m$C(O)R$^{26}$;
—(CHR$^{24}$)$_m$C(O)N(R$^{27}$)R$^{28}$;
—(CHR$^{24}$)$_m$OR$^{29}$;
—(CHR$^{24}$)$_m$SR$^{29}$;
—(CHR$^{24}$)$_m$N(R$^{27}$)R$^{28}$;
—C(=O)R$^{32}$;
—N=C(R$^{32}$)(R$^{36}$);
—NR$^{25}$C(=O)OR$^{25}$;
—Si(R$^8$)$_3$;
—SO$_2$R$^{33}$;
$C_2$-$C_6$ alkoxy carbonyl;
$C_2$-$C_6$ alkylaminocarbonyl;
$C_2$-$C_6$ alkylcarbonyl;
sugars selected from the group consisting of beta-D-glucose-tetraacetate, rhamnose, fructose, and pentose; or
a 5- or 6-membered heteroaromatic ring selected from the group consisting of furanyl, pyridinyl, pyridinyl-N-oxide, pyrimidinyl, pyridazinyl, pyrazinyl, pyrazolyl, thiazolyl, triazinyl, thiadiazolyl, oxazolyl, triazolyl or isoxazolyl wherein each 5- or 6-member heteroaromatic ring may be optionally substituted with 1-5 $R^{20}$;

$R^{22}$ is independently:
H;
halogen;
cyano;
nitro;
$C_1$-$C_6$ alkyl;
$C_1$-$C_6$ haloalkyl;
phenyl or benzyl optionally substituted with 1-3 $R^{20}$;
$C_1$-$C_6$ hydroxyalkyl;
$C_2$-$C_6$ alkoxyalkyl;
$C_3$-$C_6$ haloalkynyl;
$C_2$-$C_6$ alkenyl;
$C_2$-$C_6$ haloalkenyl;
$C_3$-$C_6$ alkynyl;
$C_1$-$C_6$ alkoxy;
$C_1$-$C_6$ haloalkoxy;
$C_1$-$C_6$ alkylthio;
$C_1$-$C_6$ alkylamino;
$C_2$-$C_8$ dialkylamino;
$C_3$-$C_6$ cycloalkylamino;
$C_4$-$C_6$ (alkyl)cycloalkylamino;
$C_2$-$C_6$ alkylcarbonyl;
$C_2$-$C_6$ alkoxycarbonyl;
$C_2$-$C_6$ alkylaminocarbonyl;
$C_3$-$C_8$ dialkylaminocarbonyl;
$C_3$-$C_6$ trialkylsilyl;
ring-fused heteroaromatic rings selected from the group consisting of benzothiophenyl, quinolinyl, isoquinolinyl, thieno[2,3-b]pyridyl, 1-methyl-1H-thieno[2,3-c]pyrazolyl, and benzoimidazolyl, wherein each of the rings may be further substituted with 1-3 $R^{20}$; or
a 5- or 6-membered heteroaromatic ring selected from the group consisting of furanyl, pyridinyl, pyridinyl-N-oxide, pyrimidinyl, pyridazinyl, pyrazinyl, thiazolyl, triazinyl, thiadiazolyl, oxazolyl, isoxazolyl, triazolyl and thienyl;

$R^{23}$ is:
H;
halogen;
$C_1$-$C_6$ alkyl;
$C_1$-$C_6$ haloalkyl;
$C_2$-$C_6$ dialkylamino;
phenyl optionally substituted with 1-5 $R^{20}$;
ring-fused heteroaromatic rings selected from the group consisting of benzothiophenyl, quinolinyl, isoquinolinyl, thieno[2,3-b]pyridyl, 1-methyl 1H-thieno[2,3-c]pyrazolyl, benzofuranyl and benzoimidazolyl, 2,3-dihydrobenzofuran-2-yl, 4-methyl-4H-thieno[3,2-b]pyrrol-5-yl, 1-methyl-1H-indol-5-yl, imidazo[1,2-a]pyridin-2-yl, imidazo[2,1-b]thiazol-6-yl, benzothiazol-2-yl, benzo[b]thiophen-7-yl, and 1-methyl-1H-indazol-3-yl, wherein each of the rings may be further substituted with 1-3 $R^{20}$;
naphthyl;
benzo[1,3]dioxolyl;
pyrrolidinonyl;
oxetanyl;
$C_1$-$C_6$ alkylthio optionally substituted with 1-5 $R^{20}$;
a 5- or 6-membered saturated or unsaturated ring containing 1-3 heteroatoms wherein each ring may be optionally substituted with 1-3 $R^{11}$; or
a 5- or 6-membered heteroaromatic ring selected from the group consisting of furanyl, pyridinyl, pyridinyl- N-oxide, pyrimidinyl, pyridazinyl, pyrazinyl, pyrazolyl, thiazolyl, triazinyl, thiadiazolyl, oxazolyl, isoxazolyl, triazolyl, imidazolyl, thiophene-2-yl and thiophen-3-yl wherein each heteroaromatic ring may be optionally substituted with 1-3 $R^{20}$;

$R^{24}$ is H, $C_1$-$C_6$ alkyl, $C_1$-$C_6$ alkoxy, benzyl, or phenyl wherein each of the benzyl or phenyl may be optionally substituted with 1-3 $R^{20}$;

$R^{25}$ is H, $C_1$-$C_6$ alkyl, phenyl or benzyl optionally substituted with 1-3 $R^{20}$;

$R^{26}$ is:
  H;
  $C_1$-$C_6$ alkyl;
  $C_1$-$C_6$ alkoxy;
  phenyl optionally substituted with 1-3 $R^{20}$; or
  a 5- or 6 membered heteroaromatic ring selected from the group consisting of furanyl, pyridinyl, pyridinyl-N-oxide, pyrimidinyl, pyridazinyl, pyrazinyl, thiazolyl, triazinyl, thiadiazolyl, oxazolyl, triazolyl and isoxazolyl;

$R^{27}$ and $R^{28}$ are independently:
  H;
  benzyl or phenyl wherein each of the benzyl or phenyl may be optionally substituted with 1-3 $R^{20}$; or
  a 5- or 6-membered saturated or unsaturated ring containing 1-3 heteroatoms wherein each ring may be optionally substituted with 1-3 $R^{11}$;

$R^{29}$ is:
  H;
  $C_1$-$C_6$ alkoxyalkyl;
  benzyl, benzoyl, or phenyl wherein each of the benzyl, benzoyl, or phenyl may be optionally substituted with 1-3 $R^{20}$; or
  a 5- or 6-membered saturated or unsaturated ring containing 1-3 heteroatoms wherein each ring may be optionally substituted with 1-3 $R^{11}$;

$R^{30}$ is independently halogen, cyano, nitro, $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$-$C_8$ dialkylamino, $C_3$-$C_8$ dialkylaminocarbonyl, $C_3$-$C_6$ trialkylsilyl, thiazolyl, phenyl, pyrimidinyl, or pyridyl, wherein the thiazolyl, phenyl, pyridyl, or pyrimidinyl may be optionally substituted with 1-3 $R^{20}$;

$R^{31}$ is independently halogen, cyano, nitro, $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$-$C_8$ dialkylamino, $C_3$-$C_8$ dialkylaminocarbonyl, or $C_3$-$C_6$ trialkylsilyl;

$R^{32}$ is independently:
  $C_1$-$C_6$ alkyl, $C_1$-$C_6$ haloalkyl, $C_1$-$C_6$ hydroxyalkyl, $C_2$-$C_6$ alkoxyalkyl, $C_2$-$C_6$ haloalkoxyalkyl, $C_2$-$C_6$ alkenyl, $C_2$-$C_6$ haloalkenyl, $C_3$-$C_6$ alkynyl, $C_3$-$C_6$ haloalkynyl, hydroxyl, $C_1$-$C_6$ alkoxy, $C_1$-$C_6$ haloalkoxy, $C_2$-$C_6$ alkenyloxy, $C_2$-$C_6$ haloalkenyloxy, $C_3$-$C_6$ alkynyloxy, $C_3$-$C_6$ haloalkynyloxy, $C_1$-$C_6$ alkylthio, $C_1$-$C_6$ alkylsulfonyl, $C_1$-$C_6$ haloalkylsulfonyl, $C_2$-$C_6$ alkenylthio, $C_2$-$C_6$ haloalkenylthio, $C_2$-$C_6$ haloalkenylsulfonyl, $C_3$-$C_6$ alkynylthio, $C_3$-$C_6$ alkynylsulfonyl, $C_3$-$C_6$ haloalkynylsulfonyl, $C_1$-$C_6$ alkylamino, $C_2$-$C_8$ dialkylamino, $C_3$-$C_8$ dialkylaminocarbonyl, $C_3$-$C_6$ trialkylsilyl;
  phenyl wherein the phenyl ring may be optionally substituted with 1-3 $R^{20}$; or
  a 5- or 6-membered saturated or unsaturated ring containing 1-3 heteroatoms wherein each ring may be optionally substituted with 1-3 $R^{11}$;

$R^{33}$ is independently:
  $C_1$-$C_6$ alkyl, $C_1$-$C_6$ haloalkyl, phenyl or thienyl optionally substituted with 1-3 $R^{20}$, or
  a 5- or 6-membered saturated or unsaturated ring containing 1-3 heteroatoms wherein each ring may be optionally substituted with 1-3 $R^{11}$;

$R^{34}$ is:
  $C_1$-$C_6$ alkyl, $C_1$-$C_6$ haloalkyl, $C_2$-$C_6$ alkoxyalkyl, $C_1$-$C_6$ alkylamino; or
  a 5- or 6-membered saturated or unsaturated ring containing 1-3 heteroatoms wherein each ring may be optionally substituted with 1-3 $R^{11}$;

$R^{35}$ is:
  $C_1$-$C_6$ alkyl, $C_2$-$C_6$ alkylcarbonyl; or
  a 5- or 6-membered saturated or unsaturated ring containing 1-3 heteroatoms wherein each ring may be optionally substituted with 1-3 $R^{11}$;

$R^{36}$ is H, cyano, $C_1$-$C_6$ alkyl, $C_1$-$C_6$ alkoxy, benzyl, or phenyl wherein each of the benzyl, or phenyl may be optionally substituted with 1-3 $R^{20}$;

alternatively $R^{32}$ and $R^{36}$ may be taken together to form:
  a 5- or 6-membered saturated or unsaturated ring containing 1-3 heteroatoms wherein each ring may be optionally substituted with 1-3 $R^{11}$; and $R^{37}$ is independently:
  H, halogen, or phenyl optionally substituted with 1-5 $R^{20}$;
  $C_1$-$C_6$ alkyl, $C_1$-$C_6$ haloalkyl, hydroxyl, $C_1$-$C_6$ alkoxy, or $C_1$-$C_6$ haloalkoxy; or
  a 5- or 6-membered saturated or unsaturated ring containing 1-3 heteroatoms wherein each ring may be optionally substituted with 1-3 $R^{11}$;

wherein the compound of formula I must include at least one of the following substituents:
  $R^3$ is —C(=N$R^{27}$)N$R^{13}R^{28}$;
  $R^4$ is hydroxyl or amino;
  $R^6$ is $C_2$-$C_6$ alkenyl optionally substituted with 1-3 $R^{30}$;
  $R^7$ is —(CH$R^{27}$)$R^{28}$, or —Si($R^8$)$_3$;
  $R^8$ is methylene-2-furanyl, —CH$R^{15}$C(O)O$R^{19}$, or benzyl optionally substituted with 1-3 $R^{30}$;
  $R^9$ is benzothiazoyl, quinazolinyl, or a 5- or 6-membered saturated or unsaturated ring containing 1-3 heteroatoms wherein each ring may be optionally substituted with 1-3 $R^{11}$;
  $R^{15}$ is $C_2$-$C_6$ alkenyl, 2-benzofuranyl, or a 5- or 6-membered saturated or unsaturated ring containing 1-3 heteroatoms wherein each ring may be optionally substituted with 1-3 $R^{11}$;
  $R^{17}$ is $C_2$-$C_6$ alkenyl, benzyl, or a 5- or 6-membered saturated or unsaturated ring containing 1-3 heteroatoms wherein each ring may be optionally substituted with 1-3 $R^{11}$;

$R^{29}$ is benzoyl.

2. The compound of claim 1, wherein $R^3$ and $R^4$ are taken together to form a 5- or 6-membered saturated or unsaturated ring containing 1-3 heteroatoms wherein each ring may be optionally substituted with 1-3 $R^{11}$.

3. The compound of claim 1, wherein $R^3$ is —C(=NR$^{27}$)NR$^{13}$R$^{28}$.

4. The compound of claim 1, wherein $R^4$ is hydroxyl or amino.

5. The compound of claim 1, wherein $R^6$ is $C_2$-$C_6$ alkenyl optionally substituted with 1-3 $R^{30}$.

6. The compound of claim 1, wherein $R^7$ is —(CHR$^{27}$)R$^{28}$, or —Si(R$^8$)$_3$.

7. The compound of claim 1, wherein $R^8$ is methylene-2-furanyl, —CHR$^{15}$C(O)OR$^{19}$, or benzyl optionally substituted with 1-3 $R^{30}$.

8. The compound of claim 1, wherein $R^9$ is benzothiazoyl, quinazolinyl, or a 5- or 6-membered saturated or unsaturated ring containing 1-3 heteroatoms wherein each ring may be optionally substituted with 1-3 $R^{11}$.

9. The compound of claim 1, wherein $R^{15}$ is $C_2$-$C_6$ alkenyl, 2-benzofuranyl, or a 5- or 6-membered saturated or unsaturated ring containing 1-3 heteroatoms wherein each ring may be optionally substituted with 1-3 $R^{11}$.

10. The compound of claim 1, wherein $R^{17}$ is $C_2$-$C_6$ alkenyl, benzyl, or a 5- or 6-membered saturated or unsaturated ring containing 1-3 heteroatoms wherein each ring may be optionally substituted with 1-3 $R^{11}$.

11. The compound of claim 1, wherein $R^{29}$ is benzoyl.

12. A composition for the control of a fungal pathogen including the compound of claim 1 and a phytologically acceptable carrier material.

13. The composition of claim 12 wherein the fungal pathogen is Apple Scab (*Venturia inaequalis*), Leaf Blotch of Wheat (*Septoria tritici*), Leaf spot of sugarbeets (*Cercospora beticola*), Leaf Spot of peanut (*Cercospora arachidicola*), and Black Sigatoka (*Mycosphaerella fijiensis*).

14. A method for the control and prevention of fungal attack on a plant, the method including the steps of:
applying a fungicidally effective amount of at least one of the compounds of claim 1 to at least one of the plant, an area adjacent to the plant, soil adapted to support growth of the plant, a root of the plant, foliage of the plant, and a seed adapted to produce the plant.

15. The method of claim 14 wherein the fungal attach is caused by Leaf Blotch of Wheat (*Septoria tritici*).

16. The compound of claim 1, wherein $R^3$ and $R^4$ are taken together to form =C(R$^{12}$)N(R$^{13}$)R$^{14}$.

17. The compound of claim 1, wherein $R^3$ and $R^4$ are taken together to form =C(R$^{12}$)N(R$^{13}$)R$^{14}$, $R^{21}$ is —(CHR$^{24}$)$_m$OR$^{29}$, and $R^{29}$ is benzoyl.

18. The compound of claim 1, wherein $R^{21}$ is —(CHR$^{24}$)$_m$OR$^{29}$.

19. The compound of claim 18, wherein $R^{24}$ is H and m is 1.

20. A compound of the formula:

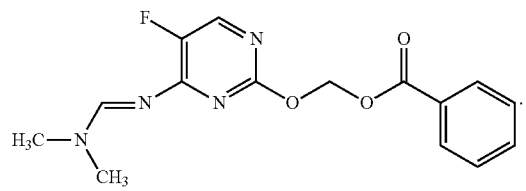 [SMILES: CN(C)/C=N/c1nc(OCOC(=O)c2ccccc2)ncc1F]

* * * * *